(12) United States Patent
Sheppard et al.

(10) Patent No.: US 10,836,720 B2
(45) Date of Patent: Nov. 17, 2020

(54) INHIBITORS OF INTEGRIN ALPHA 5 BETA 1 AND METHODS OF USE

(71) Applicant: The Regents of the University of California, Oakland, CA (US)

(72) Inventors: Dean Sheppard, Oakland, CA (US); Aparna Sundaram, San Francisco, CA (US); William F. Degrado, San Francisco, CA (US); Hyunil Jo, Lafayette, CA (US); Joel McIntosh, Pacifica, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 16/090,022

(22) PCT Filed: Mar. 31, 2017

(86) PCT No.: PCT/US2017/025432
§ 371 (c)(1),
(2) Date: Sep. 28, 2018

(87) PCT Pub. No.: WO2017/173302
PCT Pub. Date: Oct. 5, 2017

(65) Prior Publication Data
US 2019/0144386 A1    May 16, 2019

Related U.S. Application Data

(60) Provisional application No. 62/317,422, filed on Apr. 1, 2016.

(51) Int. Cl.
C07D 207/48    (2006.01)
C07D 401/12    (2006.01)
C07D 405/12    (2006.01)
C07D 453/02    (2006.01)
A61P 11/06     (2006.01)
C07D 207/16    (2006.01)

(52) U.S. Cl.
CPC ............ *C07D 207/48* (2013.01); *A61P 11/06* (2018.01); *C07D 207/16* (2013.01); *C07D 401/12* (2013.01); *C07D 405/12* (2013.01); *C07D 453/02* (2013.01)

(58) Field of Classification Search
None
See application file for complete search history.

(56) References Cited

U.S. PATENT DOCUMENTS

| | | |
|---|---|---|
| 2005/0143391 A1* | 6/2005 | Carceller Gonzalez ............ A61P 17/06 514/254.01 |
| 2006/0014966 A1 | 1/2006 | Lee et al. |
| 2007/0219252 A1 | 9/2007 | Chen et al. |
| 2010/0179119 A1* | 7/2010 | DeGrado ............ C07D 205/04 514/210.17 |
| 2012/0114667 A1 | 5/2012 | Eberlein et al. |

FOREIGN PATENT DOCUMENTS

| | | |
|---|---|---|
| WO | WO-98/53814 A1 | 12/1998 |
| WO | WO-99/06432 A1 | 2/1999 |
| WO | WO-01/12186 A1 | 2/2001 |
| WO | WO-03/084984 A1 | 10/2003 |
| WO | WO-2006/133338 A1 | 12/2006 |
| WO | WO-2015/048819 A1 | 4/2015 |
| WO | WO2015048819 | * 4/2015 |

OTHER PUBLICATIONS

Chemical Abstract Registry No. 1027961-73-4, indexed in the Registry File on STN CAS Online Jun. 13, 2008.*
Vanderslice et al., Small Molecule Agonist of Very Late Antigen-4 (VLA-4) Integrin Induces Progenitor Cell Adhesion. The Journal of Biological Chemistry, 2013, 288, 19414-19428.*
International Search Report dated Sep. 13, 2017, for PCT Application No. PCT/US2017/025432, filed Mar. 31, 2017, 5 pages.
Written Opinion dated Sep. 13, 2017, for PCT Application No. PCT/US2017/025432, filed Mar. 31, 2017, 7 pages.
Choi, S. et al. (Nov. 1, 2007, e-published Oct. 4, 2007). "Small molecule inhibitors of integrin alpha2beta1," *J Med Chem* 50(22):5457-5462.
Egger, L.A. et al. (Sep. 2003, e-published May 23, 2003). "A small molecule alpha4beta1/alpha4beta7 antagonist differentiates between the low-affinity states of alpha4beta1 and alpha4beta7: characterization of divalent cation dependence," *J Pharmacol Exp Ther* 306(3):903-913.
European Search Report dated Feb. 6, 2020, for EP Patent Application No. 17776794.4, 12 pages.
Miller, M.W. et al. (Jan. 20, 2009, e-published Jan. 13, 2009). "Small-molecule inhibitors of integrin alpha2beta1 that prevent pathological thrombus formation via an allosteric mechanism," *PNAS USA* 106(3):719-724.

* cited by examiner

*Primary Examiner* — Po-Chih Chen
(74) *Attorney, Agent, or Firm* — Edward D. Grieff; Mintz, Levin, Cohn, Ferris, Glovsky and Popeo, P.C.

(57) ABSTRACT

Disclosed herein, inter alia, are inhibitors of integrin alpha 5 beta 1 and methods of using the same.

21 Claims, 1 Drawing Sheet

Specification includes a Sequence Listing.

SEQUENCE LISTING

```
<160> NUMBER OF SEQ ID NOS: 7

<210> SEQ ID NO 1
<211> LENGTH: 3
<212> TYPE: PRT
<213> ORGANISM: Homo sapiens

<400> SEQUENCE: 1

Arg Gly Asp
1

<210> SEQ ID NO 2
<211> LENGTH: 3
<212> TYPE: PRT
<213> ORGANISM: Homo sapiens

<400> SEQUENCE: 2

Asp Gly Arg
1

<210> SEQ ID NO 3
<211> LENGTH: 6
<212> TYPE: PRT
<213> ORGANISM: Homo sapiens

<400> SEQUENCE: 3

Gly Arg Gly Asp Ser Pro
1               5

<210> SEQ ID NO 4
<211> LENGTH: 8
<212> TYPE: PRT
<213> ORGANISM: Homo sapiens

<400> SEQUENCE: 4

Cys Asn Thr Leu Lys Gly Asp Cys
1               5

<210> SEQ ID NO 5
<211> LENGTH: 6
<212> TYPE: PRT
<213> ORGANISM: Homo sapiens

<400> SEQUENCE: 5

Asn Thr Leu Lys Gly Asp
1               5
```

```
<210> SEQ ID NO 6
<211> LENGTH: 1098
<212> TYPE: PRT
<213> ORGANISM: Homo sapiens

<400> SEQUENCE: 6

Met Pro Pro Arg Gln Pro Pro Arg Gln Ala Gly Gly Gly Leu Ser Arg
1               5                   10                  15

Glu Phe Gly Lys Leu Leu Pro Ala Leu Ser His Ser Pro Leu Gly Gly
            20                  25                  30

Leu Gly Ser Gly Ser Gly Ser Val Ala Pro Gly Gln Gly Arg Ala Gly
        35                  40                  45

Ala Met Gly Ser Arg Thr Pro Glu Ser Pro Leu His Ala Val Gln Leu
    50                  55                  60

Arg Trp Gly Pro Arg Arg Arg Pro Pro Leu Leu Pro Leu Leu Leu Leu
65                  70                  75                  80

Leu Leu Pro Pro Pro Arg Val Gly Gly Phe Asn Leu Asp Ala Glu Ala
                85                  90                  95

Ala Pro Ala Val Leu Ser Gly Pro Pro Gly Ser Phe Phe Gly Phe Ser
            100                 105                 110

Val Glu Phe Tyr Arg Pro Gly Thr Asp Gly Val Ser Val Leu Val Gly
        115                 120                 125

Ala Pro Lys Ala Asn Thr Ser Gln Pro Gly Val Leu Gln Gly Gly Ala
    130                 135                 140

Val Tyr Leu Cys Pro Trp Gly Ala Ser Pro Thr Gln Cys Thr Pro Ile
145                 150                 155                 160

Glu Phe Asp Ser Lys Gly Ser Arg Leu Leu Glu Ser Ser Leu Ser Ser
                165                 170                 175

Ser Glu Gly Glu Glu Pro Val Glu Tyr Lys Ser Leu Gln Trp Phe Gly
            180                 185                 190

Ala Thr Val Arg Ala His Gly Ser Ser Ile Leu Ala Cys Ala Pro Leu
        195                 200                 205

Tyr Ser Trp Arg Thr Glu Lys Glu Pro Leu Ser Asp Pro Val Gly Thr
    210                 215                 220

Cys Tyr Leu Ser Thr Asp Asn Phe Thr Arg Ile Leu Glu Tyr Ala Pro
225                 230                 235                 240

Cys Arg Ser Asp Phe Ser Trp Ala Ala Gly Gln Gly Tyr Cys Gln Gly
                245                 250                 255

Gly Phe Ser Ala Glu Phe Thr Lys Thr Gly Arg Val Val Leu Gly Gly
            260                 265                 270

Pro Gly Ser Tyr Phe Trp Gln Gly Gln Ile Leu Ser Ala Thr Gln Glu
        275                 280                 285

Gln Ile Ala Glu Ser Tyr Tyr Pro Glu Tyr Leu Ile Asn Leu Val Gln
    290                 295                 300

Gly Gln Leu Gln Thr Arg Gln Ala Ser Ser Ile Tyr Asp Asp Ser Tyr
305                 310                 315                 320

Leu Gly Tyr Ser Val Ala Val Gly Glu Phe Ser Gly Asp Asp Thr Glu
                325                 330                 335

Asp Phe Val Ala Gly Val Pro Lys Gly Asn Leu Thr Tyr Gly Tyr Val
            340                 345                 350

Thr Ile Leu Asn Gly Ser Asp Ile Arg Ser Leu Tyr Asn Phe Ser Gly
        355                 360                 365

Glu Gln Met Ala Ser Tyr Phe Gly Tyr Ala Val Ala Ala Thr Asp Val
    370                 375                 380
```

-continued

Asn Gly Asp Gly Leu Asp Asp Leu Leu Val Gly Ala Pro Leu Leu Met
385                 390                 395                 400

Asp Arg Thr Pro Asp Gly Arg Pro Gln Glu Val Gly Arg Val Tyr Val
            405                 410                 415

Tyr Leu Gln His Pro Ala Gly Ile Glu Pro Thr Pro Thr Leu Thr Leu
            420                 425                 430

Thr Gly His Asp Glu Phe Gly Arg Phe Gly Ser Ser Leu Thr Pro Leu
            435                 440                 445

Gly Asp Leu Asp Gln Asp Gly Tyr Asn Asp Val Ala Ile Gly Ala Pro
450                 455                 460

Phe Gly Glu Thr Gln Gln Gly Val Val Phe Val Phe Pro Gly Gly
465                 470                 475                 480

Pro Gly Gly Leu Gly Ser Lys Pro Ser Gln Val Leu Gln Pro Leu Trp
            485                 490                 495

Ala Ala Ser His Thr Pro Asp Phe Phe Gly Ser Ala Leu Arg Gly Gly
            500                 505                 510

Arg Asp Leu Asp Gly Asn Gly Tyr Pro Asp Leu Ile Val Gly Ser Phe
            515                 520                 525

Gly Val Asp Lys Ala Val Val Tyr Arg Gly Arg Pro Ile Val Ser Ala
530                 535                 540

Ser Ala Ser Leu Thr Ile Phe Pro Ala Met Phe Asn Pro Glu Glu Arg
545                 550                 555                 560

Ser Cys Ser Leu Glu Gly Asn Pro Val Ala Cys Ile Asn Leu Ser Phe
            565                 570                 575

Cys Leu Asn Ala Ser Gly Lys His Val Ala Asp Ser Ile Gly Phe Thr
            580                 585                 590

Val Glu Leu Gln Leu Asp Trp Gln Lys Gln Lys Gly Gly Val Arg Arg
            595                 600                 605

Ala Leu Phe Leu Ala Ser Arg Gln Ala Thr Leu Thr Gln Thr Leu Leu
610                 615                 620

Ile Gln Asn Gly Ala Arg Glu Asp Cys Arg Glu Met Lys Ile Tyr Leu
625                 630                 635                 640

Arg Asn Glu Ser Glu Phe Arg Asp Lys Leu Ser Pro Ile His Ile Ala
            645                 650                 655

Leu Asn Phe Ser Leu Asp Pro Gln Ala Pro Val Asp Ser His Gly Leu
            660                 665                 670

Arg Pro Ala Leu His Tyr Gln Ser Lys Ser Arg Ile Glu Asp Lys Ala
            675                 680                 685

Gln Ile Leu Leu Asp Cys Gly Glu Asp Asn Ile Cys Val Pro Asp Leu
690                 695                 700

Gln Leu Glu Val Phe Gly Glu Gln Asn His Val Tyr Leu Gly Asp Lys
705                 710                 715                 720

Asn Ala Leu Asn Leu Thr Phe His Ala Gln Asn Val Gly Glu Gly Gly
            725                 730                 735

Ala Tyr Glu Ala Glu Leu Arg Val Thr Ala Pro Pro Glu Ala Glu Tyr
            740                 745                 750

Ser Gly Leu Val Arg His Pro Gly Asn Phe Ser Ser Leu Ser Cys Asp
            755                 760                 765

Tyr Phe Ala Val Asn Gln Ser Arg Leu Leu Val Cys Asp Leu Gly Asn
            770                 775                 780

Pro Met Lys Ala Gly Ala Ser Leu Trp Gly Gly Leu Arg Phe Thr Val
785                 790                 795                 800

Pro His Leu Arg Asp Thr Lys Lys Thr Ile Gln Phe Asp Phe Gln Ile 805                 810                 815
Leu Ser Lys Asn Leu Asn Asn Ser Gln Ser Asp Val Val Ser Phe Arg
            820                 825                 830

Leu Ser Val Glu Ala Gln Ala Gln Val Thr Leu Asn Gly Val Ser Lys
            835                 840                 845

Pro Glu Ala Val Leu Phe Pro Val Ser Asp Trp His Pro Arg Asp Gln
850                 855                 860

Pro Gln Lys Glu Asp Leu Gly Pro Ala Val His His Val Tyr Glu
865                 870                 875                 880

Leu Ile Asn Gln Gly Pro Ser Ser Ile Ser Gln Gly Val Leu Glu Leu
                885                 890                 895

Ser Cys Pro Gln Ala Leu Glu Gly Gln Gln Leu Leu Tyr Val Thr Arg
                900                 905                 910

Val Thr Gly Leu Asn Cys Thr Thr Asn His Pro Ile Asn Pro Lys Gly
            915                 920                 925

Leu Glu Leu Asp Pro Glu Gly Ser Leu His His Gln Gln Lys Arg Glu
            930                 935                 940

Ala Pro Ser Arg Ser Ser Ala Ser Ser Gly Pro Gln Ile Leu Lys Cys
945                 950                 955                 960

Pro Glu Ala Glu Cys Phe Arg Leu Arg Cys Glu Leu Gly Pro Leu His
                965                 970                 975

Gln Gln Glu Ser Gln Ser Leu Gln Leu His Phe Arg Val Trp Ala Lys
                980                 985                 990

Thr Phe Leu Gln Arg Glu His Gln Pro Phe Ser Leu Gln Cys Glu Ala
            995                 1000                1005

Val Tyr Lys Ala Leu Lys Met Pro Tyr Arg Ile Leu Pro Arg Gln
    1010                1015                1020

Leu Pro Gln Lys Glu Arg Gln Val Ala Thr Ala Val Gln Trp Thr
    1025                1030                1035

Lys Ala Glu Gly Ser Tyr Gly Val Pro Leu Trp Ile Ile Ile Leu
    1040                1045                1050

Ala Ile Leu Phe Gly Leu Leu Leu Leu Gly Leu Leu Ile Tyr Ile
    1055                1060                1065

Leu Tyr Lys Leu Gly Phe Phe Lys Arg Ser Leu Pro Tyr Gly Thr
    1070                1075                1080

Ala Met Glu Lys Ala Gln Leu Lys Pro Pro Ala Thr Ser Asp Ala
    1085                1090                1095

<210> SEQ ID NO 7
<211> LENGTH: 798
<212> TYPE: PRT
<213> ORGANISM: Homo sapiens

<400> SEQUENCE: 7

Met Asn Leu Gln Pro Ile Phe Trp Ile Gly Leu Ile Ser Ser Val Cys
1               5                   10                  15

Cys Val Phe Ala Gln Thr Asp Glu Asn Arg Cys Leu Lys Ala Asn Ala
            20                  25                  30

Lys Ser Cys Gly Glu Cys Ile Gln Ala Gly Pro Asn Cys Gly Trp Cys
        35                  40                  45

Thr Asn Ser Thr Phe Leu Gln Glu Gly Met Pro Thr Ser Ala Arg Cys
    50                  55                  60

Asp Asp Leu Glu Ala Leu Lys Lys Lys Gly Cys Pro Pro Asp Asp Ile
65                  70                  75                  80

-continued

```
Glu Asn Pro Arg Gly Ser Lys Asp Ile Lys Lys Asn Lys Asn Val Thr
                 85                  90                  95

Asn Arg Ser Lys Gly Thr Ala Glu Lys Leu Lys Pro Glu Asp Ile Thr
            100                 105                 110

Gln Ile Gln Pro Gln Gln Leu Val Leu Arg Leu Arg Ser Gly Glu Pro
        115                 120                 125

Gln Thr Phe Thr Leu Lys Phe Lys Arg Ala Glu Asp Tyr Pro Ile Asp
    130                 135                 140

Leu Tyr Tyr Leu Met Asp Leu Ser Tyr Ser Met Lys Asp Asp Leu Glu
145                 150                 155                 160

Asn Val Lys Ser Leu Gly Thr Asp Leu Met Asn Glu Met Arg Arg Ile
                165                 170                 175

Thr Ser Asp Phe Arg Ile Gly Phe Gly Ser Phe Val Glu Lys Thr Val
            180                 185                 190

Met Pro Tyr Ile Ser Thr Thr Pro Ala Lys Leu Arg Asn Pro Cys Thr
        195                 200                 205

Ser Glu Gln Asn Cys Thr Ser Pro Phe Ser Tyr Lys Asn Val Leu Ser
    210                 215                 220

Leu Thr Asn Lys Gly Glu Val Phe Asn Glu Leu Val Gly Lys Gln Arg
225                 230                 235                 240

Ile Ser Gly Asn Leu Asp Ser Pro Glu Gly Gly Phe Asp Ala Ile Met
                245                 250                 255

Gln Val Ala Val Cys Gly Ser Leu Ile Gly Trp Arg Asn Val Thr Arg
            260                 265                 270

Leu Leu Val Phe Ser Thr Asp Ala Gly Phe His Phe Ala Gly Asp Gly
        275                 280                 285

Lys Leu Gly Gly Ile Val Leu Pro Asn Asp Gly Gln Cys His Leu Glu
    290                 295                 300

Asn Asn Met Tyr Thr Met Ser His Tyr Tyr Asp Tyr Pro Ser Ile Ala
305                 310                 315                 320

His Leu Val Gln Lys Leu Ser Glu Asn Asn Ile Gln Thr Ile Phe Ala
                325                 330                 335

Val Thr Glu Glu Phe Gln Pro Val Tyr Lys Glu Leu Lys Asn Leu Ile
            340                 345                 350

Pro Lys Ser Ala Val Gly Thr Leu Ser Ala Asn Ser Ser Asn Val Ile
        355                 360                 365

Gln Leu Ile Ile Asp Ala Tyr Asn Ser Leu Ser Ser Glu Val Ile Leu
    370                 375                 380

Glu Asn Gly Lys Leu Ser Glu Gly Val Thr Ile Ser Tyr Lys Ser Tyr
385                 390                 395                 400

Cys Lys Asn Gly Val Asn Gly Thr Gly Glu Asn Gly Arg Lys Cys Ser
                405                 410                 415

Asn Ile Ser Ile Gly Asp Glu Val Gln Phe Glu Ile Ser Ile Thr Ser
            420                 425                 430

Asn Lys Cys Pro Lys Lys Asp Ser Asp Ser Phe Lys Ile Arg Pro Leu
        435                 440                 445

Gly Phe Thr Glu Glu Val Glu Val Ile Leu Gln Tyr Ile Cys Glu Cys
    450                 455                 460

Glu Cys Gln Ser Glu Gly Ile Pro Glu Ser Pro Lys Cys His Glu Gly
465                 470                 475                 480

Asn Gly Thr Phe Glu Cys Gly Ala Cys Arg Cys Asn Glu Gly Arg Val
                485                 490                 495

Gly Arg His Cys Glu Cys Ser Thr Asp Glu Val Asn Ser Glu Asp Met
```

-continued

```
                500                505                510
Asp Ala Tyr Cys Arg Lys Glu Asn Ser Ser Glu Ile Cys Ser Asn Asn
            515                520                525

Gly Glu Cys Val Cys Gly Gln Cys Val Cys Arg Lys Arg Asp Asn Thr
            530                535            540

Asn Glu Ile Tyr Ser Gly Lys Phe Cys Glu Cys Asp Asn Phe Asn Cys
545                550                555                560

Asp Arg Ser Asn Gly Leu Ile Cys Gly Gly Asn Gly Val Cys Lys Cys
            565                570                575

Arg Val Cys Glu Cys Asn Pro Asn Tyr Thr Gly Ser Ala Cys Asp Cys
            580                585                590

Ser Leu Asp Thr Ser Thr Cys Glu Ala Ser Asn Gly Gln Ile Cys Asn
            595                600                605

Gly Arg Gly Ile Cys Glu Cys Gly Val Cys Lys Cys Thr Asp Pro Lys
            610                615            620

Phe Gln Gly Gln Thr Cys Glu Met Cys Gln Thr Cys Leu Gly Val Cys
625                630                635                640

Ala Glu His Lys Glu Cys Val Gln Cys Arg Ala Phe Asn Lys Gly Glu
            645                650                655

Lys Lys Asp Thr Cys Thr Gln Glu Cys Ser Tyr Phe Asn Ile Thr Lys
            660                665                670

Val Glu Ser Arg Asp Lys Leu Pro Gln Pro Val Gln Pro Asp Pro Val
            675                680                685

Ser His Cys Lys Glu Lys Asp Val Asp Asp Cys Trp Phe Tyr Phe Thr
            690                695            700

Tyr Ser Val Asn Gly Asn Asn Glu Val Met Val His Val Val Glu Asn
705                710                715                720

Pro Glu Cys Pro Thr Gly Pro Asp Ile Ile Pro Ile Val Ala Gly Val
            725                730                735

Val Ala Gly Ile Val Leu Ile Gly Leu Ala Leu Leu Leu Ile Trp Lys
            740                745            750

Leu Leu Met Ile Ile His Asp Arg Arg Glu Phe Ala Lys Phe Glu Lys
            755                760                765

Glu Lys Met Asn Ala Lys Trp Asp Thr Gly Glu Asn Pro Ile Tyr Lys
            770                775                780

Ser Ala Val Thr Thr Val Val Asn Pro Lys Tyr Glu Gly Lys
785                790                795
```

INHIBITORS OF INTEGRIN ALPHA 5 BETA 1 AND METHODS OF USE

CROSS-REFERENCES TO RELATED APPLICATIONS

This application is a U.S. national stage under 35 U.S.C. § 371 of International Application No. PCT/US2017/025432 filed Mar. 31, 2017, which claims priority to U.S. Provisional Application No. 62/317,422 filed Apr. 1, 2016, which are incorporated herein by reference in their entirety and for all purposes.

STATEMENT AS TO RIGHTS TO INVENTIONS MADE UNDER FEDERALLY SPONSORED RESEARCH AND DEVELOPMENT

This invention was made with government support under grant numbers F32 HL112588, U19 AI070412, R01 HL102292, and U19 AI077439 awarded by the National Institutes of Health. The government has certain rights in the invention.

BACKGROUND

Despite its high prevalence, current therapeutic options for asthma are quite limited. There are a paucity of effective treatments for asthma. Pharmacological modulation of the α5β1 integrin by small molecules presents one route to test the role of the α5β1 integrin in asthma. There is a need in the art for potent, selective α5β1 integrin inhibitors. Provided herein are solutions to these and other problems in the art.

BRIEF SUMMARY OF THE INVENTION

Herein are provided, inter alia, methods for treating asthma using an α5β1 inhibitor and compositions of α5β1 inhibitors.

In an aspect is provided a compound having the formula:

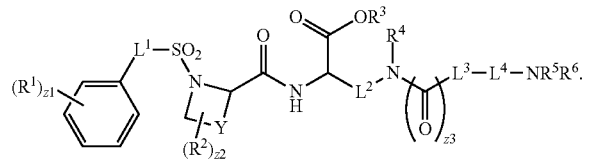

$R^1$ is independently halogen, $-N_3$, $-CX^1_3$, $-CHX^1_2$, $-CH_2X^1$, $-OCX^1_3$, $-OCH_2X^1$, $-OCHX^1_2$, $-CN$, $-SO_{n1}R^{1D}$, $-SO_{v1}NR^{1A}R^{1B}$, $-OSO_{v1}R^{1D}$, $-NHC(O)NR^{1A}R^{1B}$, $-N(O)_{m1}$, $-NR^{1A}R^{1B}$, $-C(O)R^{1C}$, $-C(O)-OR^{1C}$, $-C(O)NR^{1A}R^{1B}$, $-OR^{1D}$, $-NR^{1A}SO_2R^{1D}$, $-NR^{1A}C(O)R^{1C}$, $-NR^{1A}C(O)OR^{1C}$, $-NR^{1A}OR^{1C}$, $-ONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl. $L^1$ is a bond or substituted or unsubstituted alkylene, or substituted or unsubstituted heteroalkylene. Y is a bond, $-C-$, $-C-C-$, $-C=C-$, $-C-C-C-$, $-C=C-C-$, $-C-C=C-$, $-O-C-$, $-C-O-$, $-C-O-C$, $-S-C-$, $-C-S-$, or $-C-S-C-$; $R^2$ is independently halogen, $-CX^2_3$, $-CHX^2_2$, $-CH_2X^2$, $-OCX^2_3$, $-OCH_2X^2$, $-OCHX^2_2$, $-CN$, $-SO_{n2}R^{2D}$, $-SO_{v2}NR^{2A}R^{2B}$, $-NHC(O)NR^{2A}R^{2B}$, $-N(O)_{m2}$, $-NR^{2A}R^{2B}$, $-C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl. $R^3$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a prodrug moiety. $R^4$ is independently hydrogen, $-CX^4_3$, $-CN$, $-COOH$, $-CONH_2$, $-CHX^4_2$, $-CH_2X^4$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $L^2$ is unsubstituted alkylene. $L^3$ is a bond, $-O-$, $-S-$, $-N(R^7)-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^7$ is hydrogen, $-CN$, $-COOH$, $-CX^7_3$, substituted or unsubstituted alkyl, or substituted or unsubstituted heteroalkyl. $L^4$ is $-O-$, $-S-$, $-N(R^8)-$, $-C(O)-$, $C(O)O-$, $-S(O)-$, $-S(O)_2-$, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene. $R^8$ is hydrogen, $-CN$, $-COOH$, $-CX^8_3$, substituted or unsubstituted alkyl, or substituted or unsubstituted heteroalkyl. $R^5$ and $R^6$ are independently hydrogen,

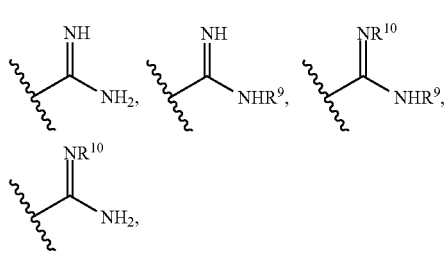

substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^5$ and $R^6$ may optionally be joined to form a substituted or unsubstituted heterocycloalkyl or substituted or unsubstituted heteroaryl. $R^9$ is hydrogen, halogen, $-N_3$, $-CX^9_3$, $-CHX^9_2$, $-CH_2X^9$, $-CN$, $-CHO$, $-OH$, $-NH_2$, $-COOH$, $-CONH_2$, $-NO_2$, $-SH$, $-SO_2$, $-SO_2CH_3$, $-SO_3H$, $-SO_4H$, $-SO_2NH_2$, $-NHNH_2$, $-ONH_2$, $-NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{10}$ is hydrogen, halogen, $-N_3$, $-CX^{10}_3$, $-CHX^{10}_2$, $-CH_2X^{10}$, $-CN$, $-CHO$, $-OH$, $-NH_2$, $-COOH$, $-CONH_2$, $-NO_2$, $-SH$, $-SO_2$, $-SO_2CH_3$, $-SO_3H$, $-SO_4H$, $-SO_2NH_2$, $-NHNH_2$, $-ONH_2$, $-NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Each $R^{1A}$, $R^{1B}$, $R^{1C}$, $R^{1D}$, $R^{2A}$, $R^{2B}$, $R^{2C}$, $R^{2D}$, is independently hydrogen, $-CX_3$, $-CN$, $-COOH$, $-CONH_2$, $-CHX_2$, $-CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{1A}$ and $R^{1B}$ substituents bonded to the same nitrogen atom may optionally be joined to form a substituted or unsubstituted heterocycloalkyl or substituted or unsubstituted heteroaryl. $R^{2A}$ and $R^{2B}$ substituents bonded to the same nitrogen atom may optionally be joined to form a substituted or unsubstituted heterocycloalkyl or substituted or unsubstituted heteroaryl. Each X, $X^1$, $X^2$, $X^4$, $X^7$, $X^8$, $X^9$, and $X^{10}$ are independently $-F$, $-Cl$, $-Br$, or $-I$. The symbols n1 and n2 are independently an integer from 0 to 4. The symbols m1, m2, v1 and v2 are independently 1 or 2. z1 is an integer from 0 and 5. z2 is an integer from 0 and 9. z3 is 0 or 1. In embodiments, when $R^5$ is hydrogen, $R^6$ is not hydrogen.

In another aspect is provided a pharmaceutical composition including a pharmaceutically acceptable excipient and a compound as described herein.

In an aspect is provided a method for treating asthma, the method including administering to a subject in need thereof an effective amount of a compound, or a pharmaceutically acceptable salt thereof, having the formula:

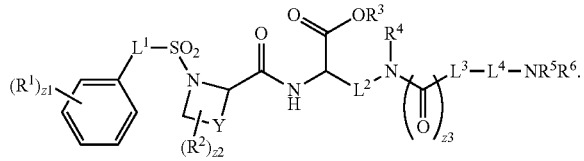

$R^1$ is independently halogen, $-N_3$, $-CX^1_3$, $-CHX^1_2$, $-CH_2X^1$, $-OCX^1_3$, $-OCH_2X^1$, $-OCHX^1_2$, $-CN$, $-SO_{n1}R^{1D}$, $-SO_{v1}NR^{1A}R^{1B}$, $-OSO_{v1}R^{1D}$, $-NHC(O)NR^{1A}R^{1B}$, $-N(O)_{m1}$, $-NR^{1A}R^{1B}$, $-C(O)R^{1C}$, $-C(O)OR^{1C}$, $-C(O)NR^{1A}R^{1B}$, $-OR^{1D}$, $-NR^{1A}SO_2R^{1D}$, $-NR^{1A}C(O)R^{1C}$, $-NR^{1A}C(O)OR^{1C}$, $-NR^{1A}OR^{1C}$, $-ONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl. $L^1$ is a bond or substituted or unsubstituted alkylene, or substituted or unsubstituted heteroalkylene. Y is a bond, $-C-$, $-C-C-$, $-C=C-$, $-C-C-C-$, $-C=C-C-$, $-C-C=C-$, $-O-C-$, $-C-O-$, $-C-O-C-$, $-S-C-$, $-C-S-$, or $-C-S-C-$; $R^2$ is independently halogen, $-CX^2_3$, $-CHX^2_2$, $-CH_2X^2$, $-OCX^2_3$, $-OCH_2X^2$, $-OCHX^2_2$, $-CN$, $-SO_{n2}R^{2D}$, $-SO_{v2}NR^{2A}R^{2B}$, $-NHC(O)NR^{2A}R^{2B}$, $-N(O)_{m2}$, $-NR^{2A}R^{2B}$, $-C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl. $R^3$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a prodrug moiety. $R^4$ is independently hydrogen, $-CX^4_3$, $-CN$, $-COOH$, $-CONH_2$, $-CHX^4_2$, $-CH_2X^4$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $L^2$ is unsubstituted alkylene. $L^3$ is a bond, $-O-$, $-S-$, $-N(R^7)-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^7$ is hydrogen, $-CN$, $-COOH$, $-CX^7_3$, substituted or unsubstituted alkyl, or substituted or unsubstituted heteroalkyl. $L^4$ is $-O-$, $-S-$, $-N(R^8)-$, $-C(O)-$, $C(O)O-$, $-S(O)-$, $-S(O)_2-$, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene. $R^8$ is hydrogen, $-CN$, $-COOH$, $-CX^8_3$, substituted or unsubstituted alkyl, or substituted or unsubstituted heteroalkyl. $R^5$ and $R^6$ are independently hydrogen,

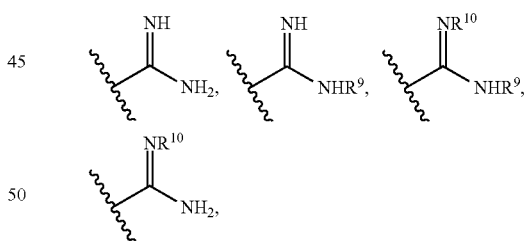

substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^5$ and $R^6$ may optionally be joined to form a substituted or unsubstituted heterocycloalkyl or substituted or unsubstituted heteroaryl. $R^9$ is hydrogen, halogen, $-N_3$, $-CX^9_3$, $-CHX^9_2$, $-CH_2X^9$, $-CN$, $-CHO$, $-OH$, $-NH_2$, $-COOH$, $-CONH_2$, $-NO_2$, $-SH$, $-SO_2$, $-SO_2CH_3$, $-SO_3H$, $-SO_4H$, $-SO_2NH_2$, $-NHNH_2$, $-ONH_2$, $-NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{10}$ is hydrogen, halogen, —$N_3$, —$CX^{10}_3$, —$CHX^{10}_2$, —$CH_2X^{10}$, —CN, —CHO, —OH, —$NH_2$, —COOH, —$CONH_2$, —$NO_2$, —SH, —$SO_2$, —$SO_2CH_3$—$SO_3H$, —$SO_4H$, —$SO_2NH_2$, —$NHNH_2$, —$ONH_2$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Each $R^{1A}$, $R^{1B}$, $R^{1C}$, $R^{1D}$, $R^{2A}R^{2B}$, $R^{2C}$, $R^{2D}$, is independently hydrogen, —$CX_3$, —CN, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{1A}$ and $R^{1B}$ substituents bonded to the same nitrogen atom may optionally be joined to form a substituted or unsubstituted heterocycloalkyl or substituted or unsubstituted heteroaryl. $R^{2A}$ and $R^{2B}$ substituents bonded to the same nitrogen atom may optionally be joined to form a substituted or unsubstituted heterocyclkyl or substituted or unsubstituted heteroaryl. Each X, $X^1$, $X^2$, $X^4$, $X^7$, $X^8$, $X^9$, and $X^{10}$ are independently —F, —Cl, —Br, or —I. The symbols n1 and n2 are independently an integer from 0 to 4. The symbols m1, m2, v1 and v2 are independently 1 or 2. z1 is an integer from 0 and 5. z2 is an integer from 0 and 9. z3 is 0 or 1.

In an aspect is provided a method of treating cancer including administering to a subject in need thereof an effective amount of a compound, or pharmaceutically acceptable salt, as described herein.

In an aspect is provided a method of treating an inflammatory disease including administering to a subject in need thereof an effective amount of a compound, or pharmaceutically acceptable salt, as described herein.

In an aspect is provided a method of treating an autoimmune disease including administering to a subject in need thereof an effective amount of a compound, or pharmaceutically acceptable salt, as described herein.

In an aspect is provided a method of detecting the presence of α5β1 integrin or inhibiting α5β1 integrin activity, the method including contacting an α5β1 integrin with a compound, or pharmaceutically acceptable salt, as described herein.

DETAILED DESCRIPTION

Figure 1A:
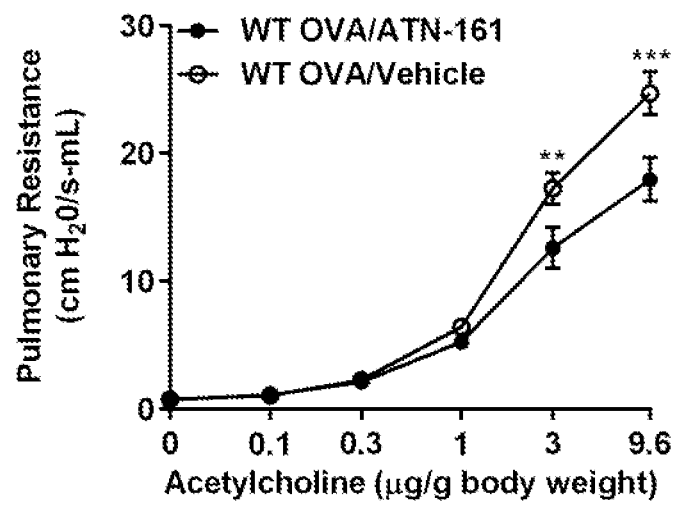
FIGS. 1A-1B. To investigate the role of α5β1 integrin in smooth muscle, wildtype (WT) mice were sensitized and challenged with ovalbumin (OVA). After intranasal administration of ATN-161, a known α5β1 inhibitor, or a vehicle control, pulmonary resistance was measured in response to increasing doses of acetylcholine (FIG. 1A). This experiment was repeated in an α5β1 knockout model. Mice homozygous for a conditional null (floxed) allele of itga5 were crossed to mice expressing rTTa under the control of the smooth muscle specific α smooth muscle actin promoter and tet-O cre and fed doxycline from conception to delete itga5 only in smooth muscle. These mice were sensitized and challenged with ovalbumin or saline, and airway hyperresponsiveness was measured in response to increasing doses of acetylcholine. Compared to littermate controls, conditional itga5 knockout mice were dramatically protected from ovalbumin-induced airway hyperresponsiveness (FIG. 1B).

Integrins are present in nearly all multi-cellular organisms and play a conserved role in mediating cell adhesion to fixed extracellular ligands and in the maintenance of tissue integrity. In invertebrates, a surprisingly small number of integrin heterodimers mediate these diverse functions. Much has been learned about the critical in vivo functions of most members of the integrin family through the use of mice with global or conditional inactivating mutations of individual subunits and through the use of heterodimer-specific blocking monoclonal antibodies. Pharmacological modulation of the α5β1 integrin by compounds described herein may be used to treat asthma. Described herein are compounds and methods of use for α5β1 integrin inhibitors.

I. DEFINITIONS

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated.

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched non-cyclic chain, or combinations thereof, including at least one carbon atom and at least one heteroatom (e.g., O, N, P, Si, or S), and wherein the nitrogen and sulfur atoms may optionally be oxidized, and the nitrogen heteroatom may optionally be quaternized. The heteroatom(s) (e.g., O, N, P, S, or Si) may be placed at any interior position of the heteroalkyl group or at the position at which the alkyl group is attached to the remainder of the molecule. Examples include, but are not limited to:

—$CH_2$—$CH_2$—O—$CH_3$, —$CH_2$—$CH_2$—NH—$CH_3$, —$CH_2$—$CH_2$—N($CH_3$)—$CH_3$, —$CH_2$—$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O) NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, non-aromatic cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, 3-hydroxy-cyclobut-3-enyl-1,2, dione, adamantanyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. A heterocycloalkyl moiety may include one ring heteroatom (e.g., O, N, S, Si, or P). A heterocycloalkyl moiety may include two optionally different ring heteroatoms (e.g., O, N, S, Si, or P). A heterocycloalkyl moiety may include three optionally different ring heteroatoms (e.g., O, N, S, Si, or P). A heterocycloalkyl moiety may include four optionally different ring heteroatoms (e.g., O, N, S, Si, or P). A heterocycloalkyl moiety may include five optionally different ring heteroatoms (e.g., O, N, S, Si, or P). A heterocycloalkyl moiety may include up to optionally different ring heteroatoms (e.g., O, N, S, Si, or P).

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of aryl and heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene. A heteroaryl moiety may include one ring heteroatom (e.g., O, N, or S). A heteroaryl moiety may include two optionally different ring heteroatoms (e.g., O, N, or S). A heteroaryl moiety may include three optionally different ring heteroatoms (e.g., O, N, or S). A heteroaryl moiety may include four optionally different ring heteroatoms (e.g., O, N, or S). A heteroaryl moiety may include five optionally different ring heteroatoms (e.g., O, N, or S). An aryl moiety may have a single ring. An aryl moiety may have two optionally different rings. An aryl moiety may have three optionally different rings. An aryl moiety may have four optionally different rings. A heteroaryl moiety may have one ring. A heteroaryl moiety may have two optionally different rings. A heteroaryl moiety may have three optionally different rings. A heteroaryl moiety may have four optionally different rings. A heteroaryl moiety may have five optionally different rings.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein.

The term "oxo," as used herein, means an oxygen that is double bonded to a carbon atom.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl," "heteroalkyl,", "cycloalkyl", "heterocycloalkyl", "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRS$O_2$R', —NR'NR"R'", —ONR'R", —NR'C=(O)NR"NR'"R"", —CN, —$NO_2$, in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRS$O_2$R', —NR'NR"R'", —ONR'R", —NR'C=(O)NR"NR'"R"", —CN, —$NO_2$, —R', —$N_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula —T—C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula —A—(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:
  (i) oxo, halogen, —$CF_3$, —CN, —OH, —$NH_2$, —COOH, —$CONH_2$, —$NO_2$, —SH—$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl, and
  (ii) alkyl, heteroalkyl, cycloalkyl, heterocycloalkyl, aryl, heteroaryl, substituted with at least one substituent selected from:
    (a) oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl, and
    (b) alkyl, heteroalkyl, cycloalkyl, heterocycloalkyl, aryl, heteroaryl, substituted with at least one substituent selected from: oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents than are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Provided herein are agents (e.g. compounds, drugs, therapeutic agents) that may be in a prodrug form. Prodrugs of the compounds described herein are those compounds that readily undergo chemical changes under select physiological conditions to provide the final agents (e.g. compounds, drugs, therapeutic agents). Additionally, prodrugs can be converted to agents (e.g. compounds, drugs, therapeutic agents) by chemical or biochemical methods in an ex vivo environment. Prodrugs described herein include compounds that readily undergo chemical changes under select physiological conditions to provide agents (e.g. compounds, drugs, therapeutic agents) to a biological system (e.g. in a subject, in a cancer cell, in the extracellular space near a cancer cell).

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in the art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^{3}$H), iodine-125 ($^{125}$I), or carbon-14 ($^{14}$C). All isotopic variations of the compounds of the present invention, whether radioactive or not, are encompassed within the scope of the present invention.

The symbol "⌇" denotes the point of attachment of a chemical moiety to the remainder of a molecule or chemical formula.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

A "detectable moiety" as used herein refers to a moiety that can be covalently or noncovalently attached to a compound or biomolecule that can be detected for instance, using techniques known in the art. In embodiments, the detectable moiety is covalently attached. The detectable moiety may provide for imaging of the attached compound or biomolecule. The detectable moiety may indicate the contacting between two compounds. Exemplary detectable moieties are fluorophores, antibodies, reactive dies, radio-labeled moieties, magnetic contrast agents, and quantum dots. Exemplary fluorophores include fluorescein, rhodamine, GFP, coumarin, FITC, Alexa fluor, Cy3, Cy5, BODIPY, and cyanine dyes. Exemplary radionuclides include Fluorine-18, Gallium-68, and Copper-64. Exemplary magnetic contrast agents include gadolinium, iron oxide and iron platinum, and manganese. The detectable moiety may be covalently attached through a covalent linker to the remainder of the molecule, wherein the covalent linker forms part of the detectable moiety. Therefore, a detectable moiety may include a detectable portions (e.g. a fluorophore) and covalent linker portion. The covalent linker portion may be $L^{12}$, wherein $L^{12}$ is —O—, —C(O)—, —CO(O)—, substituted or unsubstituted alkylene, substituted or unsubstituted heteroalkylene. The covalent linker portion may be $L^{12}$, wherein $L^{12}$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

An "α5β1-inhibitor" as used herein refers to a composition (e.g. a compound, nucleic acid, polynucleotide, peptide, protein, or antibody) capable of reducing the activity of α5β1 integrin when compared to a control compound (e.g. known to have no reduction in α5β1 integrin activity) or the absence of the α5β1-inhibitor compound. An "α5β1-inhibitor compound" refers to a compound (e.g. compounds described herein) that reduce the activity of α5β1 integrin when compared to a control, such as absence of the compound or a compound with known inactivity. An "α5β1-inhibitor-antibody" refers to an antibody that reduces the activity of α5β1 integrin when compared to a control (e.g. the absence of the antibody). An "α5β1-inhibitor-RGD peptide" refers to a RGD-peptide that reduces the activity of α5β1 integrin when compared to a control (e.g. the absence of the peptide).

An "α5β1-specific moiety", "specific," "specifically", "specificity", or the like of a composition (e.g. a compound, nucleic acid, polynucleotide, peptide, protein, or antibody) refers to the composition's ability to discriminate between particular molecular targets to a significantly greater extent than other proteins in the cell (e.g. a compound having specificity towards α5β1 integrin binds to α5β1 integrin whereas the same compound displays little-to-no binding to other integrins such as αvβ1, α8β1, α2β1, αvβ3, αvβ5, or αvβ6). An "α5β1-specific compound" refers to a compound (e.g. compounds described herein) having specificity towards α5β1 integrin. An "α5β1-specific antibody" refers to an antibody having specificity towards α5β1 integrin. An "α5β1-specific RGD peptide" refers to a RGD peptide having specificity towards α5β1 integrin.

The terms "α5β1-selective," "selective," or "selectivity" or the like of a compound refers to the composition's (e.g. a compound, nucleic acid, polynucleotide, peptide, protein, or antibody) ability to cause a particular action in a particular molecular target (e.g. a compound having selectivity toward α5β1 integrin would inhibit only α5β1). An "α5β1-selective compound" refers to a compound (e.g. compounds described herein) having selectivity towards α5β1 integrin. An "α5β1-selective antibody" refers to an antibody having selectivity towards α5β1 integrin. An "α5β1-selective RGD peptide" refers to a RGD peptide having selectivity towards α5β1 integrin.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A polypeptide, or a cell is "recombinant" when it is artificial or engineered, or derived from or contains an artificial or engineered protein or nucleic acid (e.g. non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

"RGD peptide" as used herein refers to a tripeptide comprising Arg, Gly, and Asp. RGD peptides typically act as recognition sequences for integrins and in some embodiments, promote cellular adhesion via integrin binding. RGD peptides as used herein refers to naturally occurring RGD sequences, RGD mimetics (e.g. substitutions of R, G, or D with non-proteinogenic amino acids), RGD peptides covalently bound to a targeting-moiety (e.g. a molecule for targeting the peptide to a specific integrin or specific location in a cell or organism), and cyclized RGD peptides of embodiments described herein. Exemplary RGD peptides include Arg-Gly-Asp, Asp-Gly-Arg, cyclo-Gly-Arg-Gly-Asp-Ser-Pro, and KGD peptides include Cys-Asn-Thr-Leu-Lys-Gly-Asp-Cys and Asn-Thr-Leu-Lys-Gly-Asp, and those found in Ann. Rev. Cell & Dev. Biol., 1996, November, Vol. 12: 697-715 and Proteins, 1992 December; 14(4):509-15.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

For preparation of suitable antibodies of the invention and for use according to the invention, e.g., recombinant, monoclonal, or polyclonal antibodies, many techniques known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* ($3^{rd}$ ed. 1997)). Techniques for the production of single chain antibodies or recombinant antibodies (U.S. Pat. Nos. 4,946, 778, 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633, 425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain.

Humanization can be essentially performed following the method of Winter and co-workers (see, e.g., Jones et al., *Nature* 321:522-525 (1986); Riechmann et al., *Nature* 332:323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. The preferred antibodies of, and for use according to the invention include humanized and/or chimeric monoclonal antibodies.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

As defined herein, the term "activation", "activate", "activating" and the like in reference to a protein refers to conversion of a protein into a biologically active derivative from an initial inactive or deactivated state. The terms reference activation, or activating, sensitizing, or up-regulating signal transduction or enzymatic activity or the amount of a protein decreased in a disease.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In embodiments inhibition refers means negatively affecting (e.g. decreasing) the concentration or levels of the protein relative to the concentration or level of the protein in the absence of the inhibitor. In embodiments inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation).

"Patient" or "subject in need thereof" or "subject" refers to a living organism suffering from or prone to a disease or condition that can be treated by administration of a compound or pharmaceutical composition or by a method, as provided herein. Non-limiting examples include humans, other mammals, bovines, rats, mice, dogs, monkeys, goat, sheep, cows, deer, and other non-mammalian animals. In some embodiments, a patient is human. In some embodiments, a subject is human.

"Disease" or "condition" refer to a state of being or health status of a patient or subject capable of being treated with a compound, pharmaceutical composition, or method provided herein. In some embodiments, the disease is asthma. The disease may be airway hyperresponsiveness. The disease may be airway hyperresponsiveness in asthma. The disease may be angiogenesis. The disease may be a cancer (e.g., ovarian cancer, bladder cancer, head and neck cancer, brain cancer, breast cancer, lung cancer, cervical cancer, liver cancer, colorectal cancer, pancreatic cancer, glioblastoma, neuroblastoma, rhabdomyosarcoma, osteosarcoma, renal cancer, renal cell carcinoma, non-small cell lung cancer, uterine cancer, testicular cancer, anal cancer, bile duct cancer, biliary tract cancer, gastrointestinal carcinoid tumors, esophageal cancer, gall bladder cancer, appendix cancer, small intestine cancer, stomach (gastric) cancer, urinary bladder cancer, genitourinary tract cancer, endometrial cancer, nasopharyngeal cancer, head and neck squamous cell carcinoma, or prostate cancer). The disease may be an autoimmune disease (e.g., scleroderma, lupus, diabetes, or rheumatoid arthritis). The disease may be an inflammatory disease (e.g., autoimmune diseases, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, sarcoidosis, transplant rejection, interstitial cystitis, atherosclerosis, scleroderma, or atopic dermatitis). In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma.

As used herein, the term "inflammatory disease" refers to a disease or condition characterized by aberrant inflammation (e.g. an increased level of inflammation compared to a control such as a healthy person not suffering from a disease). Examples of inflammatory diseases include autoimmune diseases, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, sarcoidosis, transplant rejection, interstitial cystitis, atherosclerosis, scleroderma, and atopic dermatitis.

As used herein, the term "cancer" refers to all types of cancer, neoplasm or malignant tumors found in mammals, including leukemia, carcinomas and sarcomas. Exemplary cancers that may be treated with a compound, inhibitory nucleic acid, pharmaceutical composition, or method provided herein include breast cancer (e.g. ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g. hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, or melanoma. Additional examples include, cancer of the thyroid, endocrine system, brain, breast, cervix, colon, head & neck, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, inhibitory nucleic acid, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound, inhibitory nucleic acid, pharmaceutical composition, or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound, inhibitory nucleic acid, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound, inhibitory nucleic acid, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

The term "aberrant" as used herein refers to different from normal. When used to describe enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

A "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal) compatible with the preparation. Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

"Co-administer" it is meant that a composition described herein is administered at the same time, just prior to, or just after the administration of one or more additional therapies. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered transdermally, by a topical route, or formulated as applicator sticks, solutions, suspensions, emulsions, gels, creams, ointments, pastes, jellies, paints, powders, and aerosols.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., spodoptera) and human cells. Cells may be useful when they are naturally nonadherent or have been treated not to adhere to surfaces, for example by trypsinization.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

Pharmaceutical compositions provided by the present invention include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., reducing, eliminating, or slowing the progression of disease symptoms (e.g. symptoms of asthma). Determination of a therapeutically effective amount of a compound of the invention is well within the capabilities of those skilled in the art, especially in light of the detailed disclosure herein.

As used herein "asthma" refers to any disease or condition characterized by inflammation within the circulatory system, often accompanied with wheezing, airway restriction, shortness of breath, chest tightness, and coughing. In embodiments, asthma is characterized by airway hyperresponsiveness. In embodiments, asthma is airway hyperresponsiveness. Asthma may refer inflammation in the bronchi and bronchioles. Asthma may refer to atopic asthma. Asthma may refer to non-atopic asthma.

The compounds described herein (e.g., compound wherein $R^3$ is not hydrogen) may be prodrugs. The term "prodrug" when referring to a prodrug described herein (e.g. α5β1-inhibitor compound moiety bonded to a prodrug moiety) refers to the compound including the α5β1-inhibitor compound moiety and the prodrug moiety. A "prodrug moiety" is the portion of a prodrug that may be cleaved from the prodrug resulting in an increased activity of the non-prodrug moiety portion of the prodrug, for example an α5β1-inhibitor compound having increased α5β1-inhibitor activity relative to the prodrug of the α5β1-inhibitor compound. In embodiments, the compounds described herein are prodrugs, wherein the prodrug moiety is the component of the compound that is not an α5β1-inhibitor compound moiety and is released from the α5β1-inhibitor compound moiety upon degradation of the prodrug.

In embodiments, degradation of the prodrug includes cleavage of —$OR^3$, wherein $R^3$ is not hydrogen. In embodiments, degradation of the prodrug includes cleavage of —$R^3$, wherein $R^3$ is not hydrogen. In embodiments, an α5β1-inhibitor compound is a compound described herein wherein $R^3$ is hydrogen and a prodrug of the α5β1-inhibitor compound is the identical compound except $R^3$ is not a hydrogen. A person having ordinary skill in the art would understand that the α5β1-inhibitor compound moiety includes only those compounds compatible with the chemistry provided herein for connecting the α5β1-inhibitor compound moiety to the prodrug moiety and for release of the α5β1-inhibitor compound from the compound (prodrug) (e.g., in vivo). In embodiments, degradation of the prodrug releases an active agent (e.g., α5β1-inhibitor compound). In such compounds, the resulting active agent includes a higher level of activity compared to the level of activity of the intact prodrug.

Integrins are transmembrane proteins that mediate interactions between adhesion molecules on adjacent cells and/or the extracellular matrix (ECM). Integrins have diverse roles in several biological processes including, for example, cell migration during development and wound healing, cell differentiation, and apoptosis. Integrins typically exist as heterodimers consisting of a subunits (about 120-170 kDa in size) and 3 subunits (about 90-100 kDa in size).

The terms "α5β1" and "α5β1 integrin" refer to an integrin comprised of α5 subunit and a β1 subunit and is used according to its common, ordinary meaning. "α5β1" refers to proteins of the same or similar names, homologs, isoforms, and functional fragments thereof, so long as such fragments retain α5β1 integrin activity. The term includes any recombinant or naturally-occurring form of α5β1, or an α5β1 preprotein, or variants thereof that maintain α5β1 activity (e.g. within at least 30%, 40%, 50%, 60%, 70%, 80%, 90%, 95%, or 100% activity compared to wildtype α5β1). In embodiments, α5 has the protein sequence corresponding to RefSeq NP_002196.3. In embodiments, α5 has the protein sequence corresponding to the proteolytically processed mature version of RefSeq NP_002196.3. In embodiments, α5 has the amino acid sequence corresponding to the reference number GI: 938148811. In embodi-

II. COMPOUNDS

In an aspect is provided a compound having the formula:

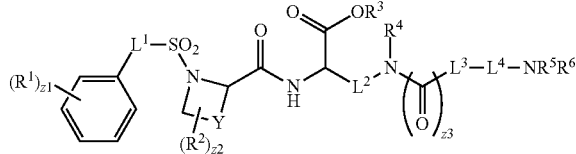

$R^1$ is independently halogen, —$CX^1_3$, —$CHX^1_2$, —$CH_2X^1$, —$OCX^1_3$, —$OCH_2X^1$, —$OCHX^1_2$, —CN, —$SO_{n1}R^{1D}$, —$SO_{v1}NR^{1A}R^{1B}$, —$NHC(O)NR^{1A}R^{1B}$, —$N(O)_{m1}$, —$NR^{1A}R^{1B}$, —$C(O)R^{1C}$, —C(O)—$OR^{1C}$, —$C(O)NR^{1A}R^{1B}$, —$OR^{1D}$, —$NR^{1A}SO_2R^{1D}$, —$NR^{1A}C(O)R^{1C}$, —$NR^{1A}C(O)OR^{1C}$, —$NR^{1A}OR^{C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl. $L^1$ is a bond or substituted or unsubstituted alkylene, or substituted or unsubstituted heteroalkylene. Y is a bond, —C—, —C—C—, —C=C—, —C—C—C—, —C=C—C—, —C—C=C—, —O—C—, —C—O—, —C—O—C, —S—C—, —C—S—, or —C—S—C—; $R^2$ is independently halogen, —$CX^2_3$, —$CHX^2_2$, —$CH_2X^2$, —$OCX^2_3$, —$OCH_2X^2$, —$OCHX^2_2$, —CN, —$SO_{n2}R^{2D}$, —$SO_{v2}NR^{2A}R^{2B}$, —$NHC(O)NR^{2A}R^{2B}$, —$N(O)_{m2}$, —$NR^{2A}R^{2B}$, —$C(O)R^{2C}$, —C(O)—$OR^{2C}$, —$C(O)NR^{2A}R^{2B}$, —$OR^{2D}$, —$NR^{2A}SO_2R^{2D}$, —$NR^{2A}C(O)R^{2C}$, —$NR^{2A}C(O)OR^{2C}$, —$NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl. $R^3$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a prodrug moiety. $R^4$ is independently hydrogen, —$CX^4_3$, —CN, —COOH, —$CONH_2$, —$CHX^4_2$, —$CH_2X^4$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $L^2$ is unsubstituted alkylene. $L^3$ is a bond, —O—, —S—, —$N(R^7)$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^7$ is hydrogen, —CN, —COOH, —$CX^7_3$, substituted or unsubstituted alkyl, or substituted or unsubstituted heteroalkyl. $L^4$ is —O—, —S—, —$N(R^8)$—, —C(O)—, C(O)O—, —S(O)—, —$S(O)_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene. $R^8$ is hydrogen, —CN, —COOH, —$CX^8_3$, substituted or unsubstituted alkyl, or substituted or unsubstituted heteroalkyl. $R^5$ and $R^6$ are independently hydrogen,

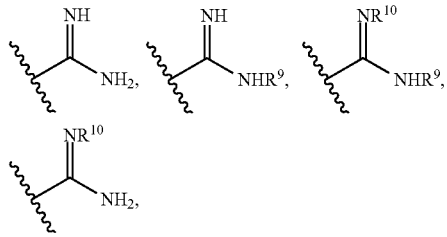

substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^5$ and $R^6$ may optionally be joined to form a substituted or unsubstituted heterocycloalkyl or substituted or unsubstituted heteroaryl. $R^9$ is hydrogen, halogen, —$N_3$, —$CX^9_3$, —$CHX^9_2$, —$CH_2X^9$, —CN, —CHO, —OH, —$NH_2$, —COOH, —$CONH_2$, —$NO_2$, —SH, —$SO_2$, —$SO_2CH_3$—$SO_3H$, —$SO_4H$, —$SO_2NH_2$, —$NHNH_2$, —$ONH_2$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{10}$ is hydrogen, halogen, —$N_3$, —$CX^{10}_3$, —$CHX^{10}_2$, —$CH_2X^{10}$, —CN, —CHO, —OH, —$NH_2$, —COOH, —$CONH_2$, —$NO_2$, —SH, —$SO_2$, —$SO_2CH_3$—$SO_3H$, —$SO_4H$, —$SO_2NH_2$, —$NHNH_2$, —$ONH_2$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Each $R^{1A}$, $R^{1B}$, $R^{1C}$, $R^{1D}$, $R^{2A}R^{2B}$, $R^{2C}$, $R^{2D}$, is independently hydrogen, —$CX_3$, —CN, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{1A}$ and $R^{1B}$ substituents bonded to the same nitrogen atom may optionally be joined to form a substituted or unsubstituted heterocycloalkyl or substituted or unsubstituted heteroaryl. $R^{2A}$ and $R^{2B}$ substituents bonded to the same nitrogen atom may optionally be joined to form a substituted or unsubstituted heterocycloalkyl or substituted or unsubstituted heteroaryl. Each X, $X^1$, $X^2$, $X^4$, $X^7$, $X^8$, $X^9$, and $X^{10}$ are independently —F, —Cl, —Br, or —I. The symbols n1 and n2 are independently an integer from 0 to 4. The symbols m1, m2, v1 and v2 are independently 1 or 2. z1 is an integer from 0 and 5. z2 is an integer from 0 and 9. z3 is 0 or 1.

In embodiments, Y is —C—C—, —C=C—, —O—C—, —C—O—, —C—O—C—, —C—S—, —S—C, or —C—S—C—. In embodiments, Y is —C—C—. In embodiments, Y is —C=C—. In embodiments, Y is —O—C—. In embodiments, Y is —C—O—. In embodiments, Y is —C—O—C—. In embodiments, Y is —C—S—. In embodiments, Y is —S—C—. In embodiments, Y is —C—S—C—.

In embodiments, the compound has the formula:

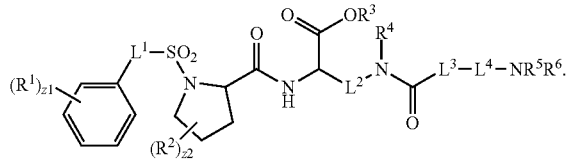

In embodiments, $R^1$ is independently halogen, —$N_3$, —$CF_3$, —$CCl_3$, —$CBr_3$, —$CI_3$, —CN, —CHO, —OH, —$NH_2$, —COOH, —$CONH_2$, —SH, —$SO_2$, —$SO_2CH_3$—$SO_3H$, —$OSO_3H$, —$SO_2NH_2$, —$NHNH_2$, —$ONH_2$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety. In embodiments, $R^1$ is independently halogen, —$N_3$, —$CF_3$, —$CCl_3$, —$CBr_3$, —$CI_3$, —CN, —CHO, —OH, —$NH_2$, —COOH, —$CONH_2$, —SH, —$SO_2$, —$SO_2CH_3$—$SO_3H$, —$OSO_3H$, —$SO_2NH_2$, —$NHNH_2$, —$ONH_2$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^1$ is independently halogen, —OMe, —SMe, —$SO_2Me$, —$SO_2Ph$, —COOH, substituted or unsubstituted $C_1$-$C_8$ alkyl, or substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted phenyl, or substituted or unsubstituted 5 to 6 membered heteroaryl; two adjacent $R^1$ substituents may optionally be joined to form a substituted or unsubstituted $C_3$-$C_8$ cycloalkyl, substituted or unsubstituted 3 to 8 membered heterocycloalkyl, substituted or unsubstituted phenyl, or substituted or unsubstituted 5 to 6 membered heteroaryl.

In embodiments, $R^1$ is $R^{11}$-substituted or unsubstituted alkyl (e.g. $C_1$-$C_8$ alkyl, $C_1$-$C_6$ alkyl, or $C_1$-$C_4$ alkyl), $R^{11}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{11}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{11}$-substituted or unsubstituted heterocycloalkyl (e.g. 3 to 8 membered heterocycloalkyl, 4 to 8 membered heterocycloalkyl, or 5 to 6 membered heterocycloalkyl), $R^{11}$-substituted aryl (e.g. $C_6$-$C_{10}$ aryl or $C_6$ aryl), or $R^{11}$-substituted or unsubstituted heteroaryl (e.g. 5 to 10 membered heteroaryl, 5 to 9 membered heteroaryl, or 5 to 6 membered heteroaryl).

In embodiments, $R^1$ is $R^{11}$-substituted alkyl (e.g. $C_1$-$C_8$ alkyl, $C_1$-$C_6$ alkyl, or $C_1$-$C_4$ alkyl), $R^{11}$-substituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{11}$-substituted cycloalkyl (e.g. $C_3$-$C_8$ cycloalkyl, $C_4$-$C_8$ cycloalkyl, or $C_5$-$C_6$ cycloalkyl), $R^{11}$-substituted heterocycloalkyl (e.g. 3 to 8 membered heterocycloalkyl, 4 to 8 membered heterocycloalkyl, or 5 to 6 membered heterocycloalkyl), $R^{11}$-substituted aryl (e.g. $C_6$-$C_{10}$ aryl or $C_6$ aryl), or $R^{11}$-substituted heteroaryl (e.g. 5 to 10 membered heteroaryl, 5 to 9 membered heteroaryl, or 5 to 6 membered heteroaryl). In embodiments, $R^1$ is an unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl).

$R^{11}$ is independently halogen, —$CX^{11}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCX^{11}_3$, —$OCHX^{11}_2$, $R^{12}$-substituted or unsubstituted alkyl (e.g. $C_1$-$C_8$ alkyl, $C_1$-$C_6$ alkyl, or $C_1$-$C_4$ alkyl), $R^{12}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{12}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{12}$-substituted or unsubstituted heterocycloalkyl (e.g. 3 to 8 membered heterocycloalkyl, 4 to 8 membered heterocycloalkyl, or 5 to 6 membered heterocycloalkyl), $R^{12}$-substituted or unsubstituted aryl (e.g. $C_6$-$C_{10}$ aryl or $C_6$ aryl), or $R^{12}$-substituted or unsubstituted heteroaryl (e.g. 5 to 10 membered heteroaryl, 5 to 9 membered heteroaryl, or 5 to 6 membered heteroaryl). $X^{11}$ is a halogen.

$R^{12}$ is independently halogen, —$CX^{12}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCX^{12}_3$, —$OCHX^{12}_2$, $R^{13}$-substituted or unsubstituted alkyl (e.g. $C_1$-$C_8$ alkyl, $C_1$-$C_6$ alkyl, or $C_1$-$C_4$ alkyl), $R^{13}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{13}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{13}$-substituted or unsubstituted heterocycloalkyl (e.g. 3 to 8 membered heterocycloalkyl, 4 to 8 membered heterocycloalkyl, or 5 to 6 membered heterocycloalkyl), $R^{13}$-substituted or unsubstituted aryl (e.g. $C_6$-$C_{10}$ aryl or $C_6$ aryl), or $R^{13}$-substituted or unsubstituted heteroaryl (e.g. 5 to 10 membered heteroaryl, 5 to 9 membered heteroaryl, or 5 to 6 membered heteroaryl). $X^{12}$ is a halogen.

In embodiments, $R^1$ is independently halogen, —$CX^1_3$, —$CHX^1_2$, —$CH_2X^1$, —$OCX^1_3$, —$OCH_2X^1$, —$OCHX^1_2$, —CN, —$SO_{n1}R^{1D}$, —$SO_{v1}NR^{1A}R^{1B}$, —NHC(O)$NR^{1A}R^{1B}$, —N(O)$_{m1}$, —$NR^{1A}R^{1B}$, —C(O)$R^{1C}$, —C(O)—$OR^{1C}$, —C(O)$NR^{1A}R^{1B}$, —$OR^{1D}$, —$NR^{1A}SO_2R^{1D}$, —$NR^{1A}C(O)R^{1C}$, —$NR^{1A}C(O)OR^{1C}$, or —$NR^{1A}OR^{1C}$. In embodiments, $R^{1A}$ is $R^{11A}$-substituted or unsubstituted alkyl (e.g. $C_1$-$C_8$ alkyl, $C_1$-$C_6$ alkyl, or $C_1$-$C_4$ alkyl), $R^{11A}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{11A}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{11A}$-substituted or unsubstituted heterocycloalkyl (e.g. 3 to 8 membered heterocycloalkyl, 4 to 8 membered heterocycloalkyl, or 5 to 6 membered heterocycloalkyl), $R^{11A}$-substituted aryl (e.g. $C_6$-$C_{10}$ aryl or $C_6$ aryl), or $R^{11A}$-substituted or unsubstituted heteroaryl (e.g. 5 to 10 membered heteroaryl, 5 to 9 membered heteroaryl, or 5 to 6 membered heteroaryl). In embodiments, $R^{1A}$ is —$CX^{1A}{}_3$, —CN, —COOH, —C(O)NH$_2$, $R^{11A}$-substituted alkyl (e.g. $C_1$-$C_8$ alkyl, $C_1$-$C_6$ alkyl, or $C_1$-$C_4$ alkyl), $R^{11A}$-substituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{11A}$-substituted cycloalkyl (e.g. $C_3$-$C_8$ cycloalkyl, $C_4$-$C_8$ cycloalkyl, or $C_5$-$C_6$ cycloalkyl), $R^{11A}$-substituted heterocycloalkyl (e.g. 3 to 8 membered heterocycloalkyl, 4 to 8 membered heterocycloalkyl, or 5 to 6 membered heterocycloalkyl), $R^{11A}$-substituted aryl (e.g. $C_6$-$C_{10}$ aryl or $C_6$ aryl), or $R^{11A}$-substituted heteroaryl (e.g. 5 to 10 membered heteroaryl, 5 to 9 membered heteroaryl, or 5 to 6 membered heteroaryl). In embodiments, $R^{1A}$ is an unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl). $X^{1A}$ is a halogen.

$R^{11A}$ is independently hydrogen, halogen, —$CX^{11A}{}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$^{11A}{}_3$, —OCHX$^{11A}{}_2$, $R^{12A}$-substituted or unsubstituted alkyl (e.g. $C_1$-$C_8$ alkyl, $C_1$-$C_6$ alkyl, or $C_1$-$C_4$ alkyl), $R^{12A}$-substituted or unsubstituted heteroalkyl (e.g. 2 to 10 membered heteroalkyl, 2 to 8 membered heteroalkyl, 4 to membered heteroalkyl, 2 to 6 membered heteroalkyl, or 2 to 4 membered heteroalkyl), $R^{12A}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{12A}$-substituted or unsubstituted heterocycloalkyl (e.g. 3 to 8 membered heterocycloalkyl, 4 to 8 membered heterocycloalkyl, or 5 to 6 membered heterocycloalkyl), $R^{12A}$-substituted or unsubstituted aryl (e.g. $C_6$-$C_{10}$ aryl or $C_6$ aryl), or $R^{12A}$-substituted or unsubstituted heteroaryl (e.g. 5 to 10 membered heteroaryl, 5 to 9 membered heteroaryl, or 5 to 6 membered heteroaryl). $X^{11A}$ is a halogen.

$R^{12A}$ is independently hydrogen, halogen, —$CX^{12A}{}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$^{12A}{}_3$, —OCHX$^{12A}{}_2$, $R^{13A}$-substituted or unsubstituted alkyl (e.g. $C_1$-$C_8$ alkyl, $C_1$-$C_6$ alkyl, or $C_1$-$C_4$ alkyl), $R^{13A}$-substituted or unsubstituted heteroalkyl (e.g. 2 to 10 membered heteroalkyl, 2 to 8 membered heteroalkyl, 4 to membered heteroalkyl, 2 to 6 membered heteroalkyl, or 2 to 4 membered heteroalkyl), $R^{13A}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{13A}$-substituted or unsubstituted heterocycloalkyl (e.g. 3 to 8 membered heterocycloalkyl, 4 to 8 membered heterocycloalkyl, or 5 to 6 membered heterocycloalkyl), $R^{13A}$-substituted or unsubstituted aryl (e.g. $C_6$-$C_{10}$ aryl or $C_6$ aryl), or $R^{13A}$-substituted or unsubstituted heteroaryl (e.g. 5 to 10 membered heteroaryl, 5 to 9 membered heteroaryl, or 5 to 6 membered heteroaryl). $X^{12A}$ is a halogen.

In embodiments, $R^{1B}$ is $R^{11B}$-substituted or unsubstituted alkyl (e.g. $C_1$-$C_8$ alkyl, $C_1$-$C_6$ alkyl, or $C_1$-$C_4$ alkyl), $R^{11B}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{11B}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{11B}$-substituted or unsubstituted heterocycloalkyl (e.g. 3 to 8 membered heterocycloalkyl, 4 to 8 membered heterocycloalkyl, or 5 to 6 membered heterocycloalkyl), $R^{11B}$-substituted or unsubstituted aryl (e.g. $C_6$-$C_{10}$ aryl or $C_6$ aryl), or $R^{11B}$-substituted or unsubstituted heteroaryl (e.g. 5 to 10 membered heteroaryl, 5 to 9 membered heteroaryl, or 5 to 6 membered heteroaryl).

In embodiments, $R^{1B}$ is —$CX^{1B}{}_3$, —CN, —COOH, —C(O)NH$_2$, $R^{11B}$-substituted alkyl (e.g. $C_1$-$C_8$ alkyl, $C_1$-$C_6$ alkyl, or $C_1$-$C_4$ alkyl), $R^{11B}$-substituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{11B}$-substituted cycloalkyl (e.g. $C_3$-$C_8$ cycloalkyl, $C_4$-$C_8$ cycloalkyl, or $C_5$-$C_6$ cycloalkyl), $R^{11B}$-substituted heterocycloalkyl (e.g. 3 to 8 membered heterocycloalkyl, 4 to 8 membered heterocycloalkyl, or 5 to 6 membered heterocycloalkyl), $R^{11B}$-substituted aryl (e.g. $C_6$-$C_{10}$ aryl or $C_6$ aryl), or $R^{11B}$-substituted heteroaryl (e.g. 5 to 10 membered heteroaryl, 5 to 9 membered heteroaryl, or 5 to 6 membered heteroaryl). In embodiments, $R^{1B}$ is an unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 10 membered heteroalkyl, 2 to 8 membered heteroalkyl, 4 to membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl). $X^{1B}$ is a halogen.

$R^{11B}$ is independently hydrogen, halogen, —$CX^{11B}{}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$^{11B}{}_3$, —OCHX$^{11B}{}_2$, $R^{12B}$-substituted or unsubstituted alkyl (e.g. $C_1$-$C_8$ alkyl, $C_1$-$C_6$ alkyl, or $C_1$-$C_4$ alkyl), $R^{12B}$-substituted or unsubstituted heteroalkyl (e.g. 2 to 10 membered heteroalkyl, 2 to 8 membered heteroalkyl, 4 to membered heteroalkyl, 2 to 6 membered heteroalkyl, or 2 to 4 membered heteroalkyl), $R^{12B}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{12B}$-substituted or unsubstituted heterocycloalkyl (e.g. 3 to 8 membered heterocycloalkyl, 4 to 8 membered heterocycloalkyl, or 5 to 6 membered heterocycloalkyl), $R^{12B}$-substituted or unsubstituted aryl (e.g. $C_6$-$C_{10}$ aryl or $C_6$ aryl), or $R^{12B}$-substituted or unsubstituted heteroaryl (e.g. 5 to 10 membered heteroaryl, 5 to 9 membered heteroaryl, or 5 to 6 membered heteroaryl). $X^{11}B$ is a halogen.

$R^{12B}$ is independently hydrogen, halogen, —$CX^{12B}{}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$^{12B}{}_3$, —OCHX$^{12B}_2$, R$^{13B}$-substituted or unsubstituted alkyl (e.g. C$_1$-C$_8$ alkyl, C$_1$-C$_6$ alkyl, or C$_1$-C$_4$ alkyl), R$^{13B}$-substituted or unsubstituted heteroalkyl (e.g. 2 to 10 membered heteroalkyl, 2 to 8 membered heteroalkyl, 4 to 6 membered heteroalkyl, 2 to 6 membered heteroalkyl, or 2 to 4 membered heteroalkyl), R$^{13B}$-substituted or unsubstituted cycloalkyl (e.g. C$_3$-C$_8$ cycloalkyl, C$_4$-C$_8$ cycloalkyl, or C$_5$-C$_6$ cycloalkyl), R$^{13B}$-substituted or unsubstituted heterocycloalkyl (e.g. 3 to 8 membered heterocycloalkyl, 4 to 8 membered heterocycloalkyl, or 5 to 6 membered heterocycloalkyl), R$^{13B}$-substituted or unsubstituted aryl (e.g. C$_6$-C$_{10}$ aryl or C$_6$ aryl), or R$^{13B}$-substituted or unsubstituted heteroaryl (e.g. 5 to 10 membered heteroaryl, 5 to 9 membered heteroaryl, or 5 to 6 membered heteroaryl).

In embodiments, R$^{1C}$ is R$^{11C}$-substituted or unsubstituted alkyl (e.g. C$_1$-C$_8$ alkyl, C$_1$-C$_6$ alkyl, or C$_1$-C$_4$ alkyl), R$^{11C}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), R$^{11C}$-substituted or unsubstituted cycloalkyl (e.g. C$_3$-C$_8$ cycloalkyl, C$_4$-C$_8$ cycloalkyl, or C$_5$-C$_6$ cycloalkyl), R$^{11C}$-substituted or unsubstituted heterocycloalkyl (e.g. 3 to 8 membered heterocycloalkyl, 4 to 8 membered heterocycloalkyl, or 5 to 6 membered heterocycloalkyl), R$^{11C}$-substituted or unsubstituted aryl (e.g. C$_6$-C$_{10}$ aryl or C$_6$ aryl), or R$^{11C}$-substituted or unsubstituted heteroaryl (e.g. 5 to 10 membered heteroaryl, 5 to 9 membered heteroaryl, or 5 to 6 membered heteroaryl).

In embodiments, R$^{11C}$ is —CX$^{1C}_3$, —CN, —COOH, —C(O)NH$_2$, R$^{11C}$-substituted alkyl (e.g. C$_1$-C$_8$ alkyl, C$_1$-C$_6$ alkyl, or C$_1$-C$_4$ alkyl), R$^{11C}$-substituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), R$^{11C}$-substituted cycloalkyl (e.g. C$_3$-C$_8$ cycloalkyl, C$_4$-C$_8$ cycloalkyl, or C$_5$-C$_6$ cycloalkyl), R$^{11C}$-substituted heterocycloalkyl (e.g. 3 to 8 membered heterocycloalkyl, 4 to 8 membered heterocycloalkyl, or 5 to 6 membered heterocycloalkyl), R$^{11C}$-substituted aryl (e.g. C$_6$-C$_{10}$ aryl or C$_6$ aryl), or R$^{11C}$-substituted heteroaryl (e.g. 5 to 10 membered heteroaryl, 5 to 9 membered heteroaryl, or 5 to 6 membered heteroaryl). In embodiments, R$^{1C}$ s an unsubstituted alkyl (e.g. C$_1$-C$_8$ alkyl, C$_1$-C$_6$ alkyl, or C$_1$-C$_4$ alkyl), unsubstituted heteroalkyl (e.g. 2 to 10 membered heteroalkyl, 2 to 8 membered heteroalkyl, 4 to 6 membered heteroalkyl, 2 to 6 membered heteroalkyl, or 2 to 4 membered heteroalkyl), unsubstituted cycloalkyl (e.g. C$_3$-C$_8$ cycloalkyl, C$_4$-C$_8$ cycloalkyl, or C$_5$-C$_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. C$_6$-C$_{10}$ aryl or C$_6$ aryl), or unsubstituted heteroaryl (e.g. 5 to 10 membered heteroaryl, 5 to 9 membered heteroaryl, or 5 to 6 membered heteroaryl). X$^{1C}$ is a halogen.

R$^{11C}$ is independently hydrogen, halogen, —CX$^{11C}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)OH, —NHOH, —OCX$^{11C}_3$, —OCHX$^{11C}_2$, R$^{12C}$-substituted or unsubstituted alkyl (e.g. C$_1$-C$_8$ alkyl, C$_1$-C$_6$ alkyl, or C$_1$-C$_4$ alkyl), R$^{12C}$-substituted or unsubstituted heteroalkyl (e.g. 2 to 10 membered heteroalkyl, 2 to 8 membered heteroalkyl, 4 to membered heteroalkyl, 2 to 6 membered heteroalkyl, or 2 to 4 membered heteroalkyl), R$^{12C}$-substituted or unsubstituted cycloalkyl (e.g. C$_3$-C$_8$ cycloalkyl, C$_4$-C$_8$ cycloalkyl, or C$_5$-C$_6$ cycloalkyl), R$^{12C}$-substituted or unsubstituted heterocycloalkyl (e.g. 3 to 8 membered heterocycloalkyl, 4 to 8 membered heterocycloalkyl, or 5 to 6 membered heterocycloalkyl), R$^{12C}$-substituted or unsubstituted aryl (e.g. C$_6$-C$_{10}$ aryl or C$_6$ aryl), or R$^{12C}$-substituted or unsubstituted heteroaryl (e.g. 5 to 10 membered heteroaryl, 5 to 9 membered heteroaryl, or 5 to 6 membered heteroaryl). X$^{11C}$ is a halogen.

R$^{12C}$ is independently hydrogen, halogen, —CX$^{12C}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)OH, —NHOH, —OCX$^{12C}_3$, —OCHX$^{12C}_2$, R$^{13C}$-substituted or unsubstituted alkyl (e.g. C$_1$-C$_8$ alkyl, C$_1$-C$_6$ alkyl, or C$_1$-C$_4$ alkyl), R$^{13C}$-substituted or unsubstituted heteroalkyl (e.g. 2 to 10 membered heteroalkyl, 2 to 8 membered heteroalkyl, 4 to membered heteroalkyl, 2 to 6 membered heteroalkyl, or 2 to 4 membered heteroalkyl), R$^{13C}$-substituted or unsubstituted cycloalkyl (e.g. C$_3$-C$_8$ cycloalkyl, C$_4$-C$_8$ cycloalkyl, or C$_5$-C$_6$ cycloalkyl), R$^{13C}$-substituted or unsubstituted heterocycloalkyl (e.g. 3 to 8 membered heterocycloalkyl, 4 to 8 membered heterocycloalkyl, or 5 to 6 membered heterocycloalkyl), R$^{13C}$-substituted or unsubstituted aryl (e.g. C$_6$-C$_{10}$ aryl or C$_6$ aryl), or R$^{13C}$-substituted or unsubstituted heteroaryl (e.g. 5 to 10 membered heteroaryl, 5 to 9 membered heteroaryl, or 5 to 6 membered heteroaryl). X$^{12C}$ is a halogen.

In embodiments, R$^{1D}$ is R$^{11D}$-substituted or unsubstituted alkyl (e.g. C$_1$-C$_8$ alkyl, C$_1$-C$_6$ alkyl, or C$_1$-C$_4$ alkyl), R$^{11D}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), R$^{11D}$-substituted or unsubstituted cycloalkyl (e.g. C$_3$-C$_8$ cycloalkyl, C$_4$-C$_8$ cycloalkyl, or C$_5$-C$_6$ cycloalkyl), R$^{11D}$-substituted or unsubstituted heterocycloalkyl (e.g. 3 to 8 membered heterocycloalkyl, 4 to 8 membered heterocycloalkyl, or 5 to 6 membered heterocycloalkyl), R$^{11D}$-substituted or unsubstituted aryl (e.g. C$_6$-C$_{10}$ aryl or C$_6$ aryl), or R$^{11D}$-substituted or unsubstituted heteroaryl (e.g. 5 to 10 membered heteroaryl, 5 to 9 membered heteroaryl, or 5 to 6 membered heteroaryl).

In embodiments, R$^{1D}$ is —CX$^{1D}_3$, —CN, —COOH, —C(O)NH$_2$, R$^{11D}$-substituted alkyl (e.g. C$_1$-C$_8$ alkyl, C$_1$-C$_6$ alkyl, or C$_1$-C$_4$ alkyl), R$^{11D}$-substituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), R$^{11D}$-substituted cycloalkyl (e.g. C$_3$-C$_8$ cycloalkyl, C$_4$-C$_8$ cycloalkyl, or C$_5$-C$_6$ cycloalkyl), R$^{11D}$-substituted heterocycloalkyl (e.g. 3 to 8 membered heterocycloalkyl, 4 to 8 membered heterocycloalkyl, or 5 to 6 membered heterocycloalkyl), R$^{11D}$-substituted aryl (e.g. C$_6$-C$_{10}$ aryl or C$_6$ aryl), or R$^{11D}$-substituted heteroaryl (e.g. 5 to 10 membered heteroaryl, 5 to 9 membered heteroaryl, or 5 to 6 membered heteroaryl). In embodiments, R$^{1D}$ is an unsubstituted alkyl (e.g. C$_1$-C$_8$ alkyl, C$_1$-C$_6$ alkyl, or C$_1$-C$_4$ alkyl), unsubstituted heteroalkyl (e.g. 2 to 10 membered heteroalkyl, 2 to 8 membered heteroalkyl, 4 to membered heteroalkyl, 2 to 6 membered heteroalkyl, or 2 to 4 membered heteroalkyl), unsubstituted cycloalkyl (e.g. C$_3$-C$_8$ cycloalkyl, C$_4$-C$_8$ cycloalkyl, or C$_5$-C$_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. C$_6$-C$_{10}$ aryl or C$_6$ aryl), or unsubstituted heteroaryl (e.g. 5 to 10 membered heteroaryl, 5 to 9 membered heteroaryl, or 5 to 6 membered heteroaryl). X$^{1D}$ is a halogen.

$R^{11D}$ is independently hydrogen, halogen, —$CX^{11D}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCX^{11D}_3$, —$OCHX^{11D}_2$, $R^{12D}$-substituted or unsubstituted alkyl (e.g. $C_1$-$C_8$ alkyl, $C_1$-$C_6$ alkyl, or $C_1$-$C_4$ alkyl), $R^{12D}$-substituted or unsubstituted heteroalkyl (e.g. 2 to 10 membered heteroalkyl, 2 to 8 membered heteroalkyl, 4 to membered heteroalkyl, 2 to 6 membered heteroalkyl, or 2 to 4 membered heteroalkyl), $R^{12D}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{12D}$-substituted or unsubstituted heterocycloalkyl (e.g. 3 to 8 membered heterocycloalkyl, 4 to 8 membered heterocycloalkyl, or 5 to 6 membered heterocycloalkyl), $R^{12D}$-substituted or unsubstituted aryl (e.g. $C_6$-$C_{10}$ aryl or $C_6$ aryl), or $R^{12D}$-substituted or unsubstituted heteroaryl (e.g. 5 to 10 membered heteroaryl, 5 to 9 membered heteroaryl, or 5 to 6 membered heteroaryl). $X^{11D}$ is a halogen.

$R^{12D}$ is independently hydrogen, halogen, —$CX^{12D}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCX^{12D}_3$, —$OCHX^{12D}_2$, $R^{13D}$-substituted or unsubstituted alkyl (e.g. $C_1$-$C_8$ alkyl, $C_1$-$C_6$ alkyl, or $C_1$-$C_4$ alkyl), $R^{13D}$-substituted or unsubstituted heteroalkyl (e.g. 2 to 10 membered heteroalkyl, 2 to 8 membered heteroalkyl, 4 to membered heteroalkyl, 2 to 6 membered heteroalkyl, or 2 to 4 membered heteroalkyl), $R^{13D}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{13D}$-substituted or unsubstituted heterocycloalkyl (e.g. 3 to 8 membered heterocycloalkyl, 4 to 8 membered heterocycloalkyl, or 5 to 6 membered heterocycloalkyl), $R^{13D}$-substituted or unsubstituted aryl (e.g. $C_6$-$C_{10}$ aryl or $C_6$ aryl), or $R^{13D}$-substituted or unsubstituted heteroaryl (e.g. 5 to 10 membered heteroaryl, 5 to 9 membered heteroaryl, or 5 to 6 membered heteroaryl). $X^{12D}$ is a halogen.

In embodiments, $R^2$ is $R^{14}$-substituted or unsubstituted alkyl (e.g. $C_1$-$C_8$ alkyl, $C_1$-$C_6$ alkyl, or $C_1$-$C_4$ alkyl), $R^{14}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{14}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{14}$-substituted or unsubstituted heterocycloalkyl (e.g. 3 to 8 membered heterocycloalkyl, 4 to 8 membered heterocycloalkyl, or 5 to 6 membered heterocycloalkyl), $R^{14}$-substituted or unsubstituted aryl (e.g. $C_6$-$C_{10}$ aryl or $C_6$ aryl), or $R^{14}$-substituted or unsubstituted heteroaryl (e.g. 5 to 10 membered heteroaryl, 5 to 9 membered heteroaryl, or 5 to 6 membered heteroaryl).

In embodiments, $R^2$ is $R^{14}$-substituted alkyl (e.g. $C_1$-$C_8$ alkyl, $C_1$-$C_6$ alkyl, or $C_1$-$C_4$ alkyl), $R^{14}$-substituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{14}$-substituted cycloalkyl (e.g. $C_3$-$C_8$ cycloalkyl, $C_4$-$C_8$ cycloalkyl, or $C_5$-$C_6$ cycloalkyl), $R^{14}$-substituted heterocycloalkyl (e.g. 3 to 8 membered heterocycloalkyl, 4 to 8 membered heterocycloalkyl, or 5 to 6 membered heterocycloalkyl), $R^{14}$-substituted aryl (e.g. $C_6$-$C_{10}$ aryl or $C_6$ aryl), or $R^{14}$-substituted heteroaryl (e.g. 5 to 10 membered heteroaryl, 5 to 9 membered heteroaryl, or 5 to 6 membered heteroaryl). In embodiments, $R^2$ is an unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl).

$R^{14}$ is independently halogen, —$CX^{14}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCX^{14}_3$, —$OCHX^{14}_2$, $R^{15}$-substituted or unsubstituted alkyl (e.g. $C_1$-$C_8$ alkyl, $C_1$-$C_6$ alkyl, or $C_1$-$C_4$ alkyl), $R^{15}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{15}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{15}$-substituted or unsubstituted heterocycloalkyl (e.g. 3 to 8 membered heterocycloalkyl, 4 to 8 membered heterocycloalkyl, or 5 to 6 membered heterocycloalkyl), $R^{15}$-substituted or unsubstituted aryl (e.g. $C_6$-$C_{10}$ aryl or $C_6$ aryl), or $R^{15}$-substituted or unsubstituted heteroaryl (e.g. 5 to 10 membered heteroaryl, 5 to 9 membered heteroaryl, or 5 to 6 membered heteroaryl). $X^{14}$ is a halogen.

$R^{15}$ is independently halogen, —$CX^{15}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCX^{15}_3$, —$OCHX^{15}_2$, $R^{16}$-substituted or unsubstituted alkyl (e.g. $C_1$-$C_8$ alkyl, $C_1$-$C_6$ alkyl, or $C_1$-$C_4$ alkyl), $R^{16}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{16}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{16}$-substituted or unsubstituted heterocycloalkyl (e.g. 3 to 8 membered heterocycloalkyl, 4 to 8 membered heterocycloalkyl, or 5 to 6 membered heterocycloalkyl), $R^{16}$-substituted or unsubstituted aryl (e.g. $C_6$-$C_{10}$ aryl or $C_6$ aryl), or $R^{16}$-substituted or unsubstituted heteroaryl (e.g. 5 to 10 membered heteroaryl, 5 to 9 membered heteroaryl, or 5 to 6 membered heteroaryl). $X^{15}$ is a halogen.

In embodiments, $R^2$ is independently halogen, —$CX^2_3$, —$CHX^2_2$, —$CH_2X^2$, —$OCX^2_3$, —$OCH_2X^2$, —$OCHX^2_2$, —CN, —$SO_{n2}R^{2D}$, —$SO_{v2}NR^{2A}R^{2B}$, —NHC(O)$NR^{2A}R^{2B}$, —N(O)$_{m2}$, —$NR^{2A}R^{2B}$, —C(O)$R^{2C}$, —C(O)—$OR^{2C}$, —C(O)$NR^{2A}R^{2B}$, —$OR^{2D}$, —$R^{2A}SO_2R^{2D}$, —$R^{2A}C(O)R^{2C}$, —$R^{2A}C(O)OR^{2C}$, or —$NR^{2A}OR^{2C}$. In embodiments, $R^{2A}$ is $R^{14A}$-substituted or unsubstituted alkyl (e.g. $C_1$-$C_8$ alkyl, $C_1$-$C_6$ alkyl, or $C_1$-$C_4$ alkyl), $R^{14A}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{14A}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{14A}$-substituted or unsubstituted heterocycloalkyl (e.g. 3 to 8 membered heterocycloalkyl, 4 to 8 membered heterocycloalkyl, or 5 to 6 membered heterocycloalkyl), $R^{14A}$-substituted or unsubstituted aryl (e.g. $C_6$-$C_{10}$ aryl or $C_6$ aryl), or $R^{14A}$-substituted or unsubstituted heteroaryl (e.g. 5 to 10 membered heteroaryl, 5 to 9 membered heteroaryl, or 5 to 6 membered heteroaryl). $X^2$ is a halogen.

In embodiments, $R^{2A}$ is $-CX^{2A}_3$, $-CN$, $-COOH$, $-C(O)NH_2$, $R^{14A}$-substituted alkyl (e.g. $C_1$-$C_8$ alkyl, $C_1$-$C_6$ alkyl, or $C_1$-$C_4$ alkyl), $R^{14A}$-substituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{14A}$-substituted cycloalkyl (e.g. $C_3$-$C_8$ cycloalkyl, $C_4$-$C_8$ cycloalkyl, or $C_5$-$C_6$ cycloalkyl), $R^{14A}$-substituted heterocycloalkyl (e.g. 3 to 8 membered heterocycloalkyl, 4 to 8 membered heterocycloalkyl, or 5 to 6 membered heterocycloalkyl), $R^{14A}$-substituted aryl (e.g. $C_6$-$C_{10}$ aryl or $C_6$ aryl), or $R^{14A}$-substituted heteroaryl (e.g. 5 to 10 membered heteroaryl, 5 to 9 membered heteroaryl, or 5 to 6 membered heteroaryl). In embodiments, $R^{2A}$ is an unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 10 membered heteroalkyl, 2 to 8 membered heteroalkyl, 4 to membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl). $X^{2A}$ is a halogen.

$R^{14A}$ is independently hydrogen, halogen, $-CX^{14A}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-OCX^{14A}_3$, $-OCHX^{14A}_2$, $R^{15A}$-substituted or unsubstituted alkyl (e.g. $C_1$-$C_8$ alkyl, $C_1$-$C_6$ alkyl, or $C_1$-$C_4$ alkyl), $R^{15A}$-substituted or unsubstituted heteroalkyl (e.g. 2 to 10 membered heteroalkyl, 2 to 8 membered heteroalkyl, 4 to membered heteroalkyl, 2 to 6 membered heteroalkyl, or 2 to 4 membered heteroalkyl), $R^{15A}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{15A}$-substituted or unsubstituted heterocycloalkyl (e.g. 3 to 8 membered heterocycloalkyl, 4 to 8 membered heterocycloalkyl, or 5 to 6 membered heterocycloalkyl), $R^{15A}$-substituted or unsubstituted aryl (e.g. $C_6$-$C_{10}$ aryl or $C_6$ aryl), or $R^{15A}$-substituted or unsubstituted heteroaryl (e.g. 5 to 10 membered heteroaryl, 5 to 9 membered heteroaryl, or 5 to 6 membered heteroaryl). $X^{14A}$ is a halogen.

$R^{15A}$ is independently hydrogen, halogen, $-CX^{15A}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-OCX^{15A}_3$, $-OCHX^{15A}_2$, $R^{6A}$-substituted or unsubstituted alkyl (e.g. $C_1$-$C_8$ alkyl, $C_1$-$C_6$ alkyl, or $C_1$-$C_4$ alkyl), $R^{16A}$-substituted or unsubstituted heteroalkyl (e.g. 2 to 10 membered heteroalkyl, 2 to 8 membered heteroalkyl, 4 to membered heteroalkyl, 2 to 6 membered heteroalkyl, or 2 to 4 membered heteroalkyl), $R^{16A}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{16A}$-substituted or unsubstituted heterocycloalkyl (e.g. 3 to 8 membered heterocycloalkyl, 4 to 8 membered heterocycloalkyl, or 5 to 6 membered heterocycloalkyl), $R^{16A}$-substituted or unsubstituted aryl (e.g. $C_6$-$C_{10}$ aryl or $C_6$ aryl), or $R^{16A}$-substituted or unsubstituted heteroaryl (e.g. 5 to 10 membered heteroaryl, 5 to 9 membered heteroaryl, or 5 to 6 membered heteroaryl). $X^{15A}$ is a halogen.

In embodiments, $R^{2B}$ is $R^{14B}$-substituted or unsubstituted alkyl (e.g. $C_1$-$C_8$ alkyl, $C_1$-$C_6$ alkyl, or $C_1$-$C_4$ alkyl), $R^{14B}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{14B}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{14B}$-substituted or unsubstituted heterocycloalkyl (e.g. 3 to 8 membered heterocycloalkyl, 4 to 8 membered heterocycloalkyl, or 5 to 6 membered heterocycloalkyl), $R^{14B}$-substituted or unsubstituted aryl (e.g. $C_6$-$C_{10}$ aryl or $C_6$ aryl), or $R^{14B}$-substituted or unsubstituted heteroaryl (e.g. 5 to 10 membered heteroaryl, 5 to 9 membered heteroaryl, or 5 to 6 membered heteroaryl).

In embodiments, $R^{2B}$ is $-CX^{2B}_3$, $-CN$, $-COOH$, $-C(O)NH_2$, $R^{14B}$-substituted alkyl (e.g. $C_1$-$C_8$ alkyl, $C_1$-$C_6$ alkyl, or $C_1$-$C_4$ alkyl), $R^{14B}$-substituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{14B}$-substituted cycloalkyl (e.g. $C_3$-$C_8$ cycloalkyl, $C_4$-$C_8$ cycloalkyl, or $C_5$-$C_6$ cycloalkyl), $R^{14B}$-substituted heterocycloalkyl (e.g. 3 to 8 membered heterocycloalkyl, 4 to 8 membered heterocycloalkyl, or 5 to 6 membered heterocycloalkyl), $R^{14B}$-substituted aryl (e.g. $C_6$-$C_{10}$ aryl or $C_6$ aryl), or $R^{14B}$-substituted heteroaryl (e.g. 5 to 10 membered heteroaryl, 5 to 9 membered heteroaryl, or 5 to 6 membered heteroaryl). In embodiments, $R^{2B}$ is an unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 10 membered heteroalkyl, 2 to 8 membered heteroalkyl, 4 to membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl).

$R^{14B}$ is independently hydrogen, halogen, $-CX^{14B}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-OCX^{14B}_3$, $-OCHX^{14B}_2$, $R^{15B}$-substituted or unsubstituted alkyl (e.g. $C_1$-$C_8$ alkyl, $C_1$-$C_6$ alkyl, or $C_1$-$C_4$ alkyl), $R^{15B}$-substituted or unsubstituted heteroalkyl (e.g. 2 to 10 membered heteroalkyl, 2 to 8 membered heteroalkyl, 4 to membered heteroalkyl, 2 to 6 membered heteroalkyl, or 2 to 4 membered heteroalkyl), $R^{15B}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{15B}$-substituted or unsubstituted heterocycloalkyl (e.g. 3 to 8 membered heterocycloalkyl, 4 to 8 membered heterocycloalkyl, or 5 to 6 membered heterocycloalkyl), $R^{15B}$-substituted or unsubstituted aryl (e.g. $C_6$-$C_{10}$ aryl or $C_6$ aryl), or $R^{15B}$-substituted or unsubstituted heteroaryl (e.g. 5 to 10 membered heteroaryl, 5 to 9 membered heteroaryl, or 5 to 6 membered heteroaryl). $X^{14B}$ is a halogen.

$R^{15B}$ is independently hydrogen, halogen, $-CX^{15B}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-OCX^{15B}_3$, $-OCHX^{15B}_2$, $R^{16B}$-substituted or unsubstituted alkyl (e.g. $C_1$-$C_8$ alkyl, $C_1$-$C_6$ alkyl, or $C_1$-$C_4$ alkyl), $R^{16B}$-substituted or unsubstituted heteroalkyl (e.g. 2 to 10 membered heteroalkyl, 2 to 8 membered heteroalkyl, 4 to membered heteroalkyl, 2 to 6 membered heteroalkyl, or 2 to 4 membered heteroalkyl), $R^{16B}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{16B}$-substituted or unsubstituted heterocycloalkyl (e.g. 3 to 8 membered heterocycloalkyl, 4 to 8 membered heterocycloalkyl, or 5 to 6 membered heterocycloalkyl), $R^{16B}$-substituted or unsubstituted aryl (e.g. $C_6$-$C_{10}$ aryl or $C_6$ aryl), or $R^{16B}$-substituted or unsubstituted heteroaryl (e.g. 5 to 10 membered heteroaryl, 5 to 9 membered heteroaryl, or 5 to 6 membered heteroaryl). $X^{15B}$ is a halogen.

In embodiments, $R^{2C}$ is $R^{14C}$-substituted or unsubstituted alkyl (e.g. $C_1$-$C_8$ alkyl, $C_1$-$C_6$ alkyl, or $C_1$-$C_4$ alkyl), $R^{14C}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{14C}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{14C}$-substituted or unsubstituted heterocycloalkyl (e.g. 3 to 8 membered heterocycloalkyl, 4 to 8 membered heterocycloalkyl, or 5 to 6 membered heterocycloalkyl), $R^{14C}$-substituted or unsubstituted aryl (e.g. $C_6$-$C_{10}$ aryl or $C_6$ aryl), or $R^{14C}$-substituted or unsubstituted heteroaryl (e.g. 5 to 10 membered heteroaryl, 5 to 9 membered heteroaryl, or 5 to 6 membered heteroaryl).

In embodiments, $R^{2C}$ is $-CX^{2C}_3$, $-CN$, $-COOH$, $-C(O)NH_2$, $R^{14C}$-substituted alkyl (e.g. $C_1$-$C_8$ alkyl, $C_1$-$C_6$ alkyl, or $C_1$-$C_4$ alkyl), $R^{14C}$-substituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{14C}$-substituted cycloalkyl (e.g. $C_3$-$C_8$ cycloalkyl, $C_4$-$C_8$ cycloalkyl, or $C_5$-$C_6$ cycloalkyl), $R^{14C}$-substituted heterocycloalkyl (e.g. 3 to 8 membered heterocycloalkyl, 4 to 8 membered heterocycloalkyl, or 5 to 6 membered heterocycloalkyl), $R^{14C}$-substituted aryl (e.g. $C_6$-$C_{10}$ aryl or $C_6$ aryl), or $R^{14C}$-substituted heteroaryl (e.g. 5 to 10 membered heteroaryl, 5 to 9 membered heteroaryl, or 5 to 6 membered heteroaryl). In embodiments, $R^{2C}$ is an unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 10 membered heteroalkyl, 2 to 8 membered heteroalkyl, 4 to membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl). $X^{2C}$ is a halogen.

$R^{14C}$ is independently hydrogen, halogen, $-CX^{14C}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-OCX^{14C}_3$, $-OCHX^{14C}_2$, $R^{15C}$-substituted or unsubstituted alkyl (e.g. $C_1$-$C_8$ alkyl, $C_1$-$C_6$ alkyl, or $C_1$-$C_4$ alkyl), $R^{15C}$-substituted or unsubstituted heteroalkyl (e.g. 2 to 10 membered heteroalkyl, 2 to 8 membered heteroalkyl, 4 to membered heteroalkyl, 2 to 6 membered heteroalkyl, or 2 to 4 membered heteroalkyl), $R^{15C}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{15C}$-substituted or unsubstituted heterocycloalkyl (e.g. 3 to 8 membered heterocycloalkyl, 4 to 8 membered heterocycloalkyl, or 5 to 6 membered heterocycloalkyl), $R^{15C}$-substituted or unsubstituted aryl (e.g. $C_6$-$C_{10}$ aryl or $C_6$ aryl), or $R^{15C}$-substituted or unsubstituted heteroaryl (e.g. 5 to 10 membered heteroaryl, 5 to 9 membered heteroaryl, or 5 to 6 membered heteroaryl). $X^{14C}$ is a halogen.

$R^{15C}$ is independently hydrogen, halogen, $-CX^{15C}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-OCX^{15C}_3$, $-OCHX^{15C}_2$, $R^{16C}$-substituted or unsubstituted alkyl (e.g. $C_1$-$C_8$ alkyl, $C_1$-$C_6$ alkyl, or $C_1$-$C_4$ alkyl), $R^{16C}$-substituted or unsubstituted heteroalkyl (e.g. 2 to 10 membered heteroalkyl, 2 to 8 membered heteroalkyl, 4 to membered heteroalkyl, 2 to 6 membered heteroalkyl, or 2 to 4 membered heteroalkyl), $R^{16C}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{16C}$-substituted or unsubstituted heterocycloalkyl (e.g. 3 to 8 membered heterocycloalkyl, 4 to 8 membered heterocycloalkyl, or 5 to 6 membered heterocycloalkyl), $R^{16C}$-substituted or unsubstituted aryl (e.g. $C_6$-$C_{10}$ aryl or $C_6$ aryl), or $R^{16C}$-substituted or unsubstituted heteroaryl (e.g. 5 to 10 membered heteroaryl, 5 to 9 membered heteroaryl, or 5 to 6 membered heteroaryl). $X^{15C}$ is a halogen.

In embodiments, $R^{2D}$ is $R^{14D}$-substituted or unsubstituted alkyl (e.g. $C_1$-$C_8$ alkyl, $C_1$-$C_6$ alkyl, or $C_1$-$C_4$ alkyl), $R^{14D}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{14D}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{14D}$-substituted or unsubstituted heterocycloalkyl (e.g. 3 to 8 membered heterocycloalkyl, 4 to 8 membered heterocycloalkyl, or 5 to 6 membered heterocycloalkyl), $R^{14D}$-substituted or unsubstituted aryl (e.g. $C_6$-$C_{10}$ aryl or $C_6$ aryl), or $R^{14D}$-substituted or unsubstituted heteroaryl (e.g. 5 to 10 membered heteroaryl, 5 to 9 membered heteroaryl, or 5 to 6 membered heteroaryl).

In embodiments, $R^{2D}$ is $-CX^{2D}_3$, $-CN$, $-COOH$, $-C(O)NH_2$, $R^{14D}$-substituted alkyl (e.g. $C_1$-$C_8$ alkyl, $C_1$-$C_6$ alkyl, or $C_1$-$C_4$ alkyl), $R^{14D}$-substituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{14D}$-substituted cycloalkyl (e.g. $C_3$-$C_8$ cycloalkyl, $C_4$-$C_8$ cycloalkyl, or $C_5$-$C_6$ cycloalkyl), $R^{14D}$-substituted heterocycloalkyl (e.g. 3 to 8 membered heterocycloalkyl, 4 to 8 membered heterocycloalkyl, or 5 to 6 membered heterocycloalkyl), $R^{14D}$-substituted aryl (e.g. $C_6$-$C_{10}$ aryl or $C_6$ aryl), or $R^{14D}$-substituted heteroaryl (e.g. 5 to 10 membered heteroaryl, 5 to 9 membered heteroaryl, or 5 to 6 membered heteroaryl). In embodiments, $R^{2D}$ is an unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 10 membered heteroalkyl, 2 to 8 membered heteroalkyl, 4 to membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl). $X^{2D}$ is a halogen.

$R^{14D}$ is independently hydrogen, halogen, $-CX^{14D}_3$, $-CN$, $-OH$, $-NH_2$, $-COOH$, $-CONH_2$, $-NO_2$, $-SH$, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$^{14D}_3$, —OCHX$^{14D}_2$, R$^{15D}$-substituted or unsubstituted alkyl (e.g. C$_1$-C$_8$ alkyl, C$_1$-C$_6$ alkyl, or C$_1$-C$_4$ alkyl), R$^{15D}$-substituted or unsubstituted heteroalkyl (e.g. 2 to 10 membered heteroalkyl, 2 to 8 membered heteroalkyl, 4 to membered heteroalkyl, 2 to 6 membered heteroalkyl, or 2 to 4 membered heteroalkyl), R$^{15D}$ substituted or unsubstituted cycloalkyl (e.g. C$_3$-C$_8$ cycloalkyl, C$_4$-C$_8$ cycloalkyl, or C$_5$-C$_6$ cycloalkyl), R$^{15D}$-substituted or unsubstituted heterocycloalkyl (e.g. 3 to 8 membered heterocycloalkyl, 4 to 8 membered heterocycloalkyl, or 5 to 6 membered heterocycloalkyl), R$^{15D}$-substituted or unsubstituted aryl (e.g. C$_6$-C$_{10}$ aryl or C$_6$ aryl), or R$^{15D}$-substituted or unsubstituted heteroaryl (e.g. 5 to 10 membered heteroaryl, 5 to 9 membered heteroaryl, or 5 to 6 membered heteroaryl). X$^{14D}$ is a halogen.

R$^{15D}$ is independently hydrogen, halogen, —CX$^{15D}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$^{15D}_3$, —OCHX$^{15D}_2$, R$^{16D}$-substituted or unsubstituted alkyl (e.g. C$_1$-C$_8$ alkyl, C$_1$-C$_6$ alkyl, or C$_1$-C$_4$ alkyl), R$^{16D}$-substituted or unsubstituted heteroalkyl (e.g. 2 to 10 membered heteroalkyl, 2 to 8 membered heteroalkyl, 4 to membered heteroalkyl, 2 to 6 membered heteroalkyl, or 2 to 4 membered heteroalkyl), R$^{16D}$-substituted or unsubstituted cycloalkyl (e.g. C$_3$-C$_8$ cycloalkyl, C$_4$-C$_8$ cycloalkyl, or C$_5$-C$_6$ cycloalkyl), R$^{16D}$-substituted or unsubstituted heterocycloalkyl (e.g. 3 to 8 membered heterocycloalkyl, 4 to 8 membered heterocycloalkyl, or 5 to 6 membered heterocycloalkyl), R$^{16D}$-substituted or unsubstituted aryl (e.g. C$_6$-C$_{10}$ aryl or C$_6$ aryl), or R$^{16D}$-substituted or unsubstituted heteroaryl (e.g. 5 to 10 membered heteroaryl, 5 to 9 membered heteroaryl, or 5 to 6 membered heteroaryl). X$^{15D}$ is a halogen.

In embodiments, R$^3$ is R$^{17}$-substituted or unsubstituted alkyl (e.g. C$_1$-C$_8$ alkyl, C$_1$-C$_6$ alkyl, or C$_1$-C$_4$ alkyl), R$^{17}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), R$^{17}$-substituted or unsubstituted cycloalkyl (e.g. C$_3$-C$_8$ cycloalkyl, C$_4$-C$_8$ cycloalkyl, or C$_5$-C$_6$ cycloalkyl), R$^{17}$-substituted or unsubstituted heterocycloalkyl (e.g. 3 to 8 membered heterocycloalkyl, 4 to 8 membered heterocycloalkyl, or 5 to 6 membered heterocycloalkyl), R$^{17}$-substituted or unsubstituted aryl (e.g. C$_6$-C$_{10}$ aryl or C$_6$ aryl), or R$^{17}$-substituted or unsubstituted heteroaryl (e.g. 5 to 10 membered heteroaryl, 5 to 9 membered heteroaryl, or 5 to 6 membered heteroaryl). In embodiments, R$^3$ is hydrogen. In embodiments, R$^3$ is an unsubstituted C$_1$-C$_4$ alkyl.

R$^3$ may be substituted or unsubstituted alkyl. R$^3$ may be substituted or unsubstituted heteroalkyl. R$^3$ may be substituted or unsubstituted cycloalkyl. R$^3$ may be substituted or unsubstituted heterocycloalkyl. R$^3$ may be substituted or unsubstituted aryl. R$^3$ may be substituted or unsubstituted heteroaryl. In embodiments, R$^3$ is an unsubstituted methyl. In embodiments, R$^3$ is an unsubstituted ethyl. In embodiments, R$^3$ is an unsubstituted propyl. In embodiments, R$^3$ is an unsubstituted isopropyl. In embodiments, R$^3$ is an unsubstituted t-butyl. In embodiments, R$^3$ is an unsubstituted butyl. In embodiments, R$^3$ is an unsubstituted C$_1$-C$_6$ alkyl. In embodiments, R$^3$ is a substituted methyl. In embodiments, R$^3$ is a substituted ethyl. In embodiments, R$^3$ is a substituted propyl. In embodiments, R$^3$ is a substituted isopropyl. In embodiments, R$^3$ is a substituted t-butyl. In embodiments, R$^3$ is a substituted butyl. In embodiments, R$^3$ is a substituted C$_1$-C$_6$ alkyl.

In embodiments, —OR$^3$ is a prodrug moiety. In embodiments, R$^3$ is a prodrug moiety. It will be understood that when R$^3$ is a prodrug moiety, the reaction that removes the prodrug moiety from the remainder of a compound described herein (e.g., prodrug) may, in embodiments, also remove the oxygen directly connected to R$^3$. In embodiments, where —OR$^3$ is removed, an —OH may replace the —OR$^3$.

In embodiments, R$^4$ is R$^{18}$-substituted or unsubstituted alkyl (e.g. C$_1$-C$_8$ alkyl, C$_1$-C$_6$ alkyl, or C$_1$-C$_4$ alkyl), R$^{18}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), R$^{18}$-substituted or unsubstituted cycloalkyl (e.g. C$_3$-C$_8$ cycloalkyl, C$_4$-C$_8$ cycloalkyl, or C$_5$-C$_6$ cycloalkyl), R$^{18}$-substituted or unsubstituted heterocycloalkyl (e.g. 3 to 8 membered heterocycloalkyl, 4 to 8 membered heterocycloalkyl, or 5 to 6 membered heterocycloalkyl), R$^{18}$-substituted or unsubstituted aryl (e.g. C$_6$-C$_{10}$ aryl or C$_6$ aryl), or R$^{18}$-substituted or unsubstituted heteroaryl (e.g. 5 to 10 membered heteroaryl, 5 to 9 membered heteroaryl, or 5 to 6 membered heteroaryl). In embodiments, R$^4$ is hydrogen. In embodiments, R$^4$ is R$^{18}$-substituted or unsubstituted alkyl (e.g. C$_1$-C$_8$ alkyl, C$_1$-C$_6$ alkyl, or C$_1$-C$_4$ alkyl).

In embodiments, R$^5$ is hydrogen,

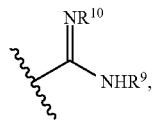

or substituted or unsubstituted heterocycloalkyl, substituted or unsubstituted aryl, or substituted or unsubstituted heteroaryl. In embodiments, R$^5$ is hydrogen. In embodiments, R$^5$ is hydrogen,

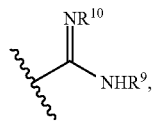

substituted or unsubstituted 3 to 8 membered heterocycloalkyl, substituted or unsubstituted phenyl, or substituted or unsubstituted 5 to 6 membered heteroaryl. In embodiments, R$^5$ is a substituted or unsubstituted 5 to 6 membered heteroaryl. In embodiments, R$^5$ is hydrogen,

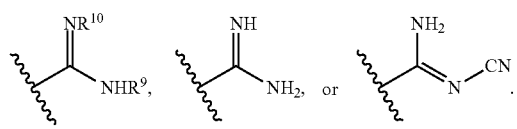

In embodiments, R$^5$ is R$^{19}$-substituted or unsubstituted alkyl (e.g. C$_1$-C$_8$ alkyl, C$_1$-C$_6$ alkyl, or C$_1$-C$_4$ alkyl), R$^{19}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), R$^{19}$-substituted or unsubstituted cycloalkyl (e.g. C$_3$-C$_8$ cycloalkyl, C$_4$-C$_8$ cycloalkyl, or C$_5$-C$_6$ cycloalkyl), R$^{19}$-substituted or unsubstituted heterocycloalkyl (e.g. 3 to 8 membered heterocycloalkyl, 4 to 8 membered heterocycloalkyl, or 5 to 6 membered heterocycloalkyl), R$^{19}$-substituted or unsubstituted aryl (e.g. C$_6$-C$_{10}$ aryl or C$_6$ aryl), or R$^{19}$-substituted or unsubstituted heteroaryl (e.g. 5 to 10 membered heteroaryl, 5 to 9 membered heteroaryl, or 5 to 6 membered heteroaryl).

In embodiments, R$^5$ is R$^{19}$-substituted alkyl (e.g. C$_1$-C$_8$ alkyl, C$_1$-C$_6$ alkyl, or C$_1$-C$_4$ alkyl), R$^{19}$-substituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), R$^{19}$-substituted cycloalkyl (e.g. C$_3$-C$_8$ cycloalkyl, C$_4$-C$_8$ cycloalkyl, or C$_5$-C$_6$ cycloalkyl), R$^{19}$-substituted heterocycloalkyl (e.g. 3 to 8 membered heterocycloalkyl, 4 to 8 membered heterocycloalkyl, or 5 to 6 membered heterocycloalkyl), R$^{19}$-substituted aryl (e.g. C$_6$-C$_{10}$ aryl or C$_6$ aryl), or R$^{19}$-substituted heteroaryl (e.g. 5 to 10 membered heteroaryl, 5 to 9 membered heteroaryl, or 5 to 6 membered heteroaryl). In embodiments, R$^5$ is an unsubstituted alkyl (e.g. C$_1$-C$_8$ alkyl, C$_1$-C$_6$ alkyl, or C$_1$-C$_4$ alkyl), unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), unsubstituted cycloalkyl (e.g. C$_3$-C$_8$ cycloalkyl, C$_4$-C$_8$ cycloalkyl, or C$_5$-C$_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. C$_6$-C$_{10}$ aryl or C$_6$ aryl), or unsubstituted heteroaryl (e.g. 5 to 10 membered heteroaryl, 5 to 9 membered heteroaryl, or 5 to 6 membered heteroaryl).

R$^{19}$ is independently halogen, —CX$^{19}$$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$^{19}$$_3$, —OCHX$^{19}$$_2$, R$^{20}$-substituted or unsubstituted alkyl (e.g. C$_1$-C$_8$ alkyl, C$_1$-C$_6$ alkyl, or C$_1$-C$_4$ alkyl), R$^{20}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), R$^{20}$-substituted or unsubstituted cycloalkyl (e.g. C$_3$-C$_8$ cycloalkyl, C$_4$-C$_8$ cycloalkyl, or C$_5$-C$_6$ cycloalkyl), R$^{20}$-substituted or unsubstituted heterocycloalkyl (e.g. 3 to 8 membered heterocycloalkyl, 4 to 8 membered heterocycloalkyl, or 5 to 6 membered heterocycloalkyl), R$^{20}$-substituted or unsubstituted aryl (e.g. C$_6$-C$_{10}$ aryl or C$_6$ aryl), or R$^{20}$-substituted or unsubstituted heteroaryl (e.g. 5 to 10 membered heteroaryl, 5 to 9 membered heteroaryl, or 5 to 6 membered heteroaryl). X$^{19}$ is a halogen.

R$^{20}$ is independently halogen, —CX$^{20}$$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$^{20}$$_3$, —OCHX$^{20}$$_2$, R$^{21}$-substituted or unsubstituted alkyl (e.g. C$_1$-C$_8$ alkyl, C$_1$-C$_6$ alkyl, or C$_1$-C$_4$ alkyl), R$^{21}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), R$^{21}$-substituted or unsubstituted cycloalkyl (e.g. C$_3$-C$_8$ cycloalkyl, C$_4$-C$_8$ cycloalkyl, or C$_5$-C$_6$ cycloalkyl), R$^{21}$-substituted or unsubstituted heterocycloalkyl (e.g. 3 to 8 membered heterocycloalkyl, 4 to 8 membered heterocycloalkyl, or 5 to 6 membered heterocycloalkyl), R$^{21}$-substituted or unsubstituted aryl (e.g. C$_6$-C$_{10}$ aryl or C$_6$ aryl), or R$^{21}$-substituted or unsubstituted heteroaryl (e.g. 5 to 10 membered heteroaryl, 5 to 9 membered heteroaryl, or 5 to 6 membered heteroaryl). X$^{20}$ is a halogen.

In embodiments, R$^6$ is hydrogen. In embodiments, R$^6$ is hydrogen,

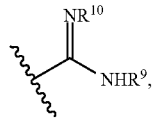

or substituted or unsubstituted heterocycloalkyl, substituted or unsubstituted aryl, or substituted or unsubstituted heteroaryl. In embodiments, R$^6$ is hydrogen,

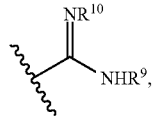

substituted or unsubstituted 3 to 8 membered heterocycloalkyl, substituted or unsubstituted phenyl, or substituted or unsubstituted 5 to 6 membered heteroaryl. In embodiments, R$^6$ is a substituted or unsubstituted 5 to 6 membered heteroaryl. In embodiments, R$^6$ is hydrogen,

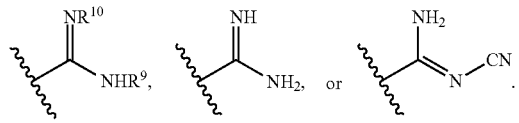

In embodiments, R$^5$ is hydrogen and R$^6$ is

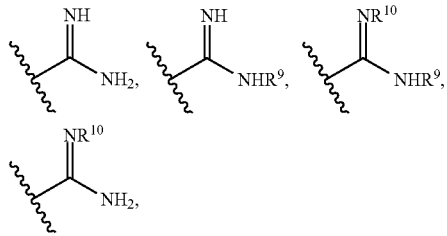

substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, R$^5$ is hydrogen and R$^6$ is

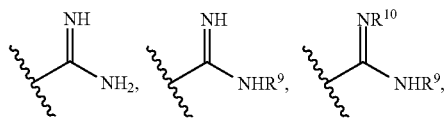

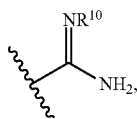

substituted or unsubstituted alkyl (e.g. $C_1$-$C_8$ alkyl, $C_1$-$C_6$ alkyl, or $C_1$-$C_4$ alkyl), substituted or unsubstituted heteroalkyl (e.g. 2 to membered heteroalkyl, 2 to 8 membered heteroalkyl, 4 to 8 membered heteroalkyl, 2 to 6 membered heteroalkyl, or 2 to 4 membered heteroalkyl), substituted or unsubstituted cycloalkyl (e.g. $C_3$-$C_8$ cycloalkyl, $C_4$-$C_8$ cycloalkyl, or $C_5$-$C_6$ cycloalkyl), substituted or unsubstituted heterocycloalkyl (e.g. 3 to 8 membered heterocycloalkyl, 4 to 8 membered heterocycloalkyl, or 5 to 6 membered heterocycloalkyl), substituted or unsubstituted aryl (e.g. $C_6$-$C_{10}$ aryl or $C_6$ aryl), or substituted or unsubstituted heteroaryl (e.g. 5 to 10 membered heteroaryl, 5 to 9 membered heteroaryl, or 5 to 6 membered heteroaryl).

In embodiments, $R^5$ is hydrogen and $R^6$ is

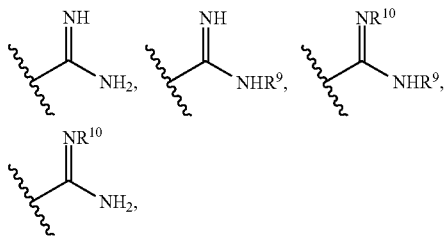

substituted or unsubstituted alkyl, substituted or unsubstituted cycloalkyl, substituted or unsubstituted heterocycloalkyl, substituted or unsubstituted aryl, or substituted or unsubstituted heteroaryl. In embodiments, $R^5$ is hydrogen and $R^6$ is

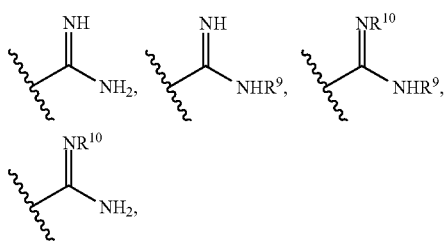

substituted or unsubstituted alkyl (e.g. $C_1$-$C_8$ alkyl, $C_1$-$C_6$ alkyl, or $C_1$-$C_4$ alkyl), substituted or unsubstituted cycloalkyl (e.g. $C_3$-$C_8$ cycloalkyl, $C_4$-$C_8$ cycloalkyl, or $C_5$-$C_6$ cycloalkyl), substituted or unsubstituted heterocycloalkyl (e.g. 3 to 8 membered heterocycloalkyl, 4 to 8 membered heterocycloalkyl, or 5 to 6 membered heterocycloalkyl), substituted or unsubstituted aryl (e.g. $C_6$-$C_{10}$ aryl or $C_6$ aryl), or substituted or unsubstituted heteroaryl (e.g. 5 to 10 membered heteroaryl, 5 to 9 membered heteroaryl, or 5 to 6 membered heteroaryl).

In embodiments, $R^5$ and $R^6$ are joined to form a substituted or unsubstituted heterocycloalkyl or substituted or unsubstituted heteroaryl. In embodiments, $R^5$ and $R^6$ are joined to form a substituted 3 to 8 membered heterocycloalkyl. In embodiments, $R^5$ and $R^6$ are joined to form a substituted 4 to 8 membered heterocycloalkyl. In embodiments, $R^5$ and $R^6$ are joined to form a substituted 5 to 6 membered heterocycloalkyl. In embodiments, $R^5$ and $R^6$ are joined to form a substituted 6 membered heterocycloalkyl. In embodiments, $R^5$ and $R^6$ are joined to form a substituted 5 membered heterocycloalkyl. In embodiments, $R^5$ and $R^6$ are joined to form an unsubstituted 3 to 8 membered heterocycloalkyl. In embodiments, $R^5$ and $R^6$ are joined to form an unsubstituted 4 to 8 membered heterocycloalkyl. In embodiments, $R^5$ and $R^6$ are joined to form an unsubstituted 5 to 6 membered heterocycloalkyl. In embodiments, $R^5$ and $R^6$ are joined to form an unsubstituted 6 membered heterocycloalkyl. In embodiments, $R^5$ and $R^6$ are joined to form an unsubstituted 5 membered heterocycloalkyl.

In embodiments, $R^5$ and $R^6$ are joined to form a substituted 5 to 10 membered heteroaryl. In embodiments, $R^5$ and $R^6$ are joined to form a substituted 5 to 9 membered heteroaryl. In embodiments, $R^5$ and $R^6$ are joined to form a substituted 5 to 6 membered heteroaryl. In embodiments, $R^5$ and $R^6$ are joined to form a substituted 5 membered heteroaryl. In embodiments, $R^5$ and $R^6$ are joined to form a substituted 6 membered heteroaryl. In embodiments, $R^5$ and $R^6$ are joined to form an unsubstituted 5 to 10 membered heteroaryl. In embodiments, $R^5$ and $R^6$ are joined to form an unsubstituted 5 to 9 membered heteroaryl. In embodiments, $R^5$ and $R^6$ are joined to form an unsubstituted 5 to 6 membered heteroaryl. In embodiments, $R^5$ and $R^6$ are joined to form an unsubstituted 5 membered heteroaryl. In embodiments, $R^5$ and $R^6$ are joined to form an unsubstituted 6 membered heteroaryl.

In embodiments, $R^5$ is hydrogen and $R^6$ is

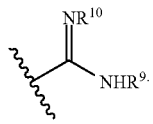

In embodiments, $R^5$ is hydrogen and $R^6$ is

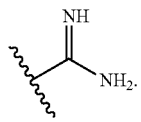

In embodiments, $R^5$ is hydrogen and $R^6$ is a substituted or unsubstituted heteroaryl. In embodiments, $R^5$ is hydrogen and $R^6$ is a substituted or unsubstituted heteroaryl (e.g. 5 to 10 membered heteroaryl, 5 to 9 membered heteroaryl, or 5 to 6 membered heteroaryl). In embodiments, $R^5$ is hydrogen and $R^6$ is a substituted or unsubstituted to 10 membered heteroaryl. In embodiments, $R^5$ is hydrogen and $R^6$ is a substituted or unsubstituted 5 to 9 membered heteroaryl. In embodiments, $R^5$ is hydrogen and $R^6$ is a substituted or unsubstituted 5 to 6 membered heteroaryl. In embodiments, $R^5$ is hydrogen and $R^6$ is a substituted or unsubstituted 5 membered heteroaryl. In embodiments, $R^5$ is hydrogen and $R^6$ is a substituted or unsubstituted 6 membered heteroaryl. In embodiments, $R^5$ is hydrogen and $R^6$ is a substituted 5 membered heteroaryl. In embodiments, $R^5$ is hydrogen and $R^6$ is a substituted 6 membered heteroaryl. In embodiments, $R^5$ is hydrogen and $R^6$ is an unsubstituted membered heteroaryl. In embodiments, $R^5$ is hydrogen and $R^6$ is an unsubstituted 6 membered heteroaryl.

In embodiments, $R^5$ is hydrogen and $R^6$ is a substituted or unsubstituted pyridinyl, substituted or unsubstituted pyrrolyl, substituted or unsubstituted furanyl, substituted or unsubstituted thiophenyl, substituted or unsubstituted imidazolyl, substituted or unsubstituted pyrazolyl, substituted or unsubstituted oxazolyl, substituted or unsubstituted thiazolyl, substituted or unsubstituted pyranyl, substituted or unsubstituted thiopyranyl, substituted or unsubstituted pyrazinyl, substituted or unsubstituted pyrimindyl, substituted or unsubstituted pyridazinyl, substituted or unsubstituted oxazinyl, substituted or unsubstituted thiazinyl, substituted or unsubstituted doxinyl, substituted or unsubstituted dithiinyl, substituted or unsubstituted azetyl, substituted or unsubstituted oxetyl, substituted or unsubstituted thietyl, substituted or unsubstituted azirinyl, substituted or unsubstituted oxirenyl or substituted or unsubstituted thienyl.

In embodiments, $R^5$ is hydrogen and $R^6$ is phenyl. In embodiments, $R^5$ is hydrogen and $R^6$ is a substituted phenyl. In embodiments, $R^5$ is hydrogen and $R^6$ is an unsubstituted phenyl. In embodiments, $R^5$ is hydrogen and $R^6$ is substituted or unsubstituted triazolyl. In embodiments, $R^5$ is hydrogen and $R^6$ is a substituted triazolyl. In embodiments, $R^5$ is hydrogen and $R^6$ is an unsubstituted triazolyl. In embodiments, $R^5$ is hydrogen and $R^6$ is substituted or unsubstituted tetrazolyl. In embodiments, $R^5$ is hydrogen and $R^6$ is a substituted tetrazolyl. In embodiments, $R^5$ is hydrogen and $R^6$ is an unsubstituted tetrazolyl. In embodiments, $R^5$ is hydrogen and $R^6$ is substituted or unsubstituted pyridinyl. In embodiments, $R^5$ is hydrogen and $R^6$ is a substituted pyridinyl. In embodiments, $R^5$ is hydrogen and $R^6$ is an unsubstituted pyridinyl. In embodiments, $R^5$ is hydrogen and $R^6$ is substituted or unsubstituted pyrrolyl. In embodiments, $R^5$ is hydrogen and $R^6$ is a substituted pyrrolyl. In embodiments, $R^5$ is hydrogen and $R^6$ is an unsubstituted pyrrolyl. In embodiments, $R^5$ is hydrogen and $R^6$ is substituted or unsubstituted furanyl. In embodiments, $R^5$ is hydrogen and $R^6$ is a substituted furanyl. In embodiments, $R^5$ is hydrogen and $R^6$ is an unsubstituted furanyl. In embodiments, $R^5$ is hydrogen and $R^6$ is substituted or unsubstituted thiophenyl. In embodiments, $R^5$ is hydrogen and $R^6$ is a substituted thiophenyl. In embodiments, $R^5$ is hydrogen and $R^6$ is an unsubstituted thiophenyl. In embodiments, $R^5$ is hydrogen and $R^6$ is substituted or unsubstituted imidazolyl. In embodiments, $R^5$ is hydrogen and $R^6$ is a substituted imidazolyl. In embodiments, $R^5$ is hydrogen and $R^6$ is an unsubstituted imidazolyl. In embodiments, $R^5$ is hydrogen and $R^6$ is substituted or unsubstituted pyrazolyl. In embodiments, $R^5$ is hydrogen and $R^6$ is a substituted pyrazolyl. In embodiments, $R^5$ is hydrogen and $R^6$ is an unsubstituted pyrazolyl. In embodiments, $R^5$ is hydrogen and $R^6$ is substituted or unsubstituted oxazolyl. In embodiments, $R^5$ is hydrogen and $R^6$ is a substituted oxazolyl. In embodiments, $R^5$ is hydrogen and $R^6$ is an unsubstituted oxazolyl. In embodiments, $R^5$ is hydrogen and $R^6$ is substituted or unsubstituted thiazolyl. In embodiments, $R^5$ is hydrogen and $R^6$ is a substituted thiazolyl. In embodiments, $R^5$ is hydrogen and $R^6$ is an unsubstituted thiazolyl. In embodiments, $R^5$ is hydrogen and $R^6$ is substituted or unsubstituted pyranyl. In embodiments, $R^5$ is hydrogen and $R^6$ is a substituted pyranyl. In embodiments, $R^5$ is hydrogen and $R^6$ is an unsubstituted pyranyl. In embodiments, $R^5$ is hydrogen and $R^6$ is substituted or unsubstituted thiopyranyl. In embodiments, $R^5$ is hydrogen and $R^6$ is a substituted thiopyranyl. In embodiments, $R^5$ is hydrogen and $R^6$ is an unsubstituted thiopyranyl. In embodiments, $R^5$ is hydrogen and $R^6$ is substituted or unsubstituted pyrazinyl. In embodiments, $R^5$ is hydrogen and $R^6$ is a substituted pyrazinyl. In embodiments, $R^5$ is hydrogen and $R^6$ is an unsubstituted pyrazinyl. In embodiments, $R^5$ is hydrogen and $R^6$ is substituted or unsubstituted pyrimindyl. In embodiments, $R^5$ is hydrogen and $R^6$ is a substituted pyrimindyl. In embodiments, $R^5$ is hydrogen and $R^6$ is an unsubstituted pyrimindyl. In embodiments, $R^5$ is hydrogen and $R^6$ is substituted or unsubstituted pyridazinyl. In embodiments, $R^5$ is hydrogen and $R^6$ is a substituted pyridazinyl. In embodiments, $R^5$ is hydrogen and $R^6$ is an unsubstituted pyridazinyl. In embodiments, $R^5$ is hydrogen and $R^6$ is substituted or unsubstituted oxazinyl. In embodiments, $R^5$ is hydrogen and $R^6$ is a substituted oxazinyl. In embodiments, $R^5$ is hydrogen and $R^6$ is an unsubstituted oxazinyl. In embodiments, $R^5$ is hydrogen and $R^6$ is substituted or unsubstituted thiazinyl. In embodiments, $R^5$ is hydrogen and $R^6$ is a substituted thiazinyl. In embodiments, $R^5$ is hydrogen and $R^6$ is an unsubstituted thiazinyl. In embodiments, $R^5$ is hydrogen and $R^6$ is substituted or unsubstituted doxinyl. In embodiments, $R^5$ is hydrogen and $R^6$ is a substituted doxinyl. In embodiments, $R^5$ is hydrogen and $R^6$ is an unsubstituted doxinyl. In embodiments, $R^5$ is hydrogen and $R^6$ is substituted or unsubstituted dithiinyl. In embodiments, $R^5$ is hydrogen and $R^6$ is a substituted dithiinyl. In embodiments, $R^5$ is hydrogen and $R^6$ is an unsubstituted dithiinyl. In embodiments, $R^5$ is hydrogen and $R^6$ is substituted or unsubstituted azetyl. In embodiments, $R^5$ is hydrogen and $R^6$ is a substituted azetyl. In embodiments, $R^5$ is hydrogen and $R^6$ is an unsubstituted azetyl. In embodiments, $R^5$ is hydrogen and $R^6$ is substituted or unsubstituted oxetyl. In embodiments, $R^5$ is hydrogen and $R^6$ is a substituted oxetyl. In embodiments, $R^5$ is hydrogen and $R^6$ is an unsubstituted oxetyl. In embodiments, $R^5$ is hydrogen and $R^6$ is substituted or unsubstituted thietyl. In embodiments, $R^5$ is hydrogen and $R^6$ is a substituted thietyl. In embodiments, $R^5$ is hydrogen and $R^6$ is an unsubstituted thietyl. In embodiments, $R^5$ is hydrogen and $R^6$ is substituted or unsubstituted azirinyl. In embodiments, $R^5$ is hydrogen and $R^6$ is a substituted azirinyl. In embodiments, $R^5$ is hydrogen and $R^6$ is an unsubstituted azirinyl. In embodiments, $R^5$ is hydrogen and $R^6$ is substituted or unsubstituted oxirenyl. In embodiments, $R^5$ is hydrogen and $R^6$ is a substituted oxirenyl. In embodiments, $R^5$ is hydrogen and $R^6$ is an unsubstituted oxirenyl. In embodiments, $R^5$ is hydrogen and $R^6$ is substituted or unsubstituted thienyl. In embodiments, $R^5$ is hydrogen and $R^6$ is a substituted thienyl. In embodiments, $R^5$ is hydrogen and $R^6$ is an unsubstituted thienyl.

In embodiments, $R^6$ is $R^{22}$-substituted or unsubstituted alkyl (e.g. $C_1$-$C_8$ alkyl, $C_1$-$C_6$ alkyl, or $C_1$-$C_4$ alkyl), $R^{22}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{22}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{22}$-substituted or unsubstituted heterocycloalkyl (e.g. 3 to 8 membered heterocycloalkyl, 4 to 8 membered heterocycloalkyl, or 5 to 6 membered heterocycloalkyl), $R^{22}$-substituted or unsubstituted aryl (e.g. $C_6$-$C_{10}$ aryl or $C_6$ aryl), or $R^{22}$-substituted or unsubstituted heteroaryl (e.g. 5 to 10 membered heteroaryl, 5 to 9 membered heteroaryl, or 5 to 6 membered heteroaryl).

In embodiments, $R^6$ is $R^{22}$-substituted alkyl (e.g. $C_1$-$C_8$ alkyl, $C_1$-$C_6$ alkyl, or $C_1$-$C_4$ alkyl), $R^{22}$-substituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{22}$-substituted cycloalkyl (e.g. $C_3$-$C_8$ cycloalkyl, $C_4$-$C_8$ cycloalkyl, or $C_5$-$C_6$ cycloalkyl), $R^{22}$-substituted heterocycloalkyl (e.g. 3 to 8 membered heterocycloalkyl, 4 to 8 membered heterocycloalkyl, or 5 to 6 membered heterocycloalkyl), $R^{22}$-substituted aryl (e.g. $C_6$-$C_{10}$ aryl or $C_6$ aryl), or $R^{22}$-substituted heteroaryl (e.g. 5 to 10 membered heteroaryl, 5 to 9 membered heteroaryl, or 5 to 6 membered heteroaryl). In embodiments, $R^6$ is an unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl).

$R^{22}$ is independently halogen, $-CX^{22}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-OCX^{22}_3$, $-OCHX^{22}_2$, $R^{23}$-substituted or unsubstituted alkyl (e.g. $C_1$-$C_8$ alkyl, $C_1$-$C_6$ alkyl, or $C_1$-$C_4$ alkyl), $R^{23}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{23}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{23}$-substituted or unsubstituted heterocycloalkyl (e.g. 3 to 8 membered heterocycloalkyl, 4 to 8 membered heterocycloalkyl, or 5 to 6 membered heterocycloalkyl), $R^{23}$-substituted or unsubstituted aryl (e.g. $C_6$-$C_{10}$ aryl or $C_6$ aryl), or $R^{23}$-substituted or unsubstituted heteroaryl (e.g. 5 to 10 membered heteroaryl, 5 to 9 membered heteroaryl, or 5 to 6 membered heteroaryl). $X^{22}$ is a halogen.

$R^{23}$ is independently halogen, $-CX^{23}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-OCX^{23}_3$, $-OCHX^{23}_2$, $R^{24}$-substituted or unsubstituted alkyl (e.g. $C_1$-$C_8$ alkyl, $C_1$-$C_6$ alkyl, or $C_1$-$C_4$ alkyl), $R^{24}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{24}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{24}$-substituted or unsubstituted heterocycloalkyl (e.g. 3 to 8 membered heterocycloalkyl, 4 to 8 membered heterocycloalkyl, or 5 to 6 membered heterocycloalkyl), $R^{24}$-substituted or unsubstituted aryl (e.g. $C_6$-$C_{10}$ aryl or $C_6$ aryl), or $R^{24}$-substituted or unsubstituted heteroaryl (e.g. 5 to 10 membered heteroaryl, 5 to 9 membered heteroaryl, or 5 to 6 membered heteroaryl). $X^{23}$ is a halogen.

In embodiments, $L^1$ is a bond. In embodiments, $L^1$ is a substituted or unsubstituted $C_1$-$C_8$ alkylene. In embodiments, $L^1$ is a substituted or unsubstituted $C_1$-$C_6$ alkylene. In embodiments, $L^1$ is a substituted or unsubstituted $C_1$-$C_4$ alkylene. In embodiments, $L^1$ is a substituted or unsubstituted $C_1$-$C_3$ alkylene. In embodiments, $L^1$ is a substituted or unsubstituted $C_1$-$C_2$ alkylene. In embodiments, $L^1$ is a substituted or unsubstituted methylene. In embodiments, $L^1$ is a substituted or unsubstituted 2 to 10 membered heteroalkylene. In embodiments, $L^1$ is a substituted or unsubstituted 2 to 8 membered heteroalkylene. In embodiments, $L^1$ is a substituted or unsubstituted 4 to 8 membered heteroalkylene. In embodiments, $L^1$ is a substituted or unsubstituted 2 to 4 membered heteroalkylene. In embodiments, $L^1$ is a substituted or unsubstituted 2 membered heteroalkylene.

In embodiments, $L^1$ is $R^{25}$-substituted or unsubstituted alkylene (e.g. $C_1$-$C_8$ alkylene, $C_1$-$C_6$ alkylene, $C_1$-$C_4$ alkylene, $C_1$-$C_3$ alkylene, $C_1$-$C_2$ alkylene, or methylene) or $R^{25}$-substituted or unsubstituted heteroalkylene (e.g. 2 to 10 membered heteroalkylene, 2 to 8 membered heteroalkylene, 4 to 8 membered heteroalkylene, 2 to 6 membered heteroalkylene, or 2 to 4 membered heteroalkylene, or 2 membered heteroalkylene). In embodiments, $L^1$ is unsubstituted alkylene (e.g. $C_1$-$C_8$ alkylene, $C_1$-$C_6$ alkylene, $C_1$-$C_4$ alkylene, $C_1$-$C_3$ alkylene, $C_1$-$C_2$ alkylene, or methylene) or unsubstituted heteroalkylene (e.g. 2 to 10 membered heteroalkylene, 2 to 8 membered heteroalkylene, 4 to 8 membered heteroalkylene, 2 to 6 membered heteroalkylene, or to 4 membered heteroalkylene, or 2 membered heteroalkylene).

In embodiments, $L^1$ is $R^{25}$-substituted alkylene (e.g. $C_1$-$C_8$ alkylene, $C_1$-$C_6$ alkylene, $C_1$-$C_4$ alkylene, $C_1$-$C_3$ alkylene, $C_1$-$C_2$ alkylene, or methylene), $R^{25}$-substituted heteroalkylene (e.g. 2 to 10 membered heteroalkylene, 2 to 8 membered heteroalkylene, 4 to 8 membered heteroalkylene, 2 to 6 membered heteroalkylene, or 2 to 4 membered heteroalkylene, or 2 membered heteroalkylene). In embodiments, $L^1$ is an unsubstituted alkylene (e.g. $C_1$-$C_8$ alkylene, $C_1$-$C_6$ alkylene, $C_1$-$C_4$ alkylene, $C_1$-$C_3$ alkylene, $C_1$-$C_2$ alkylene, or methylene), unsubstituted heteroalkylene (e.g. 2 to 10 membered heteroalkylene, 2 to 8 membered heteroalkylene, 4 to 8 membered heteroalkylene, 2 to 6 membered heteroalkylene, or 2 to 4 membered heteroalkylene, or 2 membered heteroalkylene).

$R^{25}$ is independently halogen, $-CX^{25}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-OCX^{25}_3$, $-OCHX^{25}_2$, $R^{26}$-substituted or unsubstituted alkyl (e.g. $C_1$-$C_8$ alkyl, $C_1$-$C_6$ alkyl, or $C_1$-$C_4$ alkyl), $R^{26}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{26}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{26}$-substituted or unsubstituted heterocycloalkyl (e.g. 3 to 8 membered heterocycloalkyl, 4 to 8 membered heterocycloalkyl, or 5 to 6 membered heterocycloalkyl), $R^{26}$-substituted or unsubstituted aryl (e.g. $C_6$-$C_{10}$ aryl or $C_6$ aryl), or $R^{26}$-substituted or unsubstituted heteroaryl (e.g. 5 to 10 membered heteroaryl, 5 to 9 membered heteroaryl, or 5 to 6 membered heteroaryl). $X^{25}$ is a halogen.

$R^{26}$ is independently halogen, $-CX^{26}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-OCX^{26}_3$, $-OCHX^{26}_2$, $R^{27}$-substituted or unsubstituted alkyl (e.g. $C_1$-$C_8$ alkyl, $C_1$-$C_6$ alkyl, or $C_1$-$C_4$ alkyl), $R^{27}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{27}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{27}$-substituted or unsubstituted heterocycloalkyl (e.g. 3 to 8 membered heterocycloalkyl, 4 to 8 membered heterocycloalkyl, or 5 to 6 membered heterocycloalkyl), $R^{27}$-substituted or unsubstituted aryl (e.g. $C_6$-$C_{10}$ aryl or $C_6$ aryl), or $R^{27}$-substituted or unsubstituted heteroaryl (e.g. 5 to 10 membered heteroaryl, 5 to 9 membered heteroaryl, or 5 to 6 membered heteroaryl). $X^{26}$ is a halogen.

In embodiments, $L^2$ is unsubstituted $C_1$-$C_8$ alkylene. In embodiments, $L^2$ is unsubstituted $C_1$-$C_4$ alkylene. In embodiments, $L^2$ is an unsubstituted $C_1$-$C_2$ alkylene. In embodiments, $L^2$ is an unsubstituted $C_2$ alkylene. In embodiments, $L^2$ is an unsubstituted methylene.

In embodiments, $L^3$ is a bond, substituted or unsubstituted $C_1$-$C_8$ alkylene, or substituted or unsubstituted 2 to 8 membered heteroalkylene, substituted or unsubstituted $C_3$-$C_8$ cycloalkylene, substituted or unsubstituted 3 to 8 membered heterocycloalkylene, substituted or unsubstituted phenylene, or substituted or unsubstituted 5 to 6 membered heteroarylene. In embodiments, $L^3$ is a bond. In embodiments, $L^3$ is a substituted or unsubstituted alkylene, or substituted or unsubstituted heteroalkylene. In embodiments, $L^3$ is a substituted or unsubstituted alkylene (e.g. $C_1$-$C_8$ alkylene, $C_1$-$C_6$ alkylene, or $C_1$-$C_4$ alkylene), or substituted or unsubstituted heteroalkylene (e.g. 2 to 10 membered heteroalkylene, 2 to 8 membered heteroalkylene, 4 to 8 membered heteroalkylene, 2 to 6 membered heteroalkylene, or 2 to 4 membered heteroalkylene). In embodiments, $L^3$ is a substituted or unsubstituted $C_1$-$C_8$ alkylene, or substituted or unsubstituted 2 to 8 membered heteroalkylene.

In embodiments, $L^3$ is a substituted or unsubstituted alkylene (e.g. $C_1$-$C_8$ alkylene, $C_1$-$C_6$ alkylene, or $C_1$-$C_4$ alkylene). In embodiments, $L^3$ is a substituted or unsubstituted $C_1$-$C_8$ alkylene. In embodiments, $L^3$ is a substituted or unsubstituted $C_1$-$C_6$ alkylene. In embodiments, $L^3$ is a substituted or unsubstituted $C_1$-$C_4$ alkylene. In embodiments, $L^3$ is a substituted or unsubstituted $C_1$-$C_5$ alkylene. In embodiments, $L^3$ is a substituted or unsubstituted $C_5$ alkylene. In embodiments, $L^3$ is a substituted $C_1$-$C_5$ alkylene. In embodiments, $L^3$ is a substituted $C_5$ alkylene. In embodiments, $L^3$ is an unsubstituted $C_1$-$C_5$ alkylene. In embodiments, $L^3$ is an unsubstituted $C_5$ alkylene. In embodiments, $L^3$ is a substituted or unsubstituted $C_1$-$C_4$ alkylene. In embodiments, $L^3$ is a substituted or unsubstituted $C_4$ alkylene. In embodiments, $L^3$ is a substituted $C_1$-$C_4$ alkylene. In embodiments, $L^3$ is a substituted $C_4$ alkylene. In embodiments, $L^3$ is an unsubstituted $C_1$-$C_4$ alkylene. In embodiments, $L^3$ is an unsubstituted $C_4$ alkylene. In embodiments, $L^3$ is a substituted or unsubstituted $C_1$-$C_3$ alkylene. In embodiments, $L^3$ is a substituted or unsubstituted $C_3$ alkylene. In embodiments, $L^3$ is a substituted $C_1$-$C_3$ alkylene. In embodiments, $L^3$ is a substituted $C_3$ alkylene. In embodiments, $L^3$ is an unsubstituted $C_1$-$C_3$ alkylene. In embodiments, $L^3$ is an unsubstituted $C_3$ alkylene. In embodiments, $L^3$ is a substituted or unsubstituted $C_1$-$C_2$ alkylene. In embodiments, $L^3$ is a substituted or unsubstituted $C_2$ alkylene. In embodiments, $L^3$ is a substituted $C_1$-$C_2$ alkylene. In embodiments, $L^3$ is a substituted $C_2$ alkylene. In embodiments, $L^3$ is an unsubstituted $C_1$-$C_2$ alkylene. In embodiments, $L^3$ is an unsubstituted $C_2$ alkylene.

In embodiments, $L^3$ is a substituted or unsubstituted heteroalkylene (e.g. 2 to 10 membered heteroalkylene, 2 to 8 membered heteroalkylene, 4 to 8 membered heteroalkylene, 2 to 6 membered heteroalkylene, or 2 to 4 membered heteroalkylene). In embodiments, $L^3$ is a substituted or unsubstituted 2 to 10 membered heteroalkylene. In embodiments, $L^3$ is a substituted or unsubstituted 2 to 8 membered heteroalkylene. In embodiments, $L^3$ is a substituted or unsubstituted 4 to 8 membered heteroalkylene. In embodiments, $L^3$ is a substituted or unsubstituted 2 to 6 membered heteroalkylene. In embodiments, $L^3$ is a substituted or unsubstituted 2 to 4 membered heteroalkylene. In embodiments, $L^3$ is an oxo-substituted $C_1$-$C_8$ alkylene, or oxo-substituted 2 to 8 membered heteroalkylene.

In embodiments, $L^3$ is a substituted or unsubstituted —NH—($C_1$-$C_8$ alkylene)-. In embodiments, $L^3$ is a substituted or unsubstituted —NH—($C_1$-$C_7$ alkylene)-. In embodiments, $L^3$ is a substituted or unsubstituted —NH—($C_1$-$C_6$ alkylene)-. In embodiments, $L^3$ is a substituted or unsubstituted —NH—($C_1$-$C_5$ alkylene)-. In embodiments, $L^3$ is a substituted or unsubstituted —NH—($C_1$-$C_4$ alkylene)-. In embodiments, $L^3$ is a substituted —NH—($C_1$-$C_8$ alkylene)-. In embodiments, $L^3$ is a substituted —NH—($C_1$-$C_7$ alkylene)-. In embodiments, $L^3$ is a substituted —NH—($C_1$-$C_6$ alkylene)-. In embodiments, $L^3$ is a substituted —NH—($C_1$-$C_5$ alkylene)-. In embodiments, $L^3$ is a substituted —NH—($C_1$-$C_4$ alkylene)-. In embodiments, $L^3$ is an unsubstituted —NH—($C_1$-$C_8$ alkylene)-. In embodiments, $L^3$ is an unsubstituted —NH—($C_1$-$C_7$ alkylene)-. In embodiments, $L^3$ is an unsubstituted —NH—($C_1$-$C_6$ alkylene)-. In embodiments, $L^3$ is an unsubstituted —NH—($C_1$-$C_5$ alkylene)-. In embodiments, $L^3$ is an unsubstituted —NH—($C_1$-$C_4$ alkylene)-.

In embodiments, $L^3$ is a substituted or unsubstituted —NH—($C_8$ alkylene)-. In embodiments, $L^3$ is a substituted or unsubstituted —NH—($C_7$ alkylene)-. In embodiments, $L^3$ is a substituted or unsubstituted —NH—($C_6$ alkylene)-. In embodiments, $L^3$ is a substituted or unsubstituted —NH—($C_5$ alkylene)-. In embodiments, $L^3$ is a substituted or unsubstituted —NH—($C_4$ alkylene)-. In embodiments, $L^3$ is a substituted —NH—($C_8$ alkylene)-. In embodiments, $L^3$ is a substituted —NH—($C_7$ alkylene)-. In embodiments, $L^3$ is a substituted —NH—($C_6$ alkylene)-. In embodiments, $L^3$ is a substituted —NH—($C_5$ alkylene)-. In embodiments, $L^3$ is a substituted —NH—($C_4$ alkylene)-. In embodiments, $L^3$ is an unsubstituted —NH—($C_8$ alkylene)-. In embodiments, $L^3$ is an unsubstituted —NH—($C_7$ alkylene)-. In embodiments, $L^3$ is an unsubstituted —NH—($C_6$ alkylene)-. In embodiments, $L^3$ is an unsubstituted —NH—($C_5$ alkylene)-. In embodiments, $L^3$ is an unsubstituted —NH—($C_4$ alkylene)-.

In embodiments, $L^3$ is a substituted or unsubstituted 5 membered heteroalkylene. In embodiments, $L^3$ is a substituted or unsubstituted 6 membered heteroalkylene. In embodiments, $L^3$ is a substituted or unsubstituted 7 membered heteroalkylene. In embodiments, $L^3$ is a substituted or unsubstituted 8 membered heteroalkylene. In embodiments, $L^3$ is a substituted or unsubstituted 9 membered heteroalkylene. In embodiments, $L^3$ is a substituted 5 membered heteroalkylene. In embodiments, $L^3$ is a substituted 6 membered heteroalkylene. In embodiments, $L^3$ is a substituted 7 membered heteroalkylene. In embodiments, $L^3$ is a substituted 8 membered heteroalkylene. In embodiments, $L^3$ is a substituted 9 membered heteroalkylene. In embodiments, $L^3$ is an unsubstituted 5 membered heteroalkylene. In embodiments, $L^3$ is an unsubstituted 6 membered heteroalkylene. In embodiments, $L^3$ is an unsubstituted 7 membered heteroalkylene. In embodiments, $L^3$ is an unsubstituted 8 membered heteroalkylene. In embodiments, $L^3$ is an unsubstituted 9 membered heteroalkylene.

In embodiments, $L^3$ is an oxo-substituted or unsubstituted 5 membered heteroalkylene. In embodiments, $L^3$ is an oxo-substituted or unsubstituted 6 membered heteroalkylene. In embodiments, $L^3$ is an oxo-substituted or unsubstituted 7 membered heteroalkylene. In embodiments, $L^3$ is an oxo-substituted or unsubstituted 8 membered heteroalkylene. In embodiments, $L^3$ is an oxo-substituted or unsubstituted 9 membered heteroalkylene. In embodiments, $L^3$ is an oxo-substituted 5 membered heteroalkylene. In embodiments, $L^3$ is an oxo-substituted 6 membered heteroalkylene. In embodiments, $L^3$ is an oxo-substituted 7 membered heteroalkylene. In embodiments, $L^3$ is an oxo-substituted 8 membered heteroalkylene. In embodiments, $L^3$ is an oxo-substituted 9 membered heteroalkylene. In embodiments, $L^3$ is —NH—NH—C(O)—. In embodiments, $L^3$ is —NH—C(O)—. In embodiments, $L^3$ is —NH—CH$_2$—C(O)—.

In embodiments, $L^3$ is

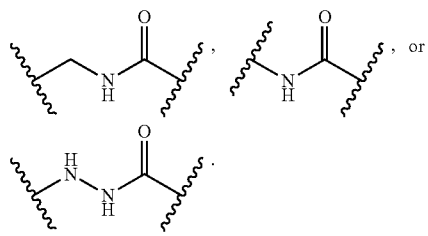

In embodiments, $L^3$ is $R^{28}$-substituted or unsubstituted alkylene (e.g. $C_1$-$C_8$ alkylene, $C_1$-$C_6$ alkylene, or $C_1$-$C_4$ alkylene), $R^{28}$-substituted or unsubstituted heteroalkylene (e.g. 2 to 10 membered heteroalkylene, 2 to 8 membered heteroalkylene, 4 to 8 membered heteroalkylene, 2 to 6 membered heteroalkylene, or 2 to 4 membered heteroalkylene), $R^{28}$-substituted or unsubstituted cycloalkylene (e.g. $C_3$-$C_8$ cycloalkylene, $C_4$-$C_8$ cycloalkylene, or $C_5$-$C_6$ cycloalkylene), $R^{28}$-substituted or unsubstituted heterocycloalkylene (e.g. 3 to 8 membered heterocycloalkylene, 4 to 8 membered heterocycloalkylene, or 5 to 6 membered heterocycloalkylene), $R^{28}$-substituted or unsubstituted arylene (e.g. $C_6$-$C_{10}$ arylene or $C_6$ arylene), or $R^{28}$-substituted or unsubstituted heteroarylene (e.g. 5 to 10 membered heteroarylene, 5 to 9 membered heteroarylene, or 5 to 6 membered heteroarylene).

In embodiments, $L^3$ is $R^{28}$-substituted alkylene (e.g. $C_1$-$C_8$ alkylene, $C_1$-$C_6$ alkylene, or $C_1$-$C_4$ alkylene), $R^{28}$-substituted heteroalkylene (e.g. 2 to 10 membered heteroalkylene, 2 to 8 membered heteroalkylene, 4 to 8 membered heteroalkylene, 2 to 6 membered heteroalkylene, or to 4 membered heteroalkylene), $R^{28}$-substituted cycloalkylene (e.g. $C_3$-$C_8$ cycloalkylene, $C_4$-$C_8$ cycloalkylene, or $C_5$-$C_6$ cycloalkylene), $R^{28}$-substituted heterocycloalkylene (e.g. 3 to 8 membered heterocycloalkylene, 4 to 8 membered heterocycloalkylene, or 5 to 6 membered heterocycloalkylene), $R^{28}$-substituted arylene (e.g. $C_6$-$C_{10}$ arylene or $C_6$ arylene), or $R^{28}$-substituted heteroarylene (e.g. 5 to 10 membered heteroarylene, 5 to 9 membered heteroarylene, or 5 to 6 membered heteroarylene).

In embodiments, $L^3$ is an unsubstituted alkylene (e.g. $C_1$-$C_8$ alkylene, $C_1$-$C_6$ alkylene, or $C_1$-$C_4$ alkylene), unsubstituted heteroalkylene (e.g. 2 to 10 membered heteroalkylene, 2 to 8 membered heteroalkylene, 4 to 8 membered heteroalkylene, 2 to 6 membered heteroalkylene, or to 4 membered heteroalkylene), unsubstituted cycloalkylene (e.g. $C_3$-$C_8$ cycloalkylene, $C_4$-$C_8$ cycloalkylene, or $C_5$-$C_6$ cycloalkylene), unsubstituted heterocycloalkylene (e.g. 3 to 8 membered heterocycloalkylene, 4 to 8 membered heterocycloalkylene, or 5 to 6 membered heterocycloalkylene), unsubstituted arylene (e.g. $C_6$-$C_{10}$ arylene or $C_6$ arylene), or unsubstituted heteroarylene (e.g. 5 to 10 membered heteroarylene, 5 to 9 membered heteroarylene, or 5 to 6 membered heteroarylene).

$R^{28}$ is independently halogen, —CX$^{28}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC═(O) NHNH$_2$, —NHC═(O)NH$_2$, —NHSO$_2$H, —NHC═(O)H, —NHC(O)OH, —NHOH, —OCX$^{28}_3$, —OCHX$^{28}_2$, $R^{29}$-substituted or unsubstituted alkyl (e.g. $C_1$-$C_8$ alkyl, $C_1$-$C_6$ alkyl, or $C_1$-$C_4$ alkyl), $R^{29}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{29}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{29}$-substituted or unsubstituted heterocycloalkyl (e.g. 3 to 8 membered heterocycloalkyl, 4 to 8 membered heterocycloalkyl, or 5 to 6 membered heterocycloalkyl), $R^{29}$-substituted or unsubstituted aryl (e.g. $C_6$-$C_{10}$ aryl or $C_6$ aryl), or $R^{29}$-substituted or unsubstituted heteroaryl (e.g. 5 to 10 membered heteroaryl, 5 to 9 membered heteroaryl, or 5 to 6 membered heteroaryl). In embodiments, $R^{28}$ is a 2 to 10 membered substituted or unsubstituted heteroalkyl. In embodiments, $R^{28}$ is a 10 membered substituted or unsubstituted heteroalkyl. In embodiments, $R^{28}$ is a substituted or unsubstituted 9 membered heteroalkyl. In embodiments, $R^{28}$ is a substituted or unsubstituted 8 membered heteroalkyl. In embodiments, $R^{28}$ is a substituted or unsubstituted 7 membered heteroalkyl. In embodiments, $R^{28}$ is a substituted or unsubstituted 6 membered heteroalkyl. In embodiments, $R^{28}$ is a substituted or unsubstituted 5 membered heteroalkyl. $X^{28}$ is a halogen.

In embodiments, $R^{28}$ is a substituted or unsubstituted alkylene (e.g. $C_1$-$C_8$ alkylene, $C_1$-$C_6$ alkylene, or $C_1$-$C_4$ alkylene). In embodiments, $R^{28}$ is a substituted alkylene (e.g. $C_1$-$C_8$ alkylene, $C_1$-$C_6$ alkylene, or $C_1$-$C_4$ alkylene). In embodiments, $R^{28}$ is an unsubstituted alkylene (e.g. $C_1$-$C_8$ alkylene, $C_1$-$C_6$ alkylene, or $C_1$-$C_4$ alkylene). In embodiments, $R^{28}$ is a substituted or unsubstituted $C_1$-$C_8$ alkylene. In embodiments, $R^{28}$ is a substituted or unsubstituted $C_1$-$C_6$ alkylene. In embodiments, $R^{28}$ is a substituted or unsubstituted $C_1$-$C_4$ alkylene. In embodiments, $R^{28}$ is a substituted or unsubstituted $C_1$-$C_2$ alkylene. In embodiments, $R^{28}$ is a substituted or unsubstituted $C_2$-$C_4$ alkylene. In embodiments, $R^{28}$ is a substituted or unsubstituted $C_4$ alkylene. In embodiments, $R^{28}$ is a substituted $C_1$-$C_8$ alkylene. In embodiments, $R^{28}$ is a substituted $C_1$-$C_6$ alkylene. In embodiments, $R^{28}$ is a substituted $C_1$-$C_4$ alkylene. In embodiments, $R^{28}$ is a substituted $C_1$-$C_2$ alkylene. In embodiments, $R^{28}$ is a substituted $C_2$-$C_4$ alkylene. In embodiments, $R^{28}$ is a substituted $C_4$ alkylene. In embodiments, $R^{28}$ is an unsubstituted $C_1$-$C_8$ alkylene. In embodiments, $R^{28}$ is an unsubstituted $C_1$-$C_6$ alkylene. In embodiments, $R^{28}$ is an unsubstituted $C_1$-$C_4$ alkylene. In embodiments, $R^{28}$ is an unsubstituted $C_1$-$C_2$ alkylene. In embodiments, $R^{28}$ is an unsubstituted $C_2$-$C_4$ alkylene. In embodiments, $R^{28}$ is an unsubstituted $C_4$ alkylene.

In embodiments, $R^{28}$ is a substituted $C_1$-$C_8$ alkylene substituted with a detectable moiety. In embodiments, $R^{28}$ is a substituted $C_1$-$C_6$ alkylene substituted with a detectable moiety. In embodiments, $R^{28}$ is a substituted $C_1$-$C_4$ alkylene substituted with a detectable moiety. In embodiments, $R^{28}$ is a substituted $C_1$-$C_2$ alkylene substituted with a detectable moiety. In embodiments, $R^{28}$ is a substituted $C_2$-$C_4$ alkylene substituted with a detectable moiety. In embodiments, $R^{28}$ is a substituted $C_4$ alkylene substituted with a detectable moiety.

In embodiments, $R^{28}$ is a substituted $C_1$-$C_8$ alkylene substituted with a fluorescein isothiocyanate detectable moiety. In embodiments, $R^{28}$ is a substituted $C_1$-$C_6$ alkylene substituted with a fluorescein isothiocyanate detectable moiety. In embodiments, $R^{28}$ is a substituted $C_1$-$C_4$ alkylene substituted with a fluorescein isothiocyanate detectable moiety. In embodiments, $R^{28}$ is a substituted $C_1$-$C_2$ alkylene substituted with a fluorescein isothiocyanate detectable moiety. In embodiments, $R^{28}$ is a substituted $C_2$-$C_4$ alkylene substituted with a fluorescein isothiocyanate detectable moiety. In embodiments, $R^{28}$ is a substituted $C_4$ alkylene substituted with a fluorescein isothiocyanate detectable moiety. In embodiments, the fluorescein isothiocyanate detectable moiety is In embodiments, the fluorescein isothiocyanate detectable moiety is In embodiments, $R^{28}$ is a substituted $C_1$-$C_8$ alkylene substituted with a thiourea-detectable moiety. In embodiments, $R^{28}$ is a substituted $C_1$-$C_6$ alkylene substituted with a thiourea-detectable moiety. In embodiments, $R^{28}$ is a substituted C—$C_4$ alkylene substituted with a thiourea-detectable moiety. In embodiments, $R^{28}$ is a substituted $C_1$-$C_2$ alkylene substituted with a thiourea-detectable moiety. In embodiments, $R^{28}$ is a substituted $C_2$-$C_4$ alkylene substituted with a thiourea-detectable moiety. In embodiments, $R^{28}$ is a substituted $C_4$ alkylene substituted with a thiourea-detectable moiety. In embodiments, $R^{28}$ is a substituted $C_1$-$C_8$ alkylene substituted with a thiourea-fluorescein detectable moiety. In embodiments, $R^{28}$ is a substituted $C_1$-$C_6$ alkylene substituted with a thiourea-fluorescein detectable moiety. In embodiments, $R^{28}$ is a substituted $C_1$-$C_4$ alkylene substituted with a thiourea-fluorescein detectable moiety. In embodiments, $R^{28}$ is a substituted $C_1$-$C_2$ alkylene substituted with a thiourea-fluorescein detectable moiety. In embodiments, $R^{28}$ is a substituted $C_2$-$C_4$ alkylene substituted with a thiourea-fluorescein detectable moiety. In embodiments, $R^{28}$ is a substituted $C_4$ alkylene substituted with a thiourea-fluorescein detectable moiety. In embodiments, the thiourea-fluorescein is In embodiments, $R^{28}$ is a substituted 2 to 10 membered heteroalkyl. In embodiments, $R^{28}$ is a substituted 10 membered heteroalkyl. In embodiments, $R^{28}$ is a substituted 9 membered heteroalkyl. In embodiments, $R^{28}$ is a substituted 8 membered heteroalkyl. In embodiments, $R^{28}$ is a substituted 7 membered heteroalkyl. In embodiments, $R^{28}$ is a substituted 6 membered heteroalkyl. In embodiments, $R^{28}$ is a substituted 5 membered heteroalkyl.

In embodiments, $R^{28}$ is a substituted 2 to 10 membered heteroalkyl substituted with a detectable moiety. In embodiments, $R^{28}$ is a substituted 2 to 8 membered heteroalkyl substituted with a detectable moiety. In embodiments, $R^{28}$ is a substituted 2 to 6 membered heteroalkyl substituted with a detectable moiety. In embodiments, $R^{28}$ is a substituted 2 to 4 membered heteroalkyl substituted with a detectable moiety. In embodiments, $R^{28}$ is a substituted 10 membered heteroalkyl substituted with a detectable moiety. In embodiments, $R^{28}$ is a substituted membered heteroalkyl substituted with a detectable moiety. In embodiments, $R^{28}$ is a substituted 8 membered heteroalkyl substituted with a detectable moiety. In embodiments, $R^{28}$ is a substituted 7 membered heteroalkyl substituted with a detectable moiety. In embodiments, $R^{28}$ is a substituted 6 membered heteroalkyl substituted with a detectable moiety. In embodiments, $R^{28}$ is a substituted 5 membered heteroalkyl substituted with a detectable moiety. In embodiments, $R^{28}$ is a substituted 4 membered heteroalkyl substituted with a detectable moiety. In embodiments, $R^{28}$ is a substituted 3 membered heteroalkyl substituted with a detectable moiety. In embodiments, $R^{28}$ is a substituted 2 membered heteroalkyl substituted with a detectable moiety.

In embodiments, $R^{28}$ is a substituted 2 to 10 membered heteroalkyl substituted with a fluorescein isothiocyanate detectable moiety. In embodiments, $R^{28}$ is a substituted 2 to 8 membered heteroalkyl substituted with a fluorescein isothiocyanate detectable moiety. In embodiments, $R^{28}$ is a substituted 2 to 6 membered heteroalkyl substituted with a fluorescein isothiocyanate detectable moiety. In embodiments, $R^{28}$ is a substituted 2 to 4 membered heteroalkyl substituted with a fluorescein isothiocyanate detectable moiety. In embodiments, $R^{28}$ is a substituted 10 membered heteroalkyl substituted with a fluorescein isothiocyanate detectable moiety. In embodiments, $R^{28}$ is a substituted 9 membered heteroalkyl substituted with a fluorescein isothiocyanate detectable moiety. In embodiments, $R^{28}$ is a substituted 8 membered heteroalkyl substituted with a fluorescein isothiocyanate detectable moiety. In embodiments, $R^{28}$ is a substituted 7 membered heteroalkyl substituted with a fluorescein isothiocyanate detectable moiety. In embodiments, $R^{28}$ is a substituted 6 membered heteroalkyl substituted with a fluorescein isothiocyanate detectable moiety. In embodiments, $R^{28}$ is a substituted 5 membered heteroalkyl substituted with a fluorescein isothiocyanate detectable moiety. In embodiments, $R^{28}$ is a substituted 4 membered heteroalkyl substituted with a fluorescein isothiocyanate detectable moiety. In embodiments, $R^{28}$ is a substituted 3 membered heteroalkyl substituted with a fluorescein isothiocyanate detectable moiety. In embodiments, $R^{28}$ is a substituted 2 membered heteroalkyl substituted with a fluorescein isothiocyanate detectable moiety. In embodiments, the fluorescein isothiocyanate detectable moiety is

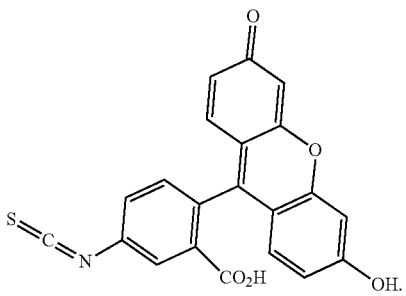 [SMILES: O=C(O)c1cc(N=C=S)ccc1-c1c2ccc(=O)cc-2oc2cc(O)ccc12]

In embodiments, the fluorescein isothiocyanate detectable moiety is

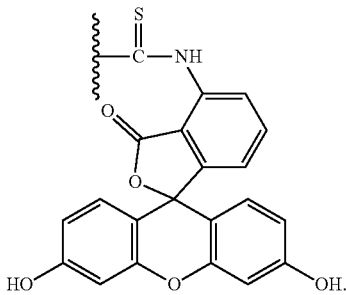 [SMILES: *C(=S)Nc1cccc2c1C(=O)OC21c2ccc(O)cc2Oc2cc(O)ccc21]

In embodiments, $R^{28}$ is a substituted 2 to 10 membered heteroalkyl substituted with a thiourea-detectable moiety. In embodiments, $R^{28}$ is a substituted 2 to 8 membered heteroalkyl substituted with a thiourea-detectable moiety. In embodiments, $R^{28}$ is a substituted 2 to 6 membered heteroalkyl substituted with a thiourea-detectable moiety. In embodiments, $R^{28}$ is a substituted 2 to 4 membered heteroalkyl substituted with a thiourea-detectable moiety. In embodiments, $R^{28}$ is a substituted 10 membered heteroalkyl substituted with a thiourea-detectable moiety. In embodiments, $R^{28}$ is a substituted 9 membered heteroalkyl substituted with a thiourea-detectable moiety. In embodiments, $R^{28}$ is a substituted 8 membered heteroalkyl substituted with a thiourea-detectable moiety. In embodiments, $R^{28}$ is a substituted 7 membered heteroalkyl substituted with a thiourea-detectable moiety. In embodiments, $R^{28}$ is a substituted 6 membered heteroalkyl substituted with a thiourea-detectable moiety. In embodiments, $R^{28}$ is a substituted 5 membered heteroalkyl substituted with a thiourea-detectable moiety. In embodiments, $R^{28}$ is a substituted 4 membered heteroalkyl substituted with a thiourea-detectable moiety. In embodiments, $R^{28}$ is a substituted 3 membered heteroalkyl substituted with a thiourea-detectable moiety. In embodiments, $R^{28}$ is a substituted 2 membered heteroalkyl substituted with a thiourea-detectable moiety.

In embodiments, $R^{28}$ is a substituted 2 to 10 membered heteroalkyl substituted with a thiourea-fluorescein detectable moiety. In embodiments, $R^{28}$ is a substituted 2 to 8 membered heteroalkyl substituted with a thiourea-fluorescein detectable moiety. In embodiments, $R^{28}$ is a substituted 2 to 6 membered heteroalkyl substituted with a thiourea-fluorescein detectable moiety. In embodiments, $R^{28}$ is a substituted 2 to 4 membered heteroalkyl substituted with a thiourea-fluorescein detectable moiety. In embodiments, $R^{28}$ is a substituted 10 membered heteroalkyl substituted with a thiourea-fluorescein detectable moiety. In embodiments, $R^{28}$ is a substituted 9 membered heteroalkyl substituted with a thiourea-fluorescein detectable moiety. In embodiments, $R^{28}$ is a substituted 8 membered heteroalkyl substituted with a thiourea-fluorescein detectable moiety. In embodiments, $R^{28}$ is a substituted 7 membered heteroalkyl substituted with a thiourea-fluorescein detectable moiety. In embodiments, $R^{28}$ is a substituted 6 membered heteroalkyl substituted with a thiourea-fluorescein detectable moiety. In embodiments, $R^{28}$ is a substituted 5 membered heteroalkyl substituted with a thiourea-fluorescein detectable moiety. In embodiments, $R^{28}$ is a substituted 4 membered heteroalkyl substituted with a thiourea-fluorescein detectable moiety. In embodiments, $R^{28}$ is a substituted 3 membered heteroalkyl substituted with a thiourea-fluorescein detectable moiety. In embodiments, $R^{28}$ is a substituted 2 membered heteroalkyl substituted with a thiourea-fluorescein detectable moiety. In embodiments, the thiourea-fluorescein is

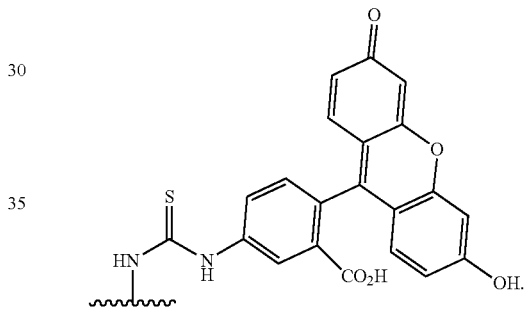

In embodiments, $R^{28}$ is a substituted 2 to 10 membered heteroalkyl. In embodiments, $R^{28}$ is a substituted 10 membered heteroalkyl. In embodiments, $R^{28}$ is a substituted 9 membered heteroalkyl. In embodiments, $R^{28}$ is a substituted 8 membered heteroalkyl. In embodiments, $R^{28}$ is a substituted 7 membered heteroalkyl. In embodiments, $R^{28}$ is a substituted 6 membered heteroalkyl. In embodiments, $R^{28}$ is a substituted 5 membered heteroalkyl.

$R^{29}$ is independently halogen, $-CX^{29}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)$NHNH_2$, $-NHC=(O)NH_2$, $-NHSO_2H$, $-NHC=(O)H$, $-NHC(O)OH$, $-NHOH$, $-OCX^{29}_3$, $-OCHX^{29}_2$, $R^{30}$-substituted or unsubstituted alkyl (e.g. $C_1$-$C_8$ alkyl, $C_1$-$C_6$ alkyl, or $C_1$-$C_4$ alkyl), $R^{30}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{30}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{30}$-substituted or unsubstituted heterocycloalkyl (e.g. 3 to 8 membered heterocycloalkyl, 4 to 8 membered heterocycloalkyl, or 5 to 6 membered heterocycloalkyl), $R^{30}$-substituted or unsubstituted aryl (e.g. $C_6$-$C_{10}$ aryl or $C_6$ aryl), or $R^{30}$-substituted or unsubstituted heteroaryl (e.g. 5 to 10 membered heteroaryl, 5 to 9 membered heteroaryl, or 5 to 6 membered heteroaryl). $X^{29}$ is a halogen.

In embodiments, $L^3$ is $N(R^7)$—. In embodiments, $R^7$ is hydrogen, —CN, —COOH, —CX$^7$$_3$, substituted or unsubstituted alkyl, or substituted or unsubstituted heteroalkyl. $X^7$ is halogen. In embodiments, $R^7$ is hydrogen, —CN, —COOH, —CX$^7$$_3$. In embodiments, $R^7$ is hydrogen. In embodiments, $R^7$ is $R^{34}$-substituted or unsubstituted alkyl (e.g. $C_1$-$C_8$ alkyl, $C_1$-$C_6$ alkyl, or $C_1$-$C_4$ alkyl), $R^{34}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{34}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{34}$-substituted or unsubstituted heterocycloalkyl (e.g. 3 to 8 membered heterocycloalkyl, 4 to 8 membered heterocycloalkyl, or 5 to 6 membered heterocycloalkyl), $R^{34}$-substituted or unsubstituted aryl (e.g. $C_6$-$C_{10}$ aryl or $C_6$ aryl), or $R^{34}$-substituted or unsubstituted heteroaryl (e.g. 5 to 10 membered heteroaryl, 5 to 9 membered heteroaryl, or 5 to 6 membered heteroaryl). $X^7$ is a halogen.

In embodiments, $R^7$ is $R^{34}$-substituted alkyl (e.g. $C_1$-$C_8$ alkyl, $C_1$-$C_6$ alkyl, or $C_1$-$C_4$ alkyl), $R^{34}$-substituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{34}$-substituted cycloalkyl (e.g. $C_3$-$C_8$ cycloalkyl, $C_4$-$C_8$ cycloalkyl, or $C_5$-$C_6$ cycloalkyl), $R^{34}$-substituted heterocycloalkyl (e.g. 3 to 8 membered heterocycloalkyl, 4 to 8 membered heterocycloalkyl, or 5 to 6 membered heterocycloalkyl), $R^{34}$-substituted aryl (e.g. $C_6$-$C_{10}$ aryl or $C_6$ aryl), or $R^{34}$-substituted heteroaryl (e.g. 5 to 10 membered heteroaryl, 5 to 9 membered heteroaryl, or 5 to 6 membered heteroaryl). In embodiments, $R^7$ is an unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl).

$R^{34}$ is independently halogen, —CX$^{34}$$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O) NHNH$_2$, —NHC=(O)NH$_2$, —NHSO$_2$H, —NHC=(O)H, —NHC(O)OH, —NHOH, —OCX$^{34}$$_3$, —OCHX$^{34}$$_2$, $R^{35}$-substituted or unsubstituted alkyl (e.g. $C_1$-$C_8$ alkyl, $C_1$-$C_6$ alkyl, or $C_1$-$C_4$ alkyl), $R^{35}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{35}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{35}$-substituted or unsubstituted heterocycloalkyl (e.g. 3 to 8 membered heterocycloalkyl, 4 to 8 membered heterocycloalkyl, or 5 to 6 membered heterocycloalkyl), $R^{35}$-substituted or unsubstituted aryl (e.g. $C_6$-$C_{10}$ aryl or $C_6$ aryl), or $R^{35}$-substituted or unsubstituted heteroaryl (e.g. 5 to 10 membered heteroaryl, 5 to 9 membered heteroaryl, or 5 to 6 membered heteroaryl). $X^{34}$ is a halogen.

$R^{35}$ is independently halogen, —CX$^{35}$$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O) NHNH$_2$, —NHC=(O)NH$_2$, —NHSO$_2$H, —NHC=(O)H, —NHC(O)OH, —NHOH, —OCX$^{35}$$_3$, —OCHX$^{35}$$_2$, $R^{36}$-substituted or unsubstituted alkyl (e.g. $C_1$-$C_8$ alkyl, $C_1$-$C_6$ alkyl, or $C_1$-$C_4$ alkyl), $R^{36}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{36}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{36}$-substituted or unsubstituted heterocycloalkyl (e.g. 3 to 8 membered heterocycloalkyl, 4 to 8 membered heterocycloalkyl, or 5 to 6 membered heterocycloalkyl), $R^{36}$-substituted or unsubstituted aryl (e.g. $C_6$-$C_{10}$ aryl or $C_6$ aryl), or $R^{36}$-substituted or unsubstituted heteroaryl (e.g. 5 to 10 membered heteroaryl, 5 to 9 membered heteroaryl, or 5 to 6 membered heteroaryl). $X^{35}$ is a halogen.

In embodiments, $L^4$ is a substituted or unsubstituted $C_1$-$C_8$ alkylene, or substituted or unsubstituted 2 to 8 membered heteroalkylene, substituted or unsubstituted $C_3$-$C_8$ cycloalkylene, substituted or unsubstituted 3 to 8 membered heterocycloalkylene, substituted or unsubstituted phenylene, or substituted or unsubstituted 5 to 6 membered heteroarylene.

In embodiments, $L^4$ is

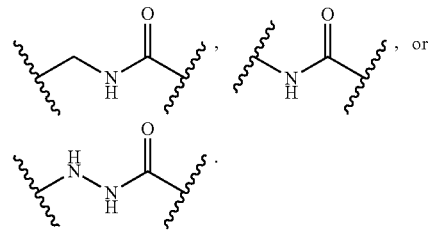

In embodiments, $L^4$ is a substituted or unsubstituted alkylene, or substituted or unsubstituted heteroalkylene. In embodiments, $L^4$ is a substituted or unsubstituted alkylene (e.g. $C_1$-$C_8$ alkylene, $C_1$-$C_6$ alkylene, or $C_1$-$C_4$ alkylene), or substituted or unsubstituted heteroalkylene (e.g. 2 to 10 membered heteroalkylene, 2 to 8 membered heteroalkylene, 4 to 8 membered heteroalkylene, 2 to 6 membered heteroalkylene, or 2 to 4 membered heteroalkylene). In embodiments, $L^4$ is a substituted or unsubstituted $C_1$-$C_8$ alkylene, or substituted or unsubstituted 2 to 8 membered heteroalkylene. In embodiments, $L^4$ is an oxo-substituted $C_1$-$C_8$ alkylene, or oxo-substituted 2 to 8 membered heteroalkylene.

In embodiments, $L^4$ is a substituted or unsubstituted alkylene (e.g. $C_1$-$C_8$ alkylene, $C_1$-$C_6$ alkylene, or $C_1$-$C_4$ alkylene). In embodiments, $L^4$ is a substituted or unsubstituted $C_1$-$C_8$ alkylene. In embodiments, $L^4$ is a substituted or unsubstituted $C_1$-$C_6$ alkylene. In embodiments, $L^4$ is a substituted or unsubstituted $C_1$-$C_4$ alkylene. In embodiments, $L^4$ is a substituted or unsubstituted $C_1$-$C_5$ alkylene. In embodiments, $L^4$ is a substituted or unsubstituted $C_5$ alkylene. In embodiments, $L^4$ is a substituted $C_1$-$C_5$ alkylene. In embodiments, $L^4$ is a substituted $C_5$ alkylene. In embodiments, $L^4$ is an unsubstituted $C_1$-$C_5$ alkylene. In embodiments, $L^4$ is an unsubstituted $C_5$ alkylene.

In embodiments, $L^4$ is a substituted or unsubstituted —NH—($C_1$-$C_8$ alkylene)-. In embodiments, $L^4$ is a substituted or unsubstituted —NH—($C_1$-$C_7$ alkylene)-. In embodiments, $L^4$ is a substituted or unsubstituted —NH—($C_1$-$C_6$ alkylene)-. In embodiments, $L^4$ is a substituted or unsubstituted —NH—($C_1$-$C_5$ alkylene)-. In embodiments, $L^4$ is a substituted or unsubstituted —NH—($C_1$-$C_4$ alkylene)-. In embodiments, $L^4$ is a substituted —NH—($C_1$-$C_8$ alkylene)-. In embodiments, $L^4$ is a substituted —NH—($C_1$-$C_7$ alkylene)-. In embodiments, $L^4$ is a substituted —NH—($C_1$-$C_6$ alkylene)-. In embodiments, $L^4$ is a substituted —NH—($C_1$-$C_5$ alkylene)-. In embodiments, $L^4$ is a substituted —NH—($C_1$-$C_4$ alkylene)-. In embodiments, $L^4$ is an unsubstituted —NH—($C_1$-$C_8$ alkylene)-. In embodiments, $L^4$ is an unsubstituted —NH—($C_1$-$C_7$ alkylene)-. In embodiments, $L^4$ is an unsubstituted —NH—($C_1$-$C_6$ alkylene)-. In embodiments, $L^4$ is an unsubstituted —NH—($C_1$-$C_5$ alkylene)-. In embodiments, $L^4$ is an unsubstituted —NH—($C_1$-$C_4$ alkylene)-.

In embodiments, $L^4$ is a substituted or unsubstituted —NH—($C_8$ alkylene)-. In embodiments, $L^4$ is a substituted or unsubstituted —NH—($C_7$ alkylene)-. In embodiments, $L^4$ is a substituted or unsubstituted —NH—($C_6$ alkylene)-. In embodiments, $L^4$ is a substituted or unsubstituted —NH—($C_5$ alkylene)-. In embodiments, $L^4$ is a substituted or unsubstituted —NH—($C_4$ alkylene)-. In embodiments, $L^4$ is a substituted —NH—($C_8$ alkylene)-. In embodiments, $L^4$ is a substituted —NH—($C_7$ alkylene)-. In embodiments, $L^4$ is a substituted —NH—($C_6$ alkylene)-. In embodiments, $L^4$ is a substituted —NH—($C_5$ alkylene)-. In embodiments, $L^4$ is a substituted —NH—($C_4$ alkylene)-. In embodiments, $L^4$ is an unsubstituted —NH—($C_8$ alkylene)-. In embodiments, $L^4$ is an unsubstituted —NH—($C_7$ alkylene)-. In embodiments, $L^4$ is an unsubstituted —NH—($C_6$ alkylene)-. In embodiments, $L^4$ is an unsubstituted —NH—($C_5$ alkylene)-. In embodiments, $L^4$ is an unsubstituted —NH—($C_4$ alkylene)-.

In embodiments, $L^4$ is a substituted or unsubstituted 5 membered heteroalkylene. In embodiments, $L^4$ is a substituted or unsubstituted 6 membered heteroalkylene. In embodiments, $L^4$ is a substituted or unsubstituted 7 membered heteroalkylene. In embodiments, $L^4$ is a substituted or unsubstituted 8 membered heteroalkylene. In embodiments, $L^4$ is a substituted or unsubstituted 9 membered heteroalkylene. In embodiments, $L^4$ is a substituted 5 membered heteroalkylene. In embodiments, $L^4$ is a substituted 6 membered heteroalkylene. In embodiments, $L^4$ is a substituted 7 membered heteroalkylene. In embodiments, $L^4$ is a substituted 8 membered heteroalkylene. In embodiments, $L^4$ is a substituted 9 membered heteroalkylene. In embodiments, $L^4$ is an unsubstituted 5 membered heteroalkylene. In embodiments, $L^4$ is an unsubstituted 6 membered heteroalkylene. In embodiments, $L^4$ is an unsubstituted 7 membered heteroalkylene. In embodiments, $L^4$ is an unsubstituted 8 membered heteroalkylene. In embodiments, $L^4$ is an unsubstituted 9 membered heteroalkylene.

In embodiments, $L^4$ is an oxo-substituted or unsubstituted 5 membered heteroalkylene. In embodiments, $L^4$ is an oxo-substituted or unsubstituted 6 membered heteroalkylene. In embodiments, $L^4$ is an oxo-substituted or unsubstituted 7 membered heteroalkylene. In embodiments, $L^4$ is an oxo-substituted or unsubstituted 8 membered heteroalkylene. In embodiments, $L^4$ is an oxo-substituted or unsubstituted 9 membered heteroalkylene. In embodiments, $L^4$ is an oxo-substituted 5 membered heteroalkylene. In embodiments, $L^4$ is an oxo-substituted 6 membered heteroalkylene. In embodiments, $L^4$ is an oxo-substituted 7 membered heteroalkylene. In embodiments, $L^4$ is an oxo-substituted 8 membered heteroalkylene. In embodiments, $L^4$ is an oxo-substituted 9 membered heteroalkylene. In embodiments, $L^4$ is —NH—NH—C(O)—. In embodiments, $L^4$ is —NH—C(O)—. In embodiments, $L^4$ is —NH—CH$_2$—C(O)—.

In embodiments, $L^4$ is a substituted or unsubstituted heteroalkylene (e.g. 2 to 10 membered heteroalkylene, 2 to 8 membered heteroalkylene, 4 to 8 membered heteroalkylene, 2 to 6 membered heteroalkylene, or 2 to 4 membered heteroalkylene). In embodiments, $L^4$ is a substituted or unsubstituted 2 to 10 membered heteroalkylene. In embodiments, $L^4$ is a substituted or unsubstituted 2 to 8 membered heteroalkylene. In embodiments, $L^4$ is a substituted or unsubstituted 4 to 8 membered heteroalkylene. In embodiments, $L^4$ is a substituted or unsubstituted 2 to 6 membered heteroalkylene. In embodiments, $L^4$ is a substituted or unsubstituted 2 to 4 membered heteroalkylene.

In embodiments, $L^4$ is a substituted or unsubstituted arylene, or substituted or unsubstituted heteroarylene. In embodiments, $L^4$ is a substituted or unsubstituted arylene. In embodiments, $L^4$ is a substituted or unsubstituted heteroarylene. In embodiments, $L^4$ is a substituted or unsubstituted phenylene, or substituted or unsubstituted 5 to 6 membered heteroarylene. In embodiments, $L^4$ is a substituted or unsubstituted phenylene. In embodiments, $L^4$ is a substituted or unsubstituted 5 to 6 membered heteroarylene. In embodiments, $L^4$ is an unsubstituted phenylene.

$L^4$ may be a substituted or unsubstituted 4 to 6 membered heterocycloalkylene. $L^4$ may be a substituted or unsubstituted 5 or 6 membered heterocycloalkylene. $L^4$ may be substituted or unsubstituted 5 membered heterocycloalkylene. $L^4$ may be a substituted or unsubstituted heterocycloalkylene such as substituted or unsubstituted pyrrolidinylene, substituted or unsubstituted imidazolidinylene, substituted or unsubstituted oxazolidinylene, substituted or unsubstituted thiazolidinylene, substituted or unsubstituted dioxolanylene, substituted or unsubstituted dithiolanylene, substituted or unsubstituted piperidinylene, substituted or unsubstituted morpholinylene, substituted or unsubstituted dioxanylene, substituted or unsubstituted dithianylene, substituted or unsubstituted aziridinylene, substituted or unsubstituted azetidinylene, substituted or unsubstituted azepinylene, substituted or unsubstituted oxiranylene, substituted or unsubstituted oxetanylene, substituted or unsubstituted tetrahydrofuranylene, or substituted or unsubstituted tetrahydropyranylene. $L^4$ may be a substituted or unsubstituted 6 membered heterocycloalkylene. $L^4$ may be an unsubstituted 6 membered heterocycloalkylene. $L^4$ may be an unsubstituted 5 membered heterocycloalkylene. $L^4$ may be substituted or unsubstituted $C_3$-$C_8$ cycloalkylene. $L^4$ may be substituted or unsubstituted 3 to 8 membered heterocycloalkylene. $L^4$ may be unsubstituted $C_3$-$C_8$ cycloalkylene. $L^4$ may be unsubstituted 3 to 8 membered heterocycloalkylene.

$L^4$ may be substituted or unsubstituted heteroarylene. $L^4$ may be substituted or unsubstituted 5 or 6 membered heteroarylene. $L^4$ may be a substituted or unsubstituted heteroarylene such as, for example, substituted or unsubstituted pyridinylene, substituted or unsubstituted pyrrolylene, substituted or unsubstituted furanylene, substituted or unsubstituted thiophenylene, substituted or unsubstituted imidazolylene, substituted or unsubstituted pyrazolylene, substituted or unsubstituted oxazolylene, substituted or unsubstituted thiazolylene, substituted or unsubstituted pyranylene, substituted or unsubstituted thiopyranylene, substituted or unsubstituted pyrazinylene, substituted or unsubstituted pyrimindylene, substituted or unsubstituted pyridazinylene, substituted or unsubstituted oxazinylene, substituted or unsubstituted thiazinylene, substituted or unsubstituted doxinylene, substituted or unsubstituted dithiinylene, substituted or unsubstituted azetylene, substituted or unsubstituted oxetylene, substituted or unsubstituted thietylene, substituted or unsubstituted azirinylene, substituted or unsubstituted oxirenylene or substituted or unsubstituted thienylene. $L^4$ may be substituted or unsubstituted pyridinylene. $L^4$ may be substituted cycloalkylene. $L^4$ may be unsubstituted cycloalkylene. $L^4$ may be substituted heterocycloalkylene. $L^4$ may be unsubstituted heterocycloalkylene. $L^4$ may be substituted $C_3$-$C_8$ cycloalkylene. $L^4$ may be unsubstituted $C_3$-$C_8$ cycloalkylene. $L^4$ may be substituted 3 to 8 membered heterocycloalkylene. $L^4$ may be unsubstituted 3 to 8 membered heterocycloalkylene. In embodiments, $L^4$ is an unsubstituted 5 to membered heteroarylene.

In embodiments, $L^4$ is $R^{31}$-substituted or unsubstituted alkylene (e.g. $C_1$-$C_8$ alkylene, $C_1$-$C_6$ alkylene, or $C_1$-$C_4$ alkylene), $R^{31}$-substituted or unsubstituted heteroalkylene (e.g. 2 to 10 membered heteroalkylene, 2 to 8 membered heteroalkylene, 4 to 8 membered heteroalkylene, 2 to 6 membered heteroalkylene, or 2 to 4 membered heteroalkylene), $R^{31}$-substituted or unsubstituted cycloalkylene (e.g. $C_3$-$C_8$ cycloalkylene, $C_4$-$C_8$ cycloalkylene, or $C_5$-$C_6$ cycloalkylene), $R^{31}$-substituted or unsubstituted heterocycloalkylene (e.g. 3 to 8 membered heterocycloalkylene, 4 to 8 membered heterocycloalkylene, or 5 to 6 membered heterocycloalkylene), $R^{31}$-substituted or unsubstituted arylene (e.g. $C_6$-$C_{10}$ arylene or $C_6$ arylene), or $R^{31}$-substituted or unsubstituted heteroarylene (e.g. 5 to 10 membered heteroarylene, 5 to 9 membered heteroarylene, or 5 to 6 membered heteroarylene).

In embodiments, $L^4$ is $R^{31}$-substituted alkylene (e.g. $C_1$-$C_6$ alkylene, $C_1$-$C_6$ alkylene, or $C_1$-$C_4$ alkylene), $R^{31}$-substituted heteroalkylene (e.g. 2 to 10 membered heteroalkylene, 2 to 8 membered heteroalkylene, 4 to 8 membered heteroalkylene, 2 to 6 membered heteroalkylene, or to 4 membered heteroalkylene), $R^{31}$-substituted cycloalkylene (e.g. $C_3$-$C_8$ cycloalkylene, $C_4$-$C_8$ cycloalkylene, or $C_5$-$C_6$ cycloalkylene), $R^{31}$-substituted heterocycloalkylene (e.g. 3 to 8 membered heterocycloalkylene, 4 to 8 membered heterocycloalkylene, or 5 to 6 membered heterocycloalkylene), $R^{31}$-substituted arylene (e.g. $C_6$-$C_{10}$ arylene or $C_6$ arylene), or $R^{31}$-substituted heteroarylene (e.g. 5 to 10 membered heteroarylene, 5 to 9 membered heteroarylene, or 5 to 6 membered heteroarylene). In embodiments, $L^4$ is an unsubstituted alkylene (e.g. $C_1$-$C_8$ alkylene, $C_1$-$C_6$ alkylene, or $C_1$-$C_4$ alkylene), unsubstituted heteroalkylene (e.g. 2 to 10 membered heteroalkylene, 2 to 8 membered heteroalkylene, 4 to 8 membered heteroalkylene, 2 to 6 membered heteroalkylene, or 2 to 4 membered heteroalkylene), unsubstituted cycloalkylene (e.g. $C_3$-$C_8$ cycloalkylene, $C_4$-$C_8$ cycloalkylene, or $C_5$-$C_6$ cycloalkylene), unsubstituted heterocycloalkylene (e.g. 3 to 8 membered heterocycloalkylene, 4 to 8 membered heterocycloalkylene, or 5 to 6 membered heterocycloalkylene), unsubstituted arylene (e.g. $C_6$-$C_{10}$ arylene or $C_6$ arylene), or unsubstituted heteroarylene (e.g. 5 to 10 membered heteroarylene, 5 to membered heteroarylene, or 5 to 6 membered heteroarylene).

$R^{31}$ is independently halogen, —$CX^{31}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)NHNH$_2$, —NHC=(O)NH$_2$, —NHSO$_2$H, —NHC=(O)H, —NHC(O)OH, —NHOH, —$OCX^{31}_3$, —$OCHX^{31}_2$, $R^{32}$-substituted or unsubstituted alkyl (e.g. $C_1$-$C_8$ alkyl, $C_1$-$C_6$ alkyl, or $C_1$-$C_4$ alkyl), $R^{32}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{32}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{32}$-substituted or unsubstituted heterocycloalkyl (e.g. 3 to 8 membered heterocycloalkyl, 4 to 8 membered heterocycloalkyl, or 5 to 6 membered heterocycloalkyl), $R^{32}$-substituted or unsubstituted aryl (e.g. $C_6$-$C_{10}$ aryl or $C_6$ aryl), or $R^{32}$-substituted or unsubstituted heteroaryl (e.g. 5 to 10 membered heteroaryl, 5 to 9 membered heteroaryl, or 5 to 6 membered heteroaryl). $X^{31}$ is a halogen.

In embodiments $R^{31}$ is

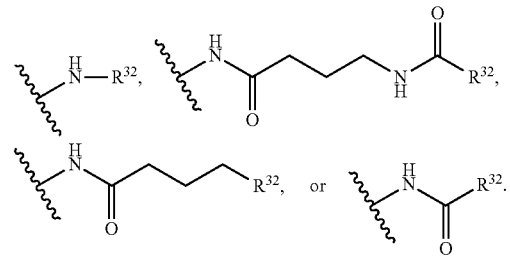

In embodiments $R^{31}$ is

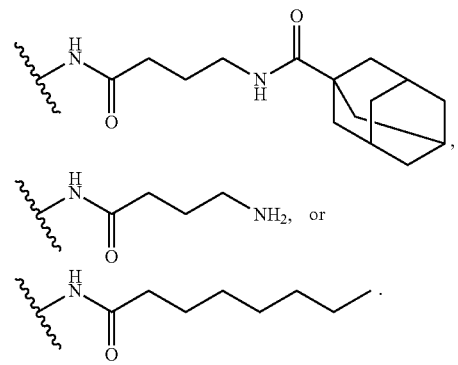

In embodiments, $R^{31}$ is a substituted or unsubstituted alkylene (e.g. $C_1$-$C_8$ alkylene, $C_1$-$C_6$ alkylene, or $C_1$-$C_4$ alkylene). In embodiments, $R^{31}$ is a substituted alkylene (e.g. $C_1$-$C_8$ alkylene, $C_1$-$C_6$ alkylene, or $C_1$-$C_4$ alkylene). In embodiments, $R^{31}$ is an unsubstituted alkylene (e.g. $C_1$-$C_8$ alkylene, $C_1$-$C_6$ alkylene, or $C_1$-$C_4$ alkylene). In embodiments, $R^{31}$ is a substituted or unsubstituted $C_1$-$C_8$ alkylene. In embodiments, $R^{31}$ is a substituted or unsubstituted $C_1$-$C_6$ alkylene. In embodiments, $R^{31}$ is a substituted or unsubstituted $C_1$-$C_4$ alkylene. In embodiments, $R^{31}$ is a substituted or unsubstituted $C_1$-$C_2$ alkylene. In embodiments, $R^{31}$ is a substituted or unsubstituted $C_2$-$C_4$ alkylene. In embodiments, $R^{31}$ is a substituted or unsubstituted $C_4$ alkylene. In embodiments, $R^{31}$ is a substituted $C_1$—C alkylene. In embodiments, $R^{31}$ is a substituted $C_1$-$C_6$ alkylene. In embodiments, $R^{31}$ is a substituted $C_1$-$C_4$ alkylene. In embodiments, $R^{31}$ is a substituted $C_1$-$C_2$ alkylene. In embodiments, $R^{31}$ is a substituted $C_2$-$C_4$ alkylene. In embodiments, $R^{31}$ is a substituted $C_4$ alkylene. In embodiments, $R^{31}$ is an unsubstituted $C_1$-$C_8$ alkylene. In embodiments, $R^{31}$ is an unsubstituted $C_1$-$C_6$ alkylene. In embodiments, $R^{31}$ is an unsubstituted $C_1$-$C_4$ alkylene. In embodiments, $R^{31}$ is an unsubstituted $C_1$-$C_2$ alkylene. In embodiments, $R^{31}$ is an unsubstituted $C_2$-$C_4$ alkylene. In embodiments, $R^{31}$ is an unsubstituted $C_4$ alkylene.

In embodiments, $R^{31}$ is a substituted $C_1$-$C_8$ alkylene substituted with a detectable moiety. In embodiments, $R^{31}$ is a substituted $C_1$-$C_6$ alkylene substituted with a detectable moiety. In embodiments, $R^{31}$ is a substituted $C_1$-$C_4$ alkylene substituted with a detectable moiety. In embodiments, $R^{31}$ is a substituted $C_1$-$C_2$ alkylene substituted with a detectable moiety. In embodiments, $R^{31}$ is a substituted $C_2$-$C_4$ alkylene substituted with a detectable moiety. In embodiments, $R^{31}$ is a substituted $C_4$ alkylene substituted with a detectable moiety.

In embodiments, $R^{31}$ is a substituted $C_1$-$C_8$ alkylene substituted with a fluorescein isothiocyanate detectable moiety. In embodiments, $R^{31}$ is a substituted $C_1$-$C_6$ alkylene substituted with a fluorescein isothiocyanate detectable moiety. In embodiments, $R^{31}$ is a substituted $C_1$-$C_4$ alkylene substituted with a fluorescein isothiocyanate detectable moiety. In embodiments, $R^{31}$ is a substituted $C_1$-$C_2$ alkylene substituted with a fluorescein isothiocyanate detectable moiety. In embodiments, $R^{31}$ is a substituted $C_2$-$C_4$ alkylene substituted with a fluorescein isothiocyanate detectable moiety. In embodiments, $R^{31}$ is a substituted $C_4$ alkylene substituted with a fluorescein isothiocyanate detectable moiety. In embodiments, the fluorescein isothiocyanate detectable moiety is In embodiments, the fluorescein isothiocyanate detectable moiety is In embodiments, $R^{31}$ is a substituted $C_1$-$C_8$ alkylene substituted with a thiourea-detectable moiety. In embodiments, $R^{31}$ is a substituted $C_1$-$C_6$ alkylene substituted with a thiourea-detectable moiety. In embodiments, $R^{31}$ is a substituted $C_1$-$C_4$ alkylene substituted with a thiourea-detectable moiety. In embodiments, $R^{31}$ is a substituted $C_1$-$C_2$ alkylene substituted with a thiourea-detectable moiety. In embodiments, $R^{31}$ is a substituted $C_2$-$C_4$ alkylene substituted with a thiourea-detectable moiety. In embodiments, $R^{31}$ is a substituted $C_4$ alkylene substituted with a thiourea-detectable moiety. In embodiments, $R^{31}$ is a substituted $C_1$-$C_8$ alkylene substituted with a thiourea-fluorescein detectable moiety. In embodiments, $R^{31}$ is a substituted $C_1$-$C_6$ alkylene substituted with a thiourea-fluorescein detectable moiety. In embodiments, $R^{31}$ is a substituted $C_1$-$C_4$ alkylene substituted with a thiourea-fluorescein detectable moiety. In embodiments, $R^{31}$ is a substituted $C_1$-$C_2$ alkylene substituted with a thiourea-fluorescein detectable moiety. In embodiments, $R^{31}$ is a substituted $C_2$-$C_4$ alkylene substituted with a thiourea-fluorescein detectable moiety. In embodiments, $R^{31}$ is a substituted $C_4$ alkylene substituted with a thiourea-fluorescein detectable moiety. In embodiments, the thiourea-fluorescein is In embodiments, $R^{31}$ is a substituted 2 to 10 membered heteroalkyl. In embodiments, $R^{31}$ is a substituted 10 membered heteroalkyl. In embodiments, $R^{31}$ is a substituted 9 membered heteroalkyl. In embodiments, $R^{31}$ is a substituted 8 membered heteroalkyl. In embodiments, $R^{31}$ is a substituted 7 membered heteroalkyl. In embodiments, $R^{31}$ is a substituted 6 membered heteroalkyl. In embodiments, $R^{31}$ is a substituted 5 membered heteroalkyl.

In embodiments, $R^{31}$ is a substituted 2 to 10 membered heteroalkyl substituted with a detectable moiety. In embodiments, $R^{31}$ is a substituted 2 to 8 membered heteroalkyl substituted with a detectable moiety. In embodiments, $R^{31}$ is a substituted 2 to 6 membered heteroalkyl substituted with a detectable moiety. In embodiments, $R^{31}$ is a substituted 2 to 4 membered heteroalkyl substituted with a detectable moiety. In embodiments, $R^{31}$ is a substituted 10 membered heteroalkyl substituted with a detectable moiety. In embodiments, $R^{31}$ is a substituted membered heteroalkyl substituted with a detectable moiety. In embodiments, $R^{31}$ is a substituted 8 membered heteroalkyl substituted with a detectable moiety. In embodiments, $R^{31}$ is a substituted 7 membered heteroalkyl substituted with a detectable moiety. In embodiments, $R^{31}$ is a substituted 6 membered heteroalkyl substituted with a detectable moiety. In embodiments, $R^{31}$ is a substituted 5 membered heteroalkyl substituted with a detectable moiety. In embodiments, $R^{31}$ is a substituted 4 membered heteroalkyl substituted with a detectable moiety. In embodiments, $R^{31}$ is a substituted 3 membered heteroalkyl substituted with a detectable moiety. In embodiments, $R^{31}$ is a substituted 2 membered heteroalkyl substituted with a detectable moiety.

In embodiments, $R^{31}$ is a substituted 2 to 10 membered heteroalkyl substituted with a fluorescein isothiocyanate detectable moiety. In embodiments, $R^{31}$ is a substituted 2 to 8 membered heteroalkyl substituted with a fluorescein isothiocyanate detectable moiety. In embodiments, $R^{31}$ is a substituted 2 to 6 membered heteroalkyl substituted with a fluorescein isothiocyanate detectable moiety. In embodiments, $R^{31}$ is a substituted 2 to 4 membered heteroalkyl substituted with a fluorescein isothiocyanate detectable moiety. In embodiments, $R^{31}$ is a substituted 10 membered heteroalkyl substituted with a fluorescein isothiocyanate detectable moiety. In embodiments, $R^{31}$ is a substituted 9 membered heteroalkyl substituted with a fluorescein isothiocyanate detectable moiety. In embodiments, $R^{31}$ is a substituted 8 membered heteroalkyl substituted with a fluorescein isothiocyanate detectable moiety. In embodiments, $R^{31}$ is a substituted 7 membered heteroalkyl substituted with a fluorescein isothiocyanate detectable moiety. In embodiments, $R^{31}$ is a substituted 6 membered heteroalkyl substituted with a fluorescein isothiocyanate detectable moiety. In embodiments, $R^{31}$ is a substituted 5 membered heteroalkyl substituted with a fluorescein isothiocyanate detectable moiety. In embodiments, $R^{31}$ is a substituted 4 membered heteroalkyl substituted with a fluorescein isothiocyanate detectable moiety. In embodiments, $R^{31}$ is a substituted 3 membered heteroalkyl substituted with a fluorescein isothiocyanate detectable moiety. In embodiments, $R^{31}$ is a substituted 2 membered heteroalkyl substituted with a fluorescein isothiocyanate detectable moiety. In embodiments, the fluorescein isothiocyanate detectable moiety is

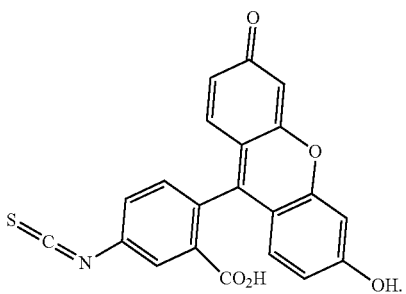 [SMILES: O=C(O)c1cc(N=C=S)ccc1-c1c2ccc(=O)cc-2oc2cc(O)ccc12]

In embodiments, the fluorescein isothiocyanate detectable moiety is

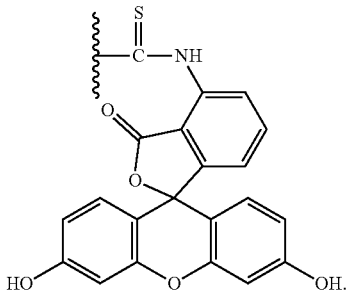 [SMILES: *C(=S)Nc1cccc2c1C(=O)OC21c2ccc(O)cc2Oc2cc(O)ccc21]

In embodiments, $R^{31}$ is a substituted 2 to 10 membered heteroalkyl substituted with a thiourea-detectable moiety. In embodiments, $R^{31}$ is a substituted 2 to 8 membered heteroalkyl substituted with a thiourea-detectable moiety. In embodiments, $R^{31}$ is a substituted 2 to 6 membered heteroalkyl substituted with a thiourea-detectable moiety. In embodiments, $R^{31}$ is a substituted 2 to 4 membered heteroalkyl substituted with a thiourea-detectable moiety. In embodiments, $R^{31}$ is a substituted 10 membered heteroalkyl substituted with a thiourea-detectable moiety. In embodiments, $R^{31}$ is a substituted 9 membered heteroalkyl substituted with a thiourea-detectable moiety. In embodiments, $R^{31}$ is a substituted 8 membered heteroalkyl substituted with a thiourea-detectable moiety. In embodiments, $R^{31}$ is a substituted 7 membered heteroalkyl substituted with a thiourea-detectable moiety. In embodiments, $R^{31}$ is a substituted 6 membered heteroalkyl substituted with a thiourea-detectable moiety. In embodiments, $R^{31}$ is a substituted 5 membered heteroalkyl substituted with a thiourea-detectable moiety. In embodiments, $R^{31}$ is a substituted 4 membered heteroalkyl substituted with a thiourea-detectable moiety. In embodiments, $R^{31}$ is a substituted 3 membered heteroalkyl substituted with a thiourea-detectable moiety. In embodiments, $R^{31}$ is a substituted 2 membered heteroalkyl substituted with a thiourea-detectable moiety.

In embodiments, $R^{31}$ is a substituted 2 to 10 membered heteroalkyl substituted with a thiourea-fluorescein detectable moiety. In embodiments, $R^{31}$ is a substituted 2 to 8 membered heteroalkyl substituted with a thiourea-fluorescein detectable moiety. In embodiments, $R^{31}$ is a substituted 2 to 6 membered heteroalkyl substituted with a thiourea-fluorescein detectable moiety. In embodiments, $R^{31}$ is a substituted 2 to 4 membered heteroalkyl substituted with a thiourea-fluorescein detectable moiety. In embodiments, $R^{31}$ is a substituted 10 membered heteroalkyl substituted with a thiourea-fluorescein detectable moiety. In embodiments, $R^{31}$ is a substituted 9 membered heteroalkyl substituted with a thiourea-fluorescein detectable moiety. In embodiments, $R^{31}$ is a substituted 8 membered heteroalkyl substituted with a thiourea-fluorescein detectable moiety. In embodiments, $R^{31}$ is a substituted 7 membered heteroalkyl substituted with a thiourea-fluorescein detectable moiety. In embodiments, $R^{31}$ is a substituted 6 membered heteroalkyl substituted with a thiourea-fluorescein detectable moiety. In embodiments, $R^{31}$ is a substituted 5 membered heteroalkyl substituted with a thiourea-fluorescein detectable moiety. In embodiments, $R^{31}$ is a substituted 4 membered heteroalkyl substituted with a thiourea-fluorescein detectable moiety. In embodiments, $R^{31}$ is a substituted 3 membered heteroalkyl substituted with a thiourea-fluorescein detectable moiety. In embodiments, $R^{31}$ is a substituted 2 membered heteroalkyl substituted with a thiourea-fluorescein detectable moiety. In embodiments, the thiourea-fluorescein is

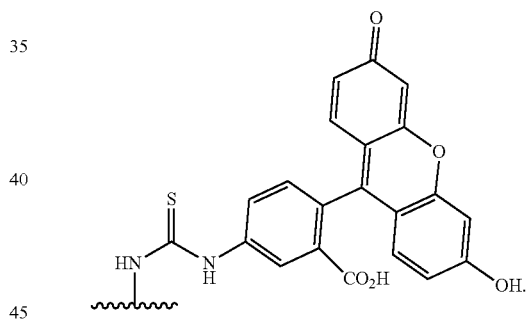

In embodiments, $R^{31}$ is $R^{32}$-substituted or unsubstituted alkyl (e.g., $C_1$-$C_8$ alkyl, $C_1$-$C_6$ alkyl, or $C_1$-$C_4$ alkyl). In embodiments, $R^{31}$ is $R^{32}$-substituted alkyl (e.g., $C_1$-$C_8$ alkyl, $C_1$-$C_6$ alkyl, or $C_1$-$C_4$ alkyl). In embodiments, $R^{31}$ is an unsubstituted alkyl (e.g., $C_1$-$C_8$ alkyl, $C_1$-$C_6$ alkyl, or $C_1$-$C_4$ alkyl).

In embodiments, $R^{31}$ is $R^{32}$-substituted or unsubstituted heteroalkyl (e.g., 2 to 10 membered heteroalkyl, 2 to 6 membered heteroalkyl, or 2 to 4 membered heteroalkyl). In embodiments, $R^{31}$ is $R^{32}$-substituted heteroalkyl (e.g., 2 to 10 membered heteroalkyl, 2 to 6 membered heteroalkyl, or 2 to 4 membered heteroalkyl). In embodiments, $R^{31}$ is an unsubstituted heteroalkyl (e.g., 2 to 10 membered heteroalkyl, 2 to 6 membered heteroalkyl, or 2 to 4 membered heteroalkyl). In embodiments, $R^{31}$ is $R^{32}$-substituted or unsubstituted 2 to 10 membered heteroalkyl. In embodiments, $R^{31}$ is $R^{32}$-substituted or unsubstituted 2 to 9 membered heteroalkyl. In embodiments, $R^{31}$ is $R^{32}$-substituted or unsubstituted 6 to 9 membered heteroalkyl.

In embodiments, $R^{31}$ is $R^{32}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{31}$ is $R^{32}$-substituted cycloalkyl (e.g., $C_3$-$C_8$ cycloalkyl, $C_3$-$C_6$ cycloalkyl, or $C_5$-$C_6$ cycloalkyl). In embodiments, $R^{31}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{31}$ is $R^{32}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{31}$ is $R^{32}$-substituted heterocycloalkyl (e.g., 3 to 8 membered heterocycloalkyl, 3 to 6 membered heterocycloalkyl, or 5 to 6 membered heterocycloalkyl). In embodiments, $R^{31}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{31}$ is $R^{32}$-substituted or unsubstituted aryl (e.g., $C_6$-$C_{10}$ aryl, $C_{10}$ aryl, or phenyl). In embodiments, $R^{31}$ is $R^{32}$-substituted aryl (e.g., $C_6$-$C_{10}$ aryl, $C_{10}$ aryl, or phenyl). In embodiments, $R^{31}$ is an unsubstituted aryl (e.g., $C_6$-$C_{10}$ aryl, $C_{10}$ aryl, or phenyl).

In embodiments, $R^{31}$ is $R^{32}$-substituted or unsubstituted heteroaryl (e.g., 5 to 10 membered heteroaryl, 5 to 9 membered heteroaryl, or 5 to 6 membered heteroaryl). In embodiments, $R^{31}$ is $R^{32}$-substituted heteroaryl (e.g., 5 to 10 membered heteroaryl, 5 to 9 membered heteroaryl, or 5 to 6 membered heteroaryl). In embodiments, $R^{31}$ is an unsubstituted heteroaryl (e.g., 5 to 10 membered heteroaryl, 5 to 9 membered heteroaryl, or 5 to 6 membered heteroaryl).

In embodiments, $R^{31}$ is a substituted 2 to 10 membered heteroalkyl. In embodiments, $R^{31}$ is a substituted 10 membered heteroalkyl. In embodiments, $R^{31}$ is a substituted 9 membered heteroalkyl. In embodiments, $R^{31}$ is a substituted 8 membered heteroalkyl. In embodiments, $R^{31}$ is a substituted 7 membered heteroalkyl. In embodiments, $R^{31}$ is a substituted 6 membered heteroalkyl. In embodiments, $R^{31}$ is a substituted 5 membered heteroalkyl.

$R^{32}$ is independently halogen, —$CX^{32}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCX^{32}_3$, —$OCHX^{32}_2$, $R^{33}$-substituted or unsubstituted alkyl (e.g. $C_1$-$C_8$ alkyl, $C_1$-$C_6$ alkyl, or $C_1$-$C_4$ alkyl), $R^{33}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{33}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{33}$-substituted or unsubstituted heterocycloalkyl (e.g. 3 to 8 membered heterocycloalkyl, 4 to 8 membered heterocycloalkyl, or 5 to 6 membered heterocycloalkyl), $R^{33}$-substituted or unsubstituted aryl (e.g. $C_6$-$C_{10}$ aryl or $C_6$ aryl), or $R^{33}$-substituted or unsubstituted heteroaryl (e.g. 5 to 10 membered heteroaryl, 5 to 9 membered heteroaryl, or 5 to 6 membered heteroaryl). $X^{32}$ is a halogen.

In embodiments, $R^{32}$ is $R^{33}$-substituted or unsubstituted alkyl (e.g., $C_1$-$C_8$ alkyl, $C_1$-$C_6$ alkyl, or $C_1$-$C_4$ alkyl). In embodiments, $R^{32}$ is $R^{33}$-substituted alkyl (e.g., $C_1$-$C_8$ alkyl, $C_1$-$C_6$ alkyl, or $C_1$-$C_4$ alkyl). In embodiments, $R^{32}$ is an unsubstituted alkyl (e.g., $C_1$-$C_8$ alkyl, $C_1$-$C_6$ alkyl, or $C_1$-$C_4$ alkyl).

In embodiments, $R^{32}$ is $R^{33}$-substituted or unsubstituted heteroalkyl (e.g., 2 to 8 membered heteroalkyl, 2 to 6 membered heteroalkyl, or 2 to 4 membered heteroalkyl). In embodiments, $R^{32}$ is $R^{33}$-substituted heteroalkyl (e.g., 2 to 8 membered heteroalkyl, 2 to 6 membered heteroalkyl, or 2 to 4 membered heteroalkyl). In embodiments, $R^{32}$ is an unsubstituted heteroalkyl (e.g., 2 to 8 membered heteroalkyl, 2 to 6 membered heteroalkyl, or 2 to 4 membered heteroalkyl). In embodiments, $R^{32}$ is $R^{33}$-substituted or unsubstituted 2 to 6 membered heteroalkyl. In embodiments, $R^{32}$ is an unsubstituted 2 to 6 membered heteroalkyl. In embodiments, $R^{32}$ is $R^{33}$-substituted 2 to 6 membered heteroalkyl.

In embodiments, $R^{32}$ is $R^{33}$-substituted or unsubstituted cycloalkyl (e.g., $C_3$-$C_{10}$ cycloalkyl, $C_3$-$C_6$ cycloalkyl, or $C_5$-$C_6$ cycloalkyl). In embodiments, $R^{32}$ is $R^{33}$-substituted cycloalkyl (e.g., $C_3$-$C_{10}$ cycloalkyl, $C_3$-$C_6$ cycloalkyl, or $C_5$-$C_6$ cycloalkyl). In embodiments, $R^{32}$ is an unsubstituted cycloalkyl (e.g., $C_3$-$C_{10}$ cycloalkyl, $C_3$-$C_6$ cycloalkyl, or $C_5$-$C_6$ cycloalkyl). In embodiments, $R^{32}$ is an unsubstituted $C_3$-$C_{10}$ cycloalkyl. In embodiments, $R^{32}$ is substituted or unsubstituted adamantanyl.

In embodiments, $R^{32}$ is $R^{33}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{32}$ is $R^{33}$-substituted heterocycloalkyl (e.g., 3 to 8 membered heterocycloalkyl, 3 to 6 membered heterocycloalkyl, or 5 to 6 membered heterocycloalkyl). In embodiments, $R^{32}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{32}$ is $R^{33}$-substituted or unsubstituted aryl (e.g., $C_6$-$C_{10}$ aryl, $C_{10}$ aryl, or phenyl). In embodiments, $R^{32}$ is $R^{33}$-substituted aryl (e.g., $C_6$-$C_{10}$ aryl, $C_{10}$ aryl, or phenyl). In embodiments, $R^{32}$ is an unsubstituted aryl (e.g., $C_6$-$C_{10}$ aryl, $C_{10}$ aryl, or phenyl).

In embodiments, $R^{32}$ is $R^{33}$-substituted or unsubstituted heteroaryl (e.g., 5 to 10 membered heteroaryl, 5 to 9 membered heteroaryl, or 5 to 6 membered heteroaryl). In embodiments, $R^{32}$ is $R^{33}$-substituted heteroaryl (e.g., 5 to 10 membered heteroaryl, 5 to 9 membered heteroaryl, or 5 to 6 membered heteroaryl). In embodiments, $R^{32}$ is an unsubstituted heteroaryl (e.g., 5 to 10 membered heteroaryl, 5 to 9 membered heteroaryl, or 5 to 6 membered heteroaryl).

In embodiments $R^{32}$ is

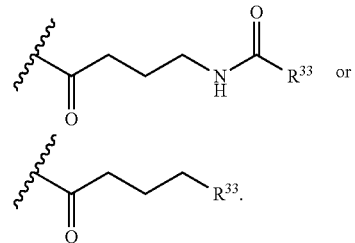

In embodiments $R^{32}$ is

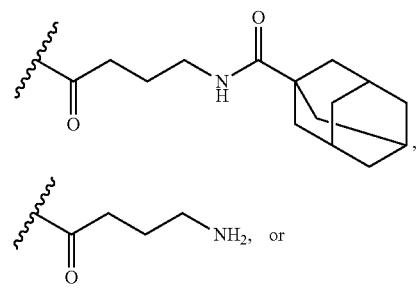

-continued

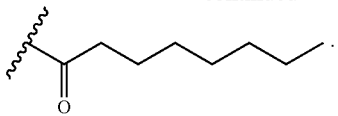

In embodiments, $R^{33}$ is an unsubstituted alkyl (e.g., $C_1$-$C_8$ alkyl, $C_1$-$C_6$ alkyl, or $C_1$-$C_4$ alkyl). In embodiments, $R^{33}$ is an unsubstituted heteroalkyl (e.g., 2 to 8 membered heteroalkyl, to 6 membered heteroalkyl, or 2 to 4 membered heteroalkyl). In embodiments, $R^{33}$ is an unsubstituted cycloalkyl (e.g., $C_3$-$C_{10}$ cycloalkyl, $C_3$-$C_6$ cycloalkyl, or $C_5$-$C_6$ cycloalkyl). In embodiments, $R^{33}$ is an unsubstituted $C_3$-$C_{10}$ cycloalkyl. In embodiments, $R^{33}$ is substituted or unsubstituted adamantanyl. In embodiments, $R^{33}$ is an unsubstituted heterocycloalkyl (e.g., 3 to 8 membered heterocycloalkyl, 3 to 6 membered heterocycloalkyl, or 5 to 6 membered heterocycloalkyl). In embodiments, $R^{33}$ is an unsubstituted aryl (e.g., $C_6$-$C_{10}$ aryl, $C_{10}$ aryl, or phenyl). In embodiments, $R^{33}$ is $R^{33}$-substituted aryl (e.g., $C_6$-$C_{10}$ aryl, $C_{10}$ aryl, or phenyl). In embodiments, $R^{33}$ is an unsubstituted aryl (e.g., $C_6$-$C_{10}$ aryl, $C_{10}$ aryl, or phenyl). In embodiments, $R^{33}$ is an unsubstituted heteroaryl (e.g., 5 to 10 membered heteroaryl, 5 to 9 membered heteroaryl, or 5 to 6 membered heteroaryl). In embodiments, $R^{33}$ is independently oxo or $NH_2$.

In embodiments, $L^4$ is $-N(R^8)-$. In embodiments, $R^8$ is hydrogen, $-CN$, $-COOH$, $-CX^8_3$, substituted or unsubstituted alkyl, or substituted or unsubstituted heteroalkyl. In embodiments, $R^8$ is hydrogen, $-CN$, $-COOH$, $-CX^8_3$. In embodiments, $R^8$ is hydrogen. In embodiments, $R^8$ is $R^{37}$-substituted or unsubstituted alkyl (e.g. $C_1$-$C_8$ alkyl, $C_1$-$C_6$ alkyl, or $C_1$-$C_4$ alkyl), $R^{37}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{37}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{37}$-substituted or unsubstituted heterocycloalkyl (e.g. 3 to 8 membered heterocycloalkyl, 4 to 8 membered heterocycloalkyl, or 5 to 6 membered heterocycloalkyl), $R^{37}$-substituted or unsubstituted aryl (e.g. $C_6$-$C_{10}$ aryl or $C_6$ aryl), or $R^{37}$-substituted or unsubstituted heteroaryl (e.g. 5 to 10 membered heteroaryl, 5 to 9 membered heteroaryl, or 5 to 6 membered heteroaryl). $X^8$ is a halogen.

In embodiments, $R^8$ is $R^{37}$-substituted alkyl (e.g. $C_1$-$C_8$ alkyl, $C_1$-$C_6$ alkyl, or $C_1$-$C_4$ alkyl), $R^{37}$-substituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{37}$-substituted cycloalkyl (e.g. $C_3$-$C_8$ cycloalkyl, $C_4$-$C_8$ cycloalkyl, or $C_5$-$C_6$ cycloalkyl), $R^{37}$-substituted heterocycloalkyl (e.g. 3 to 8 membered heterocycloalkyl, 4 to 8 membered heterocycloalkyl, or 5 to 6 membered heterocycloalkyl), $R^{37}$-substituted aryl (e.g. $C_6$-$C_{10}$ aryl or $C_6$ aryl), or $R^{37}$-substituted heteroaryl (e.g. 5 to 10 membered heteroaryl, 5 to 9 membered heteroaryl, or 5 to 6 membered heteroaryl). In embodiments, $R^8$ is an unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl).

$R^{37}$ is independently halogen, $-CX^{37}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-OCX^{37}_3$, $-OCHX^{37}_2$, $R^{38}$-substituted or unsubstituted alkyl (e.g. $C_1$-$C_8$ alkyl, $C_1$-$C_6$ alkyl, or $C_1$-$C_4$ alkyl), $R^{38}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{38}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{38}$-substituted or unsubstituted heterocycloalkyl (e.g. 3 to 8 membered heterocycloalkyl, 4 to 8 membered heterocycloalkyl, or 5 to 6 membered heterocycloalkyl), $R^{38}$-substituted or unsubstituted aryl (e.g. $C_6$-$C_{10}$ aryl or $C_6$ aryl), or $R^{38}$-substituted or unsubstituted heteroaryl (e.g. 5 to 10 membered heteroaryl, 5 to 9 membered heteroaryl, or 5 to 6 membered heteroaryl). $X^{37}$ is a halogen.

$R^{38}$ is independently halogen, $-CX^{38}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-OCX^{38}_3$, $-OCHX^{38}_2$, $R^{39}$-substituted or unsubstituted alkyl (e.g. $C_1$-$C_8$ alkyl, $C_1$-$C_6$ alkyl, or $C_1$-$C_4$ alkyl), $R^{39}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{39}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{39}$-substituted or unsubstituted heterocycloalkyl (e.g. 3 to 8 membered heterocycloalkyl, 4 to 8 membered heterocycloalkyl, or 5 to 6 membered heterocycloalkyl), $R^{39}$-substituted or unsubstituted aryl (e.g. $C_6$-$C_{10}$ aryl or $C_6$ aryl), or $R^{39}$-substituted or unsubstituted heteroaryl (e.g. 5 to 10 membered heteroaryl, 5 to 9 membered heteroaryl, or 5 to 6 membered heteroaryl). $X^{38}$ is a halogen.

In embodiments, $R^5$ is hydrogen,

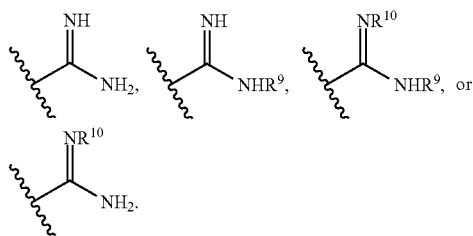

In embodiments, $R^9$ is $R^{40}$-substituted or unsubstituted alkyl (e.g. $C_1$-$C_8$ alkyl, $C_1$-$C_6$ alkyl, or $C_1$-$C_4$ alkyl), $R^{40}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{40}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{40}$-substituted or unsubstituted heterocycloalkyl (e.g. 3 to 8 membered heterocycloalkyl, 4 to 8 membered heterocycloalkyl, or 5 to 6 membered heterocycloalkyl), $R^{40}$-substituted or unsubstituted aryl (e.g. $C_6$-$C_{10}$ aryl or $C_6$ aryl), or $R^{40}$-substituted or unsubstituted heteroaryl (e.g. 5 to 10 membered heteroaryl, 5 to 9 membered heteroaryl, or 5 to 6 membered heteroaryl).

In embodiments, $R^9$ is $R^{40}$-substituted alkyl (e.g. $C_1$-$C_8$ alkyl, $C_1$-$C_6$ alkyl, or $C_1$-$C_4$ alkyl), $R^{40}$-substituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{40}$-substituted cycloalkyl (e.g. $C_3$-$C_8$ cycloalkyl, $C_4$-$C_8$ cycloalkyl, or $C_5$-$C_6$ cycloalkyl), $R^{40}$-substituted heterocycloalkyl (e.g. 3 to 8 membered heterocycloalkyl, 4 to 8 membered heterocycloalkyl, or 5 to 6 membered heterocycloalkyl), $R^{40}$-substituted aryl (e.g. $C_6$-$C_{10}$ aryl or $C_6$ aryl), or $R^{40}$-substituted heteroaryl (e.g. 5 to 10 membered heteroaryl, 5 to 9 membered heteroaryl, or 5 to 6 membered heteroaryl). In embodiments, $R^9$ is an unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl).

$R^{40}$ is independently halogen, $-CX^{40}{}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-OCX^{40}{}_3$, $-OCHX^{40}{}_2$, $R^{41}$-substituted or unsubstituted alkyl (e.g. $C_1$-$C_8$ alkyl, $C_1$-$C_6$ alkyl, or $C_1$-$C_4$ alkyl), $R^{41}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{41}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{41}$-substituted or unsubstituted heterocycloalkyl (e.g. 3 to 8 membered heterocycloalkyl, 4 to 8 membered heterocycloalkyl, or 5 to 6 membered heterocycloalkyl), $R^{41}$-substituted or unsubstituted aryl (e.g. $C_6$-$C_{10}$ aryl or $C_6$ aryl), or $R^{41}$-substituted or unsubstituted heteroaryl (e.g. 5 to 10 membered heteroaryl, 5 to 9 membered heteroaryl, or 5 to 6 membered heteroaryl). $X^{40}$ is a halogen.

$R^{41}$ is independently halogen, $-CX^{41}{}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-OCX^{41}{}_3$, $-OCHX^{41}{}_2$, $R^{42}$-substituted or unsubstituted alkyl (e.g. $C_1$-$C_8$ alkyl, $C_1$-$C_6$ alkyl, or $C_1$-$C_4$ alkyl), $R^{42}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{42}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{42}$-substituted or unsubstituted heterocycloalkyl (e.g. 3 to 8 membered heterocycloalkyl, 4 to 8 membered heterocycloalkyl, or 5 to 6 membered heterocycloalkyl), $R^{42}$-substituted or unsubstituted aryl (e.g. $C_6$-$C_{10}$ aryl or $C_6$ aryl), or $R^{42}$-substituted or unsubstituted heteroaryl (e.g. 5 to 10 membered heteroaryl, 5 to 9 membered heteroaryl, or 5 to 6 membered heteroaryl). $X^{41}$ is a halogen.

In embodiments, $R^{10}$ is $R^{43}$-substituted or unsubstituted alkyl (e.g. $C_1$-$C_8$ alkyl, $C_1$-$C_6$ alkyl, or $C_1$-$C_4$ alkyl), $R^{43}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{43}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{43}$-substituted or unsubstituted heterocycloalkyl (e.g. 3 to 8 membered heterocycloalkyl, 4 to 8 membered heterocycloalkyl, or 5 to 6 membered heterocycloalkyl), $R^{43}$-substituted or unsubstituted aryl (e.g. $C_6$-$C_{10}$ aryl or $C_6$ aryl), or $R^{43}$-substituted or unsubstituted heteroaryl (e.g. 5 to 10 membered heteroaryl, 5 to 9 membered heteroaryl, or 5 to 6 membered heteroaryl).

In embodiments, $R^{10}$ is $R^{43}$-substituted alkyl (e.g. $C_1$-$C_8$ alkyl, $C_1$-$C_6$ alkyl, or $C_1$-$C_4$ alkyl), $R^{43}$-substituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{43}$-substituted cycloalkyl (e.g. $C_3$-$C_8$ cycloalkyl, $C_4$-$C_8$ cycloalkyl, or $C_5$-$C_6$ cycloalkyl), $R^{43}$-substituted heterocycloalkyl (e.g. 3 to 8 membered heterocycloalkyl, 4 to 8 membered heterocycloalkyl, or 5 to 6 membered heterocycloalkyl), $R^{43}$-substituted aryl (e.g. $C_6$-$C_{10}$ aryl or $C_6$ aryl), or $R^{43}$-substituted heteroaryl (e.g. 5 to 10 membered heteroaryl, 5 to 9 membered heteroaryl, or 5 to 6 membered heteroaryl). In embodiments, $R^{10}$ is an unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl).

$R^{43}$ is independently halogen, $-CX^{43}{}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-OCX^{43}{}_3$, $-OCHX^{43}{}_2$, $R^{44}$-substituted or unsubstituted alkyl (e.g. $C_1$-$C_8$ alkyl, $C_1$-$C_6$ alkyl, or $C_1$-$C_4$ alkyl), $R^{44}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{44}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{44}$-substituted or unsubstituted heterocycloalkyl (e.g. 3 to 8 membered heterocycloalkyl, 4 to 8 membered heterocycloalkyl, or 5 to 6 membered heterocycloalkyl), $R^{44}$-substituted or unsubstituted aryl (e.g. $C_6$-$C_{10}$ aryl or $C_6$ aryl), or $R^{44}$-substituted or unsubstituted heteroaryl (e.g. 5 to 10 membered heteroaryl, 5 to 9 membered heteroaryl, or 5 to 6 membered heteroaryl). $X^{43}$ is a halogen.

$R^{44}$ is independently halogen, $-CX^{44}{}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-OCX^{44}{}_3$, $-OCHX^{44}{}_2$, $R^{45}$-substituted or unsubstituted alkyl (e.g. $C_1$-$C_8$ alkyl, $C_1$-$C_6$ alkyl, or $C_1$-$C_4$ alkyl), $R^{45}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{45}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{45}$-substituted or unsubstituted heterocycloalkyl (e.g. 3 to 8 membered heterocycloalkyl, 4 to 8 membered heterocycloalkyl, or 5 to 6 membered heterocycloalkyl), $R^{45}$-substituted or unsubstituted aryl (e.g. $C_6$-$C_{10}$ aryl or $C_6$ aryl), or $R^{45}$-substituted or unsubstituted heteroaryl (e.g. 5 to 10 membered heteroaryl, 5 to 9 membered heteroaryl, or 5 to 6 membered heteroaryl). $X^{44}$ is a halogen.

$R^{13}$, $R^{13A}$, $R^{13B}$, $R^{13C}$, $R^{13D}$, $R^{16}$, $R^{16A}$, $R^{16B}$, $R^{16C}$, $R^{16D}$, $R^{17}$, $R^{18}$, $R^{21}$, $R^{24}$, $R^{27}$, $R^{30}$, $R^{33}$, $R^{36}$, $R^{39}$, $R^{42}$, and $R^{45}$ are independently halogen, —$CX_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCX_3$, —$OCHX_2$, unsubstituted alkyl (e.g. $C_1$-$C_8$ alkyl, $C_1$-$C_6$ alkyl, or $C_1$-$C_4$ alkyl), unsubstituted heteroalkyl (e.g. to 10 membered heteroalkyl, 2 to 8 membered heteroalkyl, 4 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl).

In embodiments, X, $X^1$, $X^2$, $X^4$, $X^7$, $X^8$, $X^9$, $X^{10}$, $X^{11}$, $X^{11A}$, $X^{11B}$, $X^C$, $X^{11D}$, $X^{12}$, $X^{12A}$, $X^{12B}$, $X^{12C}$, $X^{12D}$, $X^{14}$, $X^{14A}$, $X^{14B}$, $X^{14C}$, $X^{14D}$, $X^{15}$, $X^{15A}$, $X^{15B}$, $X^{15C}$, $X^{15D}$, $X^{19}$, $X^{20}$, $X^{22}$, $X^{23}$, $X^{25}$, $X^{26}$, $X^{28}$, $X^{29}$, $X^{31}$, $X^{32}$, $X^{34}$, $X^{35}$, $X^{37}$, $X^{38}$, $X^{40}$, $X^{41}$, $X^{43}$, and $X^{44}$ are independently —F, —Cl, —Br, or —I. In embodiments, X is —F. In embodiments, X is —Cl. In embodiments, X is —Br. In embodiments, X is —I. In embodiments, $X^1$ is —F. In embodiments, $X^1$ is —Cl. In embodiments, $X^1$ is —Br. In embodiments, $X^1$ is —I. In embodiments, $X^2$ is —F. In embodiments, $X^2$ is —Cl. In embodiments, $X^2$ is —Br. In embodiments, $X^2$ is —I. In embodiments, $X^4$ is —F. In embodiments, $X^4$ is —Cl. In embodiments, $X^4$ is —Br. In embodiments, $X^4$ is —I. In embodiments, $X^7$ is —F. In embodiments, $X^7$ is —Cl. In embodiments, $X^7$ is —Br. In embodiments, $X^7$ is —I. In embodiments, $X^8$ is —F. In embodiments, $X^8$ is —Cl. In embodiments, $X^8$ is —Br. In embodiments, $X^8$ is —I. In embodiments, $X^9$ is —F. In embodiments, $X^9$ is —Cl. In embodiments, $X^9$ is —Br. In embodiments, $X^9$ is —I. In embodiments, $X^{10}$ is —F. In embodiments, $X^{10}$ is —Cl. In embodiments, $X^{10}$ is —Br. In embodiments, $X^{10}$ is —I. In embodiments, $X^{11}$ is —F. In embodiments, $X^{11}$ is —Cl. In embodiments, $X^{11}$ is —Br. In embodiments, $X^{11}$ is —I. In embodiments, $X^{12}$ is —F. In embodiments, $X^{12}$ is —Cl. In embodiments, $X^{12}$ is —Br. In embodiments, $X^{12}$ is —I. In embodiments, $X^{14}$ is —F. In embodiments, $X^{14}$ is —Cl. In embodiments, $X^{14}$ is —Br. In embodiments, $X^{14}$ is —I. In embodiments, $X^{15}$ is —F. In embodiments, $X^{15}$ is —Cl. In embodiments, $X^{15}$ is —Br. In embodiments, $X^{15}$ is —I.

In embodiments, $X^{19}$ is —F. In embodiments, $X^{19}$ is —Cl. In embodiments, $X^{19}$ is —Br. In embodiments, $X^{19}$ is —I. In embodiments, $X^{20}$ is —F. In embodiments, $X^{20}$ is —Cl. In embodiments, $X^{20}$ is —Br. In embodiments, $X^{20}$ is —I. In embodiments, $X^{22}$ is —F. In embodiments, $X^{22}$ is —Cl. In embodiments, $X^{22}$ is —Br. In embodiments, $X^{22}$ is —I. In embodiments, $X^{23}$ is —F. In embodiments, $X^{23}$ is —Cl. In embodiments, $X^{23}$ is —Br. In embodiments, $X^{23}$ is —I. In embodiments, $X^{25}$ is —F. In embodiments, $X^{25}$ is —Cl. In embodiments, $X^{25}$ is —Br. In embodiments, $X^{25}$ is —I. In embodiments, $X^{26}$ is —F. In embodiments, $X^{26}$ is —Cl. In embodiments, $X^{26}$ is —Br. In embodiments, $X^{26}$ is —I. In embodiments, $X^{28}$ is —F. In embodiments, $X^{28}$ is —Cl. In embodiments, $X^{28}$ is —Br. In embodiments, $X^{28}$ is —I. In embodiments, $X^{29}$ is —F. In embodiments, $X^{29}$ is —Cl. In embodiments, $X^{29}$ is —Br. In embodiments, $X^{29}$ is —I. In embodiments, $X^{31}$ is —F. In embodiments, $X^{31}$ is —C. In embodiments, $X^{31}$ is —Br. In embodiments, $X^{31}$ is —I. In embodiments, $X^{32}$ is —F. In embodiments, $X^{32}$ is —Cl. In embodiments, $X^{32}$ is —Br. In embodiments, $X^{32}$ is —I. In embodiments, $X^{34}$ is —F. In embodiments, $X^{34}$ is —Cl. In embodiments, $X^{34}$ is —Br. In embodiments, $X^{34}$ is —I. In embodiments, $X^{35}$ is —F. In embodiments, $X^{35}$ is —Cl. In embodiments, $X^{35}$ is —Br. In embodiments, $X^{35}$ is —I. In embodiments, $X^{37}$ is —F. In embodiments, $X^{37}$ is —Cl. In embodiments, $X^{37}$ is —Br. In embodiments, $X^{37}$ is —I. In embodiments, $X^{38}$ is —F. In embodiments, $X^{38}$ is —Cl. In embodiments, $X^{38}$ is —Br. In embodiments, $X^{38}$ is —I. In embodiments, $X^{40}$ is —F. In embodiments, $X^{40}$ is —Cl. In embodiments, $X^{40}$ is —Br. In embodiments, $X^{40}$ is —I. In embodiments, $X^{41}$ is —F. In embodiments, $X^{41}$ is —Cl. In embodiments, $X^{41}$ is —Br. In embodiments, $X^{41}$ is —I. In embodiments, $X^{43}$ is —F. In embodiments, $X^{43}$ is —Cl. In embodiments, $X^{43}$ is —Br. In embodiments, $X^{43}$ is —I. In embodiments, $X^{44}$ is —F. In embodiments, $X^{44}$ is —Cl. In embodiments, $X^{44}$ is —Br. In embodiments, $X^{44}$ is —I.

In embodiments, $X^{11A}$ is —F. In embodiments, $X^{11A}$ is —Cl. In embodiments, $X^{11A}$ is —Br. In embodiments, $X^{11A}$ is —I. In embodiments, $X^{12A}$ is —F. In embodiments, $X^{12A}$ is —Cl. In embodiments, $X^{12A}$ is —Br. In embodiments, $X^{12A}$ is —I. In embodiments, $X^{14A}$ is —F. In embodiments, $X^{14A}$ is —Cl. In embodiments, $X^{14A}$ is —Br. In embodiments, $X^{14A}$ is —I. In embodiments, $X^{15A}$ is —F. In embodiments, $X^{15A}$ is —Cl. In embodiments, $X^{15A}$ is —Br. In embodiments, $X^{15A}$ is —I. In embodiments, $X^{11B}$ is —F. In embodiments, $X^{11B}$ is —Cl. In embodiments, $X^{11B}$ is —Br. In embodiments, $X^{11B}$ is —I. In embodiments, $X^{12B}$ is —F. In embodiments, $X^{12B}$ is —Cl. In embodiments, $X^{12B}$ is —Br. In embodiments, $X^{12B}$ is —I. In embodiments, $X^{14B}$ is —F. In embodiments, $X^{14B}$ is —Cl. In embodiments, $X^{14B}$ is —Br. In embodiments, $X^{14B}$ is —I. In embodiments, $X^{15B}$ is —F. In embodiments, $X^{15B}$ is —Cl. In embodiments, $X^{15B}$ is —Br. In embodiments, $X^{15B}$ is —I. In embodiments, $X^{11C}$ is —F. In embodiments, $X^{11C}$ is —Cl. In embodiments, $X^{11C}$ is —Br. In embodiments, $X^{11C}$ is —I. In embodiments, $X^{12C}$ is —F. In embodiments, $X^{12C}$ is —Cl. In embodiments, $X^{12C}$ is —Br. In embodiments, $X^{12C}$ is —I. In embodiments, $X^{14C}$ is —F. In embodiments, $X^{14C}$ is —Cl. In embodiments, $X^{14C}$ is —Br. In embodiments, $X^{14C}$ is —I. In embodiments, $X^{15C}$ is —F. In embodiments, $X^{15C}$ is —Cl. In embodiments, $X^{15C}$ is —Br. In embodiments, $X^{15C}$ is —I. In embodiments, $X^{11D}$ is —F. In embodiments, $X^{11D}$ is —Cl. In embodiments, $X^{11D}$ is —Br. In embodiments, $X^{11D}$ is —I. In embodiments, $X^{12D}$ is —F. In embodiments, $X^{12D}$ is —Cl. In embodiments, $X^{12D}$ is —Br. In embodiments, $X^{12D}$ is —I. In embodiments, $X^{14D}$ is —F. In embodiments, $X^{14D}$ is —Cl. In embodiments, $X^{14D}$ is —Br. In embodiments, $X^{14D}$ is —I. In embodiments, $X^{15D}$ is —F. In embodiments, $X^{15D}$ is —Cl. In embodiments, $X^{15D}$ is —Br. In embodiments, $X^{15D}$ is —I.

In embodiments, n1 and n2 are independently an integer from 0 to 4. In embodiments, n1 and n2 are independently an integer from 0 to 3. In embodiments, n1 is 0. In embodiments, n1 is 1. In embodiments, n1 is 2. In embodiments, n1 is 3. In embodiments, n1 is 4. In embodiments, n2 is 0. In embodiments, n2 is 1. In embodiments, n2 is 2. In embodiments, n2 is 3. In embodiments, n2 is 4. In embodiments, m1, m2, v1 and v2 are independently 1 or 2. In embodiments, m1 is 1 or 2. In embodiments, m1 is 1. In embodiments, m1 is 2. In embodiments, m2 is 1 or 2. In embodiments, m2 is 1. In embodiments, m2 is 2. In embodiments, v1 is 1 or 2. In embodiments, v1 is 1. In embodiments, v1 is 2. In embodiments, v2 is 1 or 2. In embodiments, v2 is 1. In embodiments, v2 is 2.

In embodiments, z1 is an integer from 0 to 5. In embodiments, z1 is an integer from 1 to 5. In embodiments, z1 is an integer from 2 to 5. In embodiments, z1 is an integer from 3 to 5. In embodiments, z1 is 4 or 5. In embodiments, z1 is an integer from 1 to 3. In embodiments, z1 is 0. In embodiments, z1 is 1. In embodiments, z1 is 2. In embodiments, z1 is 3. In embodiments, z1 is 4. In embodiments, z1 is 5. In embodiments, z2 is an integer from 0 to 9. In embodiments, z2 is an integer from 1 to 9. In embodiments, z2 is an integer from 2 to 9. In embodiments, z2 is an integer from 0 to 5. In embodiments, z2 is an integer from 1 to 5. In embodiments, z2 is an integer from 2 to 5. In embodiments, z2 is an integer from 3 to 5. In embodiments, z2 is 4 or 5. In embodiments, z2 is an integer from 1 to 3. In embodiments, z2 is 0. In embodiments, z2 is 1. In embodiments, z2 is 2. In embodiments, z2 is 3. In embodiments, z2 is 4. In embodiments, z2 is 5. In embodiments, z2 is 6. In embodiments, z2 is 7. In embodiments, z2 is 8. In embodiments, z2 is 9.

In embodiments, where $L^3$ is substituted or unsubstituted arylene, z3 is 1. In embodiments, where $L^3$ is substituted or unsubstituted arylene, z3 is 0. In embodiments, where $L^3$ is substituted or unsubstituted heteroarylene, z3 is 1. In embodiments, where $L^3$ is substituted or unsubstituted heteroarylene, z3 is 0.

In embodiments, the compound has the formula:

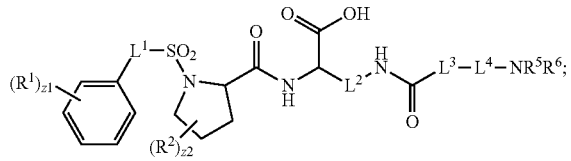

wherein $R^1$, z1, $R^2$, z2, $L^1$, $L^2$, $L^3$, $L^4$, $R^5$, and $R^6$ are as described herein.

In embodiments, the compound has the formula:

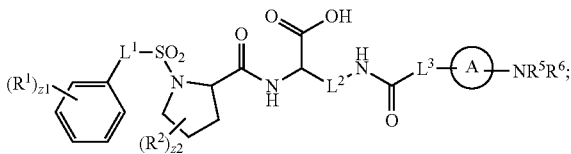

$R^1$, z1, $R^2$, z2, $L^1$, $L^2$, $L^3$, $R^5$, and $R^6$ are as described herein. Ring A is a substituted or unsubstituted cycloalkylene, substituted or unsubstituted heterocycloalkylene, substituted or unsubstituted arylene, or substituted or unsubstituted heteroarylene.

Ring A may be substituted or unsubstituted cycloalkylene. Ring A may be substituted or unsubstituted $C_3$-$C_8$ cycloalkylene. Ring A may be substituted cycloalkylene. Ring A may be substituted $C_3$-$C_8$ cycloalkylene. Ring A may be unsubstituted cycloalkylene. Ring A may be unsubstituted $C_3$-$C_8$ cycloalkylene.

Ring A may be substituted or unsubstituted 3 to 8 membered heterocycloalkylene. Ring A may be a substituted or unsubstituted 4 to 6 membered heterocycloalkylene. Ring A may be a substituted or unsubstituted 5 or 6 membered heterocycloalkylene. Ring A may be substituted or unsubstituted 5 membered heterocycloalkylene. Ring A may be substituted or unsubstituted 6 membered heterocycloalkylene. In embodiments, Ring A is a substituted or unsubstituted heterocycloalkylene (e.g., substituted or unsubstituted pyrrolidinylene, substituted or unsubstituted imidazolidinylene, substituted or unsubstituted oxazolidinylene, substituted or unsubstituted thiazolidinylene, substituted or unsubstituted dioxolanylene, substituted or unsubstituted dithiolanylene, substituted or unsubstituted piperidinylene, substituted or unsubstituted morpholinylene, substituted or unsubstituted dioxanylene, substituted or unsubstituted dithianylene, substituted or unsubstituted aziridinylene, substituted or unsubstituted azetidinylene, substituted or unsubstituted azepinylene, substituted or unsubstituted oxiranylene, substituted or unsubstituted oxetanylene, substituted or unsubstituted tetrahydrofuranylene, or substituted or unsubstituted tetrahydropyranylene.

In embodiments, Ring A is a substituted or unsubstituted $C_6$-$C_{12}$ arylene. In embodiments, Ring A is a substituted $C_6$-$C_{12}$ arylene. In embodiments, Ring A is an unsubstituted $C_6$-$C_{12}$ arylene. In embodiments, Ring A is a substituted or unsubstituted $C_6$-$C_{10}$ arylene. In embodiments, Ring A is a substituted $C_6$-$C_{10}$ arylene. In embodiments, Ring A is an unsubstituted $C_6$-$C_{10}$ arylene. In embodiments, Ring A is an unsubstituted phenylene. In embodiments, Ring A is a substituted phenylene. In embodiments, Ring A is an unsubstituted naphthylene. In embodiments, Ring A is a substituted naphthylene. In embodiments, Ring A is an unsubstituted biphenyl. In embodiments, Ring A is a substituted biphenyl.

In embodiments, Ring A is a substituted or unsubstituted 5 to 10 membered heteroarylene. In embodiments, Ring A is a substituted 5 to 10 membered heteroarylene. In embodiments, Ring A is an unsubstituted 5 to 10 membered heteroarylene. In embodiments, Ring A is a substituted or unsubstituted 5 to 6 membered heteroarylene. In embodiments, Ring A is a substituted 5 to 6 membered heteroarylene. In embodiments, Ring A is an unsubstituted 5 to 6 membered heteroarylene. In embodiments, Ring A is a substituted or unsubstituted 5 membered heteroarylene. In embodiments, Ring A is a substituted 5 membered heteroarylene. In embodiments, Ring A is an unsubstituted 5 membered heteroarylene. In embodiments, Ring A is a substituted or unsubstituted 6 membered heteroarylene. In embodiments, Ring A is a substituted 6 membered heteroarylene. In embodiments, Ring A is an unsubstituted 6 membered heteroarylene.

Ring A may be unsubstituted triazolylene. Ring A may be substituted triazolylene. Ring A may be unsubstituted tetrazolylene. Ring A may be substituted tetrazolylene. In embodiments, Ring A is substituted or unsubstituted pyridylene. Ring A may be substituted or unsubstituted heteroarylene. Ring A may be a substituted or unsubstituted heteroarylene such as, for example, substituted or unsubstituted pyridinylene, substituted or unsubstituted pyrrolylene, substituted or unsubstituted furanylene, substituted or unsubstituted thiophenylene, substituted or unsubstituted imidazolylene, substituted or unsubstituted pyrazolylene, substituted or unsubstituted oxazolylene, substituted or unsubstituted thiazolylene, substituted or unsubstituted pyranylene, substituted or unsubstituted thiopyranylene, substituted or unsubstituted pyrazinylene, substituted or unsubstituted pyrimindylene, substituted or unsubstituted pyridazinylene, substituted or unsubstituted oxazinylene, substituted or unsubstituted thiazinylene, substituted or unsubstituted doxinylene, substituted or unsubstituted dithiinylene, substituted or unsubstituted azetylene, substituted or unsubstituted oxetylene, substituted or unsubstituted thietylene, substituted or unsubstituted azirinylene, substituted or unsubstituted oxirenylene or substituted or unsubstituted thienylene. Ring A may be substituted or unsubstituted pyridinylene.

In embodiments, the compound has the formula:

$R^1$, z1, $L^1$, $L^3$, $L^4$, $R^5$, and $R^6$ are as described herein.

In embodiments, the compound has the formula:

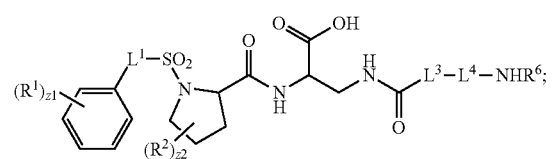

$R^1$, z1, $R^2$, z2, $L^1$, $L^3$, $L^4$, and $R^6$ are as described herein.

In embodiments, the compound has the formula:

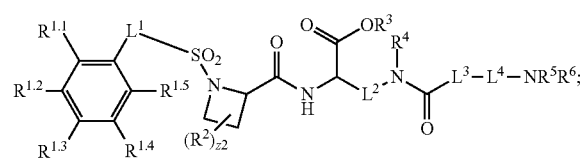

$R^2$, z2, Y, $R^3$, $R^4$, $L^1$, $L^2$, $L^3$, $L^4$, $R^5$, and $R^6$ are as described herein. $R^{11}$, $R^{12}$, $R^{13}$, $R^{14}$, and $R^{15}$ are each independently a moiety of $R^1$ as described herein, including in embodiments.

In some embodiments, a compound as described herein may include multiple instances of $R^1$, $R^2$, and/or other variables. In such embodiments, each variable may optional be different and be appropriately labeled to distinguish each group for greater clarity. For example, where each $R^1$ and/or $R^2$ is different, they may be referred to, for example, as $R^{1.1}$, $R^{1.2}$, $R^{1.3}$, $R^{1.4}$, $R^{1.5}$, $R^{2.1}$, $R^{2.2}$, $R^{2.3}$, $R^{2.4}$, $R^{2.5}$, $R^{2.6}$, $R^{2.7}$, $R^{2.8}$, $R^{2.9}$, respectively, wherein the definition of $R^1$ is assumed by $R^{1.1}$, $R^{1.2}$, $R^{1.3}$, $R^{1.4}$, $R^{1.5}$; $R^2$ is assumed by $R^{2.1}$, $R^{2.2}$, $R^{2.3}$, $R^{2.4}$, $R^{2.5}$, $R^{2.6}$, $R^{2.7}$, $R^{2.8}$, $R^{2.9}$. The variables used within a definition of $R^1$, $R^2$, and/or other variables that appear at multiple instances and are different may similarly be appropriately labeled to distinguish each group for greater clarity. In some embodiments, the compound is a compound described herein (e.g., in an aspect, embodiment, example, claim, or table).

In embodiments,

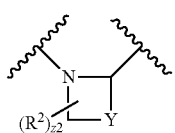

has the formula:

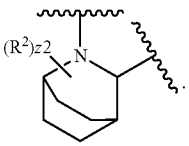

In embodiments,

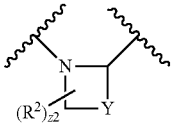

has the formula:

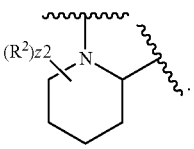

In embodiments,

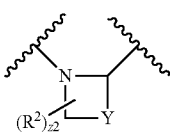

has the formula:

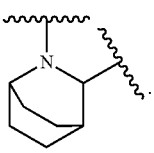

In embodiments,

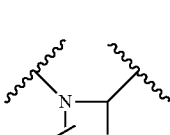

has the formula:

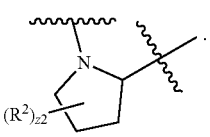

In embodiments,

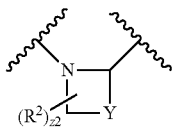

has the formula:

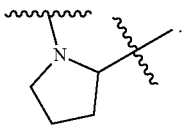 [SMILES: *C1CCCN1*]

In embodiments, the compound has the formula:

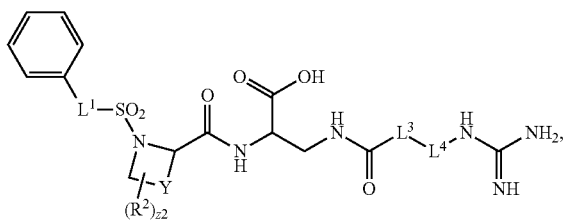

wherein $R^2$, z2, $L^1$, $L^3$, and $L^4$ are as described herein.

In embodiments, the compound has the formula:

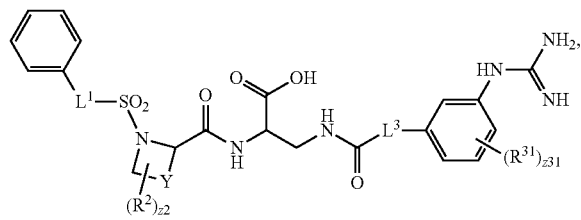

wherein $R^2$, z2, $L^1$, $L^3$, and $R^{31}$ are as described herein and z31 is an integer from 0 to 4. In embodiments, z31 is 0 or 1. In embodiments, z31 is 0. In embodiments, z31 is 1. In embodiments, z31 is 2. In embodiments, z31 is 3. In embodiments, z31 is 4.

In embodiments, the compound has the formula:

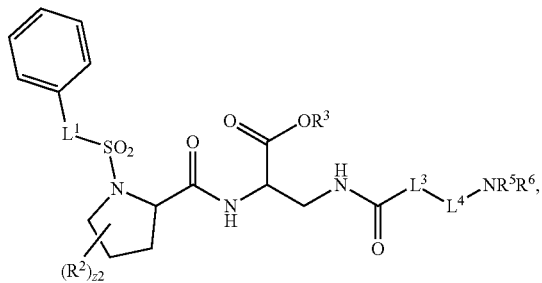

wherein $L^1$, $R^2$, z2, $R^3$, $L^3$, $L^4$, $R^5$, and $R^6$ are as described herein.

In embodiments, the compound has the formula:

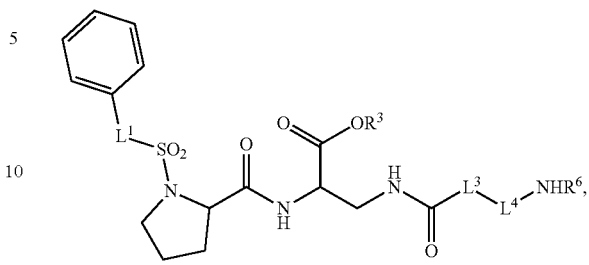

wherein $L^1$, $R^3$, $L^3$, $L^4$, and $R^6$ are as described herein.

In embodiments, the compound has the formula:

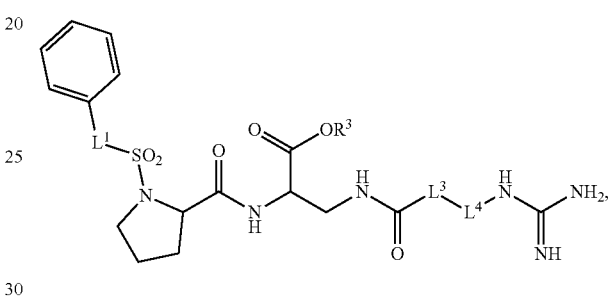

wherein $L^1$, $R^3$, $L^3$, and $L^4$ are as described herein.

In embodiments, the compound has the formula:

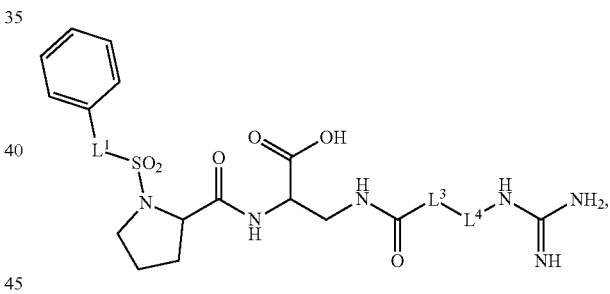

wherein $L^1$, $L^3$, and $L^4$ are as described herein.

In embodiments, the compound has the formula:

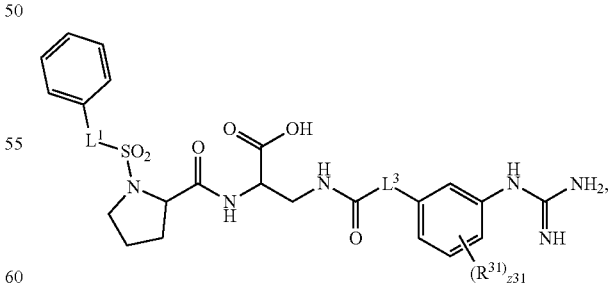

wherein $L^1$, $L^3$, and $R^{31}$ are as described herein and z31 is an integer from 0 to 4. In embodiments, z31 is 0 or 1. In embodiments, z31 is 0. In embodiments, z31 is 1. In embodiments, z31 is 2. In embodiments, z31 is 3. In embodiments, z31 is 4.

In embodiments, the compound has the formula:

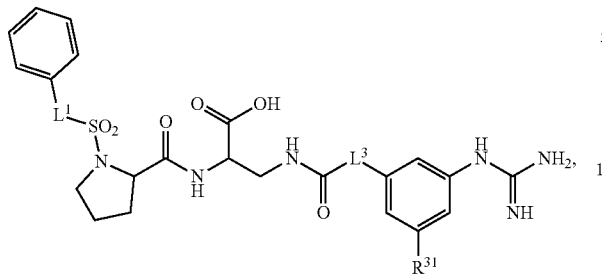

wherein $L^1$, $L^3$, and $R^{31}$ are as described herein.

In embodiments, the compound has the formula:

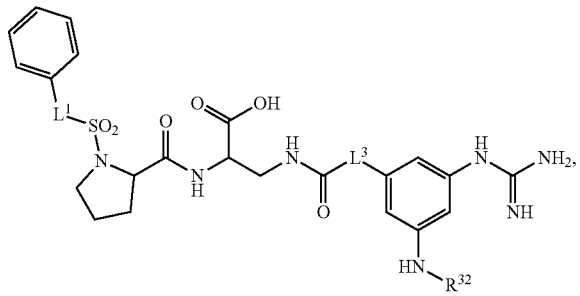

wherein $L^1$, $L^3$, and $R^{32}$ are as described herein.

In embodiments, the compound has the formula:

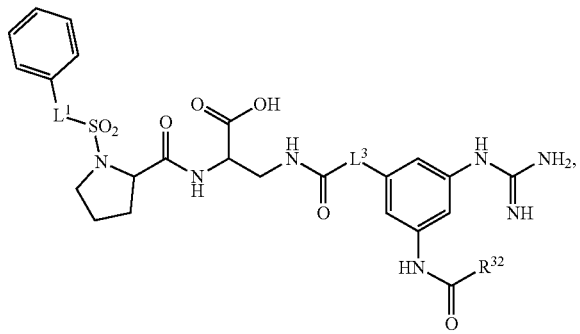

wherein $L^1$, $L^3$, and $R^{32}$ are as described herein. In embodiments, $R^{32}$ is a substituted or unsubstituted alkyl or substituted or unsubstituted heteroalkyl. In embodiments, $R^{32}$ is a substituted or unsubstituted $C_1$-$C_8$ alkyl. In embodiments, $R^{32}$ is a substituted or unsubstituted $C_1$-$C_4$ alkyl. In embodiments, $R^{32}$ is a substituted or unsubstituted $C_1$-$C_3$ alkyl. In embodiments, $R^{32}$ is a substituted or unsubstituted 2 to 10 membered heteroalkyl. In embodiments, $R^{32}$ is a substituted or unsubstituted 2 to 8 membered heteroalkyl. In embodiments, $R^{32}$ is a substituted or unsubstituted 4 to 8 membered heteroalkyl. In embodiments, $R^{32}$ is a substituted or unsubstituted 2 to 6 membered heteroalkyl. In embodiments, $R^{32}$ is a substituted or unsubstituted 2 to 4 membered heteroalkyl.

In embodiments, the compound has the formula:

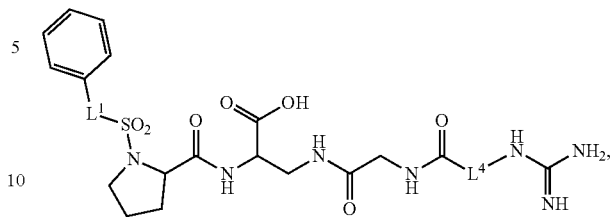

wherein $L^1$ and $L^4$ are as described herein.

In embodiments, the compound has the formula:

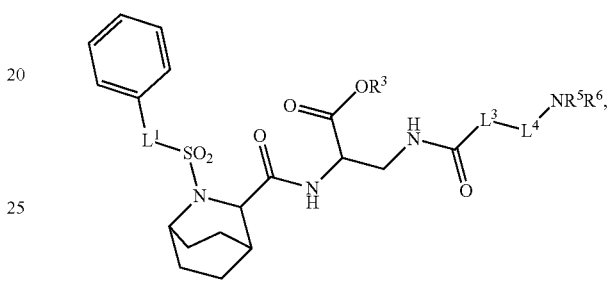

wherein $L^1$, $R^3$, $L^3$, $L^4$, $R^5$, and $R^6$ are as described herein.

In embodiments, the compound has the formula:

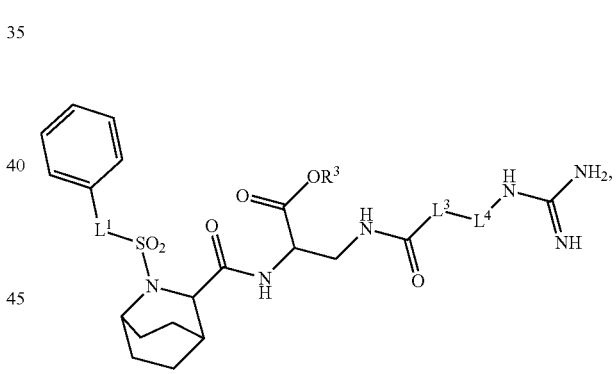

wherein $L^1$, $R^3$, $L^3$, and $L^4$ are as described herein.

In embodiments, the compound has the formula:

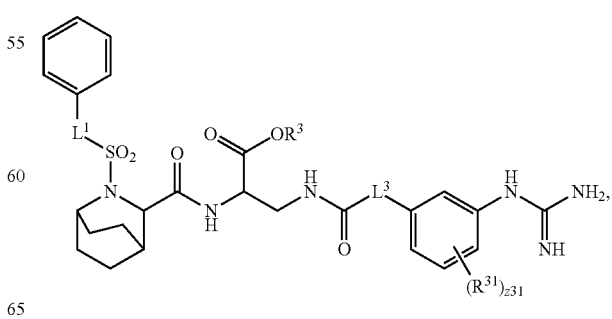

wherein $L^1$, $R^3$, $L^3$, $R^{31}$, and z31 are as described herein.

In embodiments, the compound has the formula:
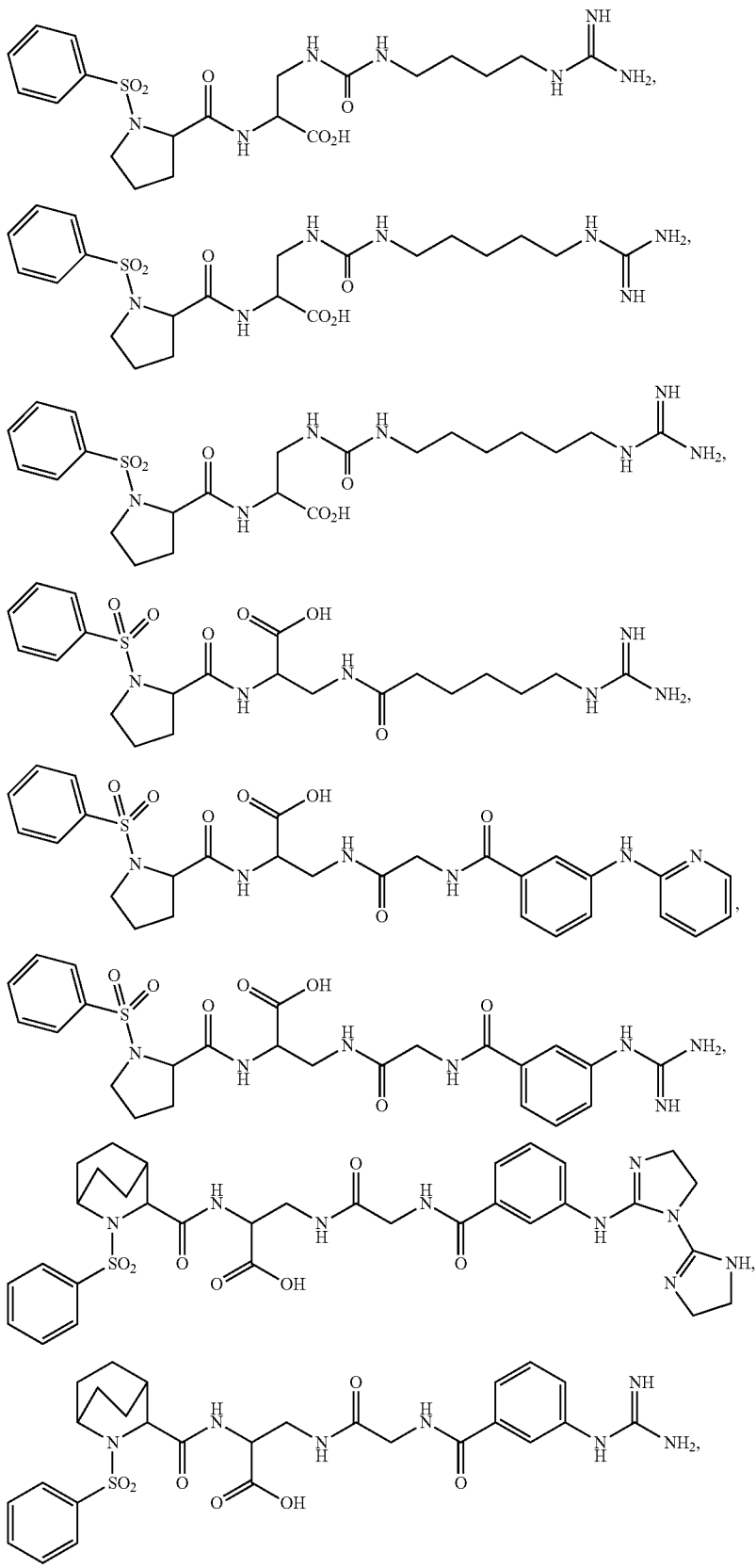

-continued
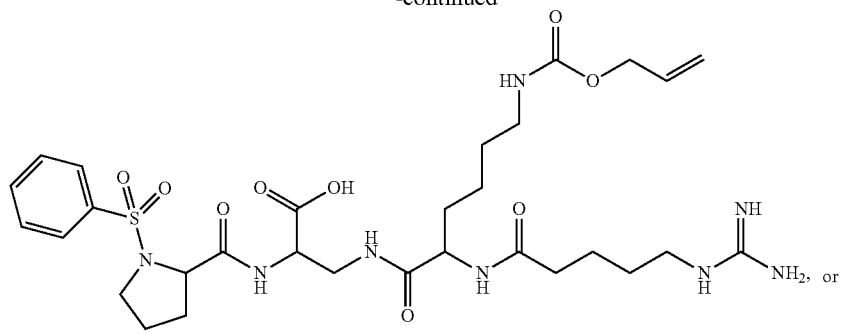
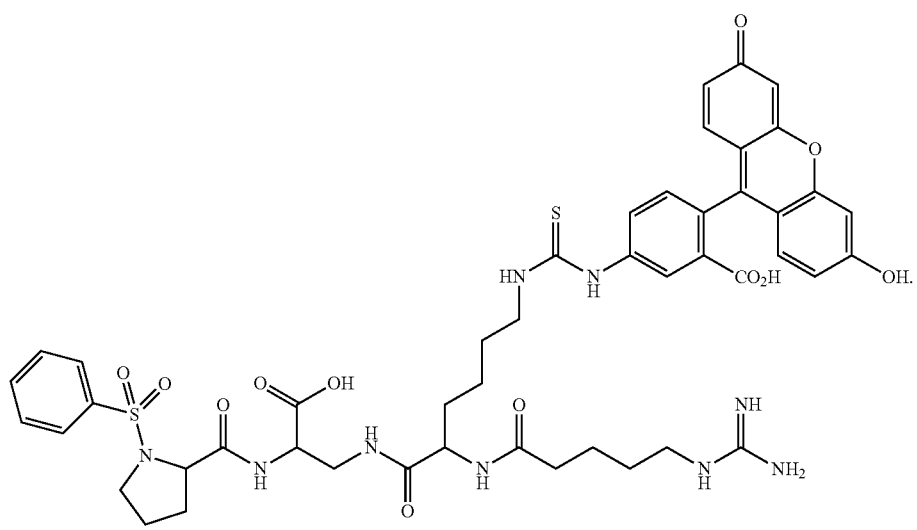
In embodiments, the compound has the formula:
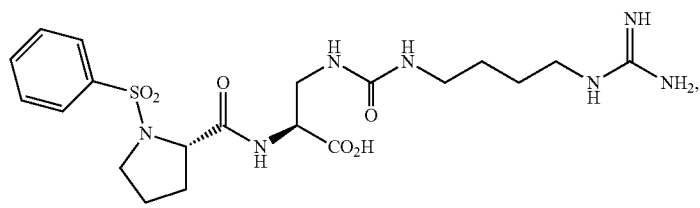
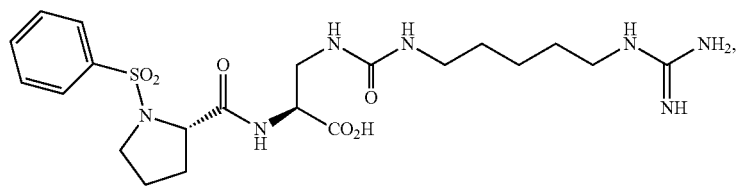
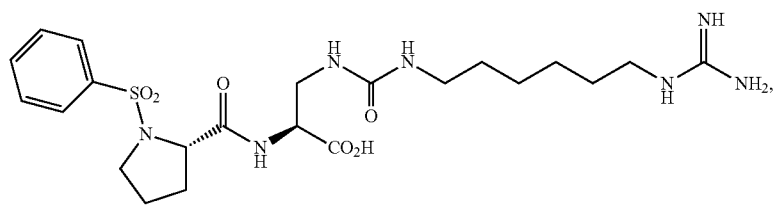

-continued
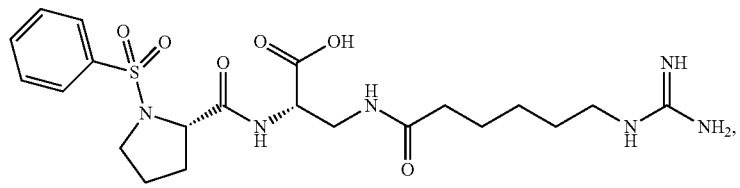
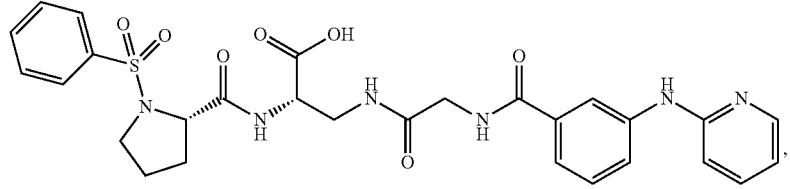
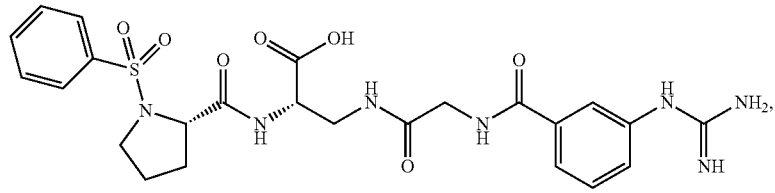
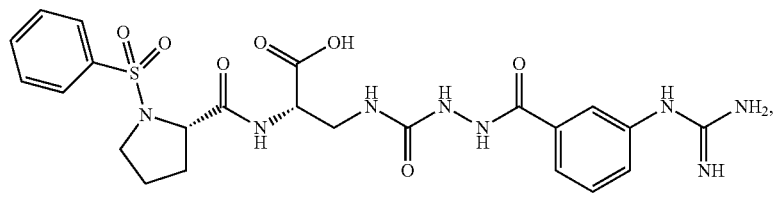
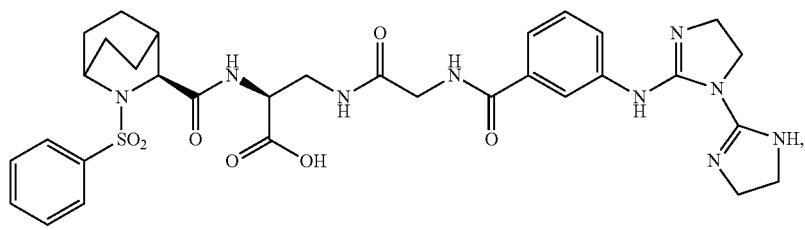
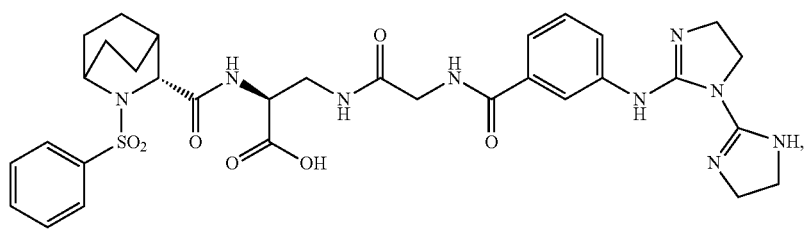
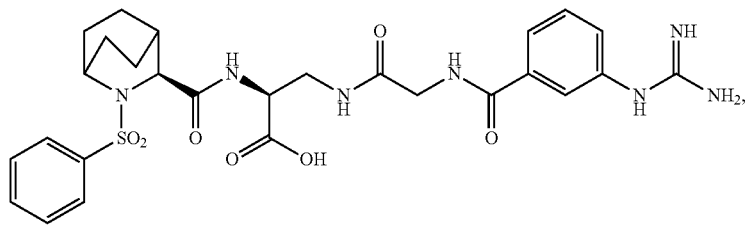
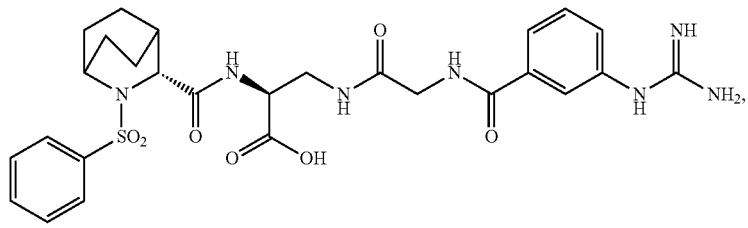

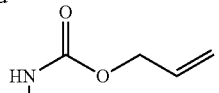
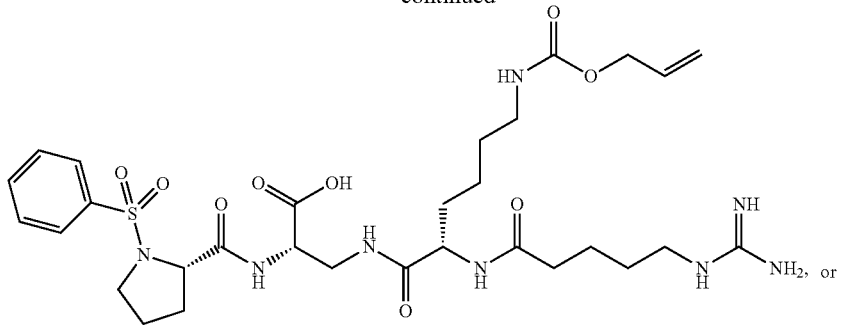
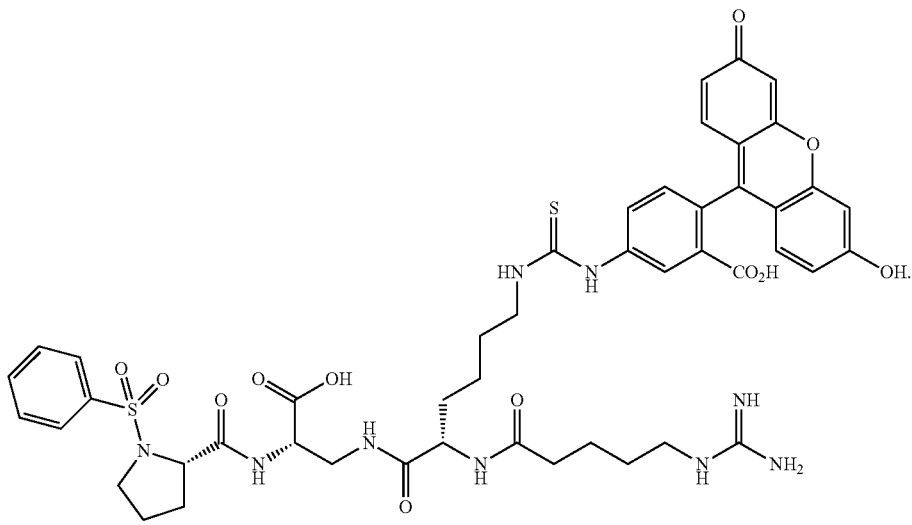
In embodiments, the compound has the formula:
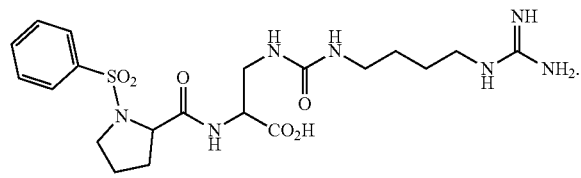 [SMILES: N=C(N)NCCCCNC(=O)NCC(NC(=O)C1CCCN1S(=O)(=O)c1ccccc1)C(=O)O]
In embodiments, the compound has the formula:
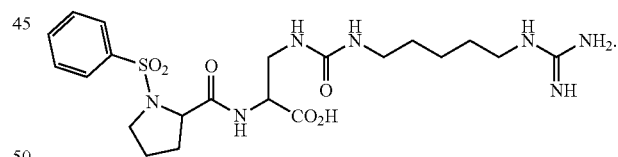
In embodiments, the compound has the formula:
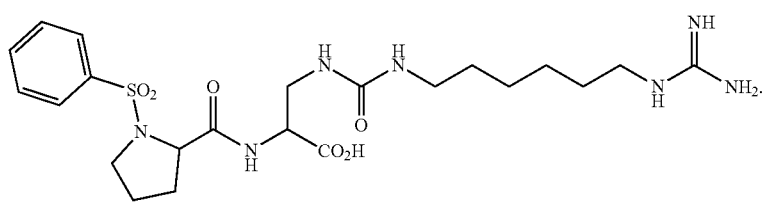 [SMILES: N=C(N)NCCCCCCNC(=O)NCC(NC(=O)C1CCCN1S(=O)(=O)c1ccccc1)C(=O)O]

In embodiments, the compound has the formula:
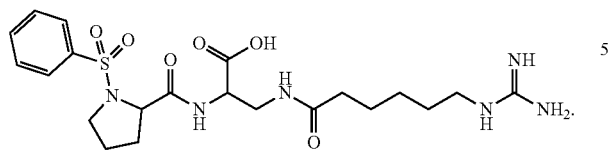
In embodiments, the compound has the formula:
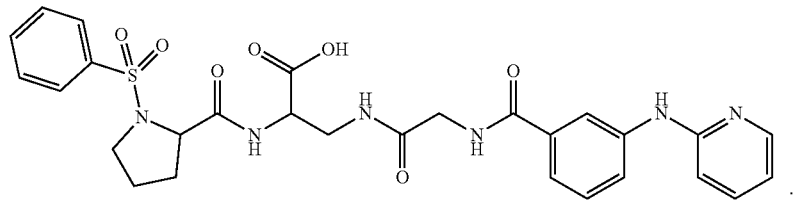 [SMILES: O=C(CNC(=O)c1cccc(Nc2ccccn2)c1)NCC(NC(=O)C1CCCN1S(=O)(=O)c1ccccc1)C(=O)O]
In embodiments, the compound has the formula:
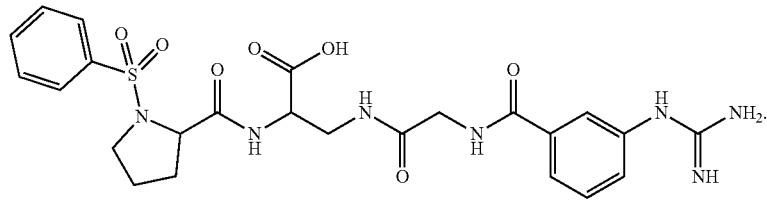 [SMILES: N=C(N)Nc1cccc(C(=O)NCC(=O)NCC(NC(=O)C2CCCN2S(=O)(=O)c2ccccc2)C(=O)O)c1]
In embodiments, the compound has the formula:
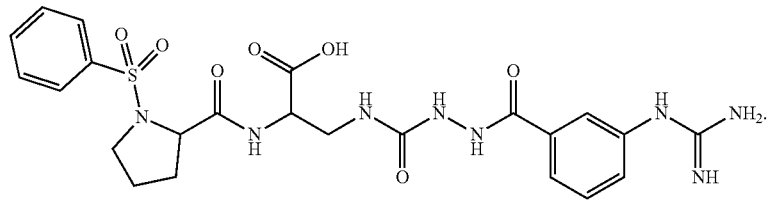 [SMILES: N=C(N)Nc1cccc(C(=O)NNC(=O)NCC(NC(=O)C2CCCN2S(=O)(=O)c2ccccc2)C(=O)O)c1]
In embodiments, the compound has the formula:
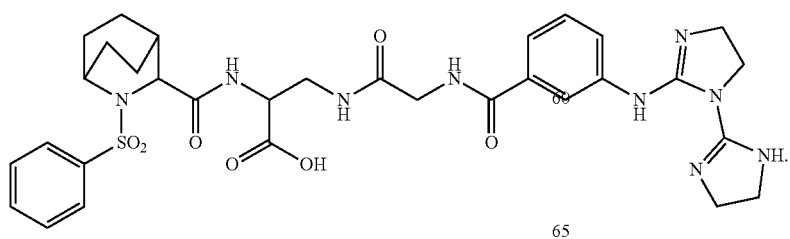

In embodiments, the compound has the formula:
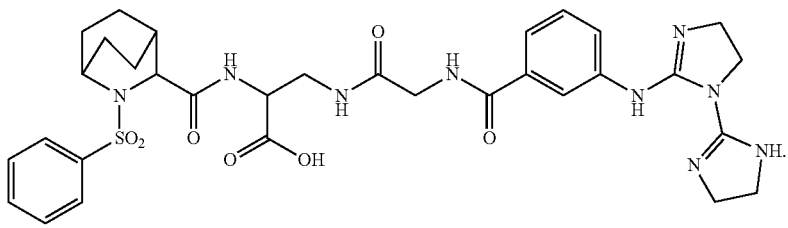 [SMILES: O=C(CNC(=O)c1cccc(NC2=NCCN2C2=NCCN2)c1)NCC(NC(=O)C1C2CCC(CC2)N1S(=O)(=O)c1ccccc1)C(=O)O]
In embodiments, the compound has the formula:
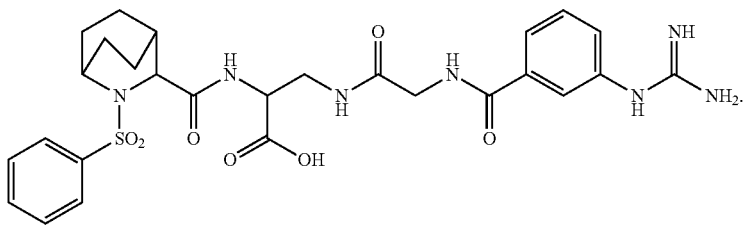 [SMILES: N=C(N)Nc1cccc(C(=O)NCC(=O)NCC(NC(=O)C2C3CCC(CC3)N2S(=O)(=O)c2ccccc2)C(=O)O)c1]
In embodiments, the compound has the formula:
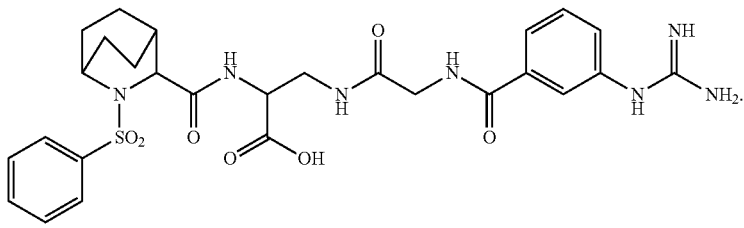 [SMILES: N=C(N)Nc1cccc(C(=O)NCC(=O)NCC(NC(=O)C2C3CCC(CC3)N2S(=O)(=O)c2ccccc2)C(=O)O)c1]
In embodiments, the compound has the formula:
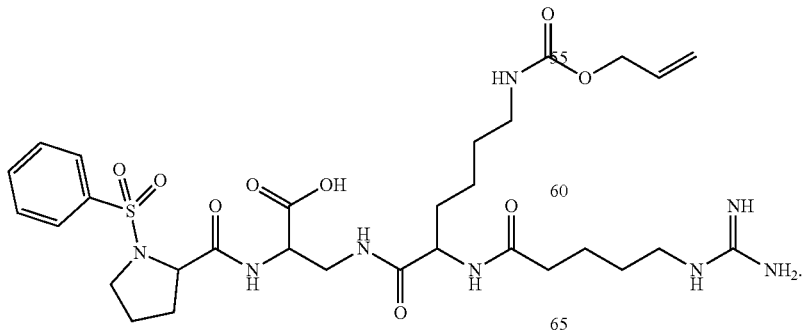

In embodiments, the compound has the formula:
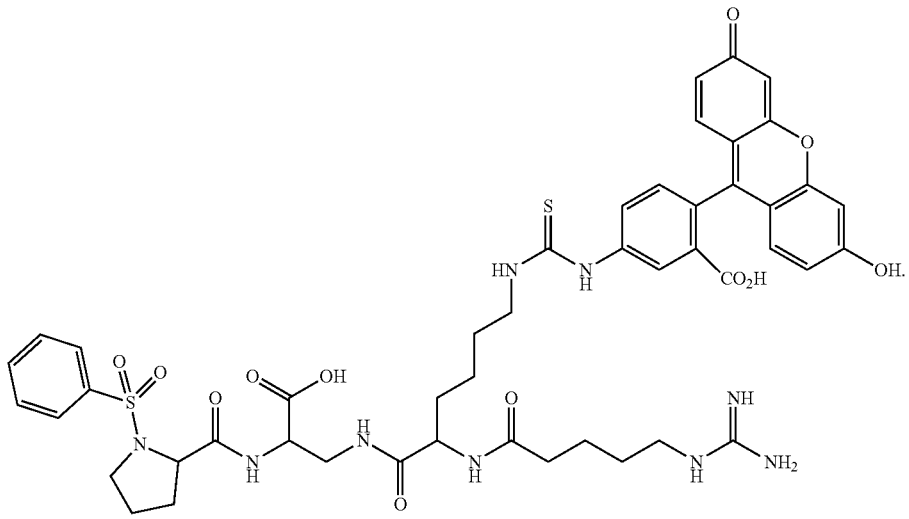 [SMILES: N=C(N)NCCCCC(=O)NC(CCCCNC(=S)Nc1ccc(-c2c3ccc(=O)cc-3oc3cc(O)ccc23)c(C(=O)O)c1)C(=O)NCC(NC(=O)C1CCCN1S(=O)(=O)c1ccccc1)C(=O)O]
In embodiments, the compound has the formula:
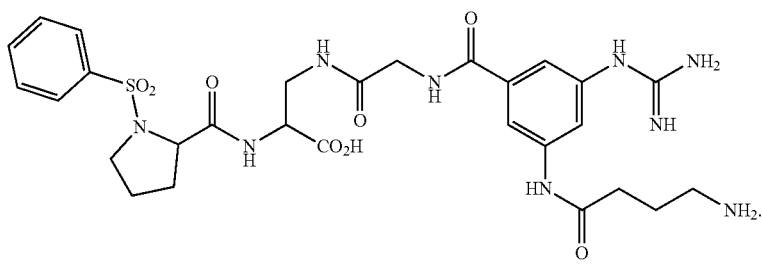 [SMILES: N=C(N)Nc1cc(NC(=O)CCCN)cc(C(=O)NCC(=O)NCC(NC(=O)C2CCCN2S(=O)(=O)c2ccccc2)C(=O)O)c1]
In embodiments, the compound has the formula:
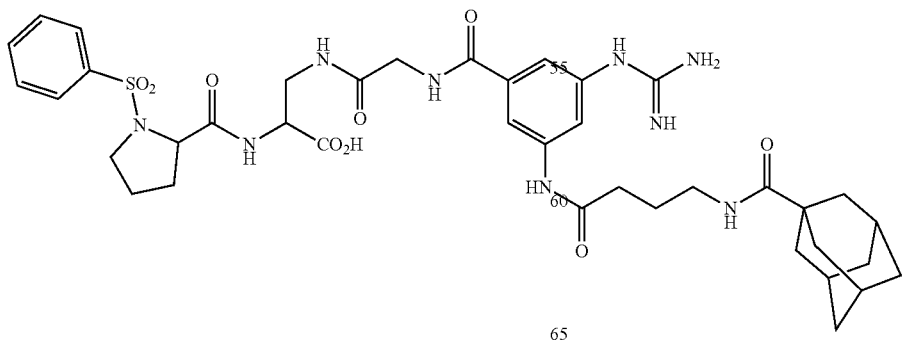

In embodiments, the compound has the formula:

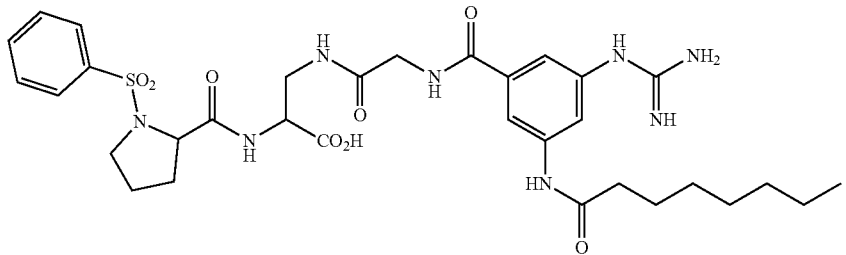

In embodiments, the compound has the formula:

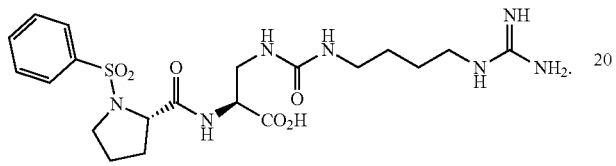

In embodiments, the compound has the formula:

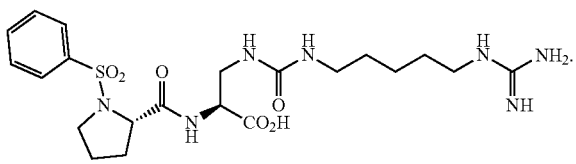 [SMILES: N=C(N)NCCCCCNC(=O)NC[C@H](NC(=O)[C@@H]1CCCN1S(=O)(=O)c1ccccc1)C(=O)O]

In embodiments, the compound has the formula:

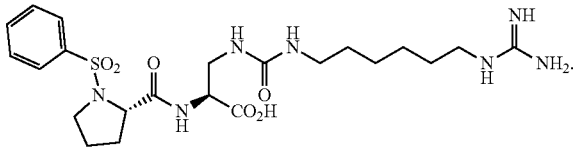 [SMILES: N=C(N)NCCCCCCNC(=O)NC[C@H](NC(=O)[C@@H]1CCCN1S(=O)(=O)c1ccccc1)C(=O)O]

In embodiments, the compound has the formula:

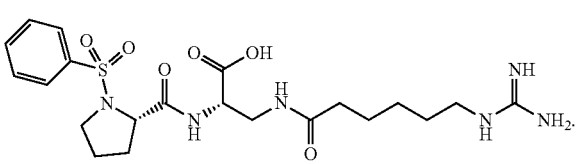 [SMILES: N=C(N)NCCCCCC(=O)NC[C@H](NC(=O)[C@@H]1CCCN1S(=O)(=O)c1ccccc1)C(=O)O]

In embodiments, the compound has the formula:

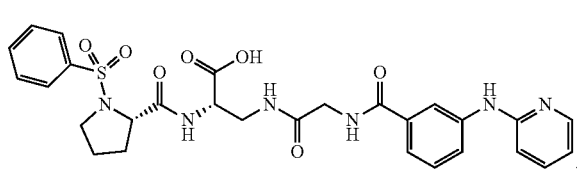 [SMILES: O=C(CNC(=O)c1cccc(Nc2ccccn2)c1)NC[C@H](NC(=O)[C@@H]1CCCN1S(=O)(=O)c1ccccc1)C(=O)O]

In embodiments, the compound has the formula:

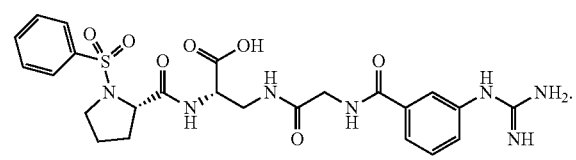 [SMILES: N=C(N)Nc1cccc(C(=O)NCC(=O)NC[C@H](NC(=O)[C@@H]2CCCN2S(=O)(=O)c2ccccc2)C(=O)O)c1]

In embodiments, the compound has the formula:

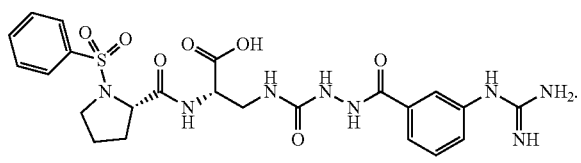 [SMILES: N=C(N)Nc1cccc(C(=O)NNC(=O)NC[C@H](NC(=O)[C@@H]2CCCN2S(=O)(=O)c2ccccc2)C(=O)O)c1]

In embodiments, the compound has the formula:

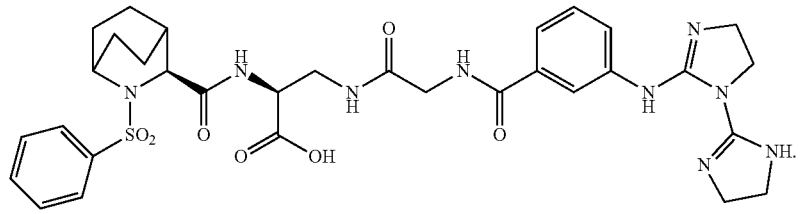 [SMILES: O=C(CNC(=O)c1cccc(NC2=NCCN2C2=NCCN2)c1)NC[C@H](NC(=O)[C@@H]1C2CCC(CC2)N1S(=O)(=O)c1ccccc1)C(=O)O]

In embodiments, the compound has the formula:
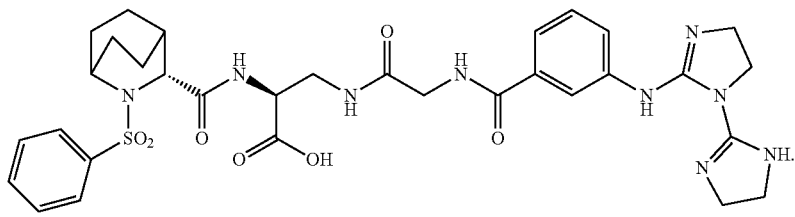 [SMILES: O=C(CNC(=O)c1cccc(NC2=NCCN2C2=NCCN2)c1)NC[C@H](NC(=O)[C@H]1C2CCC(CC2)N1S(=O)(=O)c1ccccc1)C(=O)O]
In embodiments, the compound has the formula:
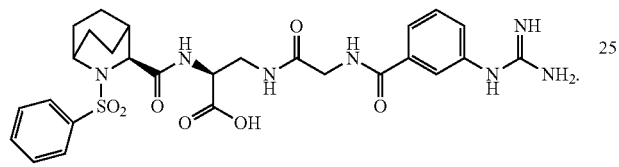
In embodiments, the compound has the formula:
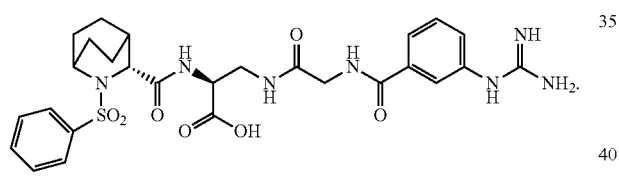
In embodiments, the compound has the formula:
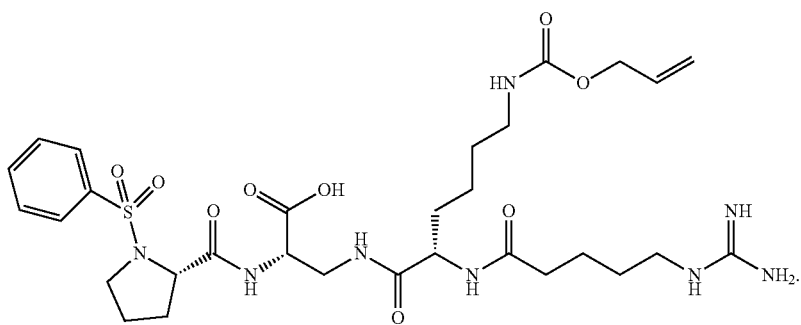 [SMILES: C=CCOC(=O)NCCCC[C@H](NC(=O)CCCCNC(=N)N)C(=O)NC[C@H](NC(=O)[C@@H]1CCCN1S(=O)(=O)c1ccccc1)C(=O)O]

In embodiments, the compound has the formula:
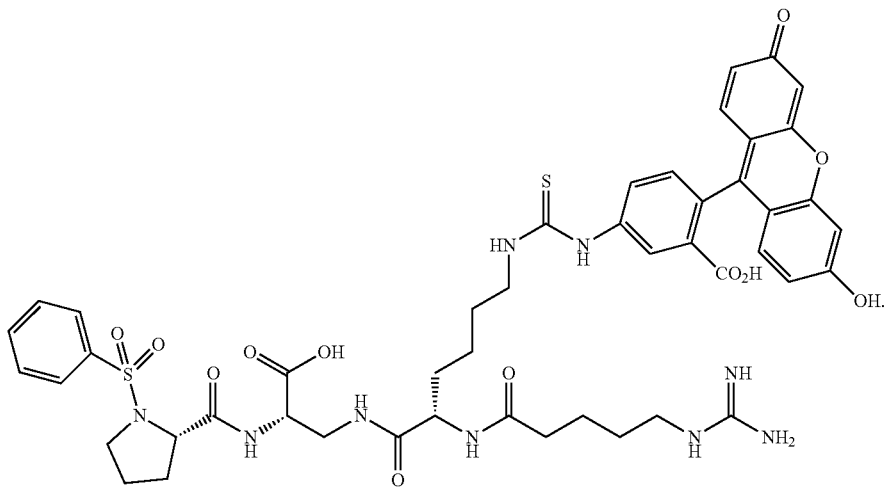 [SMILES: N=C(N)NCCCCC(=O)N[C@@H](CCCCNC(=S)Nc1ccc(-c2c3ccc(=O)cc-3oc3cc(O)ccc23)c(C(=O)O)c1)C(=O)NC[C@H](NC(=O)[C@@H]1CCCN1S(=O)(=O)c1ccccc1)C(=O)O]
In embodiments, the compound has the formula:
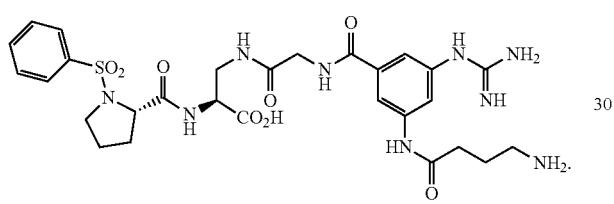
In embodiments, the compound has the formula:
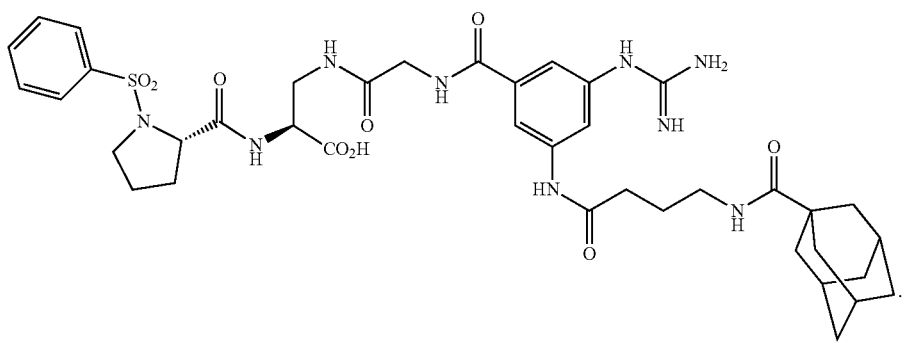 [SMILES: N=C(N)Nc1cc(NC(=O)CCCNC(=O)C23CC4CC(CC(C4)C2)C3)cc(C(=O)NCC(=O)NC[C@H](NC(=O)[C@@H]2CCCN2S(=O)(=O)c2ccccc2)C(=O)O)c1]
In embodiments, the compound has the formula:
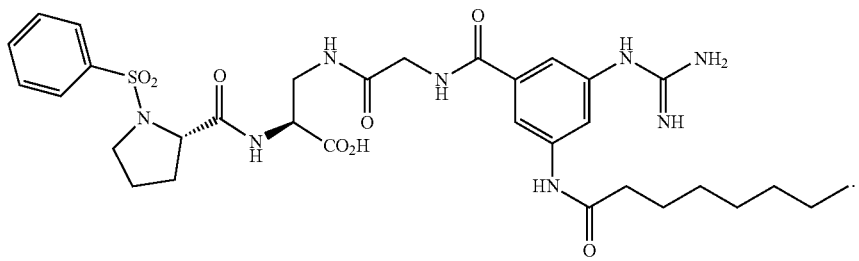 [SMILES: CCCCCCCC(=O)Nc1cc(NC(=N)N)cc(C(=O)NCC(=O)NC[C@H](NC(=O)[C@@H]2CCCN2S(=O)(=O)c2ccccc2)C(=O)O)c1]

In embodiments, the compound is HIJ-1094, HIJ-1099, HIJ-1204, HIJ-1437, HIJ-1483, or HIJ-1491. In embodiments, the compound is HIJ-1094. In embodiments, the compound is HIJ-1099. In embodiments, the compound is HIJ-1204. In embodiments, the compound is HIJ-1437. In embodiments, the compound is HIJ-1483. In embodiments, the compound is HIJ-1491.

In embodiments, when $R^5$ is hydrogen $R^6$ is not hydrogen. In embodiments, when $R^5$ is hydrogen $R^6$ is not a substituted or unsubstituted $C_1$-$C_6$ alkyl. In embodiments, when $R^5$ is hydrogen $R^6$ is not a substituted $C_1$-$C_6$ alkyl. In embodiments, when $R^5$ is hydrogen $R^6$ is not an unsubstituted $C_1$-$C_6$ alkyl. In embodiments, when $R^5$ is hydrogen $R^6$ is not a substituted or unsubstituted $C_1$-$C_4$ alkyl. In embodiments, when $R^5$ is hydrogen $R^6$ is not a substituted $C_1$-$C_4$ alkyl. In embodiments, when $R^5$ is hydrogen $R^6$ is not an unsubstituted $C_1$-$C_4$ alkyl. In embodiments, when $R^5$ is hydrogen $R^6$ is not a substituted or unsubstituted $C_1$-$C_2$ alkyl. In embodiments, when $R^5$ is hydrogen $R^6$ is not a substituted $C_1$-$C_4$ alkyl. In embodiments, when $R^5$ is hydrogen $R^6$ is not an unsubstituted $C_1$-$C_4$ alkyl.

In embodiments, $R^6$ is not hydrogen. In embodiments, $R^6$ is not a substituted or unsubstituted $C_1$-$C_6$ alkyl. In embodiments, $R^6$ is not a substituted $C_1$-$C_6$ alkyl. In embodiments, $R^6$ is not an unsubstituted $C_1$-$C_6$ alkyl. In embodiments, $R^6$ is not a substituted or unsubstituted $C_1$-$C_4$ alkyl. In embodiments, $R^6$ is not a substituted $C_1$-$C_4$ alkyl. In embodiments, $R^6$ is not an unsubstituted $C_1$-$C_4$ alkyl. In embodiments, $R^6$ is not a substituted or unsubstituted $C_1$-$C_2$ alkyl. In embodiments, $R^6$ is not a substituted $C_1$-$C_4$ alkyl. In embodiments, $R^6$ is not an unsubstituted $C_1$-$C_4$ alkyl.

In embodiments, $R^5$ is not hydrogen. In embodiments, $R^5$ is not a substituted or unsubstituted $C_1$-$C_6$ alkyl. In embodiments, $R^5$ is not a substituted $C_1$-$C_6$ alkyl. In embodiments, $R^5$ is not an unsubstituted $C_1$-$C_6$ alkyl. In embodiments, $R^5$ is not a substituted or unsubstituted $C_1$-$C_4$ alkyl. In embodiments, $R^5$ is not a substituted $C_1$-$C_4$ alkyl. In embodiments, $R^5$ is not an unsubstituted $C_1$-$C_4$ alkyl. In embodiments, $R^5$ is not a substituted or unsubstituted $C_1$-$C_2$ alkyl. In embodiments, $R^5$ is not a substituted $C_1$-$C_4$ alkyl. In embodiments, $R^5$ is not an unsubstituted $C_1$-$C_4$ alkyl.

In embodiments, when $R^5$ is hydrogen $R^6$ is not a 2 to 6 membered heteroalkyl. In embodiments, when $R^5$ is hydrogen $R^6$ is not a substituted 2 to 6 membered heteroalkyl. In embodiments, when $R^5$ is hydrogen $R^6$ is not an unsubstituted 2 to 6 membered heteroalkyl. In embodiments, when $R^5$ is hydrogen $R^6$ is not a substituted 2 to 6 membered heteroalkyl. In embodiments, when $R^5$ is hydrogen $R^6$ is not

[structure: -C(O)-O-tert-butyl]

In embodiments, when $R^5$ is hydrogen $R^6$ is not

[structure: -C(O)-O-methyl]

In embodiments when $R^5$ is hydrogen $R^6$ is not

[structure: -C(O)-O-ethyl]

In embodiments, when $R^5$ is hydrogen $R^6$ is not

[structure: -C(O)-O-propyl]

In embodiments, when $R^5$ is hydrogen $R^6$ is not

[structure: -C(O)-O-butyl]

In embodiments, when $R^5$ is hydrogen $R^6$ is not

[structure: -C(O)-O-benzyl]

In embodiments, when $R^5$ is hydrogen $R^6$ is not —C(O)-(substituted or unsubstituted heteroalkyl). In embodiments, when $R^5$ is hydrogen $R^6$ is not —C(O)-(unsubstituted heteroalkyl). In embodiments, when $R^5$ is hydrogen $R^6$ is not —C(O)-(substituted heteroalkyl). In embodiments, when $R^5$ is hydrogen $R^6$ is not —C(O)—O-(substituted or unsubstituted heteroalkyl). In embodiments, when $R^5$ is hydrogen $R^6$ is not —C(O)—O-(unsubstituted heteroalkyl). In embodiments, when $R^5$ is hydrogen $R^6$ is not —C(O)—O-(substituted heteroalkyl).

In embodiments, $R^6$ is not —C(O)-(substituted or unsubstituted heteroalkyl). In embodiments, $R^6$ is not —C(O)-(unsubstituted heteroalkyl). In embodiments, $R^6$ is not —C(O)-(substituted heteroalkyl). In embodiments, $R^6$ is not —C(O)—O-(substituted or unsubstituted heteroalkyl). In embodiments, $R^6$ is not —C(O)—O-(unsubstituted heteroalkyl). In embodiments, $R^6$ is not —C(O)—O-(substituted heteroalkyl). In embodiments, $R^5$ is not —C(O)-(substituted or unsubstituted heteroalkyl). In embodiments, $R^5$ is not —C(O)-(unsubstituted heteroalkyl). In embodiments, $R^5$ is not —C(O)-(substituted heteroalkyl). In embodiments, $R^5$ is not —C(O)—O-(substituted or unsubstituted heteroalkyl). In embodiments, $R^5$ is not —C(O)—O-(unsubstituted heteroalkyl). In embodiments, $R^5$ is not —C(O)—O-(substituted heteroalkyl).

In embodiments, $R^6$ is not a 2 to 6 membered heteroalkyl. In embodiments, $R^6$ is not a substituted 2 to 6 membered heteroalkyl. In embodiments, $R^6$ is not an unsubstituted 2 to 6 membered heteroalkyl. In embodiments, $R^6$ is not a substituted 2 to 6 membered heteroalkyl. In embodiments, $R^6$ is not

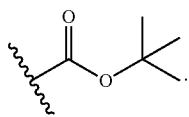 [SMILES: *C(=O)OC(C)(C)C]

In embodiments, R⁶ is not

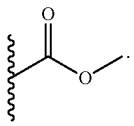

In embodiments, R⁶ is not

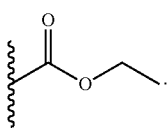 [SMILES: *C(=O)OCC]

In embodiments, R⁶ is not

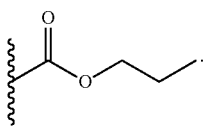 [SMILES: *C(=O)OCCC]

In embodiments, R⁶ is not

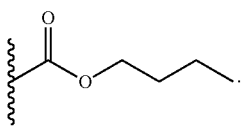 [SMILES: *C(=O)OCCCC]

In embodiments, R⁶ is not

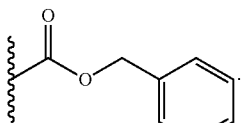

In embodiments, R⁵ is not a 2 to 6 membered heteroalkyl. In embodiments, R⁵ is not a substituted 2 to 6 membered heteroalkyl. In embodiments, R⁵ is not an unsubstituted 2 to 6 membered heteroalkyl. In embodiments, R⁵ is not a substituted 2 to 6 membered heteroalkyl. In embodiments, R⁵ is not

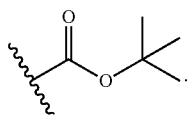 [SMILES: *C(=O)OC(C)(C)C]

In embodiments, R⁵ is not

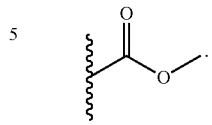

In embodiments, R⁵ is not

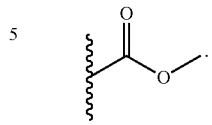

In embodiments, R⁵ is not

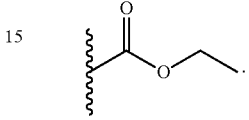

In embodiments, R⁵ is not

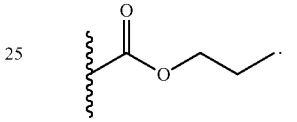

In embodiments, R⁵ is not

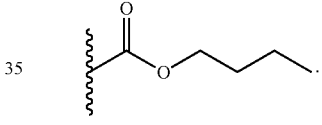

In embodiments, R⁵ is not

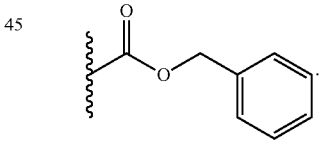

In embodiments, R¹ is not NO₂. In embodiments, $R^{1.3}$ is not NO₂.

In embodiments, the compound does not have the formula:

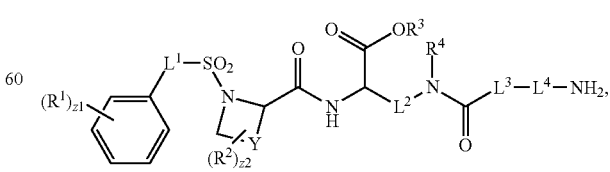

wherein R¹, z1, L¹, R², z2, Y, L², R⁴, L³, and L⁴ are as described herein.

In embodiments, the compound does not have the formula:

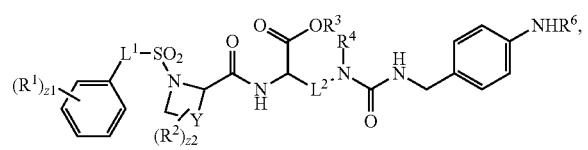

wherein $R^1$, z1, $L^1$, $R^2$, z2, Y, $L^2$, $R^4$, and $R^6$ are as described herein. In embodiments, the compound does not have the formula:

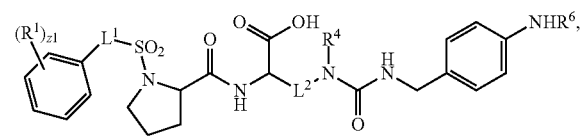

wherein $R^1$, z1, $L^1$, $L^2$, $R^4$, and $R^6$ are as described herein. In embodiments, the compound does not have the formula:

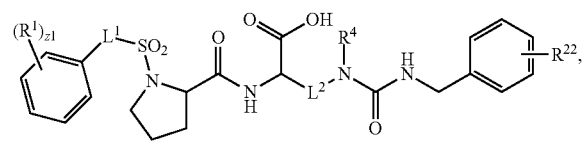

wherein $R^1$, z1, $L^1$, $L^2$, $R^4$, and $R^{22}$ are as described herein. In embodiments, the compound does not have the formula:

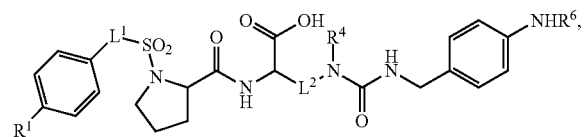

wherein $R^1$, z1, $L^1$, $L^2$, $R^4$, and $R^6$ are as described herein. In embodiments, the compound does not have the formula:

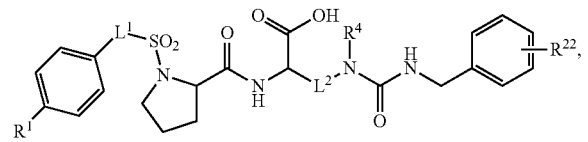

wherein $R^1$, z1, $L^1$, $L^2$, $R^4$, and $R^{22}$ are as described herein. In embodiments, $R^6$ is not hydrogen. In embodiments, $R^6$ is not a substituted or unsubstituted $C_1$-$C_6$ alkyl. In embodiments, $R^6$ is not a substituted $C_1$-$C_6$ alkyl. In embodiments, $R^6$ is not an unsubstituted $C_1$-$C_6$ alkyl. In embodiments, $R^6$ is not a substituted or unsubstituted $C_1$-$C_4$ alkyl. In embodiments, $R^6$ is not a substituted $C_1$-$C_4$ alkyl. In embodiments, $R^6$ is not an unsubstituted $C_1$-$C_4$ alkyl. In embodiments, $R^6$ is not a substituted or unsubstituted $C_1$-$C_2$ alkyl. In embodiments, $R^6$ is not a substituted $C_1$-$C_4$ alkyl. In embodiments, $R^6$ is not an unsubstituted $C_1$-$C_4$ alkyl. In embodiments, $R^6$ is not —C(O)-(substituted or unsubstituted heteroalkyl). In embodiments, $R^6$ is not —C(O)-(unsubstituted heteroalkyl). In embodiments, $R^6$ is not —C(O)-(substituted heteroalkyl). In embodiments, $R^6$ is not —C(O)—O-(substituted or unsubstituted heteroalkyl). In embodiments, $R^6$ is not —C(O)—O-(unsubstituted heteroalkyl). In embodiments, $R^6$ is not —C(O)—O-(substituted heteroalkyl). In embodiments, $R^6$ is not hydrogen.

In embodiments, $R^6$ is not a substituted or unsubstituted cycloalkyl, substituted or unsubstituted heterocycloalkyl, substituted or unsubstituted aryl, or substituted or unsubstituted heteroaryl. $R^6$ is not substituted or unsubstituted cycloalkyl. $R^6$ is not substituted or unsubstituted $C_3$-$C_8$ cycloalkyl. $R^6$ is not substituted cycloalkyl. $R^6$ is not substituted $C_3$-$C_8$ cycloalkyl. $R^6$ is not unsubstituted cycloalkyl. $R^6$ is not unsubstituted $C_3$-$C_8$ cycloalkyl.

$R^6$ is not substituted or unsubstituted 3 to 8 membered heterocycloalkyl. $R^6$ is not a substituted or unsubstituted 4 to 6 membered heterocycloalkyl. $R^6$ is not a substituted or unsubstituted 5 or 6 membered heterocycloalkyl. $R^6$ is not substituted or unsubstituted 5 membered heterocycloalkyl. $R^6$ is not substituted or unsubstituted 6 membered heterocycloalkyl. In embodiments, $R^6$ is not a substituted or unsubstituted heterocycloalkyl (e.g., substituted or unsubstituted pyrrolidinyl, substituted or unsubstituted imidazolidinyl, substituted or unsubstituted oxazolidinyl, substituted or unsubstituted thiazolidinyl, substituted or unsubstituted dioxolanyl, substituted or unsubstituted dithiolanyl, substituted or unsubstituted piperidinyl, substituted or unsubstituted morpholinyl, substituted or unsubstituted dioxanyl, substituted or unsubstituted dithianyl, substituted or unsubstituted aziridinyl, substituted or unsubstituted azetidinyl, substituted or unsubstituted azepinyl, substituted or unsubstituted oxiranyl, substituted or unsubstituted oxetanyl, substituted or unsubstituted tetrahydrofuranyl, or substituted or unsubstituted tetrahydropyranyl.

In embodiments, $R^6$ is not a substituted or unsubstituted $C_6$-$C_{12}$ aryl. In embodiments, $R^6$ is not a substituted $C_6$-$C_{12}$ aryl. In embodiments, $R^6$ is an unsubstituted $C_6$-$C_{12}$ aryl. In embodiments, $R^6$ is not a substituted or unsubstituted $C_6$-$C_{10}$ aryl. In embodiments, $R^6$ is not a substituted $C_6$-$C_{10}$ aryl. In embodiments, $R^6$ is an unsubstituted $C_6$-$C_{10}$ aryl. In embodiments, $R^6$ is an unsubstituted phenyl. In embodiments, $R^6$ is not a substituted phenyl. In embodiments, $R^6$ is an unsubstituted naphthyl. In embodiments, $R^6$ is not a substituted naphthyl. In embodiments, $R^6$ is an unsubstituted biphenyl. In embodiments, $R^6$ is not a substituted biphenyl.

In embodiments, $R^6$ is not a substituted or unsubstituted 5 to 10 membered heteroaryl. In embodiments, $R^6$ is not a substituted 5 to 10 membered heteroaryl. In embodiments, $R^6$ is an unsubstituted 5 to 10 membered heteroaryl. In embodiments, $R^6$ is not a substituted or unsubstituted 5 to 6 membered heteroaryl. In embodiments, $R^6$ is not a substituted 5 to 6 membered heteroaryl. In embodiments, $R^6$ is an unsubstituted 5 to 6 membered heteroaryl. In embodiments, $R^6$ is not a substituted or unsubstituted 5 membered heteroaryl. In embodiments, $R^6$ is not a substituted 5 membered heteroaryl. In embodiments, $R^6$ is an unsubstituted 5 membered heteroaryl. In embodiments, $R^6$ is not a substituted or unsubstituted 6 membered heteroaryl. In embodiments, $R^6$ is not a substituted 6 membered heteroaryl. In embodiments, $R^6$ is an unsubstituted 6 membered heteroaryl.

In embodiments, $R^6$ is not unsubstituted triazolyl. In embodiments, $R^6$ is not substituted triazolyl. In embodiments, $R^6$ is not unsubstituted tetrazolyl. In embodiments, $R^6$ is not substituted tetrazolyl. In embodiments, $R^6$ is not substituted or unsubstituted pyridyl. $R^6$ is not substituted or unsubstituted heteroaryl. $R^6$ is not a substituted or unsubstituted heteroaryl such as, for example, substituted or unsubstituted pyridinyl, substituted or unsubstituted pyrrolyl, substituted or unsubstituted furanyl, substituted or unsubstituted thiophenyl, substituted or unsubstituted imidazolyl, substituted or unsubstituted pyrazolyl, substituted or unsubstituted oxazolyl, substituted or unsubstituted thiazolyl, substituted or unsubstituted pyranyl, substituted or unsubstituted thiopyranyl, substituted or unsubstituted pyrazinyl, substituted or unsubstituted pyrimindyl, substituted or unsubstituted pyridazinyl, substituted or unsubstituted oxazinyl, substituted or unsubstituted thiazinyl, substituted or unsubstituted doxinyl, substituted or unsubstituted dithiinyl, substituted or unsubstituted azetyl, substituted or unsubstituted oxetyl, substituted or unsubstituted thietyl, substituted or unsubstituted azirinyl, substituted or unsubstituted oxirenyl or substituted or unsubstituted thienyl. $R^6$ is not substituted or unsubstituted pyridinyl.

III. Pharmaceutical Compositions

In an aspect is provided a pharmaceutical composition including a compound described herein, or pharmaceutically acceptable salt thereof, and a pharmaceutically acceptable excipient.

In embodiments of the pharmaceutical compositions, the compound, or pharmaceutically acceptable salt thereof, is included in a therapeutically effective amount.

In embodiments of the pharmaceutical compositions, the pharmaceutical composition includes a second agent (e.g. therapeutic agent). In embodiments of the pharmaceutical compositions, the pharmaceutical composition includes a second agent (e.g. therapeutic agent) in a therapeutically effective amount. In embodiments of the pharmaceutical compositions, the second agent is an agent for treating asthma. In embodiments of the pharmaceutical compositions, the second agent is an agent for treating cancer. In embodiments, the second agent is an anti-cancer agent. In embodiments, the second agent is a chemotherapeutic. In embodiments, the second agent is an anti-inflammatory agent. In embodiments, the second agent is an anti-autoimmune disease agent.

IV. METHODS OF USE

In an aspect is provided a method for treating asthma, the method including administering to a subject in need thereof an effective amount of a compound as described herein.

Provided herein are methods for treating asthma. In embodiments, the asthma is severe asthma. In embodiments, the asthma is acute severe asthma. In embodiments, the asthma is moderate asthma. In one aspect, is a method for treating asthma by administering to a subject in need thereof an α5β3-inhibitor (e.g., where the α5β3-inhibitor is a compound having a formulae described herein, including embodiments thereof). In an embodiment, is a method for treating asthma by administering to a subject in need thereof a therapeutically effective amount of an α5β1-inhibitor, where the α5β1-inhibitor is an α5β1-inhibitor compound having the formulae described herein, including embodiments thereof. The α5β1-inhibitor compound may be a compound having a formula described herein, including embodiments thereof. The α5β1-inhibitor compound may be a pharmaceutical composition as described herein, including embodiments thereof. In embodiments, the compound is HIJ-1094, HIJ-1099, HIJ-1204, HIJ-1437, HIJ-1483, or HIJ-1491.

In an aspect is provided a method of treating cancer including administering to a subject in need thereof an effective amount of a compound described herein. In embodiments, the cancer is ovarian cancer, bladder cancer, head and neck cancer, brain cancer, breast cancer, lung cancer, cervical cancer, liver cancer, colorectal cancer, pancreatic cancer, glioblastoma, neuroblastoma, rhabdomyosarcoma, osteosarcoma, renal cancer, renal cell carcinoma, non-small cell lung cancer, uterine cancer, testicular cancer, anal cancer, bile duct cancer, biliary tract cancer, gastrointestinal carcinoid tumors, esophageal cancer, gall bladder cancer, appendix cancer, small intestine cancer, stomach (gastric) cancer, urinary bladder cancer, genitourinary tract cancer, endometrial cancer, nasopharyngeal cancer, head and neck squamous cell carcinoma, or prostate cancer. In embodiments, the cancer is ovarian cancer, bladder cancer, head and neck cancer, prostate cancer, brain cancer, breast cancer, lung cancer, cervical cancer, liver cancer, bone cancer, or spinal cancer.

In an aspect is provided a method of treating an inflammatory disease including administering to a subject in need thereof an effective amount of a compound described herein.

In embodiments, the inflammatory disease is arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, ischemia reperfusion injury, stroke, sarcoidosis, transplant rejection, interstitial cystitis, atherosclerosis, scleroderma, or atopic dermatitis.

In an aspect is provided a method of treating an autoimmune disease including administering to a subject in need thereof an effective amount of a compound described herein.

In embodiments, the autoimmune disease is arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, sarcoidosis, transplant rejection, interstitial cystitis, atherosclerosis, scleroderma, or atopic dermatitis.

In an aspect is provided a method of detecting the presence of α5β1 integrin or inhibiting α5β1 integrin activity, the method including contacting an α5β1 integrin with a compound as described herein.

In embodiments, the method includes administering a second agent (e.g. therapeutic agent). In embodiments, the method includes administering a second agent (e.g. therapeutic agent) in a therapeutically effective amount. In embodiments, the second agent is an agent for treating cancer. In embodiments, the second agent is an anti-cancer agent. In embodiments, the second agent is a chemotherapeutic. In embodiments, the second agent is an anti-inflammatory agent.

In embodiments, the method includes detecting the presence of α5β1 integrin and inhibiting α5β1 integrin activity. In embodiments, the method includes detecting the presence of α5β1 integrin. In embodiments, the method includes inhibiting α5β1 integrin activity.

Further provided herein are methods of detecting α5β1 expression in a cell. In one aspect is a method of detecting α5β1 expression in a cell by contacting a cell with an α5β1-specific moiety (e.g., compound described herein) and allowing the α5β1-specific moiety to bind to the cell. The α5β1-specific moiety is detected, thereby detecting α5β1 expression in a cell. The detection may be performed using techniques known in the art (e.g. fluorescence detection or radiolabel detection). The cell may form part of an organism (e.g. a human).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

IV. EMBODIMENTS

Embodiments contemplated herein include embodiments P1 to P111 following.

Embodiment P1

A compound having the formula:

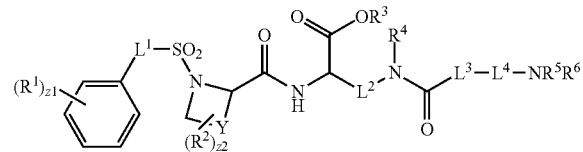

wherein, $R^1$ is independently halogen, $-CX^1_3$, $-CHX^1_2$, $-CH_2X^1$, $-OCX^1_3$, $-OCH_2X^1$, $-OCHX^1_2$, $-CN$, $-SO_{n1}R^{1D}$, $-SO_{v1}NR^{1A}R^{1B}$, $-NHC(O)NR^{1A}R^{1B}$, $-N(O)_{m1}$, $-NR^{1A}R^{1B}$, $-C(O)R^{1C}$, $-C(O)-OR^{1C}$, $-C(O)NR^{1A}R^{1B}$, $-OR^{1D}$, $-NR^{1A}SO_2R^{1D}$, $-NR^{1A}C(O)R^{1C}$, $-NR^{1A}C(O)OR^{1C}$, $-NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl; $L^1$ is a bond or substituted or unsubstituted alkylene, or substituted or unsubstituted heteroalkylene; Y is a bond, $-C-$, $-C-C-$, $-C=C-$, $-C-C-C-$, $-C=C-C-$, $-C-C=C-$, $-O-C-$, $-C-O-$, $-C-O-C$, $-S-C-$, $-C-S-$, or $-C-S-C-$; $R^2$ is independently halogen, $-CX^2_3$, $-CHX^2_2$, $-CH_2X^2$, $-OCX^2_3$, $-OCH_2X^2$, $-OCHX^2_2$, $-CN$, $-SO_{n2}R^{2D}$, $-SO_{v2}NR^{2A}R^{2B}$, $-NHC(O)NR^{2A}R^{2B}$, $-N(O)_{m2}$, $-NR^{2A}R^{2B}$, $-C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl; $R^3$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a prodrug moiety; $R^4$ is independently hydrogen, $-CX^4_3$, $-CN$, $-COOH$, $-CONH_2$, $-CHX^4_2$, $-CH_2X^4$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $L^2$ is unsubstituted alkylene; $L^3$ is a bond, $-O-$, $-S-$, $-N(R^7)-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $R^7$ is hydrogen, $-CN$, $-COOH$, $-CX^7_3$, substituted or unsubstituted alkyl, or substituted or unsubstituted heteroalkyl; $L^4$ is $-O-$, $-S-$, $-N(R^8)-$, $-C(O)-$, $C(O)O-$, $-S(O)-$, $-S(O)_2-$, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene; $R^8$ is hydrogen, $-CN$, $-COOH$, $-CX^8_3$, substituted or unsubstituted alkyl, or substituted or unsubstituted heteroalkyl; $R^5$ and $R^6$ are independently hydrogen,

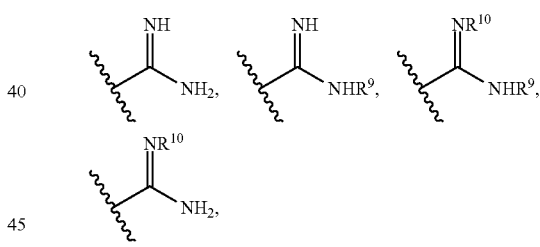

substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^5$ and $R^6$ may optionally be joined to form a substituted or unsubstituted heterocycloalkyl or substituted or unsubstituted heteroaryl; $R^9$ is hydrogen, halogen, $-N_3$, $-CX^9_3$, $-CHX^9_2$, $-CH_2X^9$, $-CN$, $-CHO$, $-OH$, $-NH_2$, $-COOH$, $-CONH_2$, $-NO_2$, $-SH$, $-SO_2$, $-SO_2CH_3-$ $SO_3H$, $-SO_4H$, $-SO_2NH_2$, $-NHNH_2$, $-ONH_2$, $-NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{10}$ is hydrogen, halogen, $-N_3$, $-CX^{10}_3$, $-CHX^{10}_2$, $-CH_2X^{10}$, $-CN$, $-CHO$, $-OH$, $-NH_2$, $-COOH$, $-CONH_2$, $-NO_2$, $-SH$, $-SO_2$, $-SO_2CH_3-$ $SO_3H$, $-SO_4H$, $-SO_2NH_2$, $-NHNH_2$, $-ONH_2$, $-NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; each $R^{1A}$, $R^{1B}$, $R^{1C}$, $R^{1D}$, $R^{2A}R^{2B}$, $R^{2C}$, $R^{2D}$, is independently hydrogen, —$CX_3$, —CN, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; each X, $X^1$, $X^2$, $X^4$, $X^7$, $X^8$, $X^9$, and $X^{10}$ are independently —F, —Cl, —Br, or —I; n1 and n2 are independently an integer from 0 to 4; and m1, m2, v1 and v2 are independently 1 or 2; z1 is an integer from 0 to 5; z2 is an integer from 0 to 9; with the proviso that when $R^5$ is hydrogen $R^6$ is not hydrogen.

Embodiment P2

The compound of embodiment P1, wherein z1 is an integer from 1 to 5.

Embodiment P3

The compound of embodiments P1 or P2, wherein Y is —C—C—, —C=C—, —O—C—, —C—O—, —C—O—C—, —C—S—, —S—C, or —C—S—C—.

Embodiment P4

The compound of any one of embodiments P1 to P3, wherein

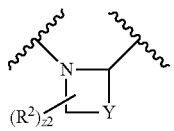

has the formula:

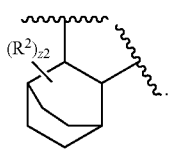

Embodiment P5

The compound of any one of embodiments P1 to P3 having the formula:

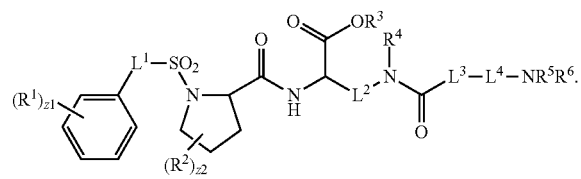

Embodiment P6

The compound of any one of embodiments P1 to P5, wherein $L^1$ is a bond.

Embodiment P7

The compound of any one of embodiments P1 to P6, wherein $R^1$ is independently halogen, —$N_3$, —$CF_3$, —$CCl_3$, —$CBr_3$, —$CI_3$, —CN, —CHO, —OH, —$NH_2$, —COOH, —$CONH_2$, —SH, —$SO_2$, —$SO_2CH_3$—$SO_3H$, —$OSO_3H$, —$SO_2NH_2$, —$NHNH_2$, —$ONH_2$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety.

Embodiment P8

The compound of any one of embodiments P1 to P6, wherein $R^1$ is independently halogen, —OMe, —SMe, —$SO_2Me$, —$SO_2Ph$, —COOH, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted phenyl, or substituted or unsubstituted 5 to 6 membered heteroaryl; two adjacent $R^1$ substituents may optionally be joined to form a substituted or unsubstituted $C_3$-$C_8$ cycloalkyl, substituted or unsubstituted 3 to 8 membered heterocycloalkyl, substituted or unsubstituted phenyl, or substituted or unsubstituted 5 to 6 membered heteroaryl.

Embodiment P9

The compound of any of embodiments P1 to P8, wherein $L^2$ is unsubstituted $C_1$-$C_2$ alkylene.

Embodiment P10

The compound of any of embodiments P1 to P8, wherein $L^2$ is unsubstituted methylene.

Embodiment P11

The compound of any of embodiments P1 to P10, wherein $R^4$ is hydrogen.

Embodiment P12

The compound of any one of embodiments P1 to P11, wherein $L^3$ is a bond, substituted or unsubstituted $C_1$-$C_8$ alkylene, or substituted or unsubstituted 2 to 8 membered heteroalkylene, substituted or unsubstituted $C_3$-$C_8$ cycloalkylene, substituted or unsubstituted 3 to 8 membered heterocycloalkylene, substituted or unsubstituted phenylene, or substituted or unsubstituted 5 to 6 membered heteroarylene.

Embodiment P13

The compound of any one of embodiments P1 to P11, wherein $L^3$ is a bond.

Embodiment P14

The compound of any one of embodiments P1 to P11, wherein $L^3$ is substituted or unsubstituted alkylene, or substituted or unsubstituted heteroalkylene.

Embodiment P15

The compound of any one of embodiments P1 to P11, wherein $L^3$ is substituted or unsubstituted $C_1$-$C_8$ alkylene, or substituted or unsubstituted 2 to 8 membered heteroalkylene.

Embodiment P16

The compound of any one of embodiments P1 to P11, wherein $L^3$ is substituted or unsubstituted 2 to 8 membered heteroalkylene.

Embodiment P17

The compound of any one of embodiments 1 to 11, wherein $L^3$ is an oxo-substituted $C_1$-$C_8$ alkylene, or oxo-substituted 2 to 8 membered heteroalkylene.

Embodiment P18

The compound of any one of embodiments P1 to P17, wherein $L^4$ is substituted or unsubstituted $C_1$-$C_8$ alkylene, or substituted or unsubstituted 2 to 8 membered heteroalkylene, substituted or unsubstituted $C_3$-$C_8$ cycloalkylene, substituted or unsubstituted 3 to 8 membered heterocycloalkylene, substituted or unsubstituted phenylene, or substituted or unsubstituted 5 to 6 membered heteroarylene.

Embodiment P19

The compound of any one of embodiments P1 to P17, wherein $L^4$ is substituted or unsubstituted alkylene, or substituted or unsubstituted heteroalkylene.

Embodiment P20

The compound of any one of embodiments P1 to P17, wherein $L^4$ is substituted or unsubstituted $C_1$-$C_8$ alkylene, or substituted or unsubstituted 2 to 8 membered heteroalkylene.

Embodiment P21

The compound of any one of embodiments P1 to P17, wherein $L^4$ is substituted or unsubstituted 2 to 8 membered heteroalkylene.

Embodiment P22

The compound of any one of embodiments P1 to P17, wherein $L^4$ is an oxo-substituted $C_1$-$C_8$ alkylene, or oxo-substituted 2 to 8 membered heteroalkylene.

Embodiment P23

The compound of any one of embodiments P1 to P17, wherein $L^4$ is substituted or unsubstituted arylene, or substituted or unsubstituted heteroarylene.

Embodiment P24

The compound of any one of embodiments P1 to P17, wherein $L^4$ is substituted or unsubstituted phenylene, or substituted or unsubstituted 5 to 6 membered heteroarylene.

Embodiment P25

The compound of any one of embodiments P1 to P17, wherein $L^4$ is unsubstituted phenylene.

Embodiment P26

The compound of any one of embodiments P1 to P25, wherein $R^5$ and $R^6$ are independently hydrogen,

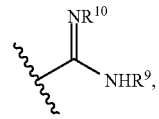

or substituted or unsubstituted heterocycloalkyl, substituted or unsubstituted aryl, or substituted or unsubstituted heteroaryl.

Embodiment P27

The compound of any one of embodiments P1 to P25, wherein $R^5$ and $R^6$ are independently hydrogen,

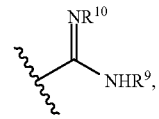

substituted or unsubstituted 3 to 8 membered heterocycloalkyl, substituted or unsubstituted phenyl, or substituted or unsubstituted 5 to 6 membered heteroaryl.

Embodiment P28

The compound of any one of embodiments P1 to P25, wherein $R^5$ is substituted or unsubstituted 5 to 6 membered heteroaryl.

Embodiment P29

The compound of any one of embodiments P1 to P25, wherein $R^6$ is substituted or unsubstituted 5 to 6 membered heteroaryl.

Embodiment P30

The compound of any one of embodiments P1 to P25, wherein $R^5$ and $R^6$ are independently hydrogen,

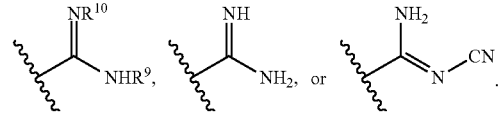

Embodiment P31

The compound of anyone of embodiments P1 to P25, wherein $R^5$ is hydrogen and $R^6$ is

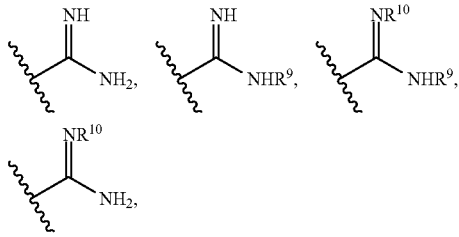

substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P32

The compound of any one of embodiments P1 to P25, wherein $R^5$ is hydrogen and $R^6$ is

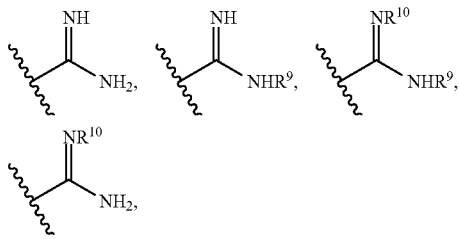

substituted or unsubstituted alkyl, substituted or unsubstituted cycloalkyl, substituted or unsubstituted heterocycloalkyl, substituted or unsubstituted aryl, or substituted or unsubstituted heteroaryl.

Embodiment P33

The compound of any one of embodiments P1 to P25, wherein $R^5$ and $R^6$ are joined to form a substituted or unsubstituted heterocycloalkyl or substituted or unsubstituted heteroaryl.

Embodiment P34

The compound of any one of embodiments P1 to P25, wherein $R^5$ is hydrogen and $R^6$ is

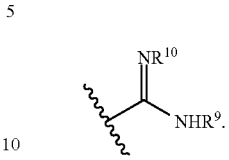

Embodiment P35

The compound of any one of embodiments P1 to P25, wherein $R^5$ is hydrogen and $R^6$ is

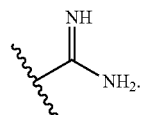 [SMILES: *C(=N)N]

Embodiment P36

The compound of any one of embodiments P1 to P25, wherein $R^5$ is hydrogen and $R^6$ is substituted or unsubstituted heteroaryl.

Embodiment P37

The compound of any one of embodiments P1 to P25, wherein $R^5$ is hydrogen and $R^6$ is substituted or unsubstituted 5 to 6 membered heteroaryl.

Embodiment P38

The compound of any one of embodiments P1 to P37, wherein $R^3$ is hydrogen.

Embodiment P39

The compound of any one of embodiments P1 to P37, wherein $R^3$ is a substituted or unsubstituted alkyl, or substituted or unsubstituted heteroalkyl.

Embodiment P40

The compound of embodiment P1, having the formula:

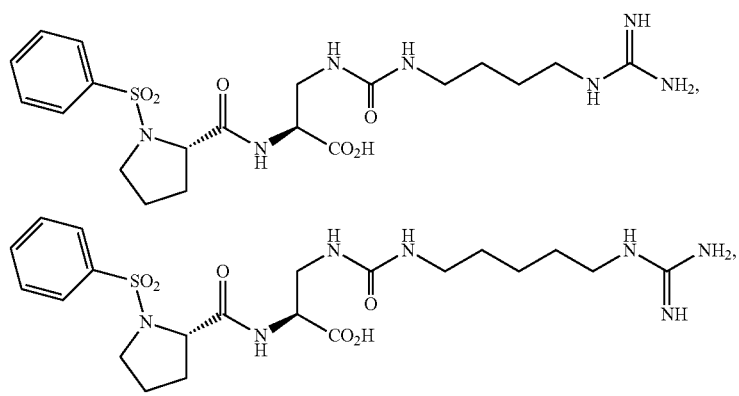

-continued
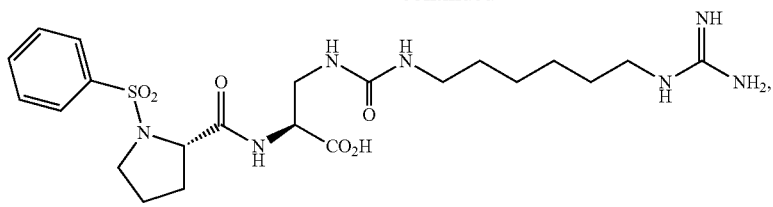
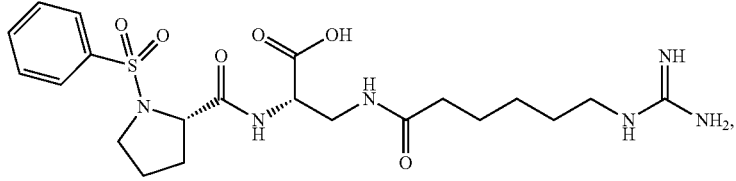
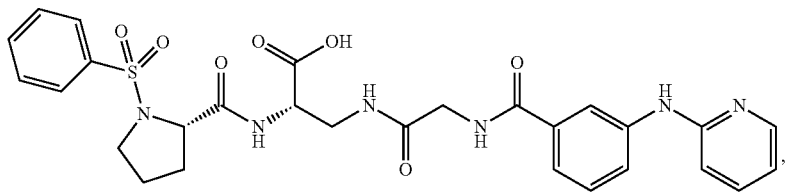
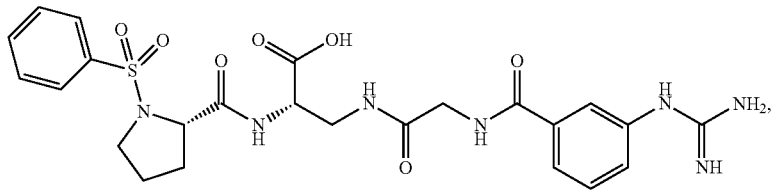
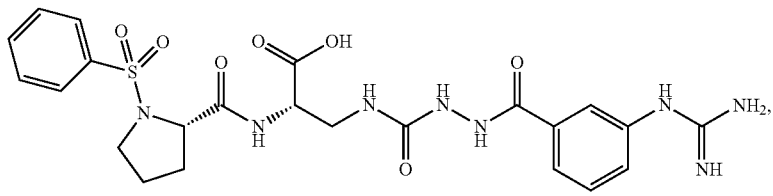
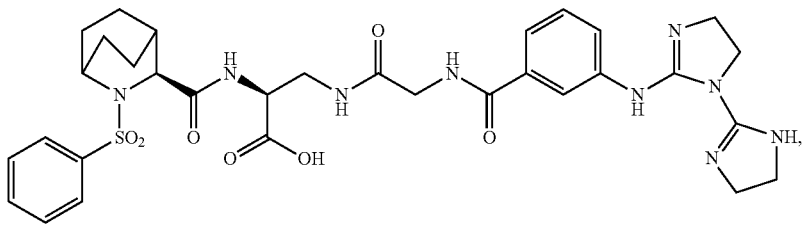
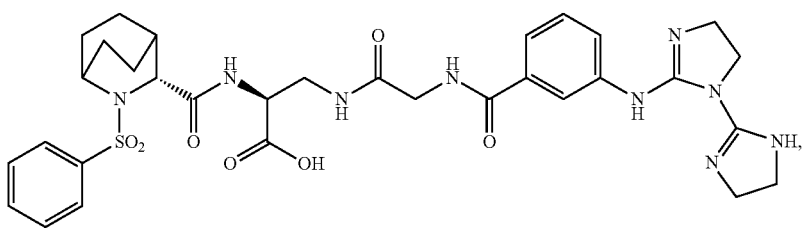
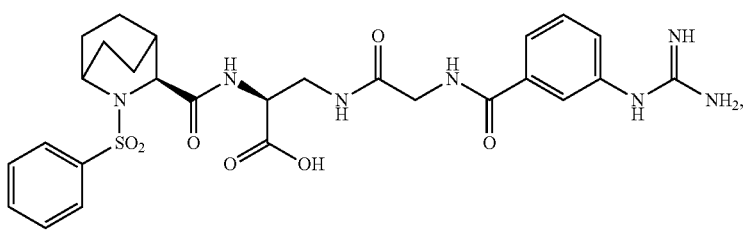

-continued
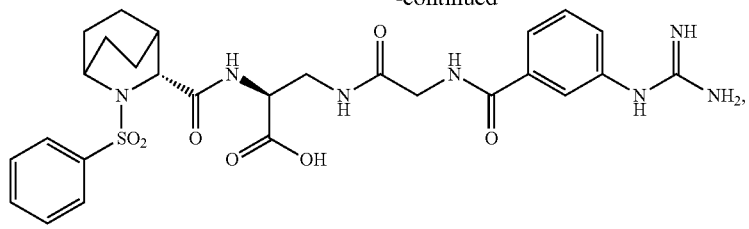
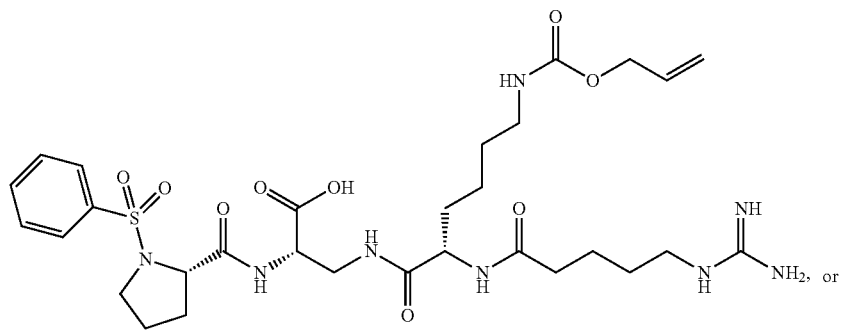
or
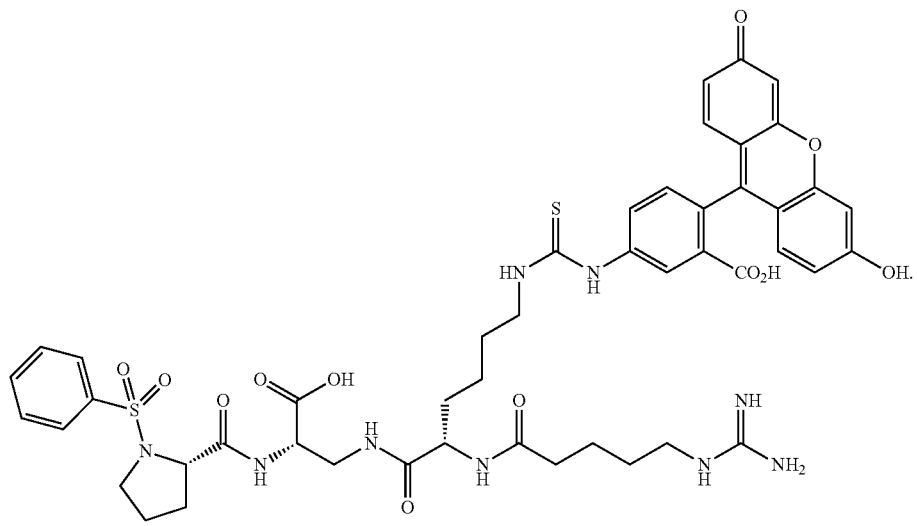
Embodiment P41
The compound of embodiment P1, having the formula:
Embodiment P42
The compound of embodiment P1, having the formula:
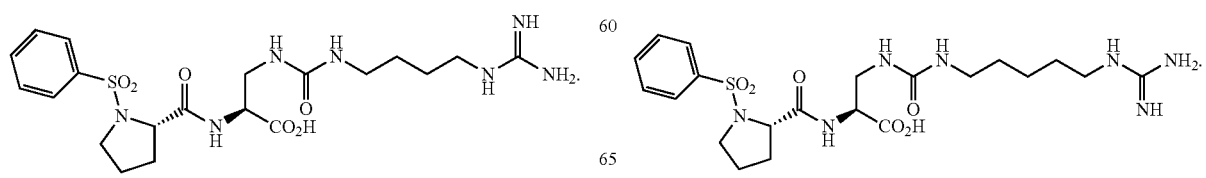

Embodiment P43
The compound of embodiment P1, having the formula:
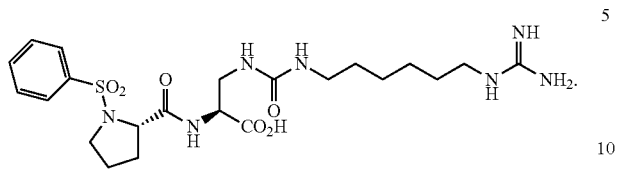
Embodiment P44
The compound of embodiment P1, having the formula:
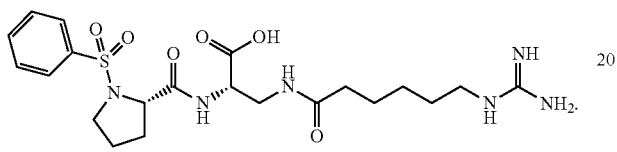
Embodiment P45
The compound of embodiment P1, having the formula:
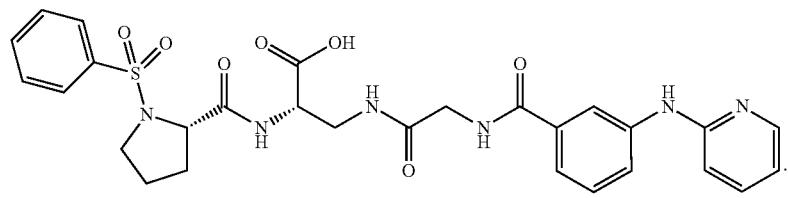 [SMILES: O=C(CNC(=O)c1cccc(Nc2ccccn2)c1)NC[C@H](NC(=O)[C@@H]1CCCN1S(=O)(=O)c1ccccc1)C(=O)O]
Embodiment P46
The compound of embodiment P1, having the formula:
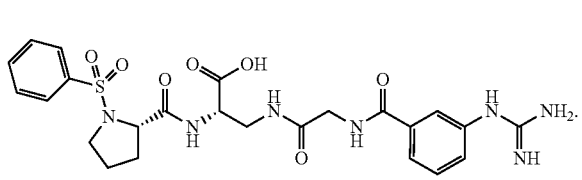 [SMILES: N=C(N)Nc1cccc(C(=O)NCC(=O)NC[C@H](NC(=O)[C@@H]2CCCN2S(=O)(=O)c2ccccc2)C(=O)O)c1]
Embodiment P47
The compound of embodiment P1, having the formula:
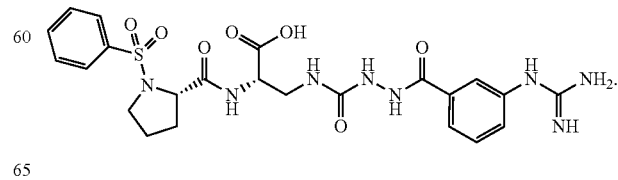

Embodiment P48
The compound of embodiments P1, having the formula:
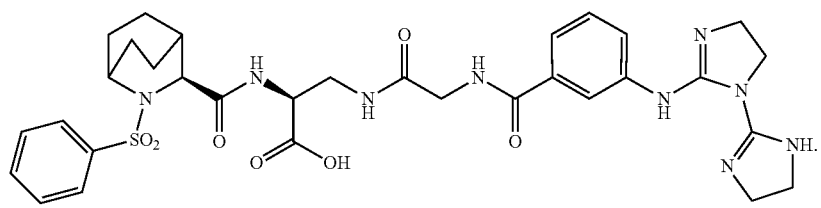 [SMILES: O=C(CNC(=O)c1cccc(NC2=NCCN2C2=NCCN2)c1)NC[C@H](NC(=O)[C@@H]1C2CCC(CC2)N1S(=O)(=O)c1ccccc1)C(=O)O]
Embodiment P49
The compound of embodiment P1, having the formula:
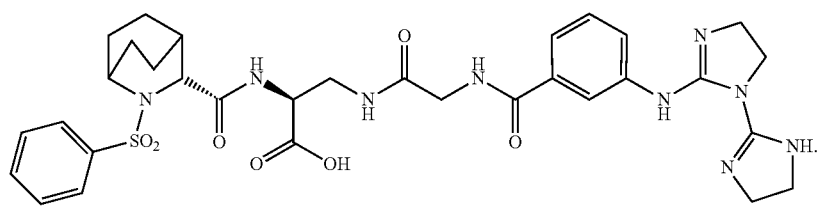
Embodiment P50
The compound of embodiment P1, having the formula:
Embodiment P51
The compound of embodiment P1, having the formula:
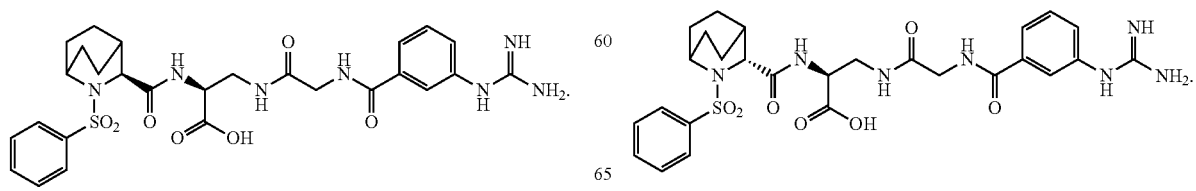

Embodiment P52

The compound of embodiment P1, having the formula:

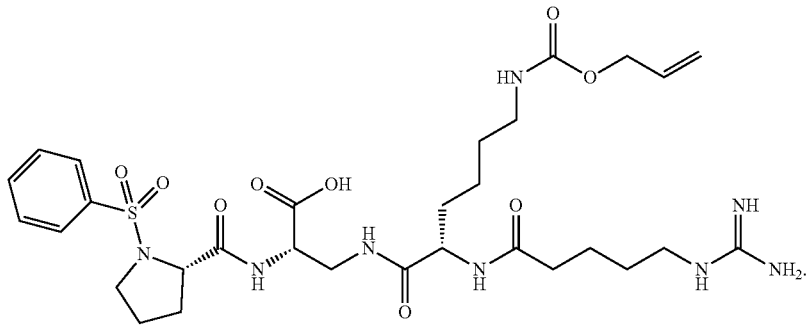 [SMILES: C=CCOC(=O)NCCCC[C@H](NC(=O)CCCCNC(=N)N)C(=O)NC[C@H](NC(=O)[C@@H]1CCCN1S(=O)(=O)c1ccccc1)C(=O)O]

Embodiment P53

The compound of embodiment P1, having the formula:

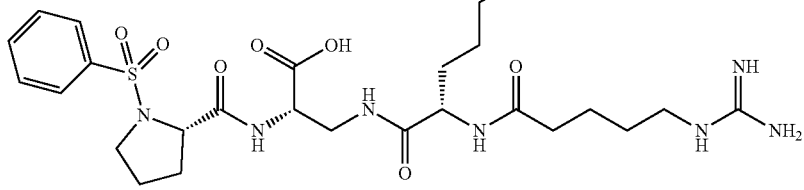

Embodiment P54

A pharmaceutical composition comprising a pharmaceutically acceptable excipient and a compound of one of embodiments P1 to P53.

Embodiment P55

A method for treating asthma, said method comprising administering to a subject in need thereof an effective amount of a compound, or a pharmaceutically acceptable salt thereof, having the formula:

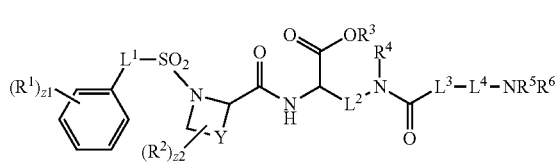

wherein, $R^1$ is independently halogen, $-CX^1_3$, $-CHX^1_2$, $-CH_2X^1$, $-OCX^1_3$, $-OCH_2X^1$, $-OCHX^1_2$, $-CN$, $-SO_{n1}R^{1D}$, $-SO_{v1}NR^{1A}R^{1B}$, $-NHC(O)NR^{1A}R^{1B}$, $-N(O)_{m1}$, $-NR^{1A}R^{1B}$, $-C(O)R^{1C}$, $-C(O)-OR^{1C}$, $-C(O)NR^{1A}R^{1B}$, $-OR^{1D}$, $-NR^{1A}SO_2R^{1D}$, $-NR^{1A}C(O)R^{1C}$, $-NR^{1A}C(O)OR^{1C}$, $-NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl; $L^1$ is a bond or substituted or unsubstituted alkylene, or substituted or unsubstituted heteroalkylene; Y is a bond, $-C-$, $-C-C-$, $-C=C-$, $-C-C-C-$, $-C=C-C-$, $-C-C=C-$, $-O-C-$, $-C-O-$, $-C-O-C-$, $-S-C-$, $-C-S-$, or $-C-S-C-$; $R^2$ is independently halogen, $-CX^2_3$, $-CHX^2_2$, $-CH_2X^2$, $-OCX^2_3$, $-OCH_2X^2$, $-OCHX^2_2$, $-CN$, $-SO_{n2}R^{2D}$, $-SO_{v2}NR^{2A}R^{2B}$, $-NHC(O)NR^{2A}R^{2B}$, $-N(O)_{m2}$, $-NR^{2A}R^{2B}$, $-C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, —NR$^{2A}$C(O)OR$^{2C}$, —NR$^{2A}$OR$^{2C}$, —SO$_2$Ph, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; two adjacent R$^2$ substituents may optionally be joined to form a substituted or unsubstituted cycloalkyl, substituted or unsubstituted heterocycloalkyl, substituted or unsubstituted aryl, or substituted or unsubstituted heteroaryl; R$^3$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a prodrug moiety; R$^4$ is independently hydrogen, —CX$^4_3$, —CN, —COOH, —CONH$_2$, —CHX$^4_2$, —CH$_2$X$^4$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; L$^2$ is unsubstituted alkylene; L$^3$ is a bond, —O—, —S—, —N(R$^7$)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; R$^7$ is hydrogen, —CN, —COOH, —CX$^7_3$, substituted or unsubstituted alkyl, or substituted or unsubstituted heteroalkyl; L$^4$ is —O—, —S—, —N(R$^8$)—, —C(O)—, C(O)O—, —S(O)—, —S(O)$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene; R$^8$ is hydrogen, —CN, —COOH, —CX$^8_3$, substituted or unsubstituted alkyl, or substituted or unsubstituted heteroalkyl; R$^5$ and R$^6$ are independently hydrogen,

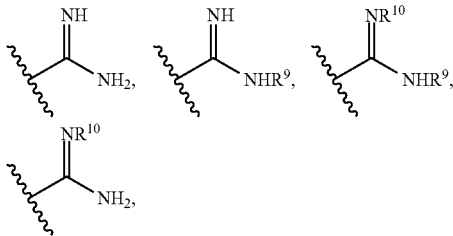

substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^5$ and R$^6$ may optionally be joined to form a substituted or unsubstituted heterocycloalkyl or substituted or unsubstituted heteroaryl; R$^9$ is hydrogen, halogen, —N$_3$, —CX$^9_3$, —CHX$^9_2$, —CH$_2$X$^9$, —CN, —CHO, —OH, —NH$_2$, —COOH, —CONH$_2$, —NO$_2$, —SH, —SO$_2$, —SO$_2$CH$_3$— SO$_3$H, —SO$_4$H, —SO$_2$NH$_2$, —NHNH$_2$, —ONH$_2$, —NHC (O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{10}$ is hydrogen, halogen, —N$_3$, —CX$^{10}_3$, —CHX$^{10}_2$, —CH$_2$X$^{10}$, —CN, —CHO, —OH, —NH$_2$, —COOH, —CONH$_2$, —NO$_2$, —SH, —SO$_2$, —SO$_2$CH$_3$— SO$_3$H, —SO$_4$H, —SO$_2$NH$_2$, —NHNH$_2$, —ONH$_2$, —NHC (O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; each R$^{1A}$, R$^{1B}$, R$^{1C}$, R$^{1D}$, R$^{2A}$, R$^{2B}$, R$^{2C}$, R$^{2D}$, is independently hydrogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{1A}$ and R$^{1B}$ substituents bonded to the same nitrogen atom may optionally be joined to form a substituted or unsubstituted heterocycloalkyl or substituted or unsubstituted heteroaryl; R$^{2A}$ and R$^{2B}$ substituents bonded to the same nitrogen atom may optionally be joined to form a substituted or unsubstituted heterocycloalkyl or substituted or unsubstituted heteroaryl; each X, X$^1$, X$^2$, X$^4$, X$^7$, X$^8$, X$^9$, and X$^{10}$ are independently —F, —Cl, —Br, or —I; n1 and n2 are independently an integer from 0 to 4; m1, m2, v1 and v2 are independently 1 or 2; z1 is an integer from 0 to 5; and z2 is an integer from 0 to 9.

Embodiment P56

The method of embodiment P55, wherein z1 is an integer from 1 to 5.

Embodiment P57

The method of any one of embodiments P55 or P56, wherein Y is —C—C—, —C=C—, —O—C—, —C—O—, —C—O—C—, —C—S—, —S—C, or —C—S—C—.

Embodiment P58

The method of any one of embodiments P55 to P57, wherein

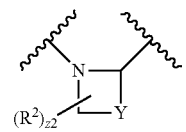

has the formula:

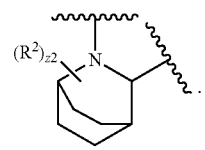

Embodiment P59

The method of any one of embodiments P55 to P57, having the formula:

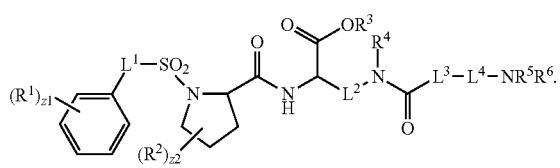

Embodiment P60

The method of any one of embodiments P55 to P59, wherein $L^1$ is a bond.

Embodiment P61

The method of any one of embodiments P55 to P60, wherein $R^1$ is independently halogen, $-N_3$, $-CF_3$, $-CCl_3$, $-CBr_3$, $-CI_3$, $-CN$, $-CHO$, $-OH$, $-NH_2$, $-COOH$, $-CONH_2$, $-SH$, $-SO_2$, $-SO_2CH_3$, $-SO_3H$, $-OSO_3H$, $-SO_2NH_2$, $-NHNH_2$, $-ONH_2$, $-NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety.

Embodiment P62

The method of any one of embodiments P55 to P60, wherein $R^1$ is independently halogen, $-OMe$, $-SMe$, $-SO_2Me$, $-SO_2Ph$, $-COOH$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted phenyl, or substituted or unsubstituted 5 to 6 membered heteroaryl; two adjacent $R^1$ substituents may optionally be joined to form a substituted or unsubstituted $C_3$-$C_8$ cycloalkyl, substituted or unsubstituted 3 to 8 membered heterocycloalkyl, substituted or unsubstituted phenyl, or substituted or unsubstituted 5 to 6 membered heteroaryl.

Embodiment P63

The method of any of embodiments P55 to P62, wherein $L^2$ is unsubstituted $C_1$-$C_2$ alkylene.

Embodiment P64

The method of any of embodiments P55 to P62, wherein $L^2$ is unsubstituted methylene.

Embodiment P65

The method of any of embodiments P55 to P64, wherein $R^4$ is hydrogen.

Embodiment P66

The method of any one of embodiments P55 to P65, wherein $L^3$ is a bond, substituted or unsubstituted $C_1$-$C_8$ alkylene, or substituted or unsubstituted 2 to 8 membered heteroalkylene, substituted or unsubstituted $C_3$-$C_8$ cycloalkylene, substituted or unsubstituted 3 to 8 membered heterocycloalkylene, substituted or unsubstituted phenylene, or substituted or unsubstituted 5 to 6 membered heteroarylene.

Embodiment P67

The method of any one of embodiments P55 to P65, wherein $L^3$ is a bond.

Embodiment P68

The method of any one of embodiments P55 to P65, wherein $L^3$ is substituted or unsubstituted alkylene, or substituted or unsubstituted heteroalkylene.

Embodiment P69

The method of any one of embodiments P55 to P65, wherein $L^3$ is substituted or unsubstituted $C_1$-$C_8$ alkylene, or substituted or unsubstituted 2 to 8 membered heteroalkylene.

Embodiment P70

The method of any one of embodiments P55 to P65, wherein $L^3$ is substituted or unsubstituted 2 to 8 membered heteroalkylene.

Embodiment P71

The method of any one of embodiments P55 to P65, wherein $L^3$ is an oxo-substituted $C_1$-$C_8$ alkylene, or oxo-substituted 2 to 8 membered heteroalkylene.

Embodiment P72

The method of any one of embodiments P55 to P71, wherein $L^4$ is substituted or unsubstituted $C_1$-$C_8$ alkylene, or substituted or unsubstituted 2 to 8 membered heteroalkylene, substituted or unsubstituted $C_3$-$C_8$ cycloalkylene, substituted or unsubstituted 3 to 8 membered heterocycloalkylene, substituted or unsubstituted phenylene, or substituted or unsubstituted 5 to 6 membered heteroarylene.

Embodiment P73

The method of any one of embodiments P55 to P71, wherein $L^4$ is substituted or unsubstituted alkylene, or substituted or unsubstituted heteroalkylene.

Embodiment P74

The method of any one of embodiments P55 to P71, wherein $L^4$ is substituted or unsubstituted $C_1$-$C_8$ alkylene, or substituted or unsubstituted 2 to 8 membered heteroalkylene.

Embodiment P75

The method of any one of embodiments P55 to P70, wherein $L^4$ is substituted or unsubstituted 2 to 8 membered heteroalkylene.

Embodiment P76

The method of any one of embodiments P55 to P71, wherein $L^4$ is an oxo-substituted $C_1$-$C_8$ alkylene, or oxo-substituted 2 to 8 membered heteroalkylene.

Embodiment P77

The method of any one of embodiments P55 to P71, wherein $L^4$ is substituted or unsubstituted arylene, or substituted or unsubstituted heteroarylene.

Embodiment P78

The method of any one of embodiments P55 to 7P1, wherein $L^4$ is substituted or unsubstituted phenylene, or substituted or unsubstituted 5 to 6 membered heteroarylene.

Embodiment P79

The method of any one of embodiments P55 to P71, wherein $L^4$ is unsubstituted phenylene.

Embodiment P80

The method of any one of embodiments P55 to P79, wherein $R^5$ and $R^6$ are independently hydrogen,

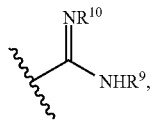

or substituted or unsubstituted heterocycloalkyl, substituted or unsubstituted aryl, or substituted or unsubstituted heteroaryl.

Embodiment P81

The method of any one of embodiments P55 to P79, wherein $R^5$ and $R^6$ are independently hydrogen,

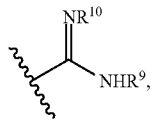

substituted or unsubstituted 3 to 8 membered heterocycloalkyl, substituted or unsubstituted phenyl, or substituted or unsubstituted 5 to 6 membered heteroaryl.

Embodiment P82

The method of any one of embodiments P55 to P79, wherein $R^5$ is substituted or unsubstituted 5 to 6 membered heteroaryl.

Embodiment P83

The method of any one of embodiments P55 to P79, wherein $R^6$ is substituted or unsubstituted 5 to 6 membered heteroaryl.

Embodiment P84

The method of any one of embodiments P55 to P79, wherein $R^5$ and $R^6$ are independently hydrogen,

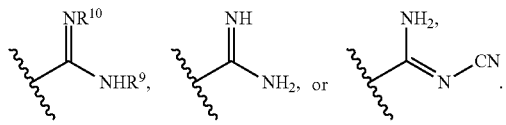

Embodiment P85

The method of any one of embodiments P55 to P79, wherein $R^5$ is hydrogen and $R^6$ is

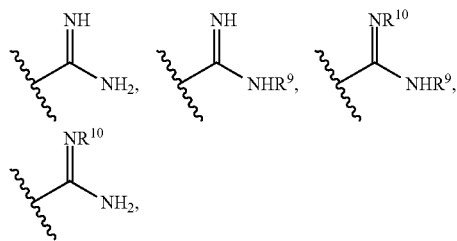

substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P86

The method of any one of embodiments 5P5 to P79, wherein $R^5$ is hydrogen and $R^6$ is

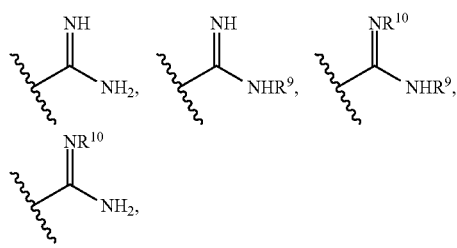

substituted or unsubstituted alkyl, substituted or unsubstituted cycloalkyl, substituted or unsubstituted heterocycloalkyl, substituted or unsubstituted aryl, or substituted or unsubstituted heteroaryl.

Embodiment P87

The method of any one of embodiments P55 to P79, wherein $R^5$ and $R^6$ are joined to form a substituted or unsubstituted heterocycloalkyl or substituted or unsubstituted heteroaryl.

Embodiment P88

The method of any one of embodiments P55 to P79, wherein $R^5$ is hydrogen and $R^6$ is

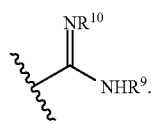

Embodiment P89

The method of any one of embodiments P55 to P79, wherein $R^5$ is hydrogen and $R^6$ is

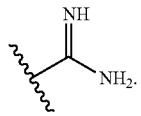 [SMILES: *C(=N)N]

Embodiment P90

The method of any one of embodiments P55 to P79, wherein $R^5$ is hydrogen and $R^6$ is substituted or unsubstituted heteroaryl.

Embodiment P91

The method of any one of embodiments P55 to P79, wherein $R^5$ is hydrogen and $R^6$ is substituted or unsubstituted 5 to 6 membered heteroaryl.

Embodiment P92

The method of any one of embodiments P55 to P91, wherein $R^3$ is hydrogen.

Embodiment P93

The method of any one of embodiments P55 to P91, wherein $R^3$ is a substituted or unsubstituted alkyl, or substituted or unsubstituted heteroalkyl.

Embodiment P94

The method of embodiment P55, having the formula:

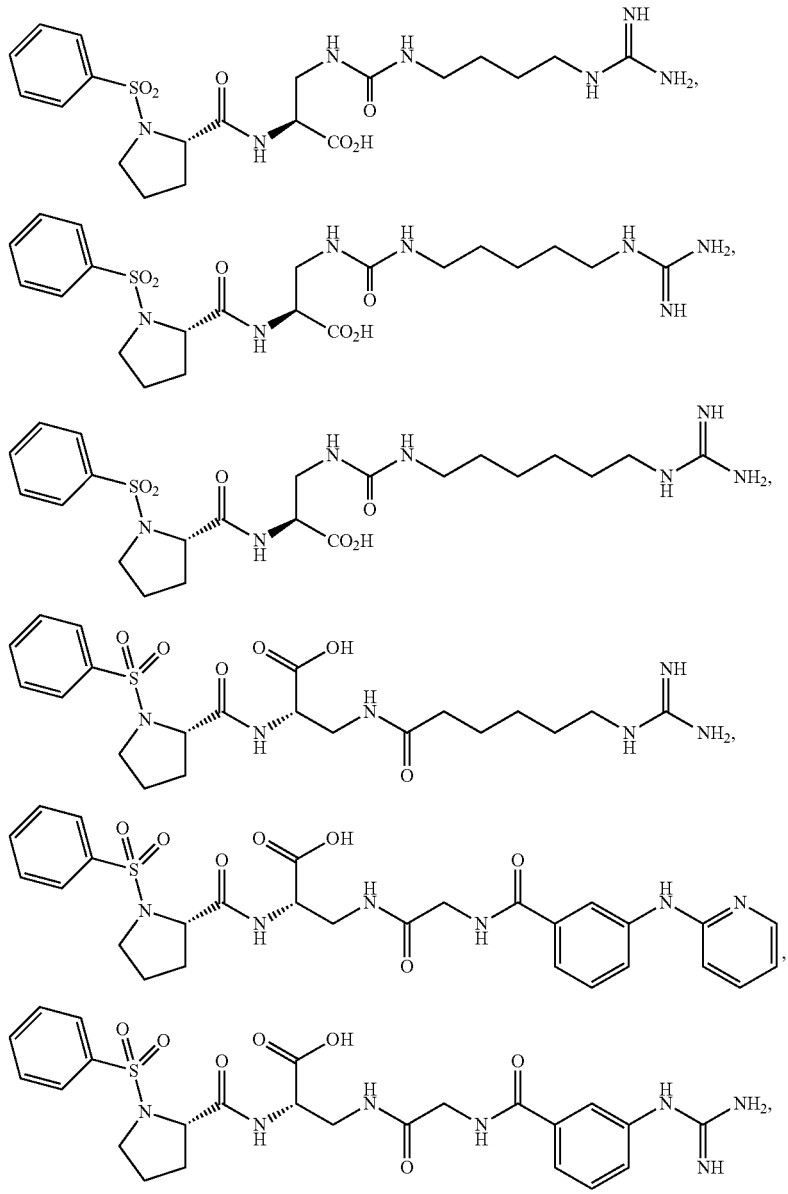

-continued
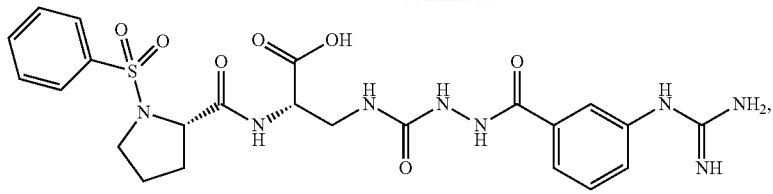
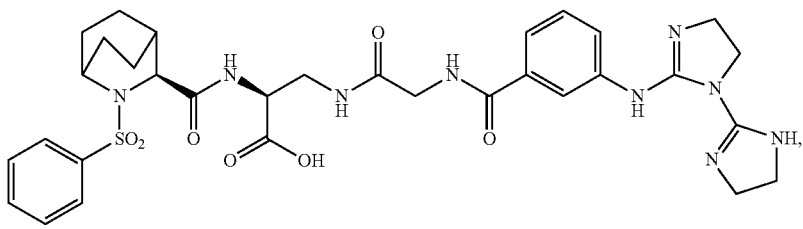
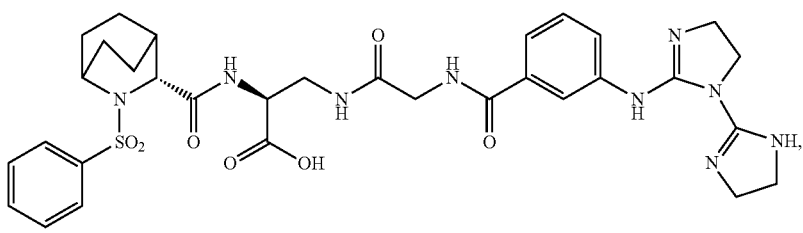
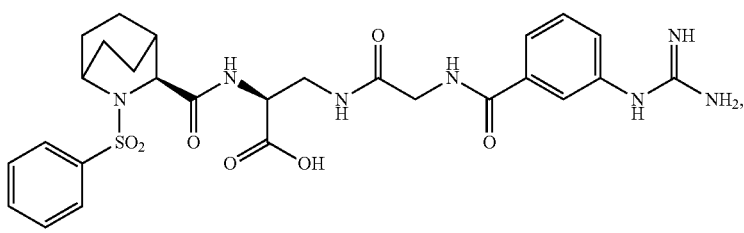
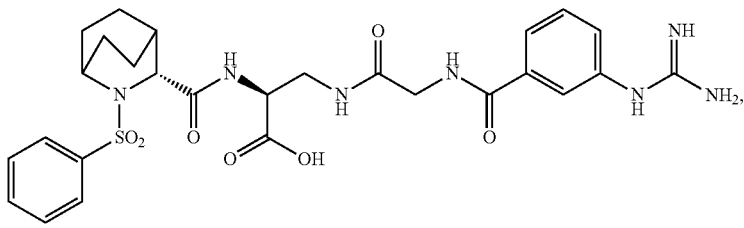
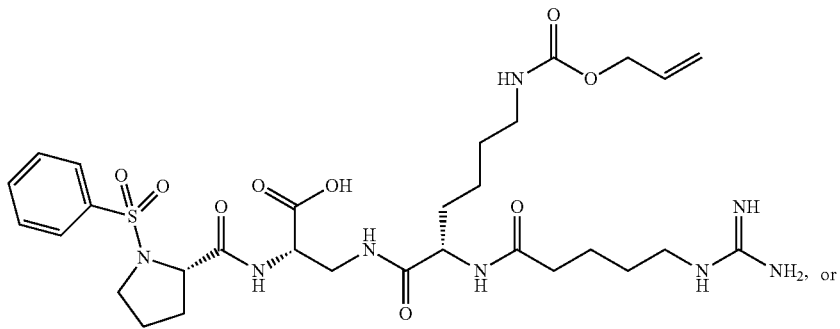

-continued

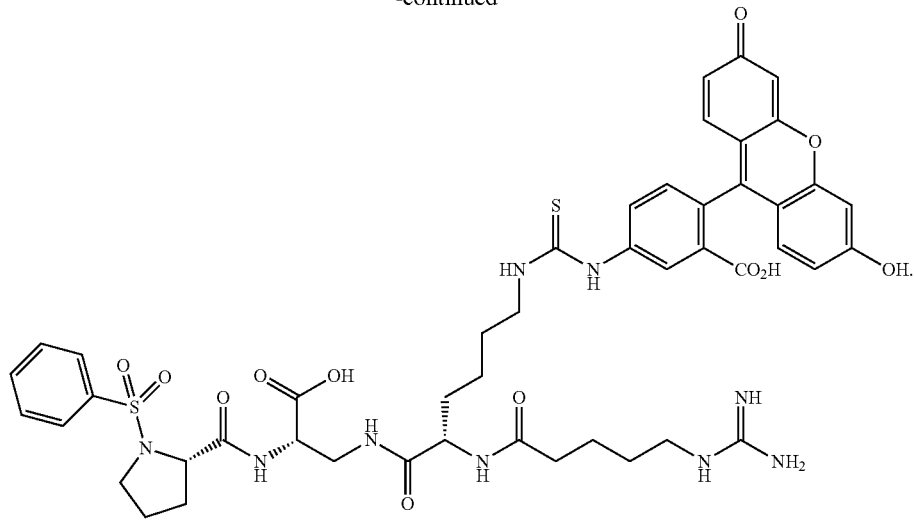

Embodiment P95

The method of embodiment P55, having the formula:

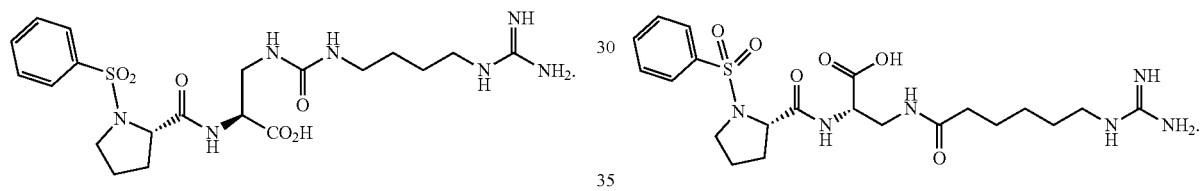

Embodiment P96

The method of embodiment P55, having the formula:

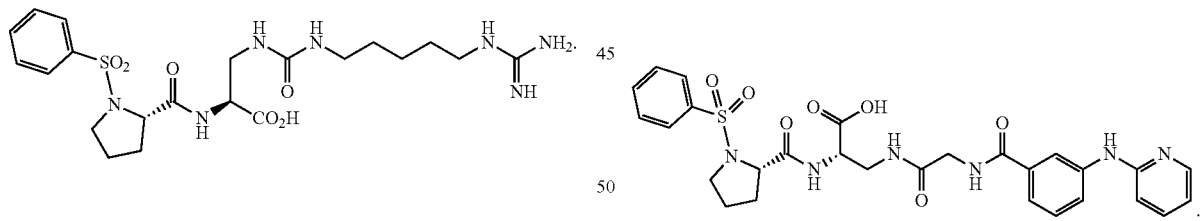

Embodiment P97

The method of embodiment P55, having the formula:

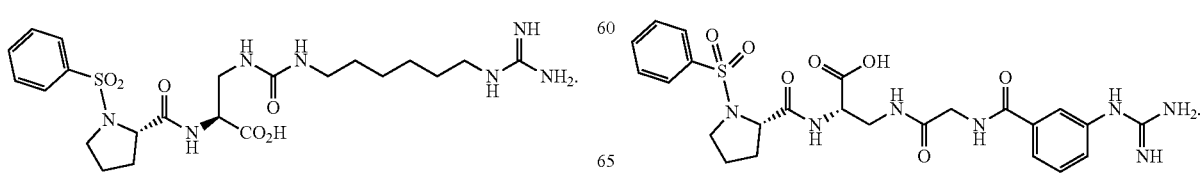

Embodiment P98

The method of embodiment P55, having the formula:

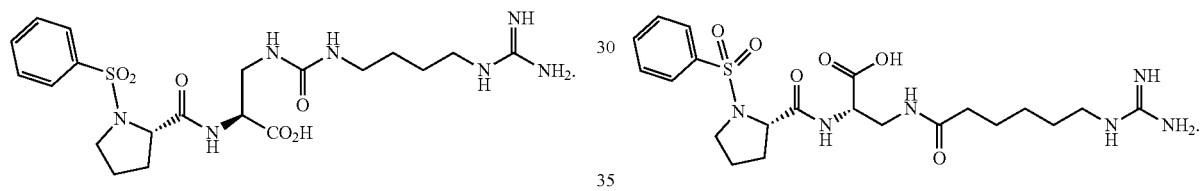

Embodiment P99

The method of embodiment P55, having the formula:

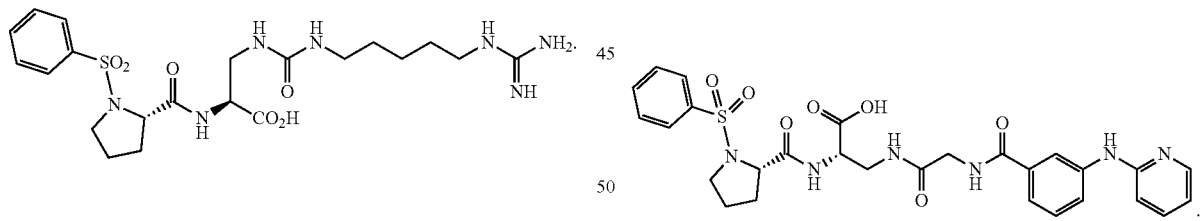

Embodiment P100

The method of embodiment P55, having the formula:

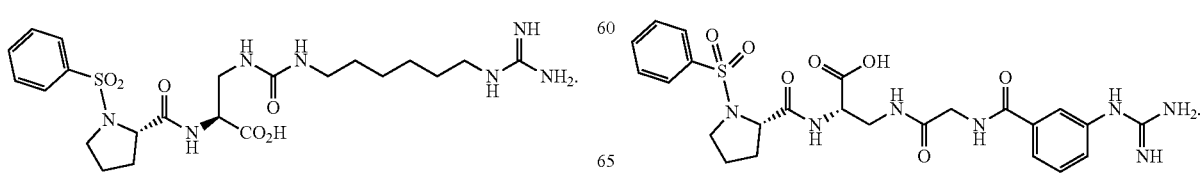

Embodiment P101
The method of embodiment P55, having the formula:
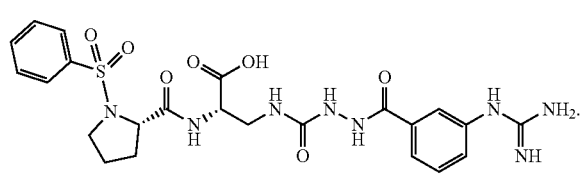 [SMILES: N=C(N)Nc1cccc(C(=O)NNC(=O)NC[C@H](NC(=O)[C@@H]2CCCN2S(=O)(=O)c2ccccc2)C(=O)O)c1]
Embodiment P102
The method of embodiment P55, having the formula:
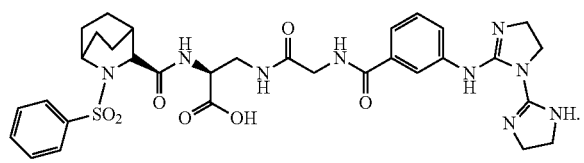
Embodiment P103
The method of embodiment P55, having the formula:
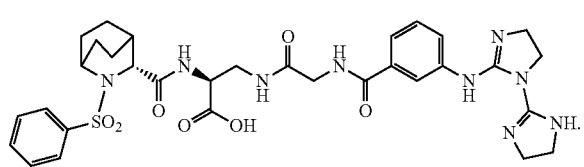 [SMILES: O=C(CNC(=O)c1cccc(NC2=NCCN2C2=NCCN2)c1)NC[C@H](NC(=O)[C@H]1C2CCC(CC2)N1S(=O)(=O)c1ccccc1)C(=O)O]
Embodiment P104
The method of embodiment P55, having the formula:
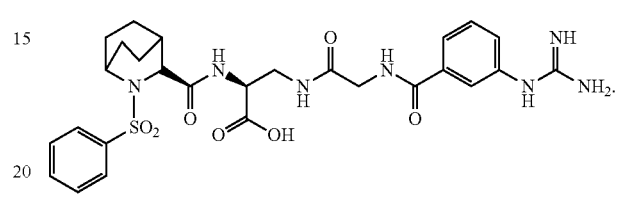
Embodiment P105
The method of embodiment P55, having the formula:
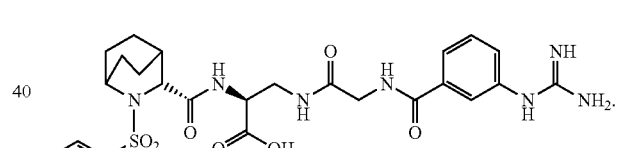
Embodiment P106
The method of embodiment P55, having the formula:
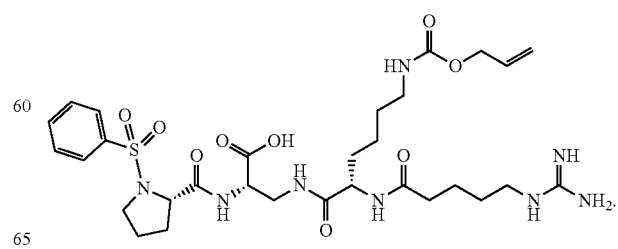

Embodiment P107

The method of embodiment P55, having the formula:

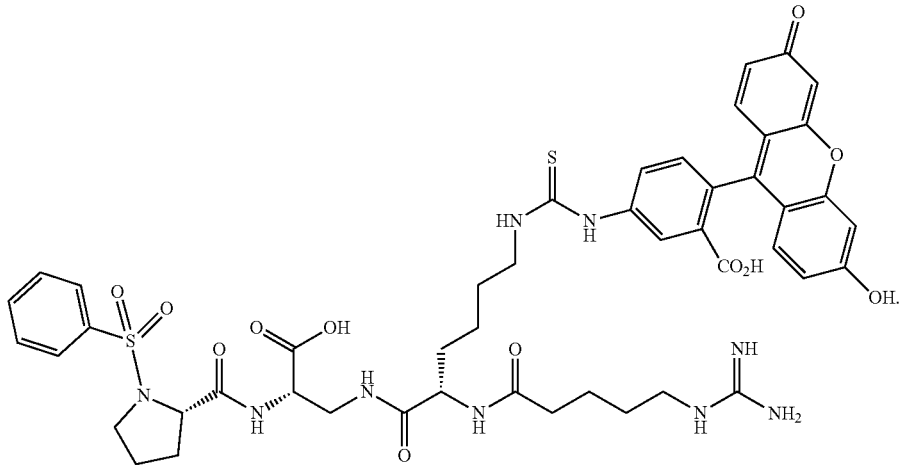 [SMILES: N=C(N)NCCCCC(=O)N[C@@H](CCCCNC(=S)Nc1ccc(-c2c3ccc(=O)cc-3oc3cc(O)ccc23)c(C(=O)O)c1)C(=O)NC[C@H](NC(=O)[C@@H]1CCCN1S(=O)(=O)c1ccccc1)C(=O)O]

Embodiment P108

A method of detecting the presence of α5β1 integrin or inhibiting α5β1 integrin activity, said method comprising contacting an α5β1 integrin with a compound having the formula: A method for treating asthma, said method comprising administering to a subject in need thereof an effective amount of a compound, or a pharmaceutically acceptable salt thereof, having the formula:

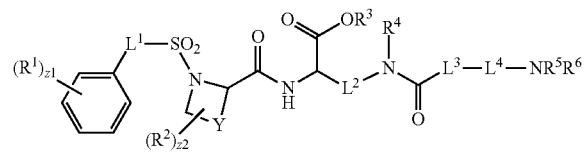

wherein, $R^1$ is independently halogen, —$CX^1_3$, —$CHX^1_2$, —$CH_2X^1$, —$OCX^1_3$, —$OCH_2X^1$, —$OCHX^1_2$, —CN, —$SO_{n1}R^{1D}$, —$SO_{v1}NR^{1A}R^{1B}$, —$NHC(O)NR^{1A}R^{1B}$, —$N(O)_{m1}$, —$NR^{1A}R^{1B}$, —$C(O)R^{1C}$, —$C(O)$—$OR^{1C}$, —$C(O)NR^{1A}R^{1B}$, —$OR^{1D}$, —$NR^{1A}SO_2R^{1D}$, —$NR^{1A}C(O)R^{1C}$, —$NR^{1A}C(O)OR^{1C}$, —$NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl; $L^1$ is a bond or substituted or unsubstituted alkylene, or substituted or unsubstituted heteroalkylene; Y is a bond, —C—, —C—C—, —C=C—, —C—C—C—, —C=C—C—, —C—C=C—, —O—C—, —C—O—, —C—O—C—, —S—C—, —C—S—, or —C—S—C—; $R^2$ is independently halogen, —$CX^2_3$, —$CHX^2_2$, —$CH_2X^2$, —$OCX^2_3$, —$OCH_2X^2$, —$OCHX^2_2$, —CN, —$SO_{n2}R^{2D}$, —$SO_{v2}NR^{2A}R^{2B}$, —$NHC(O)NR^{2A}R^{2B}$, —$N(O)_{m2}$, —$NR^{2A}R^{2B}$, —$C(O)R^{2C}$, —$C(O)$—$OR^{2C}$, —$C(O)NR^{2A}R^{2B}$, —$OR^{2D}$, —$NR^{2A}SO_2R^{2D}$, —$NR^{2A}C(O)R^{2C}$, —$NR^{2A}C(O)OR^{2C}$, —$NR^{2A}OR^{2C}$, —$SO_2Ph$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl; $R^3$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a prodrug moiety; $R^4$ is independently hydrogen, —$CX^4_3$, —CN, —COOH, —$CONH_2$, —$CHX^4_2$, —$CH_2X^4$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $L^2$ is unsubstituted alkylene; $L^3$ is a bond, —O—, —S—, —$N(R^7)$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $R^7$ is hydrogen, —CN, —COOH, —$CX^7_3$, substituted or unsubstituted alkyl, or substituted or unsubstituted heteroalkyl; $L^4$ is —O—, —S—, —$N(R^8)$—, —C(O)—, C(O)O—, —S(O)—, —$S(O)_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene; $R^8$ is hydrogen, —CN, —COOH, —$CX^8_3$, substituted or unsubstituted alkyl, or substituted or unsubstituted heteroalkyl; $R^5$ and $R^6$ are independently hydrogen,

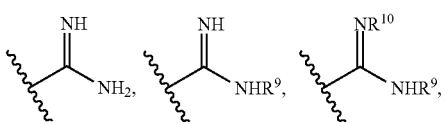

-continued

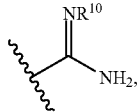

substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^5$ and $R^6$ may optionally be joined to form a substituted or unsubstituted heterocycloalkyl or substituted or unsubstituted heteroaryl; $R^9$ is hydrogen, halogen, —$N_3$, —$CX^9_3$, —$CHX^9_2$, —$CH_2X^9$, —CN, —CHO, —OH, —$NH_2$, —COOH, —$CONH_2$, —$NO_2$, —SH, —$SO_2$, —$SO_2CH_3$—$SO_3H$, —$SO_4H$, —$SO_2NH_2$, —$NHNH_2$, —$ONH_2$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{10}$ is hydrogen, halogen, —$N_3$, —$CX^{10}_3$, —$CHX^{10}_2$, —$CH_2X^{10}$, —CN, —CHO, —OH, —$NH_2$, —COOH, —$CONH_2$, —$NO_2$, —SH, —$SO_2$, —$SO_2CH_3$—$SO_3H$, —$SO_4H$, —$SO_2NH_2$, —$NHNH_2$, —$ONH_2$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; each $R^{1A}$, $R^{1B}$, $R^{1C}$, $R^{1D}$, $R^{2A}$, $R^{2B}$, $R^{2C}$, $R^{2D}$, is independently hydrogen, —$CX_3$, —CN, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; each X, $X^1$, $X^2$, $X^4$, $X^7$, $X^8$, $X^9$, and $X^{10}$ are independently —F, —Cl, —Br, or —I; n1 and n2 are independently an integer from 0 to 4; m1, m2, v1 and v2 are independently 1 or 2; z1 is an integer from 0 to 5; and z2 is an integer from 0 to 9.

Embodiment P109

The method of embodiment P108, wherein said method comprises detecting the presence of α5β1 integrin and inhibiting α5β1 integrin activity.

Embodiment P110

The method of embodiment P108, wherein said method comprises detecting the presence of α5β1 integrin.

Embodiment P111

The method of embodiment P108, wherein said method comprises inhibiting α5β1 integrin activity.

IV. ADDITIONAL EMBODIMENTS

Embodiment 1

A compound having the formula:

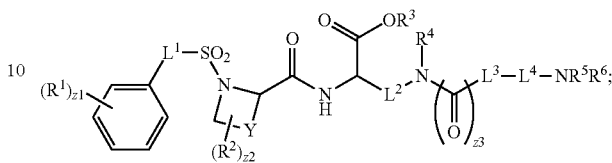

wherein, $R^1$ is independently halogen, —$N_3$, —$CX^1_3$, —$CHX^1_2$, —$CH_2X^1$, —$OCX^1_3$, —$OCH_2X^1$, —$OCHX^1_2$, —CN, —$SO_{n1}R^{1D}$, —$SO_{v1}NR^{1A}R^{1B}$, —$OSO_{v1}R^{1D}$, —NHC(O)$NR^{1A}R^{1B}$, —N(O)$_{m1}$, —$NR^{1A}R^{1B}$, —C(O)$R^{1C}$, —C(O)—$OR^{1C}$, —C(O)$NR^{1A}R^{1B}$, —$OR^{1D}$, —$NR^{1A}SO_2R^{1D}$, —$NR^{1A}C(O)R^{1C}$, —$NR^{1A}C(O)OR^{1C}$, —$NR^{1A}OR^{1C}$, —$ONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl; $L^1$ is a bond or substituted or unsubstituted alkylene, or substituted or unsubstituted heteroalkylene; Y is a bond, —C—, —C—C—, —C=C—, —C—C—C—, —C=C—C—, —C—C=C—, —O—C—, —C—O—, —C—O—C—, —S—C—, —C—S—, or —C—S—C—; $R^2$ is independently halogen, —$CX^2_3$, —$CHX^2_2$, —$CH_2X^2$, —$OCX^2_3$, —$OCH_2X^2$, —$OCHX^2_2$, —CN, —$SO_{n2}R^{2D}$, —$SO_{v2}NR^{2A}R^{2B}$, —NHC(O)$NR^{2A}R^{2B}$, —N(O)$_{m2}$, —$NR^{2A}R^{2B}$, —C(O)$R^{2C}$, —C(O)—$OR^{2C}$, —C(O)$NR^{2A}R^{2B}$, —$OR^{2D}$, —$NR^{2A}SO_2R^{2D}$, —$NR^{2A}C(O)R^{2C}$, —$NR^{2A}C(O)OR^{2C}$, —$NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl; $R^3$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a prodrug moiety; $R^4$ is independently hydrogen, —$CX^4_3$, —CN, —COOH, —$CONH_2$, —$CHX^4_2$, —$CH_2X^4$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $L^2$ is unsubstituted alkylene; $L^3$ is a bond, —O—, —S—, —N($R^7$)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $R^7$ is hydrogen, —CN, —COOH, —$CX^7_3$, substituted or unsubstituted alkyl, or substituted or unsubstituted heteroalkyl; $L^4$ is —O—, —S—, —N(R$^8$)—, —C(O)—, C(O)O—, —S(O)—, —S(O)$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene; R$^8$ is hydrogen, —CN, —COOH, —CX$^8$$_3$, substituted or unsubstituted alkyl, or substituted or unsubstituted heteroalkyl; R$^5$ and R$^6$ are independently hydrogen,

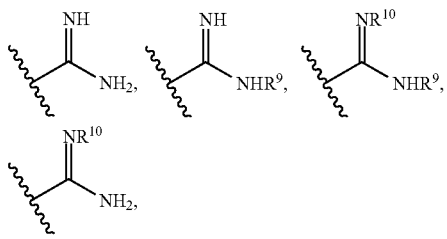

substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R and R$^6$ may optionally be joined to form a substituted or unsubstituted heterocycloalkyl or substituted or unsubstituted heteroaryl; R$^9$ is hydrogen, halogen, —N$_3$, —CX$^9$$_3$, —CHX$^9$$_2$, —CH$_2$X$^9$, —CN, —CHO, —OH, —NH$_2$, —COOH, —CONH$_2$, —NO$_2$, —SH, —SO$_2$, —SO$_2$CH$_3$—SO$_3$H, —SO$_4$H, —SO$_2$NH$_2$, —NHNH$_2$, —ONH$_2$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{10}$ is hydrogen, halogen, —N$_3$, —CX$^{10}$$_3$, —CHX$^{10}$$_2$, —CH$_2$X$^{10}$, —CN, —CHO, —OH, —NH$_2$, —COOH, —CONH$_2$, —NO$_2$, —SH, —SO$_2$, —SO$_2$CH$_3$—SO$_3$H, —SO$_4$H, —SO$_2$NH$_2$, —NHNH$_2$, —ONH$_2$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; each R$^{1A}$, R$^{1B}$, R$^{1C}$, R$^{1D}$, R$^{2A}$R$^{2B}$, R$^{2C}$, R$^{2D}$, is independently hydrogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{1A}$ and R$^{1B}$ substituents bonded to the same nitrogen atom may optionally be joined to form a substituted or unsubstituted heterocycloalkyl or substituted or unsubstituted heteroaryl; R$^{2A}$ and R$^{2B}$ substituents bonded to the same nitrogen atom may optionally be joined to form a substituted or unsubstituted heterocycloalkyl or substituted or unsubstituted heteroaryl; each X, X$^1$, X$^2$, X$^4$, X$^7$, X$^8$, X$^9$, and X$^{10}$ are independently —F, —Cl, —Br, or —I; n1 and n2 are independently an integer from 0 to 3; m1, m2, v1 and v2 are independently 1 or 2; z1 is an integer from 0 to 5; z2 is an integer from 0 to 9; and z3 is 0 or 1; with the proviso that when R$^5$ is hydrogen R$^6$ is not hydrogen.

Embodiment 2

The compound according to embodiment 1 having the formula:

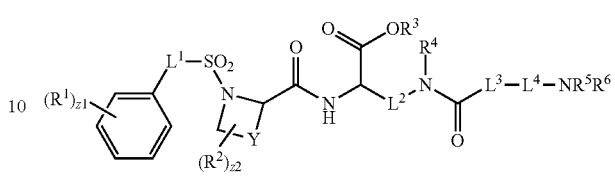

wherein,
R$^1$ is independently halogen, —CX$^1$$_3$, —CHX$^1$$_2$, —CH$_2$X$^1$, —OCX$^1$$_3$, —OCH$_2$X$^1$, —OCHX$^1$$_2$, —CN, —SO$_n$R$^{1D}$, —SO$_{v1}$NR$^{1A}$R$^{1B}$, —NHC(O)NR$^{1A}$R$^{1B}$, —N(O)$_{m1}$, —NR$^{1A}$R$^{1B}$, —C(O)R$^{1C}$, —C(O)—OR$^{1C}$, —C(O)NR$^{1A}$R$^{1B}$, —OR$^{1D}$, —NR$^{1A}$SO$_2$R$^{1D}$, —NR$^{1A}$C(O)R$^{1C}$, —NR$^{1A}$C(O)OR$^{1C}$, —NR$^{1A}$OR$^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety; two adjacent R$^1$ substituents may optionally be joined to form a substituted or unsubstituted cycloalkyl, substituted or unsubstituted heterocycloalkyl, substituted or unsubstituted aryl, or substituted or unsubstituted heteroaryl; L$^1$ is a bond or substituted or unsubstituted alkylene, or substituted or unsubstituted heteroalkylene; Y is a bond, —C—, —C—C—, —C=C—, —C—C—C—, —C=C—C—, —C—C=C—, —O—C—, —C—O—, —C—O—C, —S—C—, —C—S—, or —C—S—C—; R$^2$ is independently halogen, —CX$^2$$_3$, —CHX$^2$$_2$, —CH$_2$X$^2$, —OCX$^2$$_3$, —OCH$_2$X$^2$, —OCHX$^2$$_2$, —CN, —SO$_n$R$^{2D}$, —SO$_{v2}$NR$^{2A}$R$^{2B}$, —NHC(O)NR$^{2A}$R$^{2B}$, —N(O)$_{m2}$, —R$^{2A}$R$^{2B}$, —C(O)R$^{2C}$, —C(O)—OR$^{2C}$, —C(O)NR$^{2A}$R$^{2B}$, —OR$^{2D}$, —NR$^{2A}$SO$_2$R$^{2D}$, —NR$^{2A}$C(O)R$^{2C}$, —NR$^{2A}$C(O)OR$^{2C}$, —NR$^{2A}$OR$^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; two adjacent R$^2$ substituents may optionally be joined to form a substituted or unsubstituted cycloalkyl, substituted or unsubstituted heterocycloalkyl, substituted or unsubstituted aryl, or substituted or unsubstituted heteroaryl; R$^3$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a prodrug moiety; R$^4$ is independently hydrogen, —CX$^4$$_3$, —CN, —COOH, —CONH$_2$, —CHX$^4$$_2$, —CH$_2$X$^4$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; L$^2$ is unsubstituted alkylene; L$^3$ is a bond, —O—, —S—, —N(R$^7$)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; R$^7$ is hydrogen, —CN, —COOH, —CX$^7$$_3$, substituted or unsubstituted alkyl, or substituted or unsubstituted heteroalkyl; L$^4$ is —O—, —S—, —N(R$^8$)—, —C(O)—, C(O)O—, —S(O)—, —S(O)$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene; $R^8$ is hydrogen, —CN, —COOH, —$CX^8_3$, substituted or unsubstituted alkyl, or substituted or unsubstituted heteroalkyl; $R^5$ and $R^6$ are independently hydrogen,

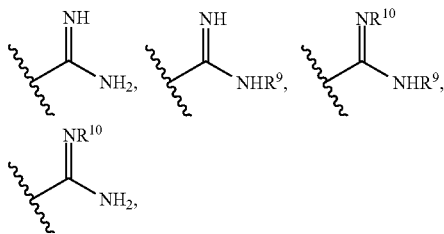

substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^5$ and $R^6$ may optionally be joined to form a substituted or unsubstituted heterocycloalkyl or substituted or unsubstituted heteroaryl; $R^9$ is hydrogen, halogen, —$N_3$, —$CX^9_3$, —$CHX^9_2$, —$CH_2X^9$, —CN, —CHO, —OH, —$NH_2$, —COOH, —$CONH_2$, —$NO_2$, —SH, —$SO_2$, —$SO_2CH_3$—$SO_3H$, —$SO_4H$, —$SO_2NH_2$, —$NHNH_2$, —$ONH_2$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{10}$ is hydrogen, halogen, —$N_3$, —$CX^{10}_3$, —$CHX^{10}_2$, —$CH_2X^{10}$, —CN, —CHO, —OH, —$NH_2$, —COOH, —$CONH_2$, —$NO_2$, —SH, —$SO_2$, —$SO_2CH_3$—$SO_3H$, —$SO_4H$, —$SO_2NH_2$, —$NHNH_2$, —$ONH_2$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; each $R^{1A}$, $R^{1B}$, $R^{1C}$, $R^{1D}$, $R^{2A}$, $R^{2B}$, $R^{2C}$, $R^{2D}$, is independently hydrogen, —$CX_3$, —CN, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; each X, $X^1$, $X^2$, $X^4$, $X^7$, $X^8$, $X^9$, and $X^{10}$ are independently —F, —Cl, —Br, or —I; n1 and n2 are independently an integer from 0 to 4; m1, m2, v1 and v2 are independently 1 or 2; z1 is an integer from 0 to 5; and z2 is an integer from 0 to 9; with the proviso that when $R^5$ is hydrogen $R^6$ is not hydrogen.

Embodiment 3

The compound of embodiment 1, wherein z1 is an integer from 1 to 5.

Embodiment 4

The compound of embodiment 1, wherein z1 is 0.

Embodiment 5

The compound of any one of embodiments 1 to 3, wherein Y is —C—C—, —C=C—, —O—C—, —C—O—, —C—O—C—, —C—S—, —S—C, or —C—S—C—.

Embodiment 6

The compound of any one of embodiments 1 to 5, wherein

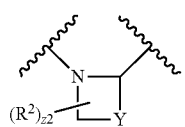

has the formula:

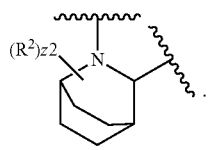

Embodiment 7

The compound of any one of embodiments 1 to 5 having the formula:

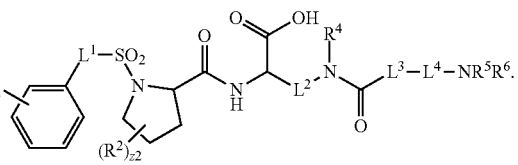

Embodiment 8

The compound of any one of embodiments 1 to 7, wherein $L^1$ is a bond.

Embodiment 9

The compound of any one of embodiments 1 to 8, wherein $R^1$ is independently halogen, —$N_3$, —$CF_3$, —$CCl_3$, —$CBr_3$, —$CI_3$, —CN, —CHO, —OH, —$NH_2$, —COOH, —$CONH_2$, —SH, —$SO_2$, —$SO_2CH_3$—$SO_3H$, —$SO_2NH_2$, —$NHNH_2$, —$ONH_2$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety.

Embodiment 10

The compound of any one of embodiments 1 to 8, wherein $R^1$ is independently halogen, —OMe, —SMe, —$SO_2$Me, —SO$_2$Ph, —COOH, substituted or unsubstituted C$_1$-C$_8$ alkyl, substituted or unsubstituted 2 to 8 membered heteroalkyl, substituted or unsubstituted C$_3$-C$_8$ cycloalkyl, substituted or unsubstituted 3 to 8 membered heterocycloalkyl, substituted or unsubstituted phenyl, or substituted or unsubstituted 5 to 6 membered heteroaryl; two adjacent R$^1$ substituents may optionally be joined to form a substituted or unsubstituted C$_3$-C$_8$ cycloalkyl, substituted or unsubstituted 3 to 8 membered heterocycloalkyl, substituted or unsubstituted phenyl, or substituted or unsubstituted 5 to 6 membered heteroaryl.

Embodiment 11

The compound of any of embodiments 1 to 10, wherein L$^2$ is unsubstituted C$_1$-C$_2$ alkylene.

Embodiment 12

The compound of any of embodiments 1 to 10, wherein L$^2$ is unsubstituted methylene.

Embodiment 13

The compound of any of embodiments 1 to 12, wherein R$^4$ is hydrogen.

Embodiment 14

The compound of any one of embodiments 1 to 13, wherein L$^3$ is a bond, substituted or unsubstituted C$_1$-C$_8$ alkylene, or substituted or unsubstituted 2 to 8 membered heteroalkylene, substituted or unsubstituted C$_3$-C$_8$ cycloalkylene, substituted or unsubstituted 3 to 8 membered heterocycloalkylene, substituted or unsubstituted phenylene, or substituted or unsubstituted 5 to 6 membered heteroarylene.

Embodiment 15

The compound of any one of embodiments 1 to 13, wherein L$^3$ is a bond.

Embodiment 16

The compound of any one of embodiments 1 to 13, wherein L$^3$ is substituted or unsubstituted alkylene, or substituted or unsubstituted heteroalkylene.

Embodiment 17

The compound of any one of embodiments 1 to 13, wherein L$^3$ is substituted or unsubstituted C$_1$-C$_8$ alkylene, or substituted or unsubstituted 2 to 8 membered heteroalkylene.

Embodiment 18

The compound of any one of embodiments 1 to 13, wherein L$^3$ is substituted or unsubstituted 2 to 8 membered heteroalkylene.

Embodiment 19

The compound of any one of embodiments 1 to 13, wherein L$^3$ is an oxo-substituted C$_1$-C$_8$ alkylene, or oxo-substituted 2 to 8 membered heteroalkylene.

Embodiment 20

The compound of any one of embodiments 1 to 19, wherein L$^4$ is substituted or unsubstituted C$_1$-C$_8$ alkylene, or substituted or unsubstituted 2 to 8 membered heteroalkylene, substituted or unsubstituted C$_3$-C$_8$ cycloalkylene, substituted or unsubstituted 3 to 8 membered heterocycloalkylene, substituted or unsubstituted phenylene, or substituted or unsubstituted 5 to 6 membered heteroarylene.

Embodiment 21

The compound of any one of embodiments 1 to 19, wherein L$^4$ is substituted or unsubstituted alkylene, or substituted or unsubstituted heteroalkylene.

Embodiment 22

The compound of any one of embodiments 1 to 19, wherein L$^4$ is substituted or unsubstituted C$_1$-C$_8$ alkylene, or substituted or unsubstituted 2 to 8 membered heteroalkylene.

Embodiment 23

The compound of any one of embodiments 1 to 19, wherein L$^4$ is substituted or unsubstituted 2 to 8 membered heteroalkylene.

Embodiment 24

The compound of any one of embodiments 1 to 19, wherein L$^4$ is an oxo-substituted C$_1$-C$_8$ alkylene, or oxo-substituted 2 to 8 membered heteroalkylene.

Embodiment 25

The compound of any one of embodiments 1 to 19, wherein L$^4$ is substituted or unsubstituted arylene, or substituted or unsubstituted heteroarylene.

Embodiment 26

The compound of any one of embodiments 1 to 19, wherein L$^4$ is substituted or unsubstituted phenylene, or substituted or unsubstituted 5 to 6 membered heteroarylene.

Embodiment 27

The compound of any one of embodiments 1 to 19, wherein L$^4$ is unsubstituted phenylene.

Embodiment 28

The compound of any one of embodiments 1 to 27, wherein R$^5$ and R$^6$ are independently hydrogen,

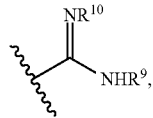

or substituted or unsubstituted heterocycloalkyl, substituted or unsubstituted aryl, or substituted or unsubstituted heteroaryl.

Embodiment 29

The compound of any one of embodiments 1 to 27, wherein $R^5$ and $R^6$ are independently hydrogen,

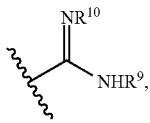

substituted or unsubstituted 3 to 8 membered heterocycloalkyl, substituted or unsubstituted phenyl, or substituted or unsubstituted 5 to 6 membered heteroaryl.

Embodiment 30

The compound of any one of embodiments 1 to 27, wherein $R^5$ is substituted or unsubstituted 5 to 6 membered heteroaryl.

Embodiment 31

The compound of any one of embodiments 1 to 27, wherein $R^6$ is substituted or unsubstituted 5 to 6 membered heteroaryl.

Embodiment 32

The compound of any one of embodiments 1 to 27, wherein $R^5$ and $R^6$ are independently hydrogen,

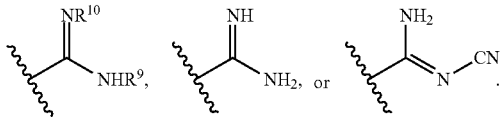

Embodiment 33

The compound of any one of embodiments 1 to 27, wherein $R^5$ is hydrogen and $R^6$ is

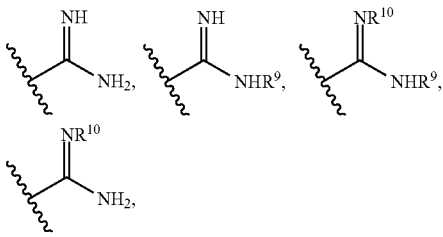

substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 34

The compound of any one of embodiments 1 to 27, wherein $R^5$ is hydrogen and $R^6$ is

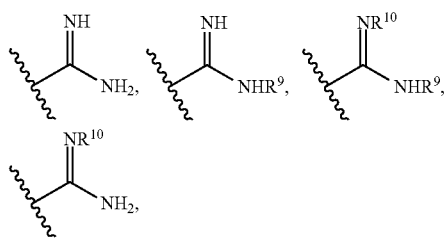

substituted or unsubstituted alkyl, substituted or unsubstituted cycloalkyl, substituted or unsubstituted heterocycloalkyl, substituted or unsubstituted aryl, or substituted or unsubstituted heteroaryl.

Embodiment 35

The compound of any one of embodiments 1 to 27, wherein $R^5$ and $R^6$ are joined to form a substituted or unsubstituted heterocycloalkyl or substituted or unsubstituted heteroaryl.

Embodiment 36

The compound of any one of embodiments 1 to 27, wherein $R^5$ is hydrogen and $R^6$ is

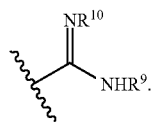

Embodiment 37

The compound of any one of embodiments 1 to 27, wherein $R^5$ is hydrogen and $R^6$ is

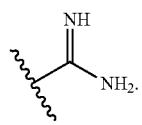

Embodiment 38

The compound of any one of embodiments 1 to 27, wherein $R^5$ is hydrogen and $R^6$ is substituted or unsubstituted heteroaryl.

Embodiment 39

The compound of any one of embodiments 1 to 27, wherein $R^5$ is hydrogen and $R^6$ is substituted or unsubstituted 5 to 6 membered heteroaryl.

Embodiment 40

The compound of any one of embodiments 1 to 39, wherein $R^3$ is hydrogen.

Embodiment 41
The compound of any one of embodiments 1 to 39, wherein R³ is a substituted or unsubstituted alkyl, or substituted or unsubstituted heteroalkyl.
Embodiment 42
The compound of embodiment 1, having the formula:
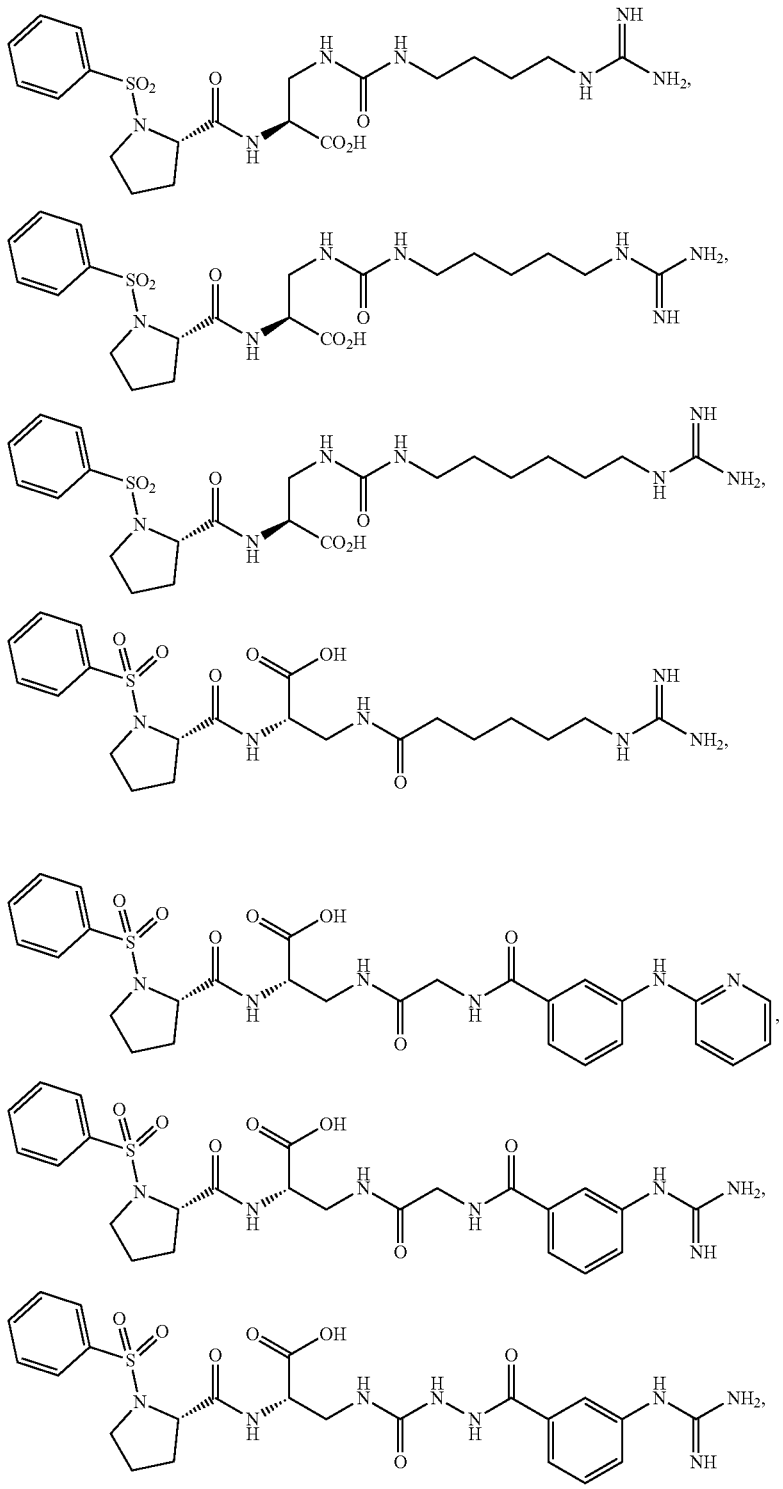

-continued
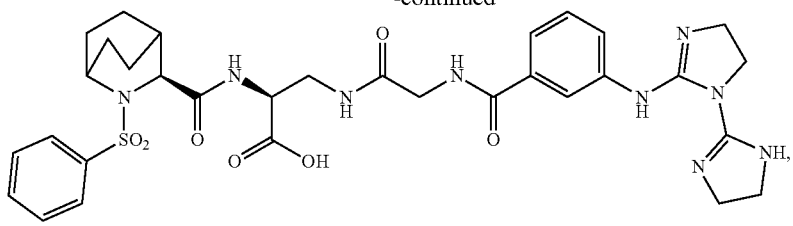
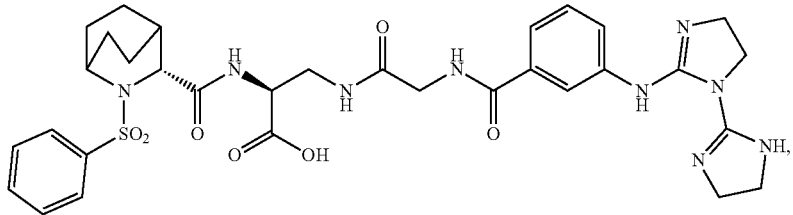
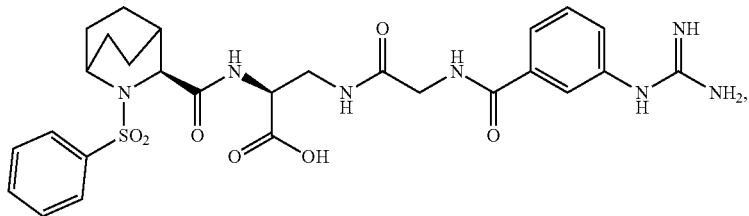
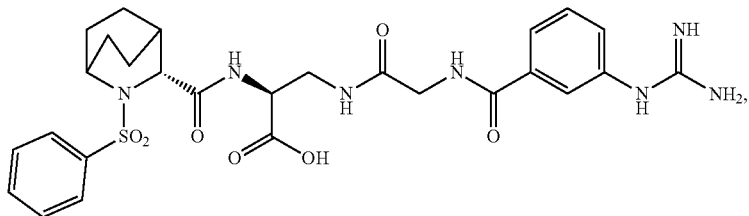
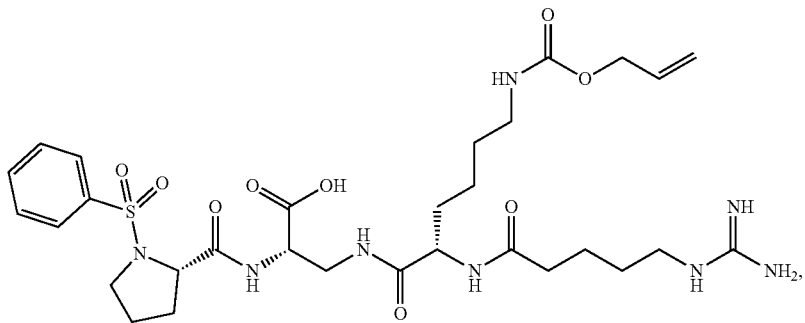
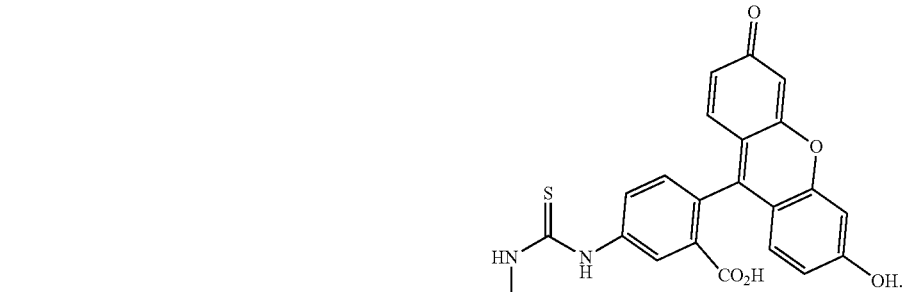
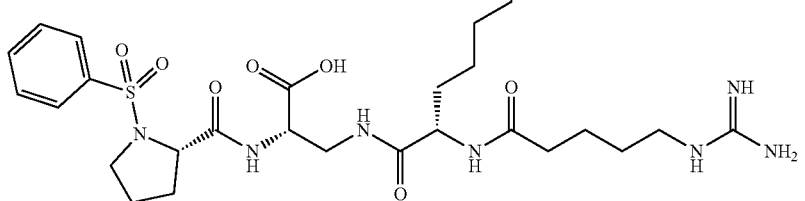

-continued
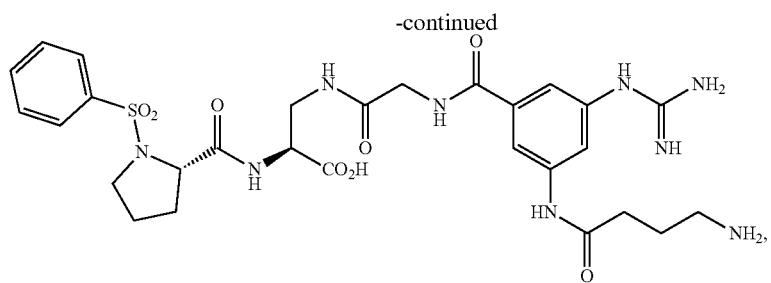
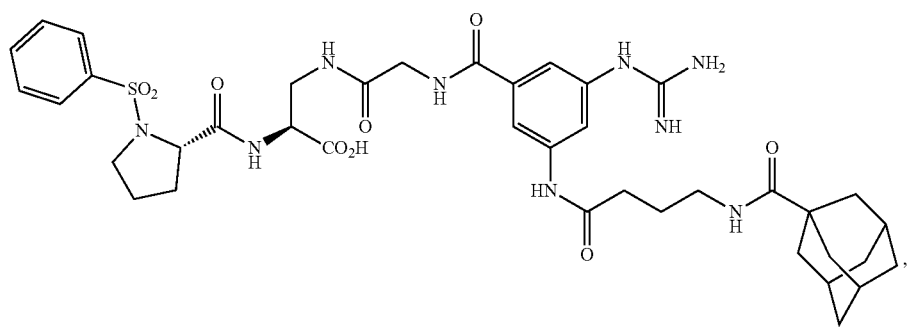
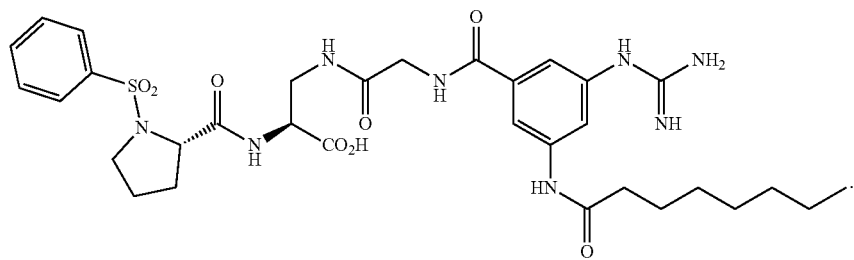
Embodiment 43
The compound of embodiment 1, having the formula:
Embodiment 44
The compound of embodiment 1, having the formula:
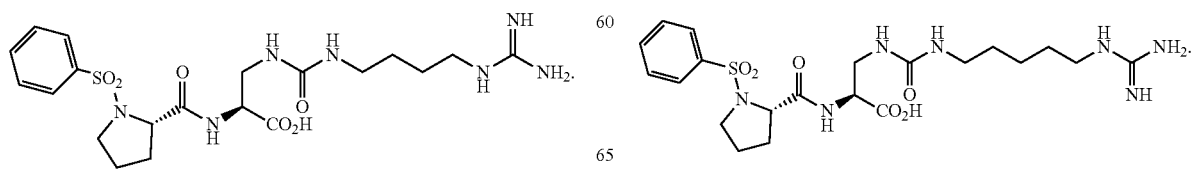

Embodiment 45
The compound of embodiment 1, having the formula:
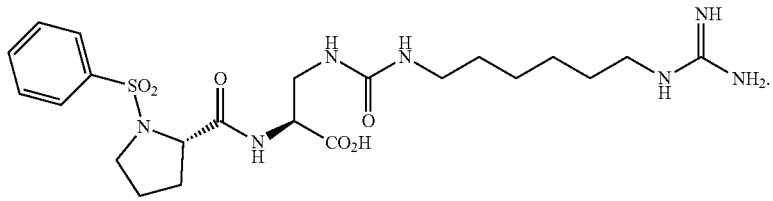 [SMILES: N=C(N)NCCCCCCNC(=O)NC[C@H](NC(=O)[C@@H]1CCCN1S(=O)(=O)c1ccccc1)C(=O)O]
Embodiment 46
The compound of embodiment 1, having the formula:
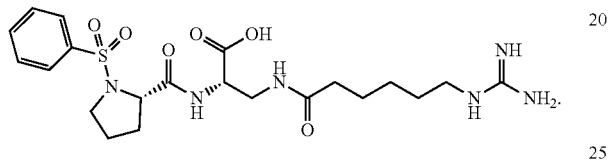
47. The compound of embodiment 1, having the formula:
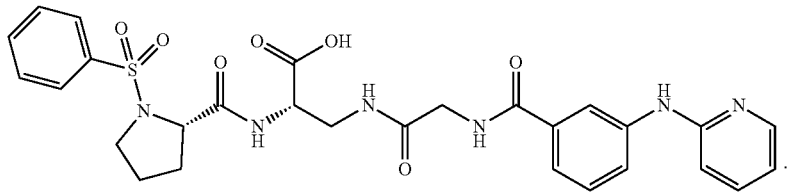 [SMILES: O=C(CNC(=O)c1cccc(Nc2ccccn2)c1)NC[C@H](NC(=O)[C@@H]1CCCN1S(=O)(=O)c1ccccc1)C(=O)O]
Embodiment 48
The compound of embodiment 1, having the formula:
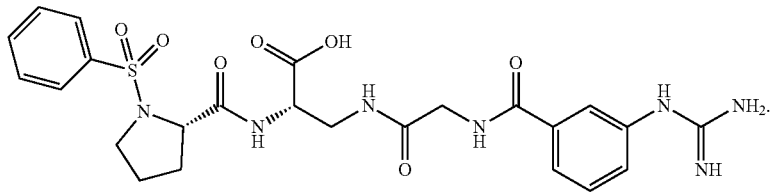 [SMILES: N=C(N)Nc1cccc(C(=O)NCC(=O)NC[C@H](NC(=O)[C@@H]2CCCN2S(=O)(=O)c2ccccc2)C(=O)O)c1]
Embodiment 49
The compound of embodiment 1, having the formula:
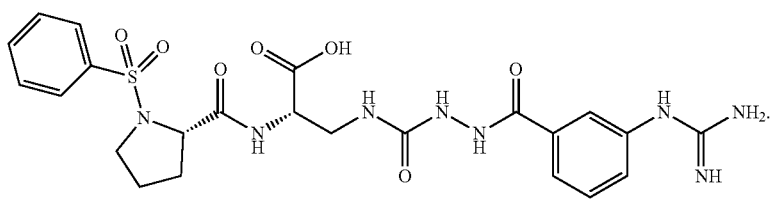 [SMILES: N=C(N)Nc1cccc(C(=O)NNC(=O)NC[C@H](NC(=O)[C@@H]2CCCN2S(=O)(=O)c2ccccc2)C(=O)O)c1]

Embodiment 50
The compound of embodiment 1, having the formula:
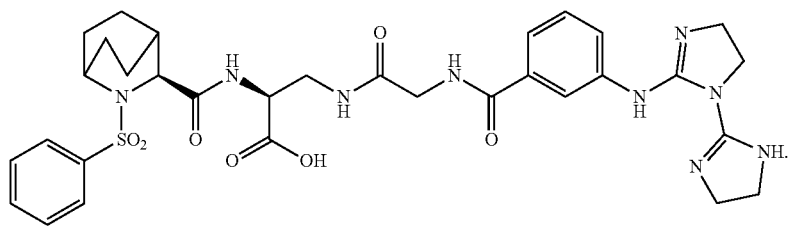 [SMILES: O=C(CNC(=O)c1cccc(NC2=NCCN2C2=NCCN2)c1)NC[C@H](NC(=O)[C@@H]1C2CCC(CC2)N1S(=O)(=O)c1ccccc1)C(=O)O]
Embodiment 51
The compound of embodiment 1, having the formula:
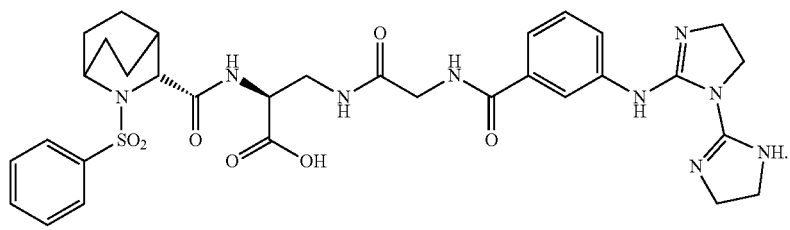
Embodiment 52
The compound of embodiment 1, having the formula:
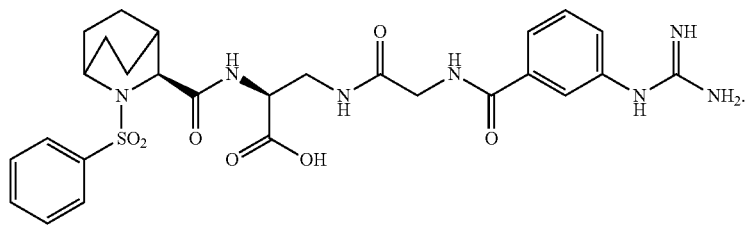 [SMILES: N=C(N)Nc1cccc(C(=O)NCC(=O)NC[C@H](NC(=O)[C@@H]2C3CCC(CC3)N2S(=O)(=O)c2ccccc2)C(=O)O)c1]
Embodiment 53
The compound of embodiment 1, having the formula:
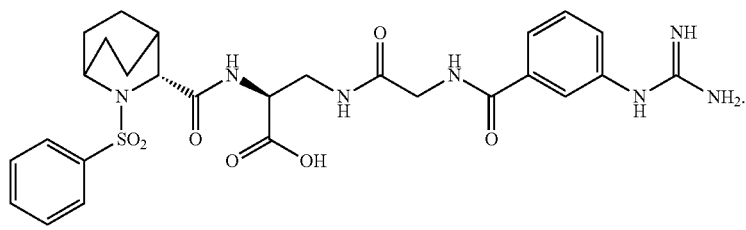 [SMILES: N=C(N)Nc1cccc(C(=O)NCC(=O)NC[C@H](NC(=O)[C@H]2C3CCC(CC3)N2S(=O)(=O)c2ccccc2)C(=O)O)c1]

Embodiment 54
The compound of embodiment 1, having the formula:
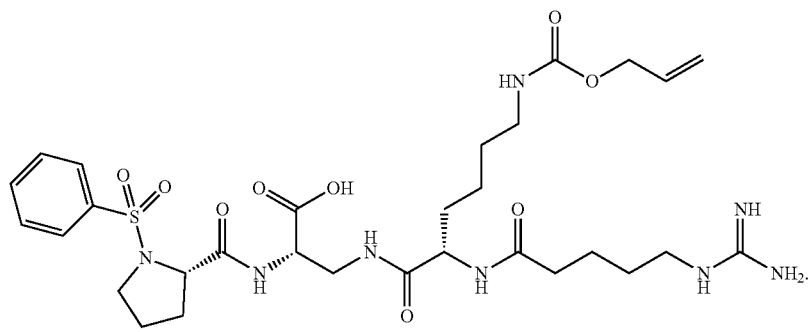 [SMILES: C=CCOC(=O)NCCCC[C@H](NC(=O)CCCCNC(=N)N)C(=O)NC[C@H](NC(=O)[C@@H]1CCCN1S(=O)(=O)c1ccccc1)C(=O)O]
Embodiment 55
The compound of embodiment 1, having the formula:
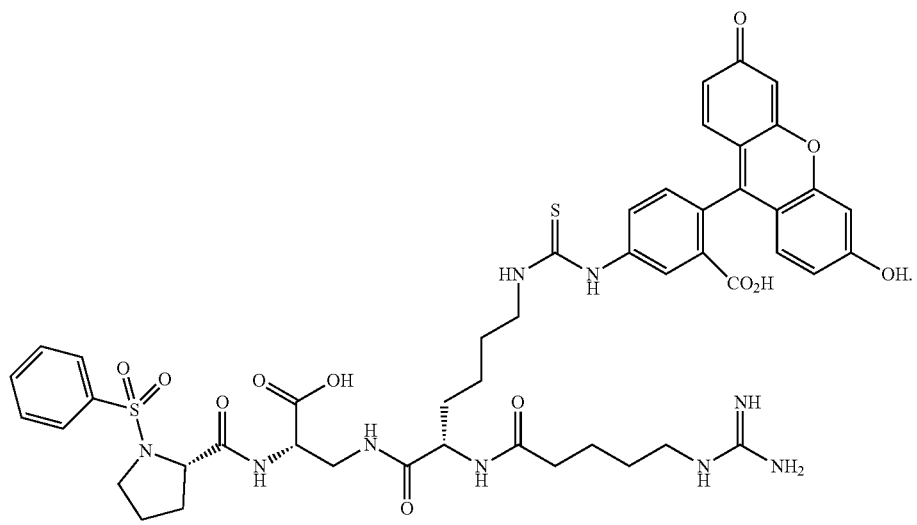 [SMILES: N=C(N)NCCCCC(=O)N[C@@H](CCCCNC(=S)Nc1ccc(-c2c3ccc(=O)cc-3oc3cc(O)ccc23)c(C(=O)O)c1)C(=O)NC[C@H](NC(=O)[C@@H]1CCCN1S(=O)(=O)c1ccccc1)C(=O)O]
Embodiment 56
The compound of embodiment 1, having the formula:
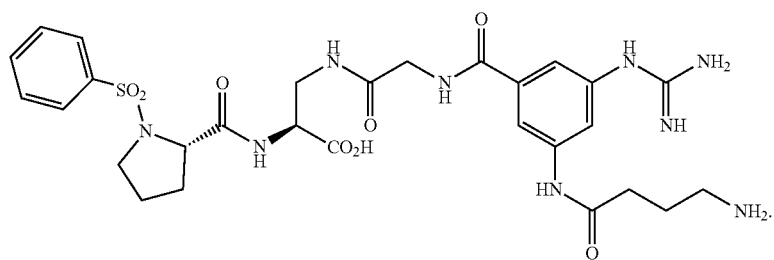 [SMILES: N=C(N)Nc1cc(NC(=O)CCCN)cc(C(=O)NCC(=O)NC[C@H](NC(=O)[C@@H]2CCCN2S(=O)(=O)c2ccccc2)C(=O)O)c1]

Embodiment 57

The compound of embodiment 1, having the formula:

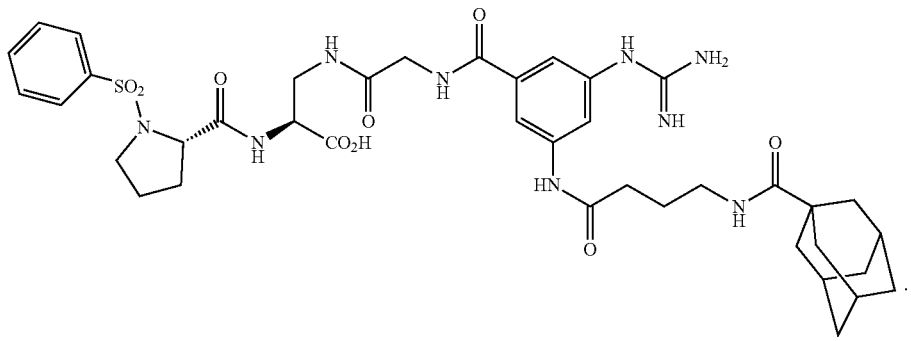 [SMILES: N=C(N)Nc1cc(NC(=O)CCCNC(=O)C23CC4CC(CC(C4)C2)C3)cc(C(=O)NCC(=O)NC[C@H](NC(=O)[C@@H]2CCCN2S(=O)(=O)c2ccccc2)C(=O)O)c1]

Embodiment 58

The compound of embodiment 1, having the formula:

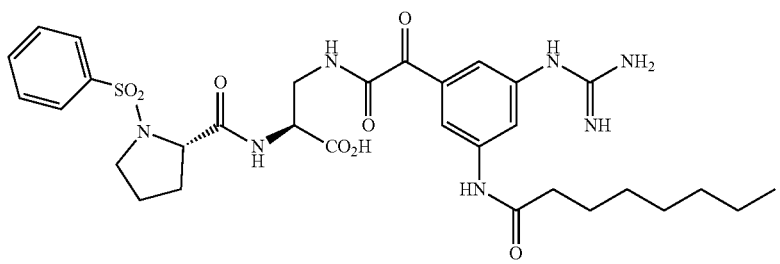

Embodiment 59

A pharmaceutical composition comprising a pharmaceutically acceptable excipient and a compound of one of embodiments 1 to 55.

Embodiment 60

A method for treating asthma, said method comprising administering to a subject in need thereof an effective amount of a compound, or a pharmaceutically acceptable salt thereof, having the formula:

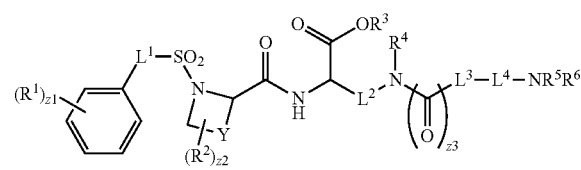

wherein, $R^1$ is independently halogen, —$N_3$, —$CX^1{}_3$, —$CHX^1{}_2$, —$CH_2X$, —$OCX^1{}_3$, —$OCH_2X^1$, —$OCHX^1{}_2$, —CN, —$SO_{n1}R^{1D}$, —$SO_{v1}NR^{1A}R^{1B}$, —$OSO_{v1}R^{1D}$, —$NHC(O)NR^{1A}R^{1B}$, —$N(O)_{m1}$, —$NR^{1A}R^{1B}$, —$C(O)R^{1C}$, —$C(O)$—$OR^{1C}$, —$C(O)NR^{1A}R^{1B}$, —$OR^{1D}$, —$NR^{1A}SO_2R^{1D}$, —$NR^{1A}C(O)R^{1C}$, —$NR^{1A}C(O)OR^{1C}$, —$NR^{1A}OR^{1C}$, —$ONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl;

$L^1$ is a bond or substituted or unsubstituted alkylene, or substituted or unsubstituted heteroalkylene; Y is a bond, —C—, —C—C—, —C=C—, —C—C—C—, —C=C—C—, —C—C=C—, —O—C—, —C—O—, —C—O—C, —S—C—, —C—S—, or —C—S—C—; $R^2$ is independently halogen, —$CX^2{}_3$, —$CHX^2{}_2$, —$CH_2X^2$, —$OCX^2{}_3$, —$OCH_2X^2$, —$OCHX^2{}_2$, —CN, —$SO_nR^{2D}$, —$SO_{v2}NR^{2A}R^{2B}$, —$NHC(O)NR^{2A}R^{2B}$, —$N(O)_{m2}$, —$NR^{2A}R^{2B}$, —$C(O)R^{2C}$, —$C(O)$—$OR^{2C}$, —$C(O)NR^{2A}R^{2B}$, —$OR^{2D}$, —$NR^{2A}SO_2R^{2D}$, —$NR^{2A}C(O)R^{2C}$, —$NR^{2A}C(O)OR^{2C}$, —$NR^{2A}OR^{2C}$, —$SO_2Ph$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl; $R^3$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a prodrug moiety; $R^4$ is independently hydrogen, —$CX^4{}_3$, —CN, —COOH, —$CONH_2$, —$CHX^4{}_2$, —$CH_2X^4$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; L² is unsubstituted alkylene; L³ is a bond, —O—, —S—, —N(R⁷)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; R⁷ is hydrogen, —CN, —COOH, —CX⁷₃, substituted or unsubstituted alkyl, or substituted or unsubstituted heteroalkyl; L⁴ is —O—, —S—, —N(R⁸)—, —C(O)—, C(O)O—, —S(O)—, —S(O)₂—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene; R⁸ is hydrogen, —CN, —COOH, —CX⁸₃, substituted or unsubstituted alkyl, or substituted or unsubstituted heteroalkyl; R⁵ and R⁶ are independently hydrogen,

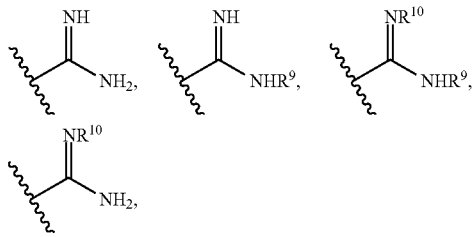

substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R⁵ and R⁶ may optionally be joined to form a substituted or unsubstituted heterocycloalkyl or substituted or unsubstituted heteroaryl; R⁹ is hydrogen, halogen, —N₃, —CX⁹₃, —CHX⁹₂, —CH₂X⁹, —CN, —CHO, —OH, —NH₂, —COOH, —CONH₂, —NO₂, —SH, —SO₂, —SO₂CH₃—SO₃H, —SO₄H, —SO₂NH₂, —NHNH₂, —ONH₂, —NHC(O)NHNH₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R¹⁰ is hydrogen, halogen, —N₃, —CX¹⁰₃, —CHX¹⁰₂, —CH₂X¹⁰, —CN, —CHO, —OH, —NH₂, —COOH, —CONH₂, —NO₂, —SH, —SO₂, —SO₂CH₃—SO₃H, —SO₄H, —SO₂NH₂, —NHNH₂, —ONH₂, —NHC(O)NHNH₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; each $R^{1A}$, $R^{1B}$, $R^{1C}$, $R^{1D}$, $R^{2A}$, $R^{2B}$, $R^{2C}$, $R^{2D}$, is independently hydrogen, —CX₃, —CN, —COOH, —CONH₂, —CHX₂, —CH₂X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; each X, $X^1$, $X^2$, $X^4$, $X^7$, $X^8$, $X^9$, and $X^{10}$ are independently —F, —Cl, —Br, or —I; n1 and n2 are independently an integer from 0 to 3; m1, m2, v1 and v2 are independently 1 or 2; z1 is an integer from 0 to 5; z2 is an integer from 0 to 9; and z3 is 0 or 1.

Embodiment 61

The method of embodiment 60, wherein z1 is an integer from 1 to 5.

Embodiment 62

The method of one of embodiments 60 or 61, wherein Y is —C—C—, —C=C—, —O—C—, —C—O—, —C—O—C—, —C—S—, —S—C, or —C—S—C—.

Embodiment 63

The method of any one of embodiments 60 to 62, wherein

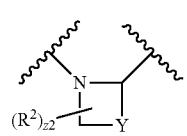

has the formula:

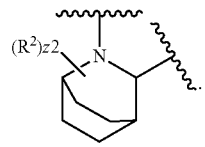

Embodiment 64

The method of any one of embodiments 60 to 62 having the formula:

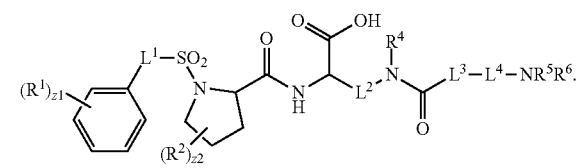

Embodiment 65

The method of any one of embodiments 60 to 64, wherein L¹ is a bond.

Embodiment 66

The method of any one of embodiments 60 to 65, wherein R¹ is independently halogen, —N₃, —CF₃, —CCl₃, —CBr₃, —CI₃, —CN, —CHO, —OH, —NH₂, —COOH, —CONH₂, —SH, —SO₂, —SO₂CH₃—SO₃H, —OSO₃H, —SO₂NH₂, —NHNH₂, —ONH₂, —NHC(O)NHNH₂, substituted or unsubstituted alkyl, substituted or unsubstituted heteroalkyl, substituted or unsubstituted cycloalkyl, substi-

Embodiment 67

The method of any one of embodiments 60 to 65, wherein $R^1$ is independently halogen, —OMe, —SMe, —SO$_2$Me, —SO$_2$Ph, —COOH, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted phenyl, or substituted or unsubstituted 5 to 6 membered heteroaryl; two adjacent $R^1$ substituents may optionally be joined to form a substituted or unsubstituted $C_3$-$C_8$ cycloalkyl, substituted or unsubstituted 3 to 8 membered heterocycloalkyl, substituted or unsubstituted phenyl, or substituted or unsubstituted 5 to 6 membered heteroaryl.

Embodiment 68

The method of any of embodiments 60 to 67, wherein $L^2$ is unsubstituted $C_1$-$C_2$ alkylene.

Embodiment 69

The method of any of embodiments 60 to 67, wherein $L^2$ is unsubstituted methylene.

Embodiment 70

The method of any of embodiments 60 to 69, wherein $R^4$ is hydrogen.

Embodiment 71

The method of any one of embodiments 60 to 70, wherein $L^3$ is a bond, substituted or unsubstituted $C_1$-$C_8$ alkylene, or substituted or unsubstituted 2 to 8 membered heteroalkylene, substituted or unsubstituted $C_3$-$C_8$ cycloalkylene, substituted or unsubstituted 3 to 8 membered heterocycloalkylene, substituted or unsubstituted phenylene, or substituted or unsubstituted 5 to 6 membered heteroarylene.

Embodiment 72

The method of any one of embodiments 60 to 70, wherein $L^3$ is a bond.

73. The method of any one of embodiments 60 to 70, wherein $L^3$ is substituted or unsubstituted alkylene, or substituted or unsubstituted heteroalkylene.

Embodiment 74

The method of any one of embodiments 60 to 70, wherein $L^3$ is substituted or unsubstituted $C_1$-$C_8$ alkylene, or substituted or unsubstituted 2 to 8 membered heteroalkylene.

Embodiment 75

The method of any one of embodiments 60 to 70, wherein $L^3$ is substituted or unsubstituted 2 to 8 membered heteroalkylene.

Embodiment 76

The method of any one of embodiments 60 to 70, wherein $L^3$ is an oxo-substituted $C_1$-$C_8$ alkylene, or oxo-substituted 2 to 8 membered heteroalkylene.

Embodiment 77

The method of any one of embodiments 60 to 76, wherein $L^4$ is substituted or unsubstituted $C_1$-$C_8$ alkylene, or substituted or unsubstituted 2 to 8 membered heteroalkylene, substituted or unsubstituted $C_3$-$C_8$ cycloalkylene, substituted or unsubstituted 3 to 8 membered heterocycloalkylene, substituted or unsubstituted phenylene, or substituted or unsubstituted 5 to 6 membered heteroarylene.

Embodiment 78

The method of any one of embodiments 60 to 76, wherein $L^4$ is substituted or unsubstituted alkylene, or substituted or unsubstituted heteroalkylene.

Embodiment 79

The method of any one of embodiments 60 to 76, wherein $L^4$ is substituted or unsubstituted $C_1$-$C_8$ alkylene, or substituted or unsubstituted 2 to 8 membered heteroalkylene.

Embodiment 80

The method of any one of embodiments 60 to 75, wherein $L^4$ is substituted or unsubstituted 2 to 8 membered heteroalkylene.

Embodiment 81

The method of any one of embodiments 60 to 76, wherein $L^4$ is an oxo-substituted $C_1$-$C_8$ alkylene, or oxo-substituted 2 to 8 membered heteroalkylene.

Embodiment 82

The method of any one of embodiments 60 to 76, wherein $L^4$ is substituted or unsubstituted arylene, or substituted or unsubstituted heteroarylene.

Embodiment 83

The method of any one of embodiments 60 to 76, wherein $L^4$ is substituted or unsubstituted phenylene, or substituted or unsubstituted 5 to 6 membered heteroarylene.

Embodiment 84

The method of any one of embodiments 60 to 76, wherein $L^4$ is unsubstituted phenylene.

Embodiment 85

The method of any one of embodiments 60 to 84, wherein $R^5$ and $R^6$ are independently hydrogen,

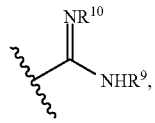

Embodiment 86

The method of any one of embodiments 60 to 84, wherein $R^5$ and $R^6$ are independently hydrogen,

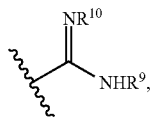

substituted or unsubstituted 3 to 8 membered heterocycloalkyl, substituted or unsubstituted phenyl, or substituted or unsubstituted 5 to 6 membered heteroaryl.

Embodiment 87

The method of any one of embodiments 60 to 84, wherein $R^5$ is substituted or unsubstituted 5 to 6 membered heteroaryl.

Embodiment 88

The method of any one of embodiments 60 to 84, wherein $R^6$ is substituted or unsubstituted 5 to 6 membered heteroaryl.

Embodiment 89

The method of any one of embodiments 60 to 84, wherein $R^5$ and $R^6$ are independently hydrogen,

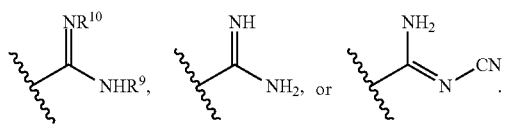

Embodiment 90

The method of any one of embodiments 60 to 84, wherein $R^5$ is hydrogen and $R^6$ is

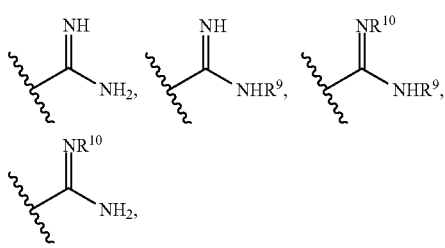

substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 91

The method of any one of embodiments 60 to 84, wherein $R^5$ is hydrogen and $R^6$ is

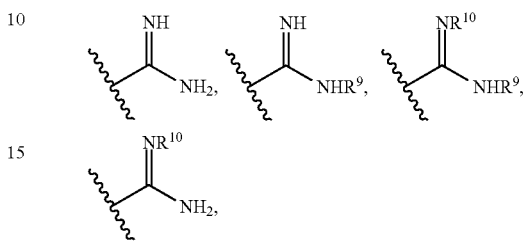

substituted or unsubstituted alkyl, substituted or unsubstituted cycloalkyl, substituted or unsubstituted heterocycloalkyl, substituted or unsubstituted aryl, or substituted or unsubstituted heteroaryl.

Embodiment 92

The method of any one of embodiments 60 to 84, wherein $R^5$ and $R^6$ are joined to form a substituted or unsubstituted heterocycloalkyl or substituted or unsubstituted heteroaryl.

Embodiment 93

The method of any one of embodiments 60 to 84, wherein $R^5$ is hydrogen and $R^6$ is

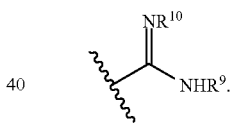

Embodiment 94

The method of any one of embodiments 60 to 84, wherein $R^5$ is hydrogen and $R^6$ is

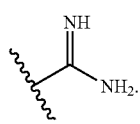

Embodiment 95

The method of any one of embodiments 60 to 84, wherein $R^5$ is hydrogen and $R^6$ is substituted or unsubstituted heteroaryl.

Embodiment 96

The method of any one of embodiments 60 to 84, wherein $R^5$ is hydrogen and $R^6$ is substituted or unsubstituted 5 to 6 membered heteroaryl.

Embodiment 97
The method of any one of embodiments 60 to 96, wherein $R^3$ is hydrogen.
Embodiment 98
The method of any one of embodiments 60 to 96, wherein $R^3$ is a substituted or unsubstituted alkyl, or substituted or unsubstituted heteroalkyl.
Embodiment 99
The method of embodiment 60, having the formula:
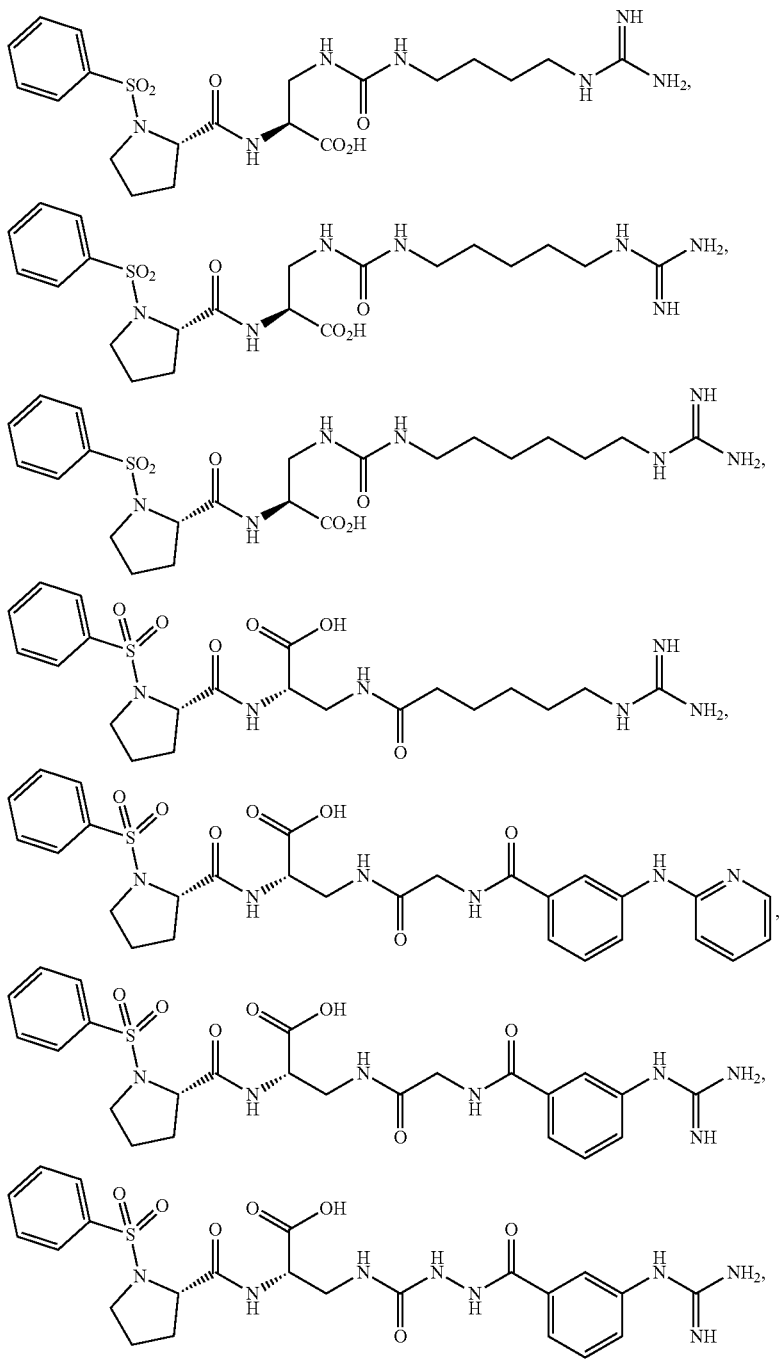

-continued
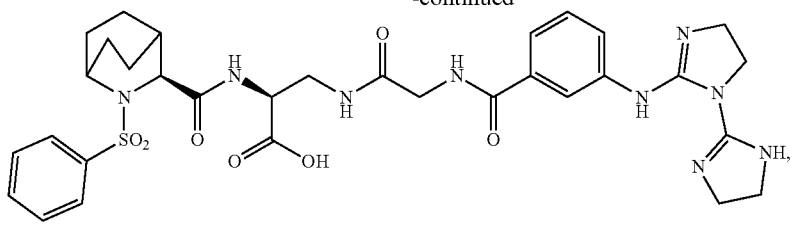
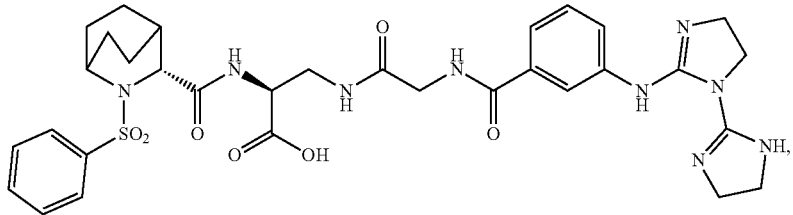
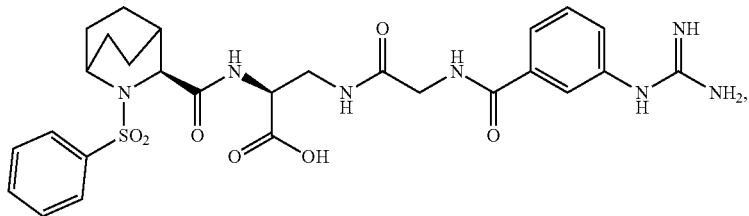
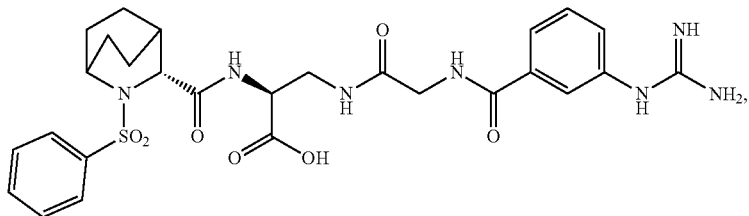
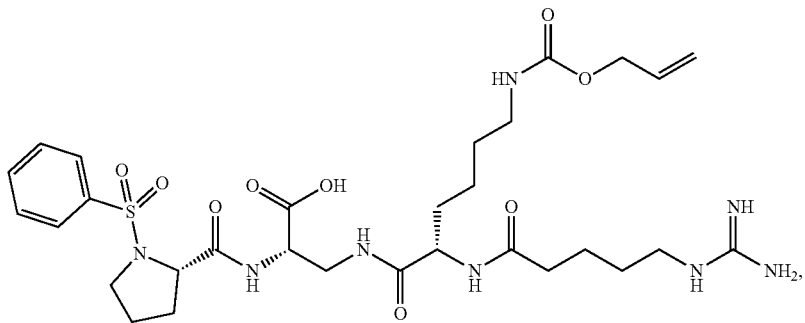
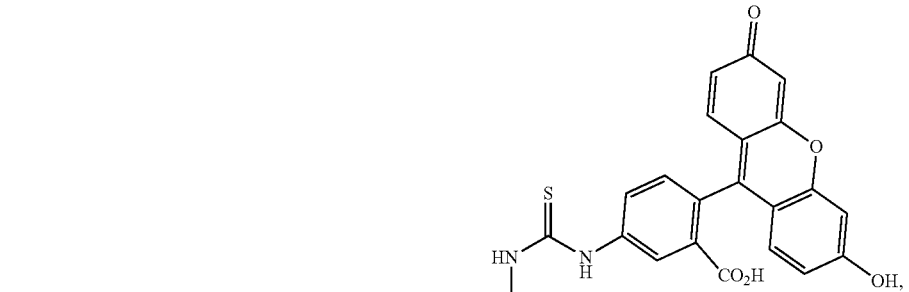
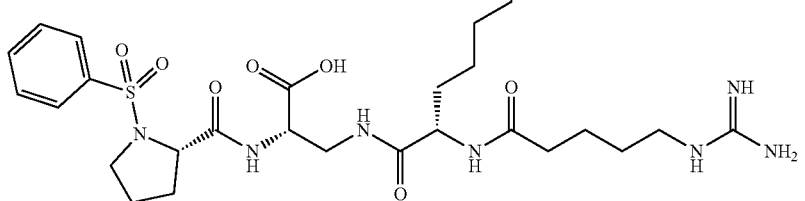

-continued
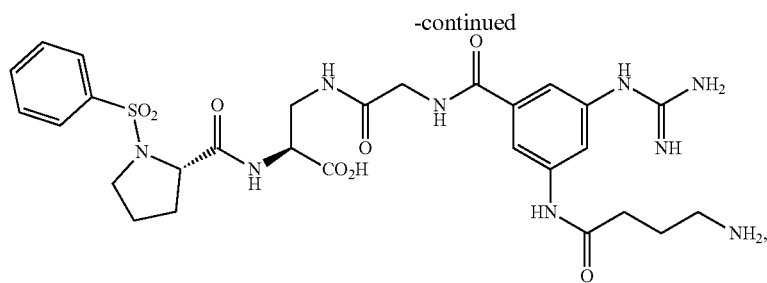
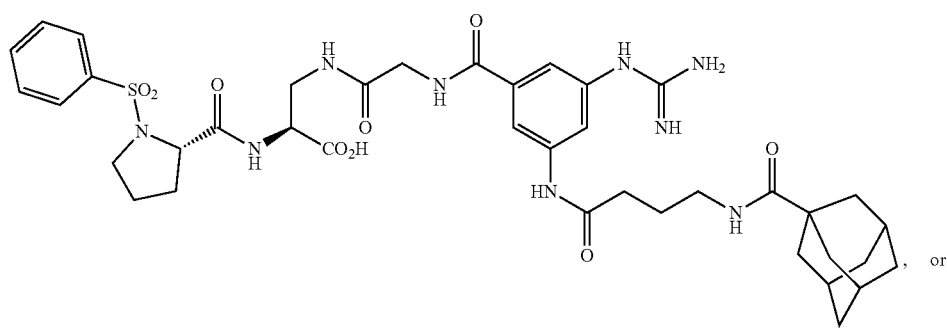, or
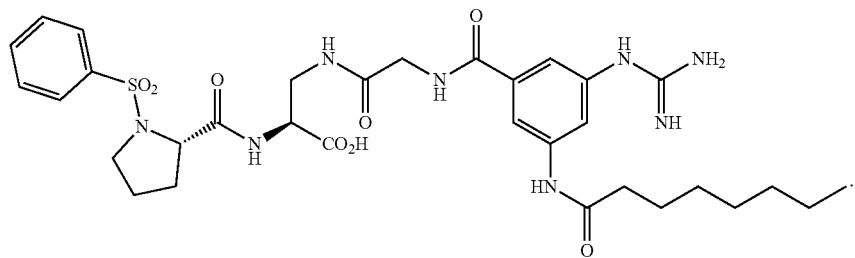
Embodiment 100
The method of embodiment 60, having the formula:
Embodiment 101
The method of embodiment 60, having the formula:
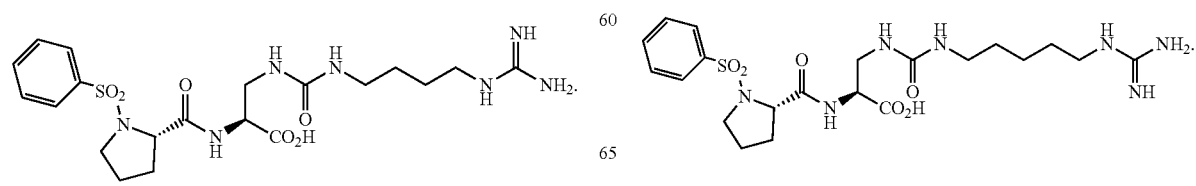

Embodiment 102
The method of embodiment 60, having the formula:
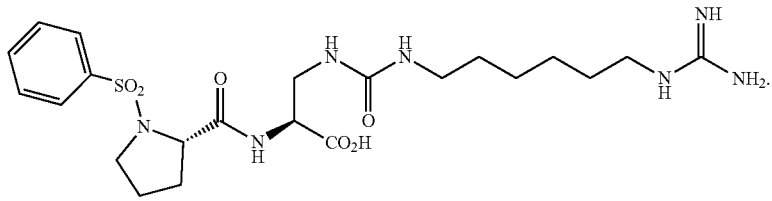 [SMILES: N=C(N)NCCCCCCNC(=O)NC[C@H](NC(=O)[C@@H]1CCCN1S(=O)(=O)c1ccccc1)C(=O)O]
Embodiment 103
The method of embodiment 60, having the formula:
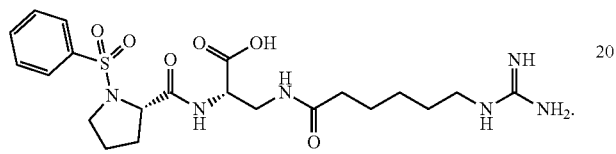
Embodiment 104
The method of embodiment 60, having the formula:
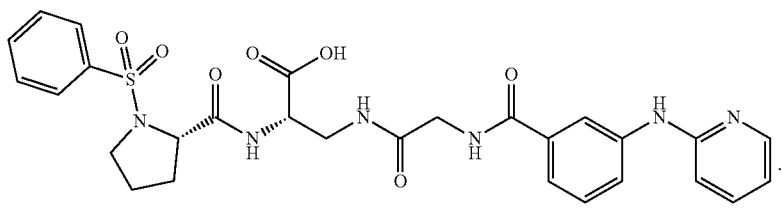 [SMILES: O=C(CNC(=O)c1cccc(Nc2ccccn2)c1)NC[C@H](NC(=O)[C@@H]1CCCN1S(=O)(=O)c1ccccc1)C(=O)O]
Embodiment 105
The method of embodiment 60, having the formula:
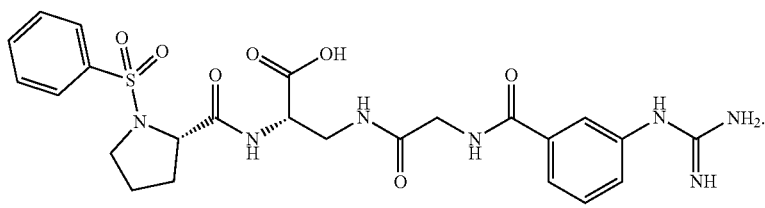
Embodiment 106
The method of embodiment 60, having the formula:
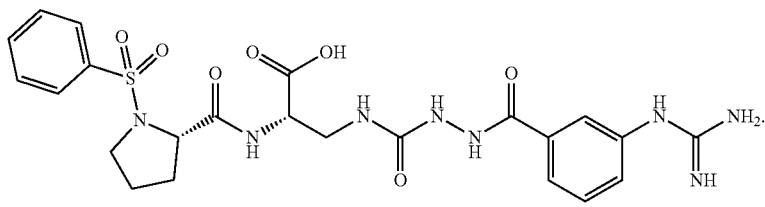 [SMILES: N=C(N)Nc1cccc(C(=O)NNC(=O)NC[C@H](NC(=O)[C@@H]2CCCN2S(=O)(=O)c2ccccc2)C(=O)O)c1]

185 186
Embodiment 107
The method of embodiment 60, having the formula:
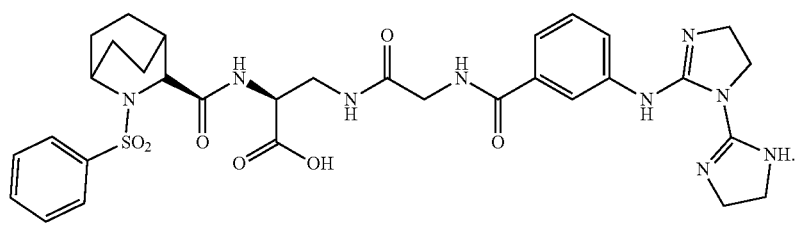
Embodiment 108
The method of embodiment 60, having the formula:
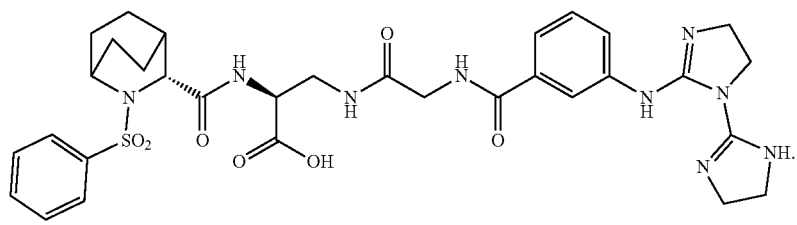 [SMILES: O=C(CNC(=O)c1cccc(NC2=NCCN2C2=NCCN2)c1)NC[C@H](NC(=O)[C@H]1C2CCC(CC2)N1S(=O)(=O)c1ccccc1)C(=O)O]
Embodiment 109
The method of embodiment 60, having the formula:
Embodiment 110
The method of embodiment 60, having the formula:
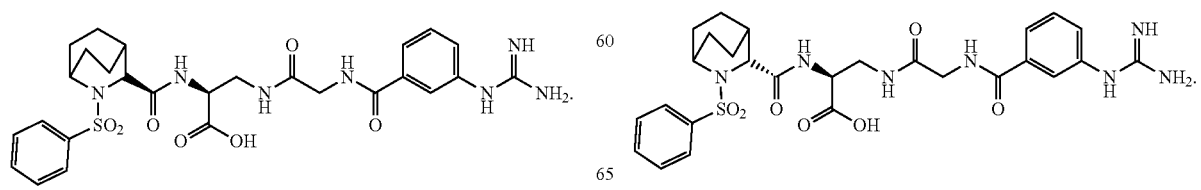

Embodiment 111
The method of embodiment 60, having the formula:
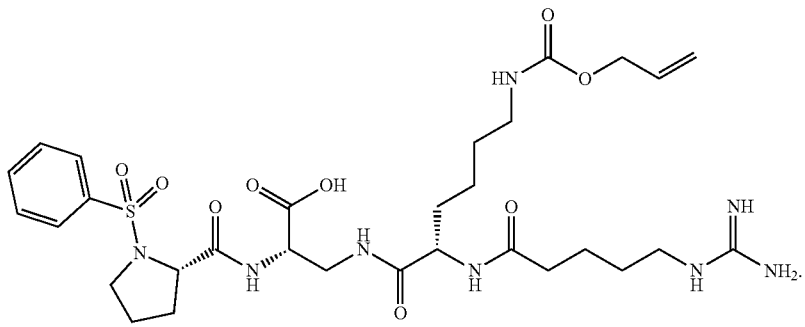 [SMILES: C=CCOC(=O)NCCCC[C@H](NC(=O)CCCCNC(=N)N)C(=O)NC[C@H](NC(=O)[C@@H]1CCCN1S(=O)(=O)c1ccccc1)C(=O)O]
Embodiment 112
The method of embodiment 60, having the formula:
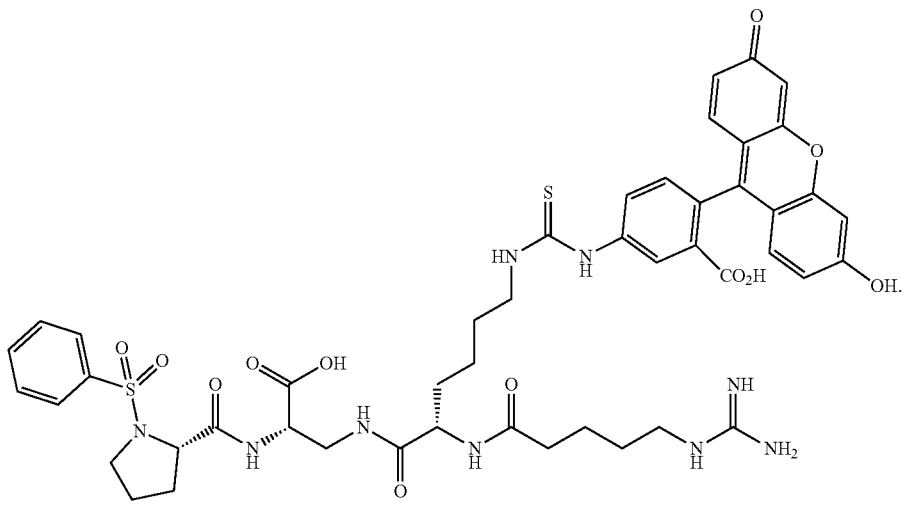 [SMILES: N=C(N)NCCCCC(=O)N[C@@H](CCCCNC(=S)Nc1ccc(-c2c3ccc(=O)cc-3oc3cc(O)ccc23)c(C(=O)O)c1)C(=O)NC[C@H](NC(=O)[C@@H]1CCCN1S(=O)(=O)c1ccccc1)C(=O)O]
Embodiment 113
The method of embodiment 60, having the formula:
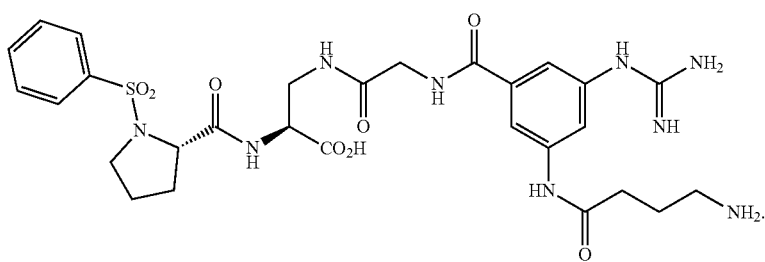 [SMILES: N=C(N)Nc1cc(NC(=O)CCCN)cc(C(=O)NCC(=O)NC[C@H](NC(=O)[C@@H]2CCCN2S(=O)(=O)c2ccccc2)C(=O)O)c1]

Embodiment 114

The method of embodiment 60, having the formula:

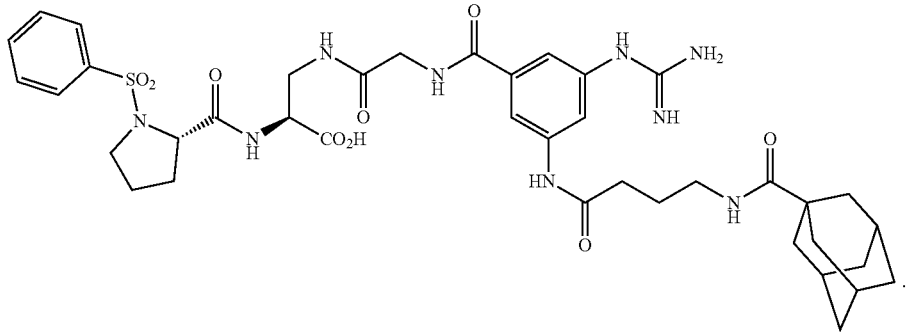 [SMILES: N=C(N)Nc1cc(NC(=O)CCCNC(=O)C23CC4CC(CC(C4)C2)C3)cc(C(=O)NCC(=O)NC[C@H](NC(=O)[C@@H]2CCCN2S(=O)(=O)c2ccccc2)C(=O)O)c1]

Embodiment 115

The method of embodiment 60, having the formula:

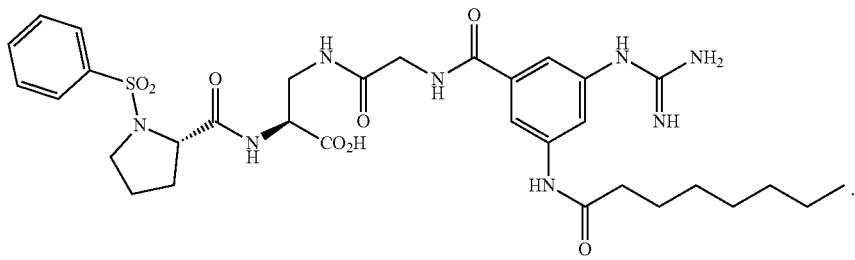 [SMILES: CCCCCCCC(=O)Nc1cc(NC(=N)N)cc(C(=O)NCC(=O)NC[C@H](NC(=O)[C@@H]2CCCN2S(=O)(=O)c2ccccc2)C(=O)O)c1]

Embodiment 116

A method of detecting the presence of α5β1 integrin or inhibiting α5β1 integrin activity, said method comprising contacting an α5β1 integrin with a compound having the formula:

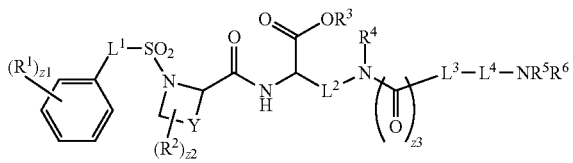

wherein, $R^1$ is independently halogen, —$N_3$, —$CX^1_3$, —$CHX^1_2$, —$CH_2X^1$, —$OCX^1_3$, —$OCH_2X^1$, —$OCHX^1_2$, —CN, —$SO_{n1}R^{1D}$, —$SO_{v1}NR^{1A}R^{1B}$, —$OSO_{v1}R^{1D}$, —$NHC(O)NR^{1A}R^{1B}$, —$N(O)_{m1}$, —$NR^{1A}R^{1B}$, —$C(O)R^{1C}$, —$C(O)$—$OR^{1C}$, —$C(O)NR^{1A}R^{1B}$, —$OR^{1D}$, —$NR^{1A}SO_2R^{1D}$, —$NR^{1A}C(O)R^{1C}$, —$NR^{1A}C(O)OR^{1C}$, —$NR^{1A}OR^{1C}$, —$ONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl; $L^1$ is a bond or substituted or unsubstituted alkylene, or substituted or unsubstituted heteroalkylene; Y is a bond, —C—, —C—C—, —C=C—, —C—C—C—, —C=C—C—, —C—C=C—, —O—C—, —C—O—, —C—O—C, —S—C—, —C—S—, or —C—S—C—; $R^2$ is independently halogen, —$CX^2_3$, —$CHX^2_2$, —$CH_2X^2$, —$OCX^2_3$, —$OCH_2X^2$, —$OCHX^2_2$, —CN, —$SO_{n2}R^{2D}$, —$SO_{v2}NR^{2A}R^{2B}$, —$NHC(O)NR^{2A}R^{2B}$, —$N(O)_{m2}$, —$NR^{2A}R^{2B}$, —$C(O)R^{2C}$, —$C(O)$—$OR^{2C}$, —$C(O)NR^{2A}R^{2B}$, —$OR^{2D}$, —$NR^{2A}SO_2R^{2D}$, —$NR^{2A}C(O)R^{2C}$, —$NR^{2A}C(O)OR^{2C}$, —$NR^{2A}OR^{2C}$, —$SO_2Ph$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl; $R^3$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a prodrug moiety; $R^4$ is independently hydrogen, —$CX^4_3$, —CN, —COOH, —$CONH_2$, —$CHX^4_2$, —$CH_2X^4$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $L^2$ is unsubstituted alkylene; $L^3$ is a bond, —O—, —S—, —$N(R^7)$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $R^7$ is hydrogen, —CN, —COOH, —CX$^7_3$, substituted or unsubstituted alkyl, or substituted or unsubstituted heteroalkyl; $L^4$ is —O—, —S—, —N($R^8$)—, —C(O)—, C(O)O—, —S(O)—, —S(O)$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene; $R^8$ is hydrogen, —CN, —COOH, —CX$^8_3$, substituted or unsubstituted alkyl, or substituted or unsubstituted heteroalkyl; $R^5$ and $R^6$ are independently hydrogen,

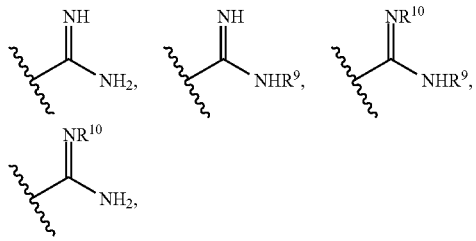

substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^5$ and $R^6$ may optionally be joined to form a substituted or unsubstituted heterocycloalkyl or substituted or unsubstituted heteroaryl; $R^9$ is hydrogen, halogen, —N$_3$, —CX$^9_3$, —CHX$^9_2$, —CH$_2$X$^9$, —CN, —CHO, —OH, —NH$_2$, —COOH, —CONH$_2$, —NO$_2$, —SH, —SO$_2$, —SO$_2$CH$_3$—SO$_3$H, —SO$_4$H, —SO$_2$NH$_2$, —NHNH$_2$, —ONH$_2$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{10}$ is hydrogen, halogen, —N$_3$, —CX$^{10}_3$, —CHX$^{10}_2$, —CH$_2$X$^{10}$, —CN, —CHO, —OH, —NH$_2$, —COOH, —CONH$_2$, —NO$_2$, —SH, —SO$_2$, —SO$_2$CH$_3$—SO$_3$H, —SO$_4$H, —SO$_2$NH$_2$, —NHNH$_2$, —ONH$_2$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; each $R^{1A}$, $R^{1B}$, $R^{1C}$, $R^{1D}$, $R^{2A}$, $R^{2B}$, $R^{2C}$, $R^{2D}$, is independently hydrogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; each X, $X^1$, $X^2$, $X^4$, $X^7$, $X^8$, $X^9$, and $X^{10}$ are independently —F, —Cl, —Br, or —I; n1 and n2 are independently an integer from 0 to 3; m1, m2, v1 and v2 are independently 1 or 2; z1 is an integer from 0 to 5; and z2 is an integer from 0 to 9; and z3 is 0 or 1.

Embodiment 117

The method of embodiment 116, wherein said method comprises detecting the presence of α5β1 integrin and inhibiting α5β1 integrin activity.

Embodiment 118

The method of embodiment 116, wherein said method comprises detecting the presence of α5β1 integrin.

Embodiment 119

The method of embodiment 116, wherein said method comprises inhibiting α5β1 integrin activity.

V. EXAMPLES

Figure 1B:
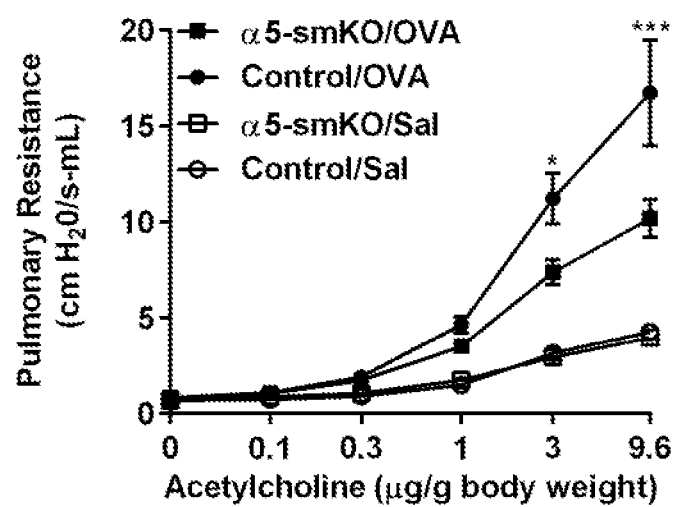

The blockade of integrin alpha 5 beta 1 provides a novel target for the treatment of asthma. As shown in FIGS. 1A and 1B, delivery of ATN-161, a low affinity yet specific inhibitor of alpha5beta1, reduces the magnitude of airway narrowing in vivo in mice sensitized and challenged with ovalbumin, a widely used model of allergic asthma. In the same model, it was found that mice with a specific deletion of this integrin in smooth muscle also have reduced airway narrowing. The intracellular actin-myosin cross-bridging pathway serves as a useful target. Modulating the interactions of the cell and the extracellular matrix impairs the ability of the smooth muscle to transmit tension effectively. The blockade of integrin alpha 5 beta 1 was tested in vitro with human cell lines as well as in vivo with a mouse model of airway hyperresponsiveness. Novel compounds as described herein, and identified in Table 1, have been synthesized and tested in vitro for their ability to inhibit cell adhesion mediated by either alpha5beta1 (adhesion of the colon carcinoma cell line SW480 to fibronectin, a response that is entirely dependent on binding of alpha5beta1 to fibronectin), or alphavbeta1 (adhesion of Chinese Hamster Ovary cells transfected with human alphav to the latency associated peptide of transforming growth factor beta, a response that is entirely dependent on binding of alphavbeta1 to LAP).

TABLE 1

Cell adhesion assay data

| Name | Structure of compound synthesized | IC50 alphavbeta1 | IC50 alpha5beta1 |
|---|---|---|---|
| HIJ-1016 | | A | B |

TABLE 1-continued

Cell adhesion assay data

| Name | Structure of compound synthesized | IC50 alphavbeta1 | IC50 alpha5beta1 |
|---|---|---|---|
| HIJ-1017 | | A | B |
| HIJ-1018 | | A | B |
| HIJ-1083 | | B | B |
| HIJ-1093 | | B | B |
| HIJ-1094 | | A | A |
| HIJ-1099 | | B | A |
| HIJ-1203 | | C | C |

TABLE 1-continued
Cell adhesion assay data
| Name | Structure of compound synthesized | IC50 alphavbeta1 | IC50 alpha5beta1 |
|---|---|---|---|
| HIJ-1204 | 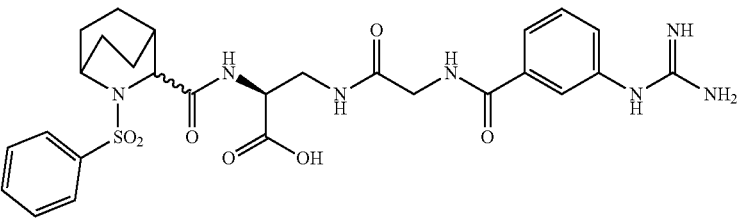 [SMILES: N=C(N)Nc1cccc(C(=O)NCC(=O)NC[C@H](NC(=O)C2C3CCC(CC3)N2S(=O)(=O)c2ccccc2)C(=O)O)c1] | C | A |
| HIJ-1213 | 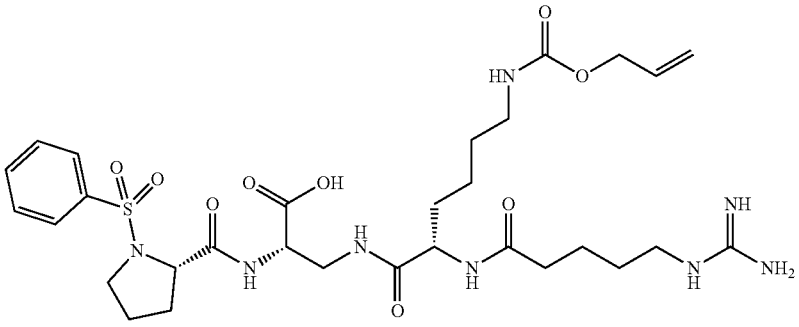 [SMILES: C=CCOC(=O)NCCCC[C@H](NC(=O)CCCCNC(=N)N)C(=O)NC[C@H](NC(=O)[C@@H]1CCCN1S(=O)(=O)c1ccccc1)C(=O)O] | C | C |
| HIJ-1216 | 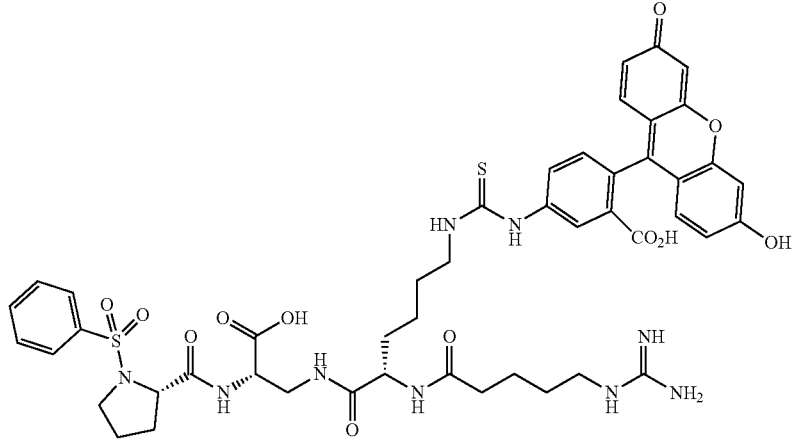 [SMILES: N=C(N)NCCCCC(=O)N[C@@H](CCCCNC(=S)Nc1ccc(-c2c3ccc(=O)cc-3oc3cc(O)ccc23)c(C(=O)O)c1)C(=O)NC[C@H](NC(=O)[C@@H]1CCCN1S(=O)(=O)c1ccccc1)C(=O)O] | C | C |
| HIJ-1437 | 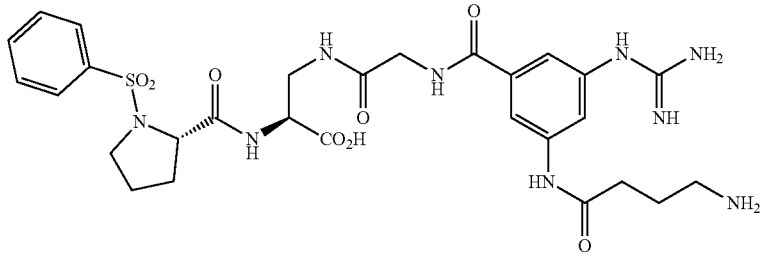 [SMILES: N=C(N)Nc1cc(NC(=O)CCCN)cc(C(=O)NCC(=O)NC[C@H](NC(=O)[C@@H]2CCCN2S(=O)(=O)c2ccccc2)C(=O)O)c1] | N/A | A |

TABLE 1-continued
Cell adhesion assay data
| Name | Structure of compound synthesized | IC50 alphavbeta1 | IC50 alpha5beta1 |
|------|-----------------------------------|------------------|------------------|
| HIJ-1483 | | N/A | A |
| HIJ-1491 | | N/A | N/A |
A Less than 100 nM
B 100 nM to 10 uM;
C Greater than 10 uM
N/A Not tested
Example 1. Syntheses of Compounds HIJ-1016, HIJ-1017 and HIJ-1018
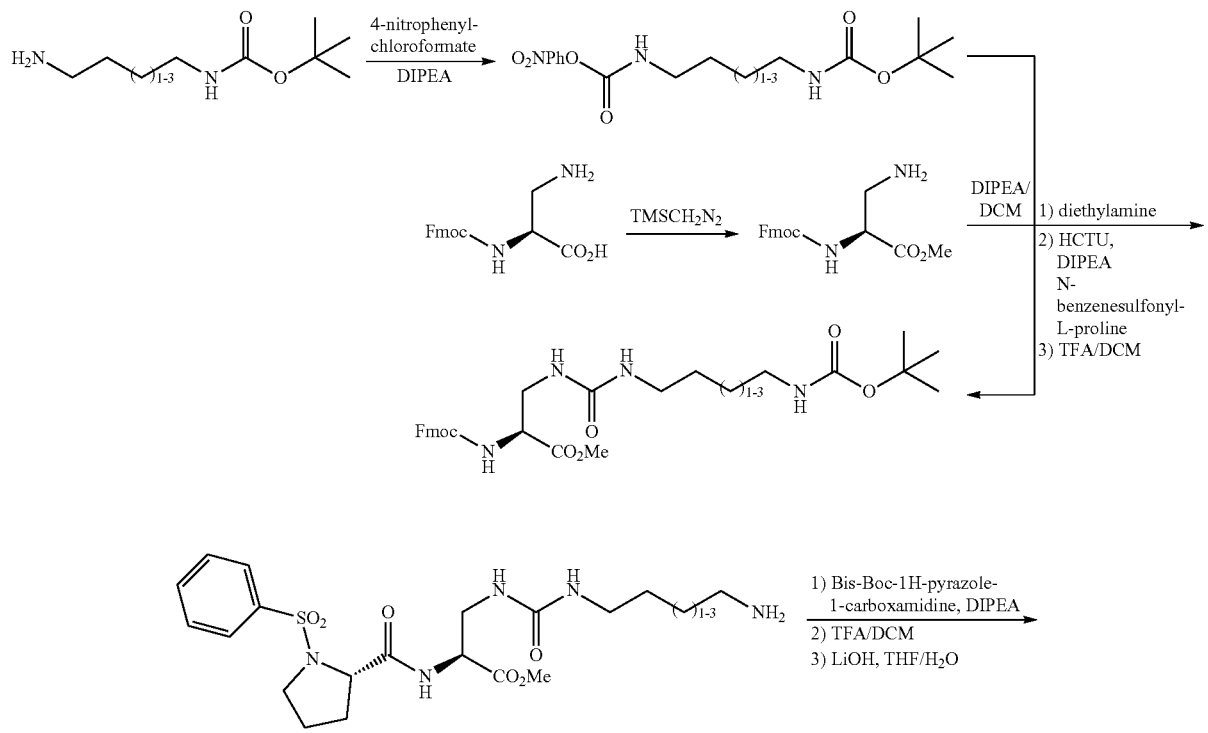

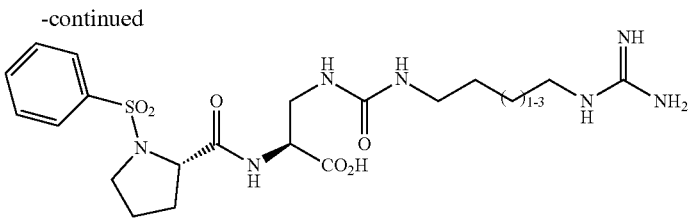

Step 1. Synthesis of 4-nitrophenylcarbamate: To a solution of mono-boc protected amine (5 mmol) and DIPEA (1.2 eq) in DCM (10 mL) was added 4-nitrophenyl chloroformate (1.1 eq) dropwise at room temperature. The mixture was stirred for 1 h and diluted with DCM. The organic layer was washed with 1M HCl and dried over $Na_2SO_4$. The volatiles were removed under reduced pressure and the residue was purified by column chromatography (0 to 10% MeOH in DCM) to yield a carbamate mixture of the following: tert-butyl (4-nitrophenyl) butane-1,4-diyldicarbamate: yield 700 mg (37%), ESI-MS 376.6 ($MNa^+$); tert-butyl (4-nitrophenyl) pentane-1,5-diyldicarbamate: yield 880 mg (45%), ESI-MS 390.9 ($MNa^+$); tert-butyl (4-nitrophenyl) hexane-1,6-diyldicarbamate: yield 700 mg (35%), ESI-MS 404.8 ($MNa^+$).

Step 2. Synthesis of methyl (S)-2-((((9H-fluoren-9-yl)methoxy)carbonyl)amino)-3-aminopropanoate: To a solution of Fmoc-DAP (15.3 mmol) in 10% methanol in DCM (55 mL) was added TMS diazomethane (10 mL, 2M solution in hexanes) dropwise at room temperature. The mixture was stirred for 5 hours and the volatiles were removed under reduced pressure. The yellow residual oil was triturated with cold diethyl ether and filtered to yield the following white solid amine product: methyl (S)-2-((((9H-fluoren-9-yl)methoxy)carbonyl)amino)-3-aminopropanoate: yield 3.1 g (60%), ESI-MS 341.7 ($MH^+$).

Step 3. Urea synthesis: The carbamate mixture from step 1, the amine product (1 mmol) from step 2, and DIPEA (2 mmol) in THF (10 mL) was stirred for 3 hours at 60° C. The volatiles were removed under reduced pressure and purified by column chromatography (0 to 10% MeOH in DCM) to yield Fmoc protected amine products: methyl (S)-14-((((9H-fluoren-9-yl)methoxy)carbonyl)amino)-2,2-dimethyl-4,11-dioxo-3-oxa-5,10,12-triazapentadecan-15-oate: yield (420 mg, 76%) ESI-MS 577.8 ($MNa^+$); methyl (S)-15-((((9H-fluoren-9-yl)methoxy)carbonyl)amino)-2,2-dimethyl-4,12-dioxo-3-oxa-5,11,13-triazahexadecan-16-oate: yield (530 mg, 93%) ESI-MS 591.9 ($MNa^+$); methyl (S)-16-((((9H-fluoren-9-yl)methoxy)carbonyl)amino)-2,2-dimethyl-4,13-dioxo-3-oxa-5,12,14-triazaheptadecan-17-oate: yield (460 mg, 79%) ESI-MS 605.9 ($MNa^+$).

Step 4. Deprotection of Fmoc protecting group: A solution of the Fmoc protected amine products from step 3 in 30% diethylamine in acetonitrile (15 mL) was stirred for 1 hour and the volatiles were removed under reduced pressure and purified by column chromatography (0 to 20% MeOH in DCM) to yield Fmoc-deprotected amine products: methyl (S)-14-amino-2,2-dimethyl-4,11-dioxo-3-oxa-5,10,12-triazapentadecan-15-oate: yield (200 mg, 79%), ESI-MS 355.8 ($MNa^+$); methyl (S)-15-amino-2,2-dimethyl-4,12-dioxo-3-oxa-5,11,13-triazahexadecan-16-oate: yield (240 mg, 74%), ESI-MS 369.7 ($MNa^+$); methyl (S)-16-amino-2,2-dimethyl-4,13-dioxo-3-oxa-5,12,14-triazaheptadecan-17-oate: yield (190 mg, 67%), ESI-MS 361.8 ($MH^+$).

Steps 5 and 6. Amidation with N-benzenesulfonyl-1-proline and deprotection of Boc protecting group: A solution of the Fmoc-deprotected amine products from step 4 and N-benzenesulfonyl-1-proline (1.1 eq), HCTU (1.05 eq) and DIPEA (2.2 eq) in DMF (0.2 M) was stirred for 3 hours at room temperature. The mixture was diluted with ethyl acetate and washed with brine. The organic layer was dried over $Na_2SO_4$ and concentrated under reduced pressure. A solution of 50% TFA in DCM (5 mL) was added to the crude residue and stirred for 2 hours. The volatiles were removed by a stream of nitrogen and precipitated by addition of cold diethyl ether. The ether was decanted after centrifuge and the crude mixture was used in the next step without further purification to yield the following amine products: methyl (S)-3-(3-(4-aminobutyl)ureido)-2-((S)-1-(phenylsulfonyl)pyrrolidine-2-carboxamido)propanoate: ESI-MS 470.6 ($MH^+$); methyl (S)-3-(3-(5-aminopentyl)ureido)-2-((S)-1-(phenylsulfonyl)pyrrolidine-2-carboxamido)propanoate: ESI-MS 484.6 ($MH^+$); methyl (S)-3-(3-(6-aminohexyl)ureido)-2-((S)-1-(phenylsulfonyl)pyrrolidine-2-carboxamido)propanoate: ESI-MS 498.7 ($MH^+$).

Step 7. Syntheses of Compounds HIJ-1016, HIJ-1017, and HIJ-1018: To a solution of the amine products from steps 5 and 6 and DIPEA (6 eq) in DMF (3 mL) was added Bis-Boc-1H-pyrazole-1-carboxamidine (2 eq) and stirred overnight at room temperature. The mixture was diluted with ethyl acetate and washed with water. The organic layer was dried over $Na_2SO_4$ and concentrated under reduced pressure. The crude mixture was treated with a solution of TFA:TIPS:$H_2O$ (95:2.5:2.5, 3 mL) and stirred for 3 hours. The volatiles were blown off by a stream of nitrogen and lyophilized. The lyophilized powder was dissolved in a solution of THF:$H_2O$ (4:1, 15 mL) and stirred for 1.5 hours. The mixture was acidified by addition of a solution of 2M $KHSO_4$ and purified by RP-HPLC (Atlantis Prep T3 OBD 19×150 mm, 5% to 65% B over 23 min, flow rate: 10 ml/min, solvent A: 0.1% TFA in $H_2O$, solvent B: 0.1% TFA in 99% acetonitrile in $H_2O$). The fractions containing the following compound products were pooled and lyophilized: [HIJ-1016]: (S)-3-(3-(4-guanidinobutyl)ureido)-2-((S)-1-(phenylsulfonyl)pyrrolidine-2-carboxamido)propanoic acid: retention time: 18.3 min, ESI-MS 498.9 ($MH^+$); [HIJ-1017]: (S)-3-(3-(5-guanidinopentyl)ureido)-2-((S)-1-(phenylsulfonyl)pyrrolidine-2-carboxamido)propanoic acid: retention time: 19.4 min, ESI-MS 512.8 ($MH^+$); [HIJ-1018]: (S)-3-(3-(6-guanidinohexyl)ureido)-2-((S)-1-(phenylsulfonyl)pyrrolidine-2-carboxamido)propanoic acid: retention time: 20.3 min, ESI-MS 526.9 ($MH^+$).

Example 2. Synthesis of HIJ-1083

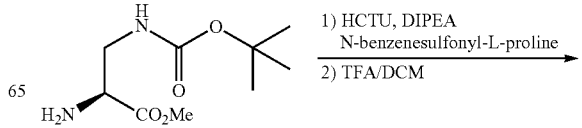

-continued

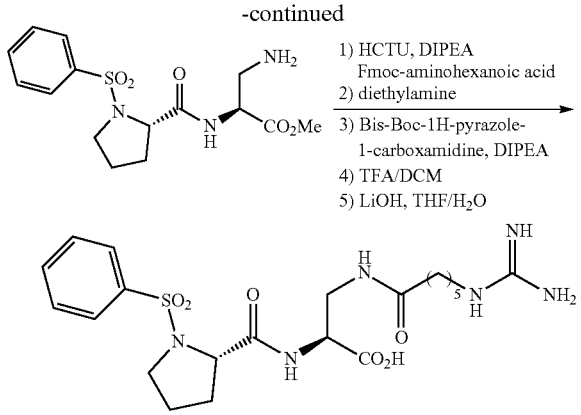

Step 1. Synthesis of N-benzenesulfonyl-Pro-DAP-OMe: To a solution of N-benzenesulfonyl proline (10 mmol) in DMF (50 mL) were added DIPEA (2 eq) and HCTU (1 eq). After stirring 1 minute to obtain a clear solution, the amine shown in the above reaction scheme (10 mmol) in DMF (5 mL) was added to the mixture and stirred overnight at room temperature. The mixture was diluted with ethyl acetate and washed with saturated $NaHCO_3$ solution and dried over $Na_2SO_4$. After concentration under reduced pressure, the crude product was dissolved in 50% TFA (25 mL) in DCM and stirred for 2.5 h. The volatiles were blown off by a stream of N2 and the residue was neutralized by addition of sat. $Na_2CO_3$ solution. The product was extracted with DCM and dried over $Na_2SO_4$ to yield the following amine product: methyl (S)-3-amino-2-((S)-1-(phenylsulfonyl)pyrrolidine-2-carboxamido)propanoate: ESI-MS 356.7 (MH$^+$).

Step 2. Synthesis of HIJ-1083: To stirred solution of Fmoc-aminohexanoic acid (1.1 eq), HCTU (1.1 eq) and DIPEA (2.2 eq) was to the amine product (200 mg) from step 1 at room temperature and stirred overnight. The mixture was diluted with ethyl acetate and washed with brine followed by drying over $Na_2SO4$. The mixture was concentrated under reduced pressure and diluted with 30% diethylamine in acetonitrile. The mixture was stirred for 2 hours and the volatiles were removed under reduced pressure. The crude product was diluted with DMF (1 mL) and Bis-boc-1H-pyrazole-1-carboxamidine (2 eq) and DIPEA (2 eq) were added at room temperature. The mixture was stirred overnight and diluted with ethyl acetate. The organic layer was washed with water and dried over $Na_2SO_4$. After concentration under reduced pressure, the residue was dissolved in 50% TFA in DCM (5 mL) and stirred for 1 hour. The volatiles were blown off by a stream of nitrogen and the residue was diluted with THF:$H_2O$ (4:1, 5 mL). LiOH was added to the mixture to make the solution pH around 11 to 12. The mixture was stirred for 1 h and acidified by addition of 1M HCl and purified by RP-HPLC. (Atlantis Prep T3 OBD 19×150 mm, 5% to 65% B over 23 min, flow rate: 10 ml/min, solvent A: 0.1% TFA in $H_2O$, solvent B: 0.1% TFA in 99% acetonitrile in $H_2O$). The fractions containing the product were pooled and lyophilized to yield compound product HIJ-1083: (S)-3-(6-guanidinohexanamido)-2-((S)-1-(phenylsulfonyl)pyrrolidine-2-carboxamido)propanoic acid: 18.7 min, ESI-MS 497.9 (MH$^+$).

Example 3. Synthesis of HIJ-1093

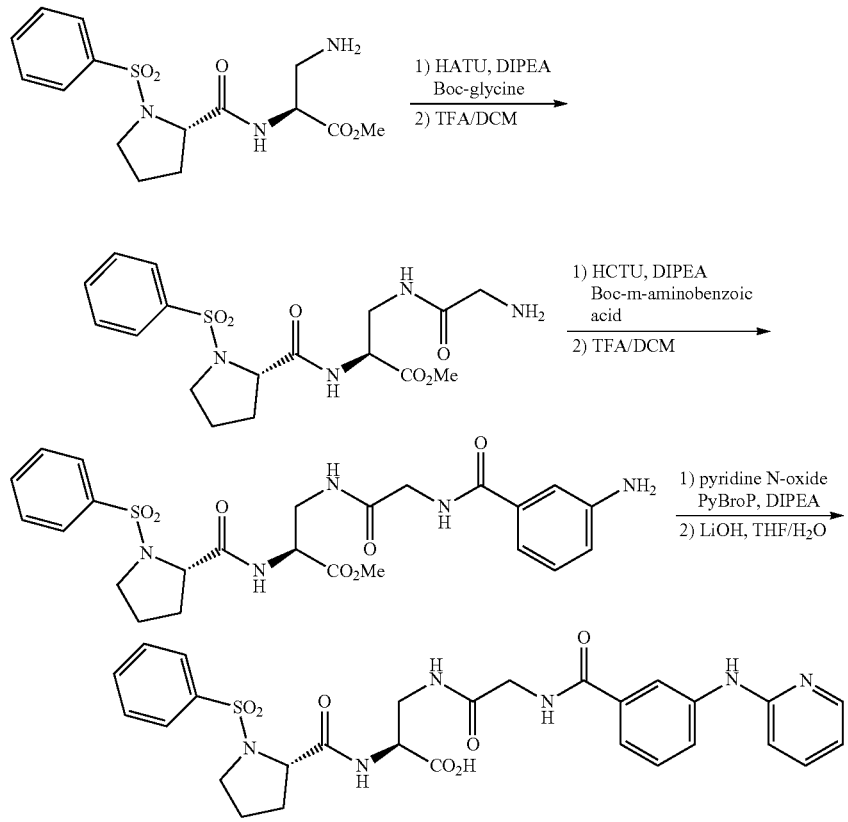

Step 1. Synthesis of N-benzenesulfonyl-Pro-DAP-Gly-OMe: To a solution of N-benzenesulfonyl-Pro-DAP-OMe (712 mg) in DMF (5 mL) were added DIPEA (2.2 eq), Boc glycine (1.1 eq) and HATU (1 eq). The mixture was stirred overnight at room temperature. The mixture was diluted with ethyl acetate and washed with saturated NaHCO₃ solution and dried over Na₂SO₄. After concentration under reduced pressure, the crude product was dissolved in 50% TFA in DCM (12 mL) and stirred 1 hour. The volatiles were removed by a stream of N₂ and the crude product was diluted with DCM and washed with sat NaHCO₃ and 1M NaOH solution. After drying over Na2SO4, the mixture was concentrated under reduced pressure to yield the amine product: methyl (S)-3-(2-aminoacetamido)-2-((S)-1-(phenylsulfonyl)pyrrolidine-2-carboxamido)propanoate: ESI-MS 413.6 (MH⁺).

Steps 2 and 3. Synthesis of N-benzenesulfonyl-Pro-DAP-Gly-Abz-OMe: To a solution of amine product from step 1 (300 mg) in DMF (3 mL) was added Boc-aminobenzoic acid (1 eq), HCTU (1 eq) and DIPEA (2 eq). The mixture was stirred overnight and diluted with ethyl acetate. The organic layer was washed with water and brine and dried over Na₂SO₄. The mixture was concentrated under reduced pressure. The crude mixture was dissolved in 50% TFA in DCM (10 mL) and stirred for 1 hour. The volatiles were removed by a stream of N₂ and diluted with DCM. The organic layer was washed with sat. Na₂CO₃ solution and dried over Na₂SO₄. After concentration under reduced pressure, half of the crude mixture (150 mg, 1.25 eq), pyridine N-oxide (19 mg, 1 eq), DIPEA (0.125 mL, 3.75 eq) were dissolved in DCM and PyBroP (120 mg, 1.3 eq) was added at room temperature. The mixture was stirred overnight and washed with water. The organic layer was concentrated and dissolved in THF:H₂O (4:1, 5 mL). LiOH (21 mg) was added to the mixture and acidified with 1M HCl after stirring for 3 h at room temperature. The mixture was purified by RP-HPLC. (Atlantis Prep T3 OBD 19×150 mm, 5% to 65% B over 23 min, flow rate: 10 ml/min, solvent A: 0.1% TFA in H₂O, solvent B: 0.1% TFA in 99% acetonitrile in H₂O). The fractions containing the product were pooled and lyophilized to yield the compound product HIJ-1093: methyl (S)-2-((S)-1-(phenylsulfonyl)pyrrolidine-2-carboxamido)-3-(2-(3-(pyridin-2-ylamino)benzamido)acetamido)propanoate: retention time 19.0 min, ESI-MS 595.9 (MH+).

Example 4. Synthesis of HIJ-1094

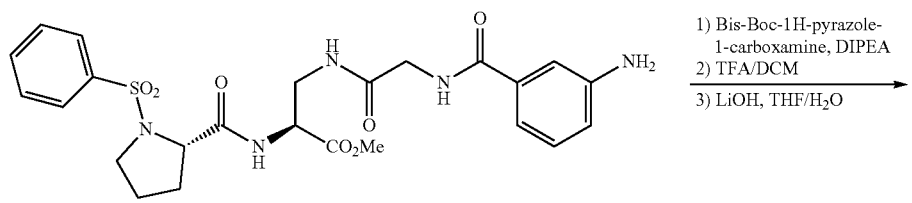

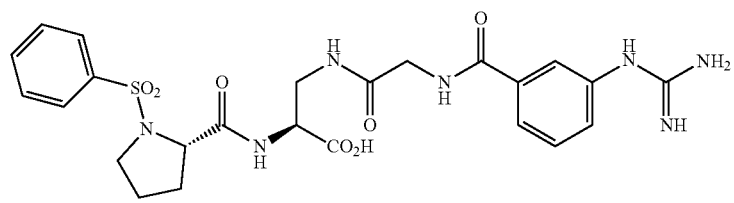

A mixture of half of the crude amine (150 mg, 1.25 eq) from synthesis of HIJ-1093 (Example 3), Bis-boc-1H-pyrazole-1-carboxamidine (2 eq), DIPEA (2 eq) in DMF (1 mL) was stirred overnight at room temperature. The mixture was diluted with DCM and washed with water. After drying over Na₂SO₄, the mixture was concentrated under reduced pressure and dissolved in 50% TFA in DCM. The mixture was stirred for 2 hours and the volatiles were removed by a stream of nitrogen. The oily residue was dissolved in THF:H₂O (4:1, 5 mL) and LiOH was added until the solution pH became app. 11 to 12. After stirring 1 hour at room temperature, the mixture was acidified with 1M HCl. The mixture was purified by RP-HPLC. (Atlantis Prep T3 OBD 19×150 mm, 5% to 65% B over 23 min, flow rate: 10 ml/min, solvent A: 0.1% TFA in H₂O, solvent B: 0.1% TFA in 99% acetonitrile in H₂O). The fractions containing the product were pooled and lyophilized to yield the compound product HIJ-1094: (S)-3-(2-(3-guanidinobenzamido)acetamido)-2-((S)-1-(phenylsulfonyl)pyrrolidine-2-carboxamido)propanoic acid: retention time 17.9 min, ESI-MS 560.9 (MH+).

Example 5. Synthesis of HIJ-1099

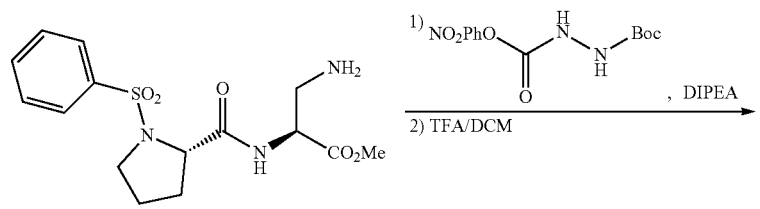

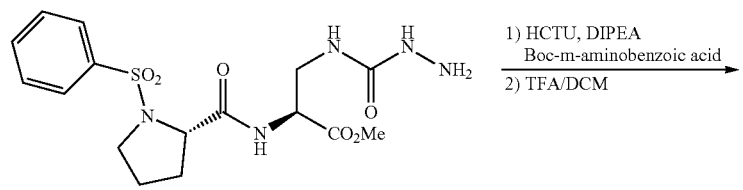

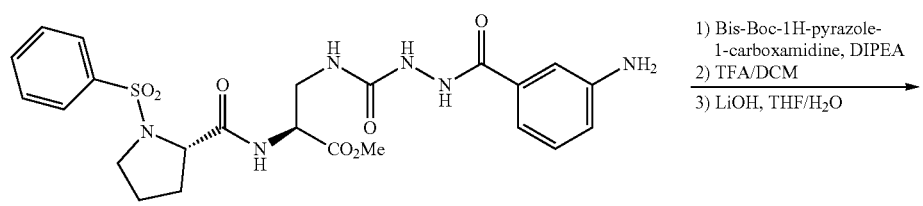

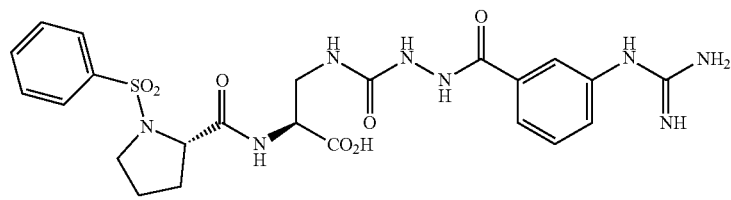

Step 1. Synthesis of N-benzenesulfonyl-Pro-DAP-azaGly-OMe: To a mixture of amine (600 mg, 1 eq) and 1-(tert-butyl) 2-(4-nitrophenyl) hydrazine-1,2-dicarboxylate (1 eq) in anhydrous DCM (4 mL) was added trimethylamine (1 eq) at room temperature, as indicated in the above scheme. The mixture was stirred 1 hour at room temperature. The mixture was diluted with DCM and washed with water. After drying over Na$_2$SO$_4$, the mixture was concentrated under reduced pressure. The crude product was dissolved in 50% TFA in DCM. The mixture was stirred for 1 hour and the volatiles were removed by a stream of nitrogen. The oily residue was dissolved in DCM again and washed with sat Na$_2$CO$_3$ solution and dried over Na$_2$SO$_4$. The organic layer was concentrated under reduced pressure to yield the amine product: methyl (S)-3-(hydrazinecarboxamido)-2-((S)-1-(phenylsulfonyl)pyrrolidine-2-carboxamido)propanoate: ESI-MS 414.6 (MH$^+$).

Steps 2 and 3. Synthesis of HIJ-1099: To a solution of the amine product (200 mg) from step 1 in DMF (2 mL) was added Boc-aminobenzoic acid (1.2 eq), HCTU (1.2 eq) and DIPEA (2.5 eq). The mixture was stirred overnight and diluted with ethyl acetate. The organic layer was washed with water and brine and dried over Na$_2$SO$_4$. The mixture was concentrated under reduced pressure. The crude mixture was dissolved in 50% TFA in DCM (5 mL) and stirred for 1 hour. The volatiles were removed by a stream of N2 and diluted with DCM. The organic layer was washed with sat. Na$_2$CO3 solution and dried over Na$_2$SO$_4$. The mixture was concentrated under reduced pressure and dissolved in DMF (2 mL). Bis-boc-1H-pyrazole-1-carboxamidine (2 eq) and DIPEA (2 eq) were added to the mixture and stirred overnight at room temperature. The mixture was diluted with ethyl acetate (50 mL) and washed with water. After drying over Na$_2$SO$_4$, the mixture was concentrated under reduced pressure and dissolved in 50% TFA in DCM. The mixture was stirred for 2 h and the volatiles were removed by a stream of nitrogen. The oily residue was dissolved in THF:H$_2$O (4:1, 5 mL) and LiOH was added until the solution pH became app. 11 to 12. After stirring 1 h at room temperature, the mixture was acidified with 1M HCl. The mixture was purified by RP-HPLC. (Atlantis Prep T3 OBD 19×150 mm, 5% to 65% B over 23 min, flow rate: 10 ml/min, solvent A: 0.1% TFA in H$_2$O, solvent B: 0.1% TFA in 99% acetonitrile in H$_2$O). The fractions containing the product were pooled and lyophilized to yield the compound product HIJ-1099: (S)-3-(2-(3-guanidinobenzoyl)hydrazine-1-carboxamido)-2-((S)-1-(phenylsulfonyl)pyrrolidine-2-carboxamido)propanoic acid: retention time 17.6 min ESI-MS 561.9 (MH$^+$).

Example 6. Synthesis of HIJ-1203

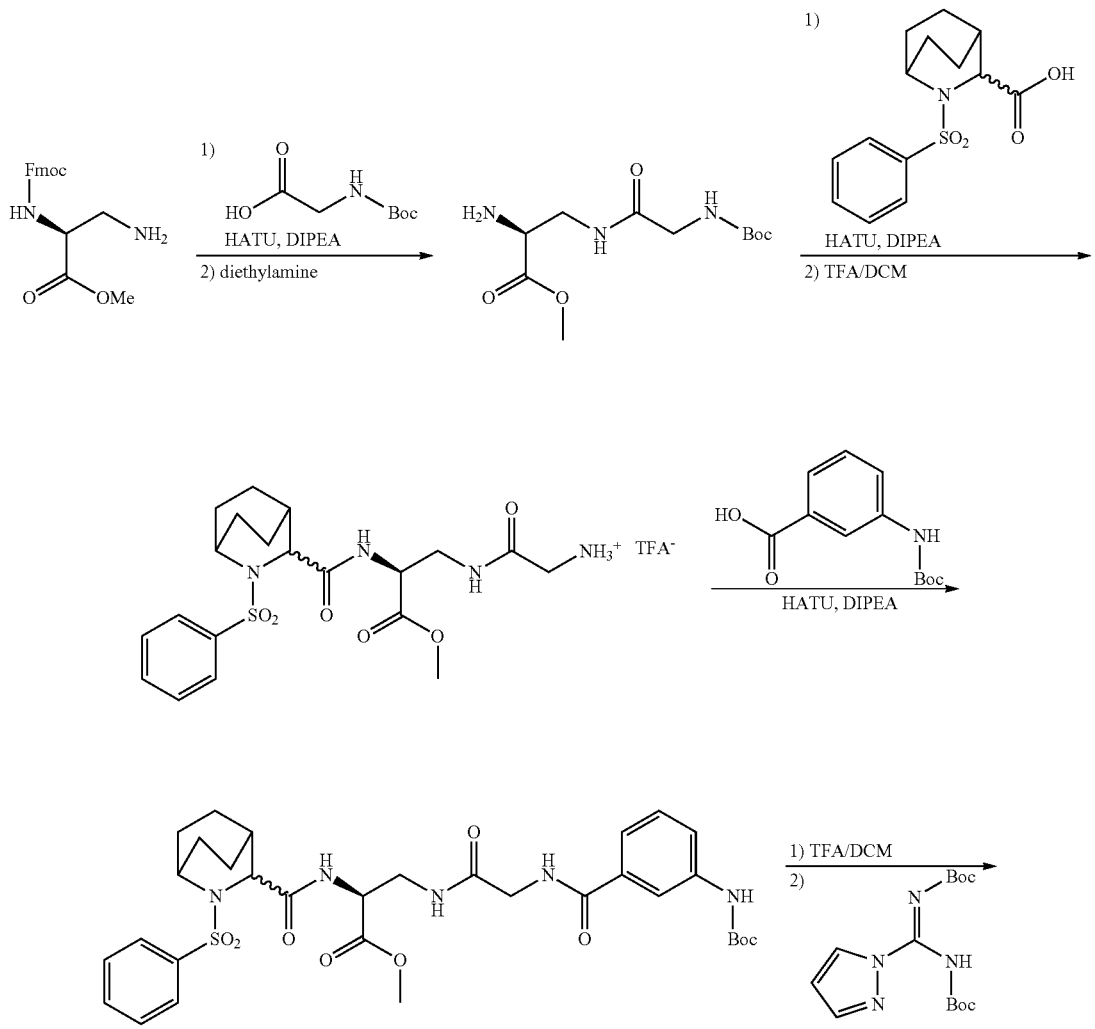

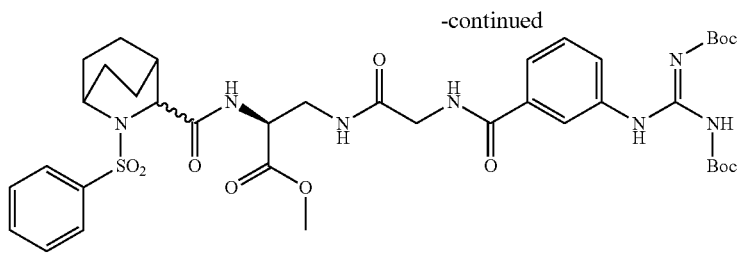

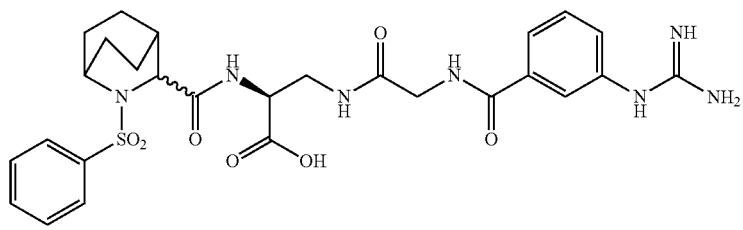

To a solution of amine (255 mg, TFA salt) in DMF (4 mL) was added Boc-glycine (1 eq), HCTU (0.95 eq) and DIPEA (4 eq) as indicated in the above reaction scheme. The mixture was stirred overnight and diluted with ethyl acetate. The organic layer was washed with water and brine and dried over $Na_2SO_4$. The mixture was concentrated under reduced pressure. The crude mixture was dissolved in 30% diethylamine in acetonitrile (6 mL) and stirred for 1 hour. The volatiles were removed under reduced pressure and the layer was separated by addition hexanes. The lower yellow layer was collected and the washing was repeated twice. The crude amine was diluted with DMF (2 mL) and a premixed solution of acid (89 mg), HATU (114 mg), and DIPEA (0.104 mL) in DMF (2 mL) was added and stirred overnight. The reaction mixture was then diluted with ethyl acetate. The organic layer was washed with water and brine and dried over $Na_2SO_4$. The mixture was concentrated under reduced pressure. The crude product was dissolved in 50% TFA in DCM (5 mL) and stirred for 3 h. The volatiles were blown off by a stream of nitrogen. The oily residue was then precipitated by addition cold diethyl ether. After centrifuge, the supernatant was decanted. The solid was then dissolved in DMF (2 mL) and Boc-3-aminobenzoic acid (71 mg), HATU (114 mg), DIPEA (0.174 mL) were added and stirred overnight. The reaction mixture was then diluted with ethyl acetate. The organic layer was washed with water and brine and dried over $Na_2SO_4$. The mixture was concentrated under reduced pressure. The crude product was then dissolved in 50% TFA in DCM (5 mL). The mixture was stirred for 2 hours and the volatiles were removed by a stream of nitrogen. The oily residue was then dissolved in ethyl acetate and washed with sat. $Na_2CO_3$ solution. After drying over $Na_2SO_4$, the mixture was concentrated under reduced pressure and dissolved in DMF (1 mL). Bis-boc-1H-pyrazole-1-carboxamidine (0.5 mmol) and DIPEA (0.5 mmol) were added to the mixture and stirred overnight at room temperature. The mixture was diluted with ethyl acetate (30 mL) and washed with water. After drying over $Na_2SO_4$, the mixture was concentrated under reduced pressure and dissolved in 50% TFA in DCM (5 mL). The mixture was stirred for 2 hours and the volatiles were removed by a stream of nitrogen. The oily residue was dissolved in THF:$H_2O$ (4:1, 5 mL) and LiOH was added until the solution pH became app. 11 to 12. After stirring 1 hour at room temperature, the mixture was acidified with 1M HCl. The mixture was purified by RP-HPLC. (Atlantis Prep T3 OBD 19×150 mm, 5% to 65% B over 23 min, flow rate: 10 ml/min, solvent A: 0.1% TFA in $H_2O$, solvent B: 0.1% TFA in 99% acetonitrile in $H_2O$). The fractions containing the product were pooled and lyophilized to yield the compound product HIJ-1203: (2S)-3-(2-(3-guanidinobenzamido)acetamido)-2-(2-(phenylsulfonyl)-2-azabicyclo[2.2.2]octane-3-carboxamido)propanoic acid: retention time 15.8 min ESI-MS 600.8 (MH$^+$).

Example 7. Synthesis of HIJ-1204

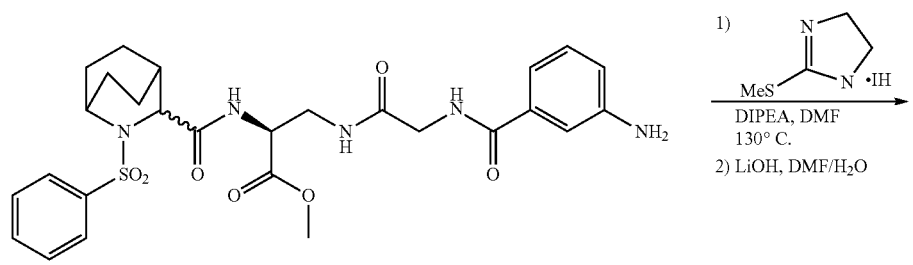

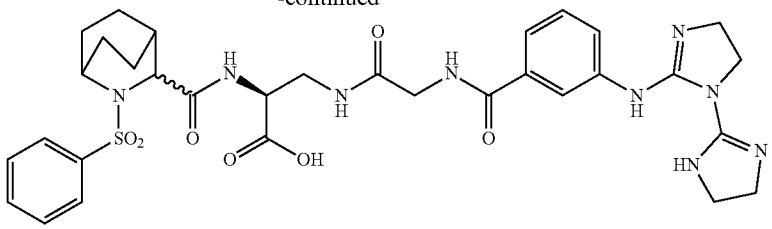

To the amine (0.087 mmol) was added 2-methylthioimidazoline (1 mmol) in DMF was added DIPEA (2 mmol) and stirred at 135° C. bath for 2 hours. The mixture was cooled down and water was added. The mixture was extracted with ethyl acetate. The volatiles were removed under reduced pressure and the crude residue was dissolved in DMF-H2O (1:1, 2 mL). LiOH (50 mg) was added and stirred at room temperature for 3 hours and the mixture was acidified (pH=4) by 1M HCl and lyophilized. The lyophilized mixture was purified by RP-HPLC. (Atlantis Prep T3 OBD 19×150 mm, 5% to 65% B over 23 min, flow rate: 10 ml/min, solvent A: 0.1% TFA in H$_2$O, solvent B: 0.1% TFA in 99% acetonitrile in H$_2$O). The fractions containing the product were pooled and lyophilized to yield the compound product HIJ-1204:(2S)-2-(2-(phenylsulfonyl)-2-azabicyclo[2.2.2]octane-3-carboxamido)-3-(2-(3-((4,4',5,5'-tetrahydro-1'H-[1,2'-biimidazol]-2-yl)amino)benzamido)acetamido)propanoic acid: retention time 16.0 min ESI-MS 695.1 (MH$^+$).

Example 8. Synthesis of HIJ-1213

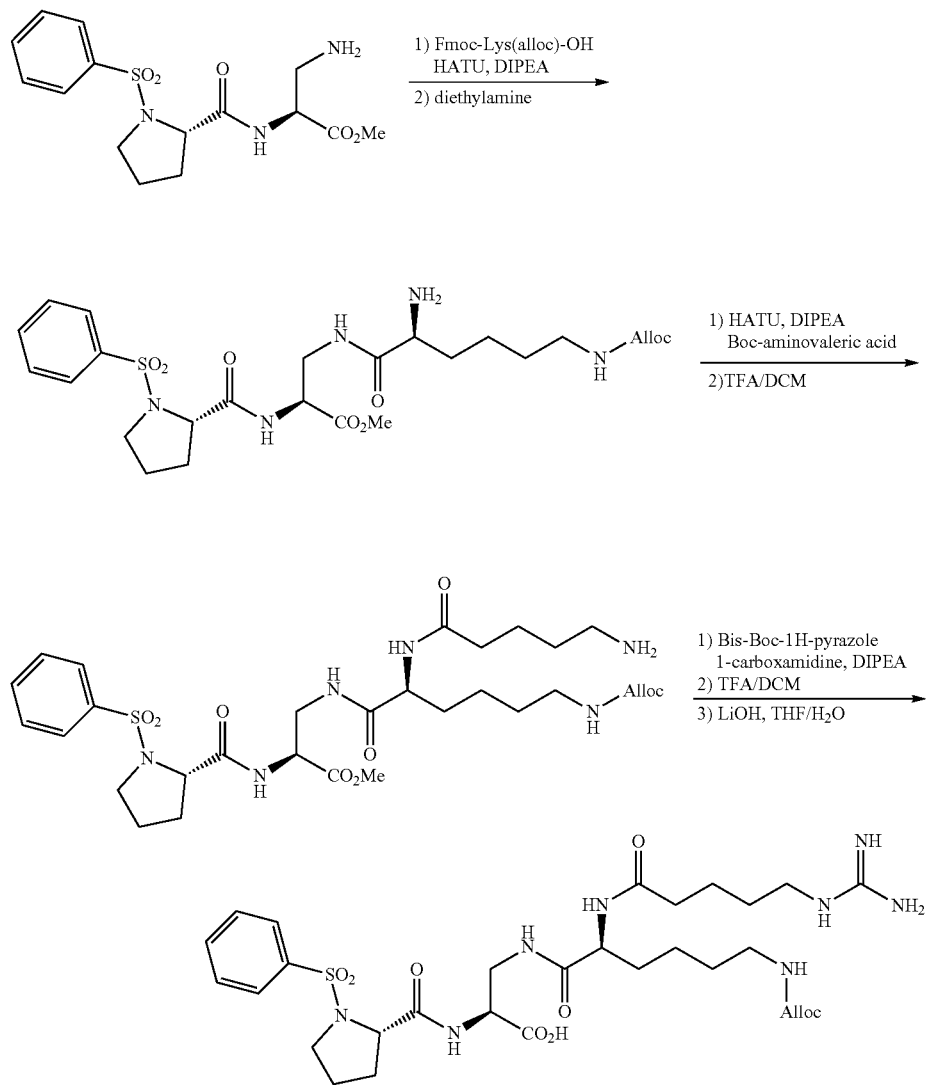

To a mixture of amine (2 mmol, TFA salt) and Fmoc-Lys (alloc)-OH (1 eq), DIPEA (5 eq) was added HATU (1 eq) and stirred overnight. The mixture was diluted with ethyl acetate and washed with water. After drying over $Na_2SO_4$, the mixture was concentrated under reduced pressure. The crude product was dissolved in 30% diethylamine in acetonitrile (15 mL) and stirred for 1 hour. The volatiles were removed under reduced pressure and the layer was separated by addition hexanes. The lower yellow layer was collected and the washing was repeated twice. The crude amine was diluted with DMF (10 mL) and Boc-aminovaleric acid (2 mmol), HATU (1.9 mmol), and DIPEA (4 mmol) were added. The mixture was stirred overnight. The reaction mixture was then diluted with ethyl acetate. The organic layer was successively washed with 1M HCl, sat. $NaHCO_3$ solution, brine and dried over $Na_2SO_4$. The mixture was concentrated under reduced pressure. The crude product was dissolved in 50% TFA in DCM (10 mL) and stirred for 3 hours. The volatiles were blown off by a stream of nitrogen. The oily residue was then precipitated by addition cold diethyl ether. After centrifuge, the supernatant was decanted. The solid was dissolved in DMF (10 mL) and Bis-boc-1H-pyrazole-1-carboxamidine (0.5 mmol) and DIPEA (0.5 mmol) were added to the mixture. After stirring overnight at room temperature, the mixture was diluted with ethyl acetate (50 mL) and washed with water. After drying over $Na_2SO_4$, the mixture was concentrated under reduced pressure and dissolved in 50% TFA in DCM (10 mL). The mixture was stirred for 2 hours and the volatiles were removed by a stream of nitrogen. The crude product was precipitated by addition of cold ether. After centrifuge, the supernatant was decanted. The solid was dissolved in $THF:H_2O$ (4:1, 10 mL) and LiOH (87 mg) was added After stirring 1 hour at room temperature, the mixture was acidified with 1M HCl. The mixture was purified by RP-HPLC. (Atlantis Prep T3 OBD 19×150 mm, 5% to 70% B over 37 min, flow rate: 10 ml/min, solvent A: 0.1% TFA in $H_2O$, solvent B: 0.1% TFA in 99% acetonitrile in $H_2O$). The fractions containing the product were pooled and lyophilized to yield the compound product HIJ-1213: (13S,17S)-13-(4-(((allyloxy)carbonyl) amino)butyl)-5,11,14-trioxo-17-((S)-1-(phenylsulfonyl)pyrrolidine-2-carboxamido)-4-oxa-6,12,15-triazaoctadec-1-en-18-oic acid: retention time 24.8 min ESI-MS 695.9 ($MH^+$).

Example 9. Synthesis of HIJ-1216

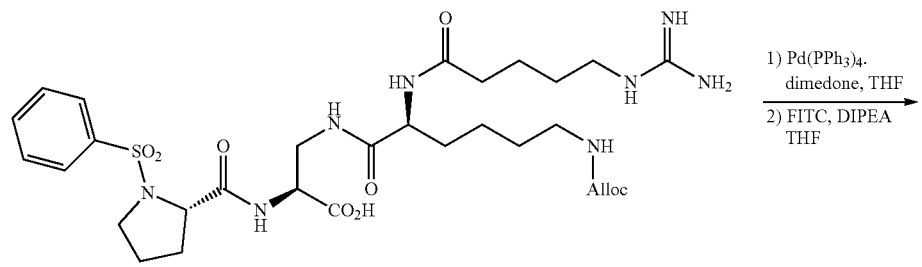

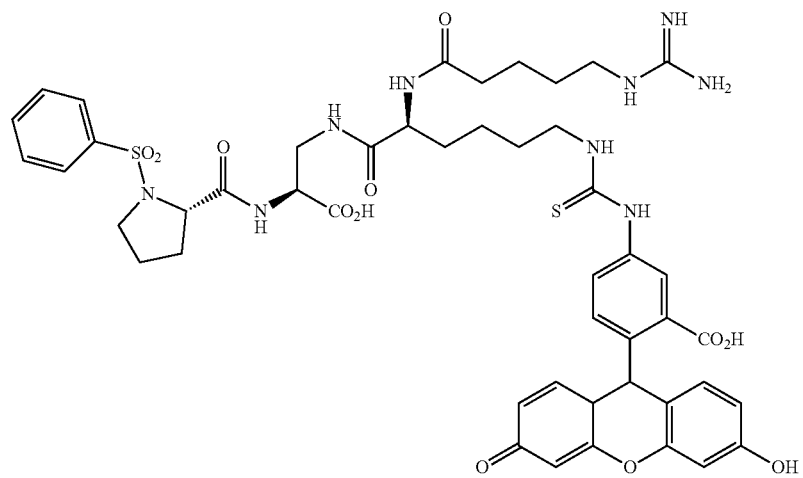

To a mixture of HIJ-1213 (Example 8) (2 mg, TFA salt) in THF (2 mL) was added dimedone (4 mg) and Pd(PPh$_3$)$_4$ (4 mg). After 1 hour, H$_2$O (1 mL) was added and additional Pd(PPh3)4 was added. After 3 hours, FITC (25 mg) and DIPEA (0.066 mL) were added and stirred overnight. The solvent was removed and purified by RP-HPLC. (Atlantis Prep T3 OBD 19×150 mm, 5% to 55% B over 14 min, flow rate: 10 ml/min, solvent A: 0.1% TFA in H$_2$O, solvent B: 0.1% TFA in 99% acetonitrile in H$_2$O). The fractions containing the product were pooled and lyophilized to yield the compound product HIJ-1216: 5-(3-((S)-6-(((S)-2-carboxy-2-((S)-1-(phenylsulfonyl)pyrrolidine-2-carboxamido)ethyl) amino)-5-(5-guanidinopentanamido)-6-oxohexyl)thioureido)-2-(6-hydroxy-3-oxo-9,9a-dihydro-3H-xanthen-9-yl) benzoic acid: retention time 19.6 min ESI-MS: 1001.1 (M$^+$).

Example 10. Synthesis of HIJ-1437

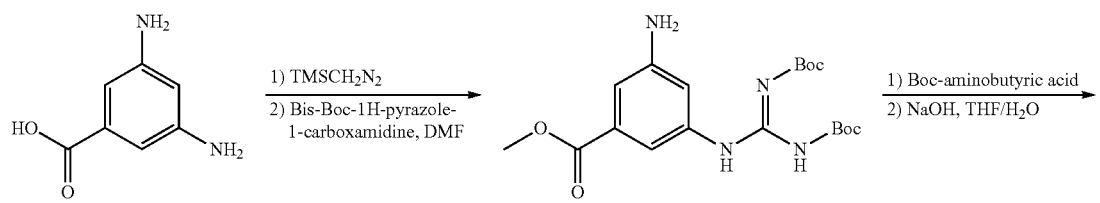

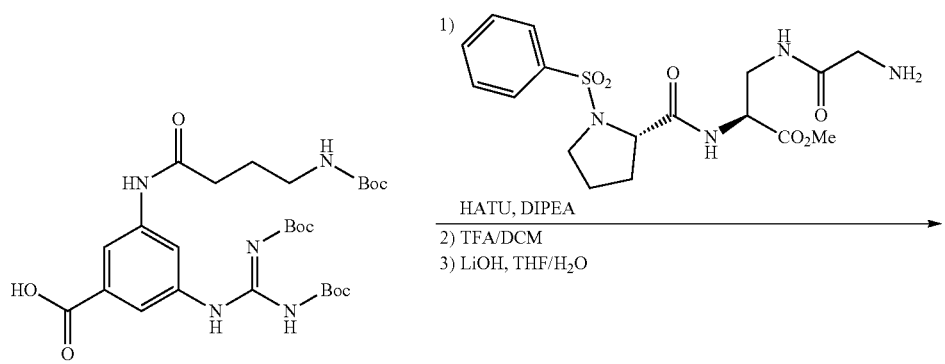

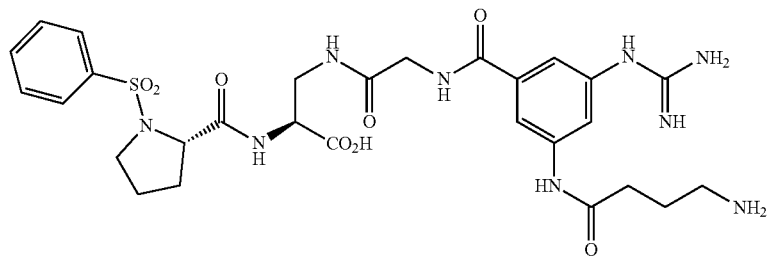

3,5-diaminobenzoic acid (10 mmol) was suspended in DCM/MeOH (2/1, 30 mL) and TMSdiazomethane (6 mL, 2M in hexanes) was added to the stirring mixture dropwise. After stirring for 1 hour, the volatiles were removed under reduced pressure. DMF (10 mL) was added to the oily residue and Bis-Boc-1H-pyrazole-1-carboxamide (2 g) was added. After 20 min, NaOH solution (1M) was added to make the solution basic (pH=10) and the aqueous layer was extracted with ethyl acetate. After drying over $Na_2SO_4$, the mixture was concentrated under reduced pressure. The crude amine was dissolved in DMF (15 mL) and Boc-aminobutyric acid (660 mg), DIPEA (1.2 mL), HATU (1.14 g) were added. The mixture was stirred overnight and diluted with ethyl acetate and washed with water. After drying over $Na_2SO_4$, the mixture was concentrated under reduced pressure. The crude product was purified by column chromatography using hexanes/ethyl acetate as eluants. (ESI-MS; 594.6 ($MH^+$)). Thus obtained ester (350 mg) was dissolved in $THF:H_2O$ (3:1, 10 mL). Then 3M NaOH (0.7 mL) and a small amount of MeOH were added and stirred 1 hour. The reaction mixture was diluted with ethyl acetate and acidified with 1M HCl. The organic layer was dried over $Na_2SO_4$ and concentrated under reduced pressure. The crude acid was dissolved in DMF (5 mL) and Benzenesulfonyl-L-Pro-Gly-OMe (145 mg), HATU (100 mg), DIPEA (0.121 mL) were added and stirred overnight. The mixture was diluted with ethyl acetate (30 mL) and washed with water. After drying over $Na_2SO_4$, the mixture was concentrated under reduced pressure and dissolved in 50% TFA in DCM (15 mL). The mixture was stirred for 2 h and the volatiles were removed by a stream of nitrogen. The oily residue was dissolved in $THF:H_2O$ (4:1, 5 mL) and LiOH (55 mg) was added. After stirring 1 hour at room temperature, the mixture was acidified with 1M HCl. The mixture was purified by RP-HPLC. (Atlantis Prep T3 OBD 19×150 mm, 5% to 65% B over 23 min, flow rate: 10 ml/min, solvent A: 0.1% TFA in $H_2O$, solvent B: 0.1% TFA in 99% acetonitrile in $H_2O$). The fractions containing the product were pooled and lyophilized to yield the compound product HIJ-1437: (S)-3-(2-(3-(4-aminobutanamido)-5-guanidinobenzamido)acetamido)-2-((S)-1-(phenylsulfonyl)pyrrolidine-2-carboxamido)propanoic acid: retention time 17.1 min, ESI-MS: 660.6 ($MH^+$).

Example 11. Synthesis of HIJ-1483

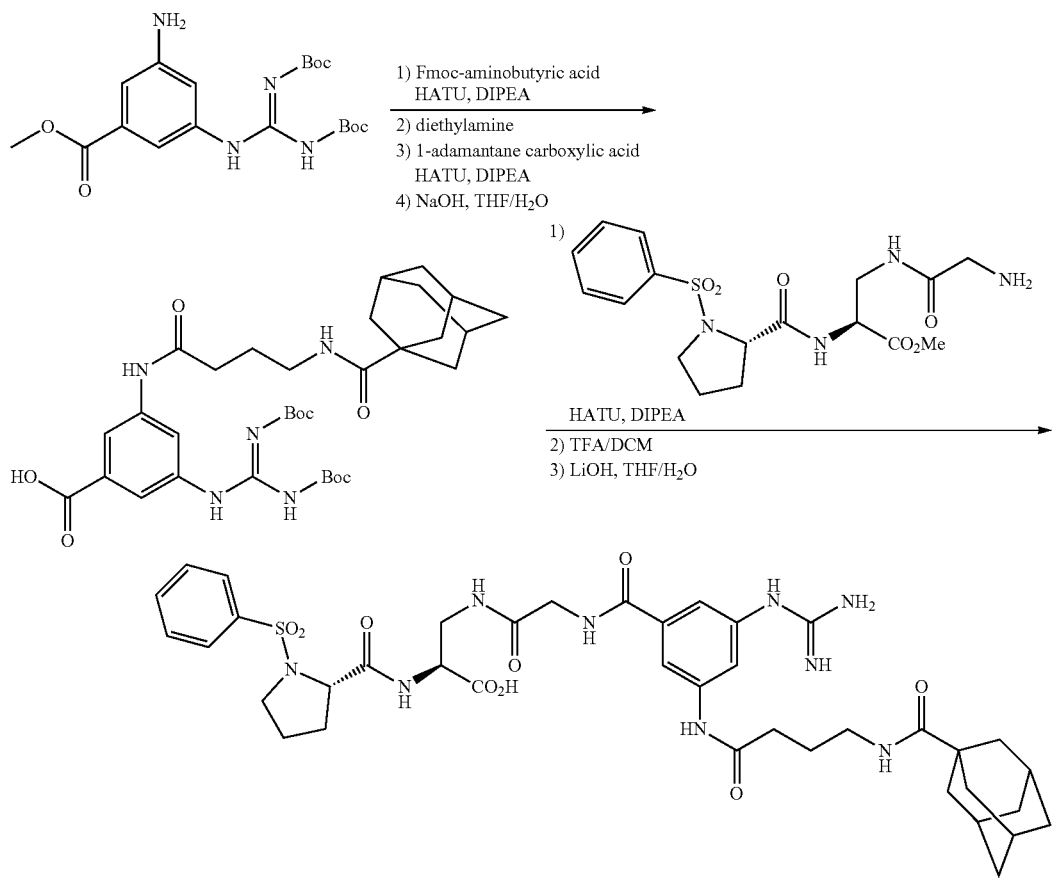 [SMILES: COC(=O)c1cc(N)cc(N/C(=N/C(=O)OC(C)(C)C)NC(=O)OC(C)(C)C)c1 ; CC(C)(C)OC(=O)/N=C(\NC(=O)OC(C)(C)C)Nc1cc(NC(=O)CCCNC(=O)C23CC4CC(CC(C4)C2)C3)cc(C(=O)O)c1 ; COC(=O)[C@H](CNC(=O)CN)NC(=O)[C@@H]1CCCN1S(=O)(=O)c1ccccc1 ; N=C(N)Nc1cc(NC(=O)CCCNC(=O)C23CC4CC(CC(C4)C2)C3)cc(C(=O)NCC(=O)NC[C@H](NC(=O)[C@@H]2CCCN2S(=O)(=O)c2ccccc2)C(=O)O)c1]

To a solution of amine (777 mg) in DMF (5 mL) were added Fmoc-aminobutyric acid (1 eq), DIPEA (2.5 eq), and HATU (1 eq) and stirred overnight. The mixture was diluted with ethyl acetate and washed with water. After drying over $Na_2SO_4$, the mixture was concentrated under reduced pressure. The crude product was dissolved in 30% diethylamine in acetonitrile (40 mL) and stirred for 2 hours. The volatiles were removed under reduced pressure and the layer was separated by addition hexanes (100 mL). The lower yellow layer was collected and the washing was repeated twice. To the crude amine (600 mg) in DMF (15 mL) were added 1-amantane carboxylic acid (1 eq), HATU (1 eq), DIPEA (2.1 eq) and stirred overnight. The mixture was diluted with ethyl acetate and washed with water. After drying over Na$_2$SO$_4$, the mixture was concentrated under reduced pressure. The crude product was purified by column chromatography using hexanes/ethyl acetate as eluants. To the above ester (120 mg) in THF-H$_2$O (4:1, 5 mL) was added NaOH (200 mg) and stirred overnight. THF was removed under reduced pressure and the solution was acidified to pH=4 by 2M KHSO$_4$. The solid precipitated, filtered and washed with water and lyophilized. To the acid (65 mg) in DMF (1 mL) was added benzenesulfonyl-L-Pro-DAP-Gly-OMe (52 mg), HATU (38 mg), and DIPEA (0.07 mL). The mixture was stirred overnight and diluted with ethyl acetate and washed with water. After drying over Na$_2$SO$_4$, the mixture was concentrated under reduced pressure and then dissolved in 50% TFA in DCM (5 mL). The mixture was stirred for 3 h and the volatiles were removed by a stream of nitrogen. The oily residue was dissolved in THF:H$_2$O (4:1, 5 mL) and LiOH (24 mg) was added. After stirring 3 h at room temperature, the mixture was acidified with 2M KHSO4. The mixture was purified by RP-HPLC. (Atlantis Prep T3 OBD 19×150 mm, 5% to 65% B over 23 min, flow rate: 10 ml/min, solvent A: 0.1% TFA in H$_2$O, solvent B: 0.1% TFA in 99% acetonitrile in H$_2$O). The fractions containing the product were pooled and lyophilized to yield the compound product HIJ-1483: (2S)-3-(2-(3-(4-((1s,3s)-adamantane-1-carboxamido)butanamido)-5-guanidinobenzamido)acetamido)-2-((S)-1-(phenylsulfonyl)pyrrolidine-2-carboxamido)propanoic acid: retention time 20.7 min, ESI-MS: 822.7 (MH$^+$).

Example 12. Synthesis of HIJ-1491

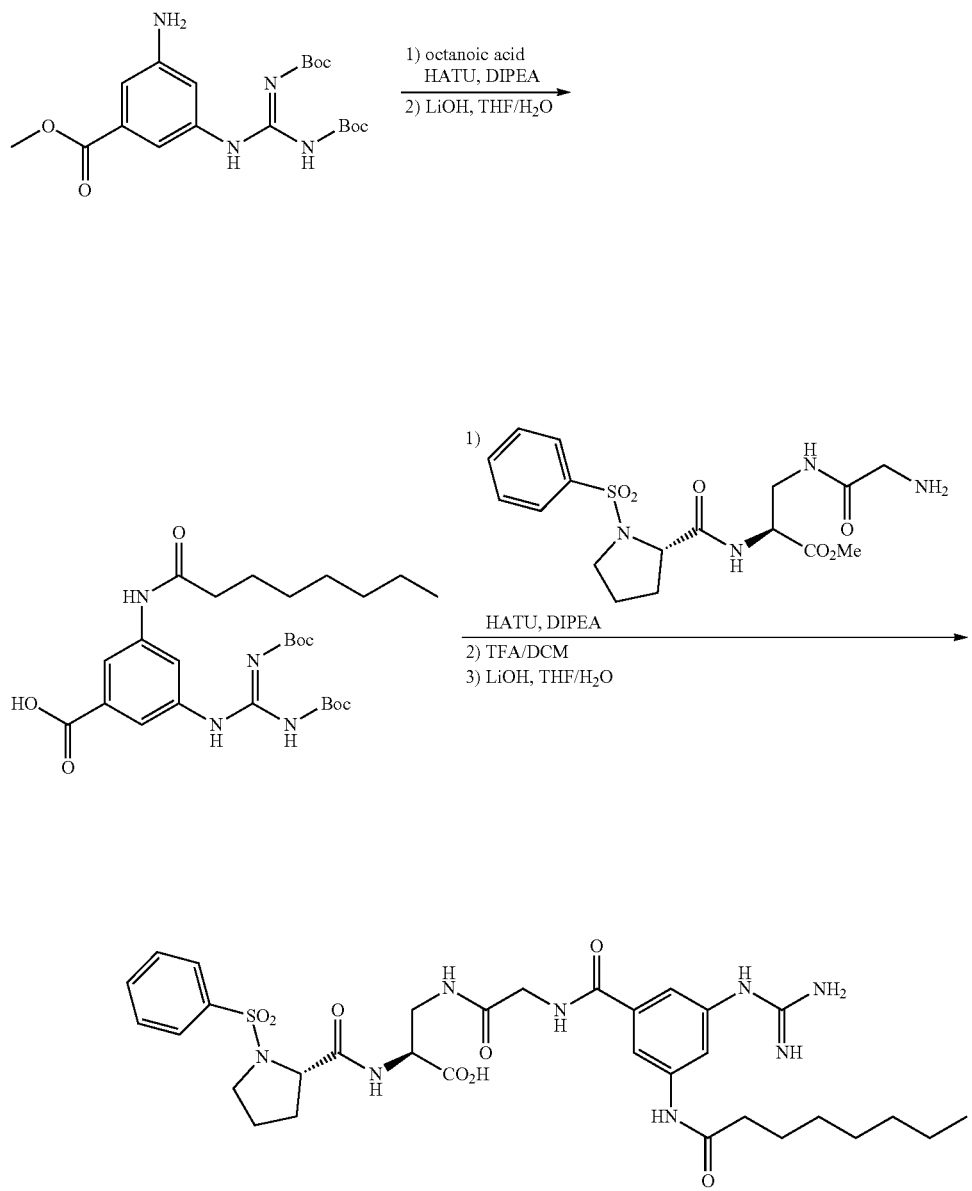

To a solution of amine (307 mg) in DMF (5 mL) were added octanoic acid (1 eq), DIPEA (2.5 eq), and HATU (1 eq) and stirred overnight. The mixture was diluted with ethyl acetate and washed with water. After drying over $Na_2SO_4$, the mixture was concentrated under reduced pressure. The crude product was purified by column chromatography using hexanes/ethyl acetate as eluants. To the above ester (53 mg) in THF-$H_2O$ (3:1, 5 mL) was added NaOH (60 mg) and and EtOH (2 mL) and stirred overnight. THF was removed under reduced pressure and diluted with ethyl acetate. The solution was acidified to pH=2 by 2M KHSO4. The organic layer was dried over $Na_2SO_4$ and concentrated under reduced pressure. To the crude acid in DMF (1 mL) was added benzenesulfonyl-L-Pro-DAP-Gly-OMe (50 mg), HATU (38 mg), and DIPEA (0.07 mL). The mixture was stirred for 72 hours and diluted with ethyl acetate and washed with water. After drying over $Na_2SO_4$, the mixture was concentrated under reduced pressure and then dissolved in 50% TFA in DCM (4 mL). The mixture was stirred for 3 hours and the volatiles were removed by a stream of nitrogen. The oily residue was dissolved in THF:$H_2O$ (3:1, 6 mL) and LiOH (32 mg) was added. After stirring 3 hours at room temperature, the mixture was acidified with 2M $KHSO_4$. The mixture was purified by RP-HPLC. (Atlantis Prep T3 OBD 19×150 mm, 5% to 65% B over 23 min, flow rate: 10 ml/min, solvent A: 0.1% TFA in $H_2O$, solvent B: 0.1% TFA in 99% acetonitrile in $H_2O$). The fractions containing the product were pooled and lyophilized to yield the compound product HIJ-1491: (S)-3-(2-(3-guanidino-5-octanamidobenzamido)acetamido)-2-((S)-1-(phenyl sulfonyl)pyrrolidine-2-carboxamido)propanoic acid: retention time 20.8 min, ESI-MS: 701.5 (MH+).

---

What is claimed is:

1. A compound having the formula:

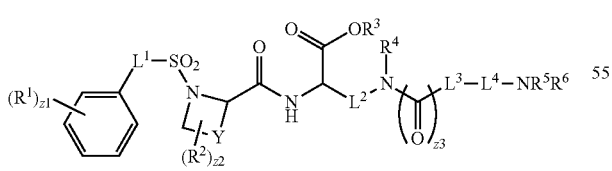

wherein, $R^1$ is independently halogen, $-N_3$, $-CX^1{}_3$, $-CHX^1{}_2$, $-CH_2X^1$, $-OCX^1{}_3$, $-OCH_2X^1$, $-OCHX^1{}_2$, $-CN$, $-SO_{n1}R^{1D}$, $-SO_{v1}NR^{1A}R^{1B}$, $-OSO_{v1}R^{1D}$, $-NHC(O)NR^{1A}R^{1B}$, $-N(O)_{m1}$, $-NR^{1A}R^{1B}$, $-C(O)R^{1C}$, $-C(O)-OR^{1C}$, $-C(O)NR^{1A}R^{1B}$, $-OR^{1D}$, $-NR^{1A}SO_2R^{1D}$, $-NR^{1A}C(O)R^{1C}$, $-NR^{1A}C(O)$ $OR^{1C}$, $-NR^{1A}OR^{1C}$, $-ONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety; or two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl;

$L^1$ is a bond, substituted or unsubstituted alkylene, or substituted or unsubstituted heteroalkylene;

Y is a bond, —C—, —C—C—, —C=C—, —C—C—C—, —C=C—C—, —C—C=C—, —O—C—, —C—O—, —C—O—C—, —S—C—, —C—S—, or —C—S—C—;

$R^2$ is independently halogen, $-CX^2{}_3$, $-CHX^2{}_2$, $-CH_2X^2$, $-OCX^2{}_3$, $-OCH_2X^2$, $-OCHX^2{}_2$, $-CN$, —SO$_{n2}$R$^{2D}$, —SO$_{v2}$NR$^{2A}$R$^{2B}$, —NHC(O)NR$^{2A}$R$^{2B}$, —N(O)$_{m2}$, —NR$^{2A}$R$^{2B}$, —C(O)R$^{2C}$, —C(O)—OR$^{2C}$, —C(O)NR$^{2A}$R$^{2B}$, —OR$^{2D}$, —NR$^{2A}$SO$_2$R$^{2D}$, —NR$^{2A}$C(O)R$^{2C}$, —NR$^{2A}$C(O)OR$^{2C}$, —NR$^{2A}$OR$^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or two adjacent R$^2$ substituents may optionally be joined to form a substituted or unsubstituted cycloalkyl, substituted or unsubstituted heterocycloalkyl, substituted or unsubstituted aryl, or substituted or unsubstituted heteroaryl;

R$^3$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a prodrug moiety;

R$^4$ is independently hydrogen, —CX$^4_3$, —CN, —COOH, —CONH$_2$, —CHX$^4_2$, —CH$_2$X$^4$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

L$^2$ is unsubstituted alkylene;

L$^3$ is a bond, —O—, —S—, —N(R$^7$)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

R$^7$ is hydrogen, —CN, —COOH, —CX$^7_3$, substituted or unsubstituted alkyl, or substituted or unsubstituted heteroalkyl;

L$^4$ is —O—, —S—, —N(R$^8$)—, —C(O)—, C(O)O—, —S(O)—, —S(O)$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

R$^8$ is hydrogen, —CN, —COOH, —CX$^8_3$, substituted or unsubstituted alkyl, or substituted or unsubstituted heteroalkyl;

R$^5$ is hydrogen,

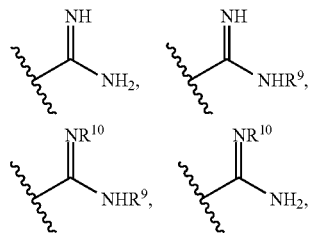

substituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or R$^5$ and R$^6$ may optionally be joined to form unsubstituted heteroaryl;

R$^6$ is

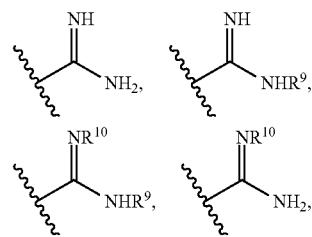

unsubstituted heteroalkyl, substituted or unsubstituted cycloalkyl, substituted or unsubstituted heterocycloalkyl, or substituted or unsubstituted heteroaryl;

R$^9$ is hydrogen, halogen, —N$_3$, —CX$^9_3$, —CHX$^9_2$, —CH$_2$X$^9$, —CN, —CHO, —OH, —NH$_2$, —COOH, —CONH$_2$, —NO$_2$, —SH, —SO$_2$, —SO$_2$CH$_3$—SO$_3$H, —SO$_4$H, —SO$_2$NH$_2$, —NHNH$_2$, —ONH$_2$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{10}$ is hydrogen, halogen, —N$_3$, —CX$^{10}_3$, —CHX$^{10}_2$, —CH$_2$X$^{10}$, —CN, —CHO, —OH, —NH$_2$, —COOH, —CONH$_2$, —NO$_2$, —SH, —SO$_2$, —SO$_2$CH$_3$—SO$_3$H, —SO$_4$H, —SO$_2$NH$_2$, —NHNH$_2$, —ONH$_2$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{1A}$, R$^{1B}$, R$^{1C}$, R$^{1D}$, R$^{2A}$, R$^{2B}$, R$^{2C}$, and R$^{2D}$ are each independently hydrogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or R$^{1A}$ and R$^{1B}$ substituents bonded to the same nitrogen atom may optionally be joined to form a substituted or unsubstituted heterocycloalkyl or substituted or unsubstituted heteroaryl; or R$^{2A}$ and R$^{2B}$ substituents bonded to the same nitrogen atom may optionally be joined to form a substituted or unsubstituted heterocycloalkyl or substituted or unsubstituted heteroaryl;

X, X$^1$, X$^2$, X$^4$, X$^7$, X$^8$, X$^9$, and X$^{10}$ are each independently —F, —Cl, —Br, or —I;

n1 and n2 are each independently an integer from 0 to 4;

m1, m2, v1 and v2 are each independently 1 or 2;

z1 is an integer from 0 to 5;

z2 is an integer from 0 to 9; and z3 is 0 or 1.

2. The compound according to claim 1 having the formula:

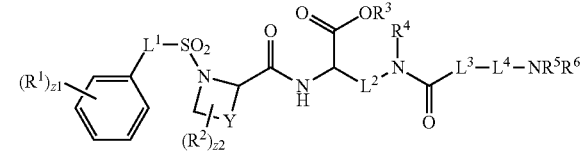

wherein,
R¹ is independently halogen, —CX¹₃, —CHX¹₂, —CH₂X¹, —OCX¹₃, —OCH₂X¹, —OCHX¹₂, —CN, —SO$_{n1}$R$^{1D}$, —SO$_{v1}$NR$^{1A}$R$^{1B}$, —NHC(O)NR$^{1A}$R$^{1B}$, —N(O)$_{m1}$, —NR$^{1A}$R$^{1B}$, —C(O)R$^{1C}$, —C(O)—OR$^{1C}$, —C(O)NR$^{1A}$R$^{1B}$, —OR$^{1D}$, —NR$^{1A}$SO₂R$^{1D}$, —NR$^{1A}$C(O)R$^{1C}$, —NR$^{1A}$C(O)OR$^{1C}$, —NR$^{1A}$OR$^{1C}$ substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety; or two adjacent R¹ substituents may optionally be joined to form a substituted or unsubstituted cycloalkyl, substituted or unsubstituted heterocycloalkyl, substituted or unsubstituted aryl, or substituted or unsubstituted heteroaryl;

L¹ is a bond, substituted or unsubstituted alkylene, or substituted or unsubstituted heteroalkylene;

Y is a bond, —C—, —C—C—, —C=C—, —C—C—C—, —C=C—C—, —C—C=C—, —O—C—, —C—O—, —C—O—C, —S—C—, —C—S—, or —C—S—C—;

R² is independently halogen, —CX²₃, —CHX²₂, —CH₂X², —OCX²₃, —OCH₂X², —OCHX²₂, —CN, —SO$_{n2}$R$^{2D}$, —SO$_{v2}$NR$^{2A}$R$^{2B}$, —NHC(O)NR$^{2A}$R$^{2B}$, —N(O)$_{m2}$, —NR$^{2A}$R$^{2B}$, —C(O)R$^{2C}$, —C(O)—OR$^{2C}$, —C(O)NR$^{2A}$R$^{2B}$, —OR$^{2D}$, —NR$^{2A}$SO₂R$^{2D}$, —NR$^{2A}$C(O)R$^{2C}$, —NR$^{2A}$C(O)OR$^{2C}$, —NR$^{2A}$OR$^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or two adjacent R² substituents may optionally be joined to form a substituted or unsubstituted cycloalkyl, substituted or unsubstituted heterocycloalkyl, substituted or unsubstituted aryl, or substituted or unsubstituted heteroaryl;

R³ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a prodrug moiety;

R⁴ is independently hydrogen, —CX⁴₃, —CN, —COOH, —CONH₂, —CHX⁴₂, —CH₂X⁴, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

L² is unsubstituted alkylene;

L³ is a bond, —O—, —S—, —N(R⁷)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

R⁷ is hydrogen, —CN, —COOH, —CX⁷₃, substituted or unsubstituted alkyl, or substituted or unsubstituted heteroalkyl;

L⁴ is —O—, —S—, —N(R⁸)—, —C(O)—, —C(O)O—, —S(O)—, —S(O)₂—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

R⁸ is hydrogen, —CN, —COOH, —CX⁸₃, substituted or unsubstituted alkyl, or substituted or unsubstituted heteroalkyl;

R⁵ is hydrogen,

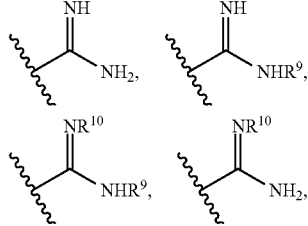

substituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or R⁵ and R⁶ may optionally be joined to form unsubstituted heteroaryl;

R⁶ is

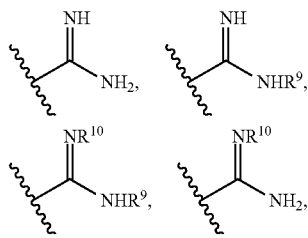

unsubstituted heteroalkyl, substituted or unsubstituted cycloalkyl, substituted or unsubstituted heterocycloalkyl, or substituted or unsubstituted heteroaryl;

R⁹ is hydrogen, halogen, —N₃, —CX⁹₃, —CHX⁹₂, —CH₂X⁹, —CN, —CHO, —OH, —NH₂, —COOH, —CONH₂, —NO₂, —SH, —SO₂, —SO₂CH₃—SO₃H, —SO₄H, —SO₂NH₂, —NHNH₂, —ONH₂, —NHC(O)NHNH₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R¹⁰ is hydrogen, halogen, —N₃, —CX¹⁰₃, —CHX¹⁰₂, —CH₂X¹⁰, —CN, —CHO, —OH, —NH₂, —COOH, —CONH₂, —NO₂, —SH, —SO₂, —SO₂CH₃—SO₃H, —SO₄H, —SO₂NH₂, —NHNH₂, —ONH₂, —NHC(O)NHNH₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{1A}$, R$^{1B}$, R$^{1C}$, R$^{1D}$, R$^{2A}$, R$^{2B}$, R$^{2C}$, and R$^{2D}$ are each independently hydrogen, —CX₃, —CN, —COOH, —CONH₂, —CHX₂, —CH₂X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or R$^{1A}$ and R$^{1B}$ substituents bonded to the same nitrogen atom may optionally be joined to form a substituted or unsubstituted heterocycloalkyl or substituted or unsubstituted heteroaryl; or R$^{2A}$ and R$^{2B}$ substituents bonded to the same nitrogen atom may optionally be joined to form a substituted or unsubstituted heterocycloalkyl or substituted or unsubstituted heteroaryl;

$X, X^1, X^2, X^4, X^7, X^8, X^9$, and $X^{10}$ are each independently —F, —Cl, —Br, or —I;

n1 and n2 are each independently an integer from 0 to 4;

m1, m2, v1 and v2 are each independently 1 or 2;

z1 is an integer from 0 to 5; and z2 is an integer from 0 to 9.

3. The compound of claim 1, wherein Y is —C—C—, —C=C—, —O—C—, —C—O—, —C—O—C—, —C—S—, —S—C, or —C—S—C—.

4. The compound of claim 1, having the formula:

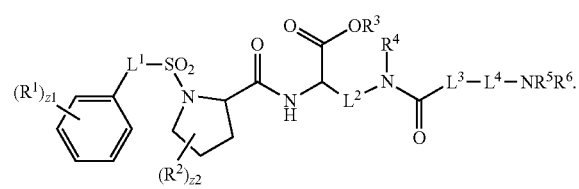

5. The compound of claim 1, wherein $R^1$ is independently halogen, —OMe, —SMe, —SO$_2$Me, —SO$_2$Ph, —COOH, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted phenyl, or substituted or unsubstituted 5 to 6 membered heteroaryl; or two adjacent $R^1$ substituents may optionally be joined to form a substituted or unsubstituted $C_3$-$C_8$ cycloalkyl, substituted or unsubstituted 3 to 8 membered heterocycloalkyl, substituted or unsubstituted phenyl, or substituted or unsubstituted 5 to 6 membered heteroaryl.

6. The compound of claim 1, wherein $L^2$ is unsubstituted $C_1$-$C_2$alkylene.

7. The compound of claim 1, wherein $L^3$ is a bond, substituted or unsubstituted $C_1$-$C_8$ alkylene, or substituted or unsubstituted 2 to 8 membered heteroalkylene.

8. The compound of claim 1, wherein:

$R^5$ is hydrogen,

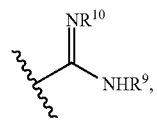

substituted or unsubstituted 3 to 8 membered heterocycloalkyl, substituted or unsubstituted phenyl, or substituted or unsubstituted 5 to 6 membered heteroaryl; and $R^6$ is

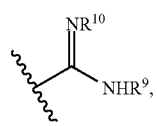

substituted or unsubstituted 3 to 8 membered heterocycloalkyl, or substituted or unsubstituted 5 to 6 membered heteroaryl.

9. The compound of claim 1, wherein:

$R^5$ is hydrogen, substituted or unsubstituted 5 to 6 membered heteroaryl,

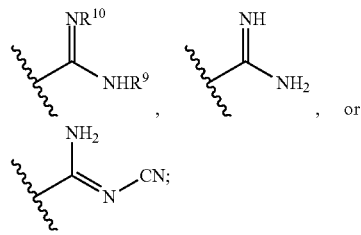

and $R^6$ is substituted or unsubstituted 5 to 6 membered heteroaryl,

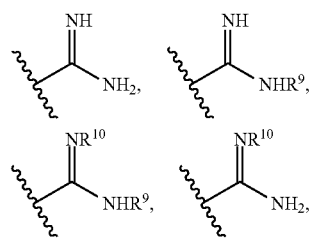

10. The compound of claim 1, wherein $R^5$ is hydrogen and $R^6$ is

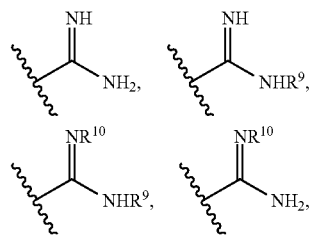

substituted or unsubstituted cycloalkyl, substituted or unsubstituted heterocycloalkyl, or substituted or unsubstituted heteroaryl.

11. The compound of claim 1, wherein $R^5$ and $R^6$ are joined to form a unsubstituted heteroaryl.

12. The compound of claim 1, wherein $R^5$ is hydrogen and $R^6$ is substituted or unsubstituted 5 to 6 membered heteroaryl or

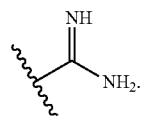

13. The compound of claim 1, wherein $R^5$ is hydrogen and $R^6$ is substituted or unsubstituted 5 to 6 membered heteroaryl.

14. The compound of claim 1, wherein $R^3$ is hydrogen, a substituted or unsubstituted alkyl, or substituted or unsubstituted heteroalkyl.

15. A compound having the formula:
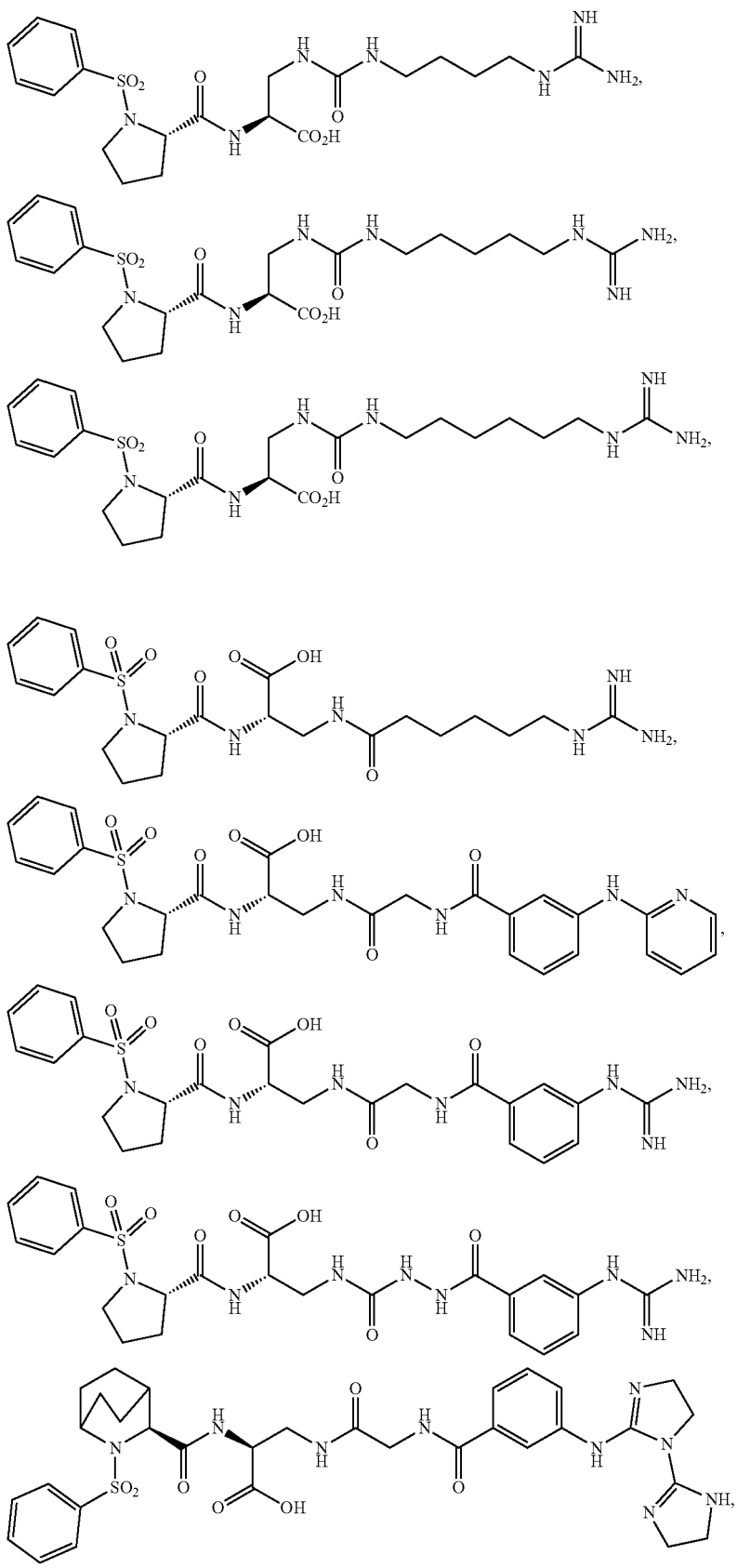

-continued
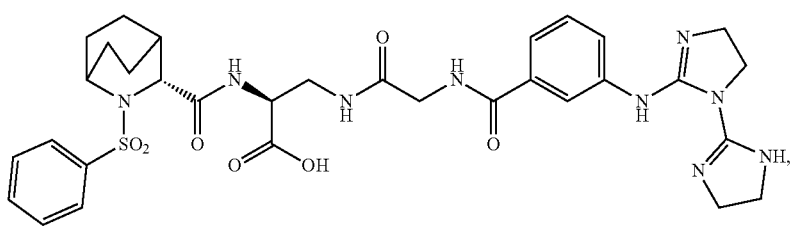
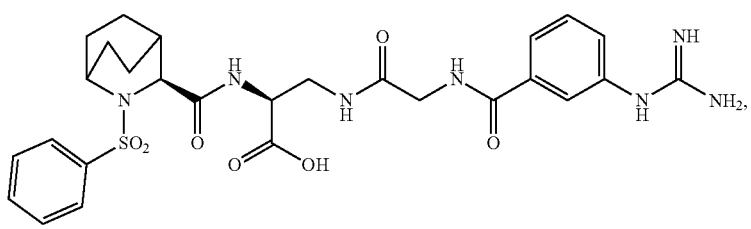
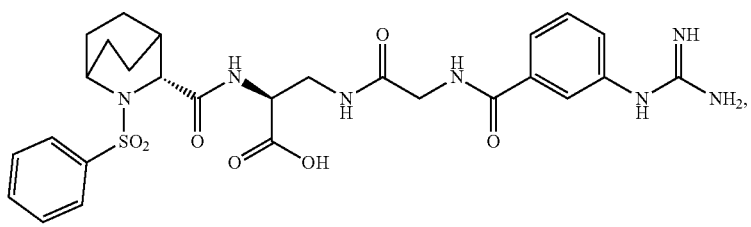
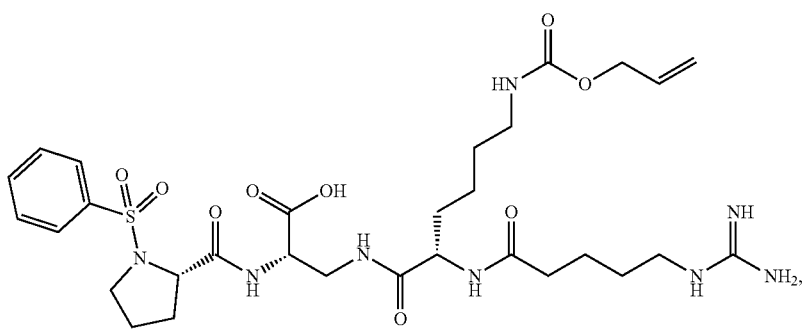
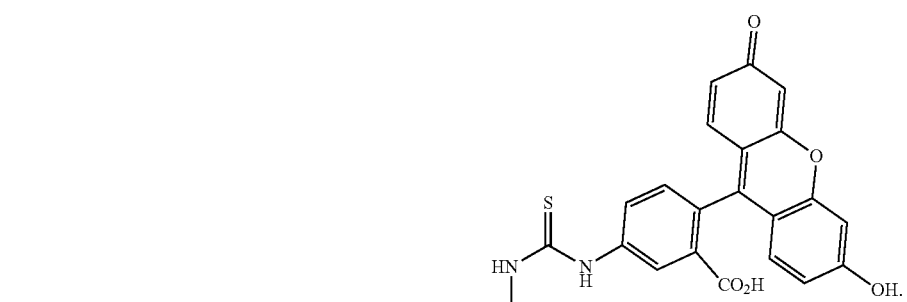
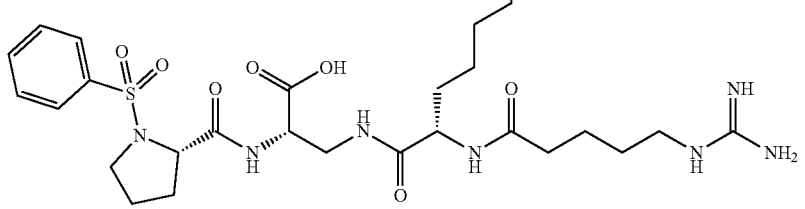

-continued

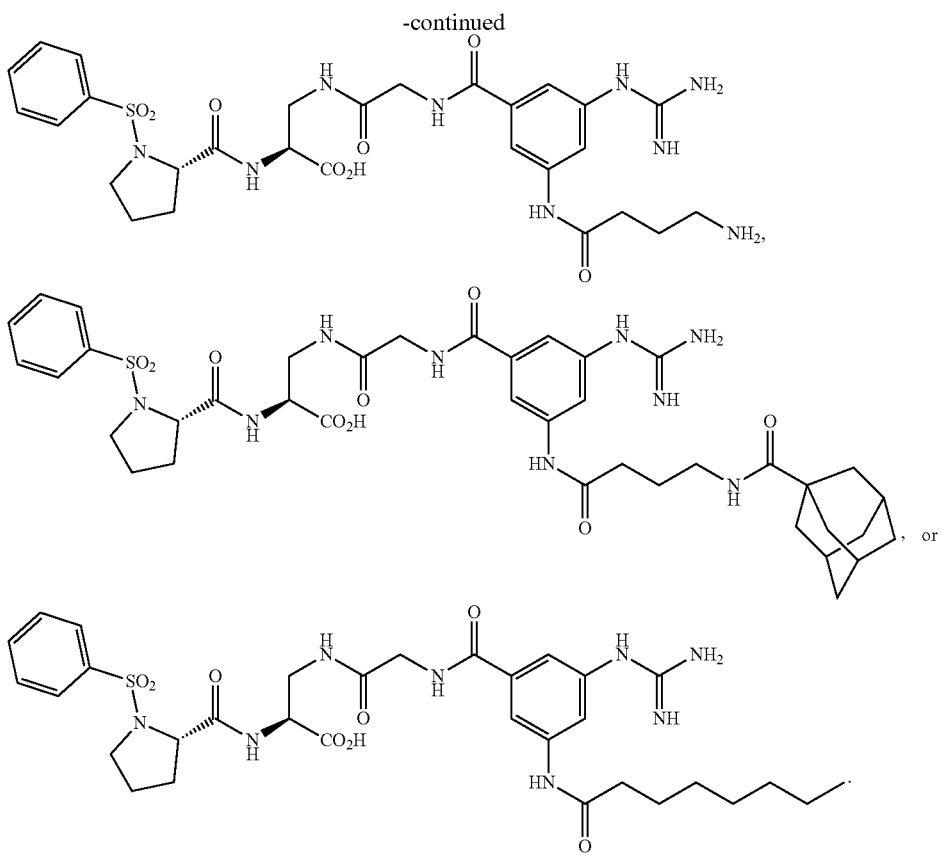

16. The compound of claim 1, wherein $R^3$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

17. The compound of claim 2, wherein $R^3$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl.

18. A pharmaceutical composition comprising the compound of claim 1 and a pharmaceutically acceptable excipient.

19. A method for treating asthma, said method comprising administering to a subject in need thereof an effective amount of the compound of claim 1 or a pharmaceutically acceptable salt thereof.

20. A method of detecting the presence of α5β1 integrin or inhibiting α5β1 integrin activity or a combination thereof, said method comprising contacting an α5β1 integrin with the compound of claim 1.

21. A method for treating asthma in a subject in need thereof, the method comprising administering to the subject an effective amount of the compound of claim 15 or a pharmaceutically acceptable salt thereof.

* * * * *